US011666641B2

(12) United States Patent
Baram et al.

(10) Patent No.: US 11,666,641 B2
(45) Date of Patent: Jun. 6, 2023

(54) CRISPR NUCLEASE

(71) Applicant: EmendoBio Inc., Wilmington, DE (US)

(72) Inventors: David Baram, Tel Aviv (IL); Lior Izhar, Tel Aviv (IL); Asael Herman, Ness-Ziona (IL); Liat Rockah, Rishon LeZion (IL); Nadav Marbach-Bar, Rehovot (IL); Nurit Meron, Ramat Gan (IL); Joseph Georgeson, Rehovot (IL)

(73) Assignee: EMENDOBIO INC., Wilmington, DE (US)

( * ) Notice: Subject to any disclaimer, the term of this patent is extended or adjusted under 35 U.S.C. 154(b) by 0 days.

(21) Appl. No.: 17/594,761

(22) PCT Filed: Apr. 30, 2020

(86) PCT No.: PCT/US2020/030782

§ 371 (c)(1),
(2) Date: Oct. 28, 2021

(87) PCT Pub. No.: WO2020/223514

PCT Pub. Date: Nov. 5, 2020

(65) Prior Publication Data

US 2022/0202913 A1 Jun. 30, 2022

Related U.S. Application Data

(60) Provisional application No. 62/841,046, filed on Apr. 30, 2019, provisional application No. 62/897,806, filed on Sep. 9, 2019, provisional application No. 62/931,630, filed on Nov. 6, 2019, provisional application No. 62/959,672, filed on Jan. 10, 2020, provisional application No. 62/991,285, filed on Mar. 18, 2020.

(51) Int. Cl.

| | |
|---|---|
| ***C12N 9/22*** | (2006.01) |
| ***A61K 38/46*** | (2006.01) |
| ***A61K 31/7105*** | (2006.01) |
| ***C12N 15/11*** | (2006.01) |
| ***C12N 15/90*** | (2006.01) |

(52) U.S. Cl.

CPC ........ *A61K 38/465* (2013.01); *A61K 31/7105* (2013.01); *C12N 9/22* (2013.01); *C12N 15/11* (2013.01); *C12N 15/907* (2013.01); *C12N 2310/20* (2017.05); *C12N 2800/80* (2013.01)

(58) Field of Classification Search

CPC ........................................................ C12N 9/22

See application file for complete search history.

(56) References Cited

U.S. PATENT DOCUMENTS

2011/0182867 A1 7/2011 Orkin

FOREIGN PATENT DOCUMENTS

| | | |
|---|---|---|
| WO | WO 2013/176772 A1 | 11/2013 |
| WO | WO 2015/134812 A1 | 9/2015 |
| WO | WO 2017/024047 A1 | 2/2017 |
| WO | WO 2017/077394 A2 | 5/2017 |

OTHER PUBLICATIONS

International Preliminary Report on Patentability dated Nov. 2, 2021, including Written Opinion of the International Searching Authority dated Nov. 16, 2020, in connection with PCT International Application No. PCT/US2020/030782.

Anders et al. "Structural basis of PAM-dependent target DNA recognition by the Cas9 endonuclease", Nature, 513, 569-573 (2014).

Briner et al. (2014) "Guide RNA functional modules direct Cas9 activity and orthogonality", Molecular Cell, 56:333-39.

Burstein et al. (2017) "New CRISPR-Cas systems from uncultivated microbes", Nature, 542:237-41.

Canver et al., "BCL11A enhancer dissection by Cas9-mediated in situ saturating mutagenesis", Nature, Nov. 12, 2015, vol. 527, pp. 192-214.

Charlesworth et al. (2019) "Identification of preexisting adaptive immunity to Cas9 proteins in humans", Nature Medicine, 25(2), 249.

Humbert et al., "Therapeutically relevant engraftment of a CRISPR-Cas9—edited HSC-enriched population with HbF reactivation in nonhuman primates", Sci. Trans. Med., Jul. 31, 2019, vol. 11, pp. 1-13.

Jiang et al. "Structures of a CRISPR-Cas9 R-loop complex primed for DNA cleavage", Science, Feb. 19, 2016; 351(6275):867-71.

Jiang and Doudna (2017) "CRISPR-Cas9 Structures and Mechanisms", Annual Review of Biophysics 46:505-29.

Jinek et al. (2012) "A programmable dual-RNA-guided DNA endonuclease in adaptive bacterial immunity", Science 337(6096):816-21.

Maxwell et al. (2018) "A detailed cell-free transcription-translation-based assay to decipher CRISPR protospacer adjacent motifs", Methods 14348-57.

Mir et al. (2019) "Type II-C CRISPR-Cas9 Biology, Mechanism and Application", ACS Chem. Biol. 13(2):357-365.

Nishimasu et al. (2014) "Crystal structure of Cas9 in complex with guide RNA and target DNA", Cell 156(5):935-49.

Nishimasu et al. (2015) "Crystal Structure of *Staphylococcus aureus* Cas9", Cell 162(5):1113-26.

Nowak et al., "Survey and Summary: Guide RNA engineering for versatile Cas9 functionality", Nucleic Acids Research, 2016, Vo. 44, No. 20, pp. 9555-9564.

Palermo et al. (2018) "Key role of the REC lobe during CRISPR-Cas9 activation by 'sensing', 'regulating', and 'locking' the catalytic HNH domain" Quarterly Reviews of Biophysics 51, e9, 1-11.

Sentmanat et al. (2018) "A Survey of Validation Strategies for CRISPR-Cas9 Editing", Scientific Reports 8:888.

(Continued)

*Primary Examiner* — Karen Cochrane Carlson
(74) *Attorney, Agent, or Firm* — Gary J. Gershik

(57) ABSTRACT

The present invention provides a non-naturally occurring composition comprising a CRISPR nuclease comprising a sequence having at least 95% identity to the amino acid sequence of SEQ ID NO: 3 or a nucleic acid molecule comprising a sequence encoding the CRISPR nuclease.

39 Claims, 15 Drawing Sheets

Specification includes a Sequence Listing.

(56) References Cited

OTHER PUBLICATIONS

Sternberg et al. "Conformational control of DNA target cleavage by CRISPR-Cas9", Nature, Nov. 5, 2015; 527(7576):110-3.
Wagner et al. (2019) "High prevalence of *Streptococcus pyogenes* Cas9-reactive T cells within the adult human population" Nature Medicine, 25(2), 242.
Zetsche et al. (2015) "Cpf1 is a single RNA-guided endonuclease of a class 2 CRIPSR-Cas system" Cell 163(3):759-71.
Database GenPept [Online] Nov. 10, 2017 (Nov. 10, 2017), "Type II CRISPR RNA-guided endonuclease Cas9 [Ezakiella peruensis]", XP93010135, retrieved from NCBI Accession No. RefSeq:WP_099951290, Database Accession No. WP 099951290.
Database GenBank [Online] Feb. 9, 2018 (Feb. 9, 2018), "Ezakiella peruensis strain M6.X2 isolate M6.X2, whole genome shotgun sequence—Cas9—locus_tag="CUU59_RS07215"—complement(78708..82820)", XP93010158, retrieved from NCBI Accession No. RefSeq:NZ_LT962471, Database Accession No. NZ_LT962471.
Cebrian-Serrano Alberto et al. (2017) "CRISPR-Cas orthologues and variants: optimizing the repertoire, specificity and delivery of genome engineering tools", Mammalian Genome, Jun. 20 2017, vol. 28, No. 7, pp. 247-261.
Jan. 9, 2023 Extended European Search Report issued in connection with European Patent Application No. 20799462.5.
International Search Report dated Nov. 16, 2020 in connection with PCT International Application No. PCT/US2020/030782.
Notification of Transmittal of the International Search Report and the Written Opinion of the International Searching Authority, or the Declaration (form PCT/ISA/220) dated Nov. 16, 2020 in connection with PCT International Application No. PCT/US2020/030782.
Written Opinion of the International Searching Authority dated Nov. 16, 2020 in connection with PCT International Application No. PCT/US2020/030782.

positions 1-4

| 1 | 2 | 3 | 4 | 5 | 6 | 7 | 8 | Ratio |
|---|---|---|---|---|---|---|---|---|
| C | G | G | G | | | | | 0.01 |
| C | G | G | A | | | | | 0.03 |
| | G | G | G | A | | | | 0.05 |
| | G | G | A | G | | | | 0.05 |
| | G | G | G | G | | | | 0.05 |
| T | G | G | G | | | | | 0.06 |
| G | G | G | A | | | | | 0.06 |
| G | G | G | G | | | | | 0.06 |
| | G | G | G | C | | | | 0.06 |
| | G | G | G | T | | | | 0.07 |
| | G | G | A | T | | | | 0.08 |
| T | G | G | A | | | | | 0.11 |
| | | G | A | A | C | | | 0.52 |
| | | G | G | C | C | | | 0.55 |
| | | G | A | T | T | | | 0.56 |
| | | G | G | A | G | | | 0.57 |
| | | G | T | G | A | | | 0.59 |
| | | | | A | T | A | G | 0.59 |
| | | A | T | T | A | | | 0.60 |
| | | | T | C | G | G | | 0.61 |

positions 1-4

| 1 | 2 | 3 | 4 | 5 | 6 | 7 | 8 | Ratio |
|---|---|---|---|---|---|---|---|---|
| C | G | G | A | | | | | 0.02 |
| | G | G | A | T | | | | 0.02 |
| A | G | G | A | | | | | 0.03 |
| G | G | G | A | | | | | 0.03 |
| | G | G | G | T | | | | 0.03 |
| | G | G | A | G | | | | 0.03 |
| | G | G | A | C | | | | 0.03 |
| C | G | G | T | | | | | 0.03 |
| | G | G | A | A | | | | 0.03 |
| T | G | G | G | | | | | 0.03 |
| | G | G | T | C | | | | 0.03 |
| C | G | G | G | | | | | 0.04 |
| | | G | A | A | C | | | 0.57 |
| | | G | G | C | C | | | 0.59 |
| | | G | T | C | T | | | 0.59 |
| | | G | A | T | T | | | 0.60 |
| | | G | C | A | A | | | 0.60 |
| | | | | A | G | G | G | 0.60 |
| | | G | G | C | G | | | 0.61 |

OMNI-50 specificity g35 and g62 DNA transfection (HeLa)

On-target g35 5′ AGTCCGGGCTGGGAGCGGGTGGGGAGCA (SEQ ID NO: 130)
On-target g62 5′ GTCAAGCCCCAGAGGCCACAGGGACAGA (SEQ ID NO: 131)
Off-target g35 5′ AGTCCTGGCTGGGAGCAGGTGGGGAGAG (SEQ ID NO: 132)
Off-target g62 5′ GCCAAGCCTCAGAGGCCACAGGGCAGCA (SEQ ID OMNI-50 specificity in g35 RNP electroporation (U2OS)

EXHIBIT B

SEQUENCE LISTING

```
<160> NUMBER OF SEQ ID NOS: 197

<210> SEQ ID NO 1
<211> LENGTH: 1100
<212> TYPE: PRT
<213> ORGANISM: Butyrivibrio sp. AC2005

<400> SEQUENCE: 1

Met Gly Tyr Thr Ile Gly Leu Asp Leu Gly Val Ala Ser Leu Gly Trp
1               5                   10                  15

Ala Val Val Asn Asp Glu Tyr Glu Val Leu Glu Ser Cys Ser Asn Ile
            20                  25                  30

Phe Pro Ala Ala Glu Ser Ala Asn Asn Val Glu Arg Arg Gly Phe Arg
        35                  40                  45

Gln Gly Arg Arg Leu Ser Arg Arg Arg Arg Thr Arg Ile Ser Asp Phe
    50                  55                  60

Arg Lys Leu Trp Glu Lys Ser Gly Phe Glu Val Pro Ser Asn Glu Leu
65                  70                  75                  80

Asn Glu Val Leu Gln Tyr Arg Ile Lys Gly Met Asn Asp Lys Leu Ser
                85                  90                  95

Glu Asp Glu Leu Tyr His Val Leu Leu Asn Ser Leu Lys His Arg Gly
            100                 105                 110

Ile Ser Tyr Leu Asp Asp Ala Asp Asp Glu Asn Ala Ser Gly Asp Tyr
        115                 120                 125

Ala Ala Ser Ile Ala Tyr Asn Glu Asn Gln Leu Lys Thr Lys Leu Pro
    130                 135                 140

Cys Glu Ile Gln Trp Glu Arg Tyr Lys Lys Tyr Gly Ala Tyr Arg Gly
145                 150                 155                 160

Asn Ile Thr Ile Gln Glu Gly Gly Glu Pro Leu Thr Leu Arg Asn Val
                165                 170                 175

Phe Thr Thr Ser Ala Tyr Glu Lys Glu Ile Gln Lys Leu Leu Asp Val
            180                 185                 190

Gln Ser Met Ser Asn Glu Lys Val Thr Lys Lys Phe Ile Asp Glu Tyr
        195                 200                 205

Leu Lys Ile Phe Ser Arg Lys Arg Glu Tyr Tyr Ile Gly Pro Gly Asn
    210                 215                 220

Lys Lys Ser Arg Thr Asp Tyr Gly Val Tyr Thr Thr Gln Lys Asn Glu
225                 230                 235                 240

Asp Gly Thr Tyr His Thr Glu Gln Asn Leu Phe Asp Lys Leu Ile Gly
                245                 250                 255

Lys Cys Ser Val Tyr Pro Asp Glu Arg Arg Ala Ala Gly Ala Thr Tyr
            260                 265                 270

Thr Ala Gln Glu Phe Asn Leu Leu Asn Asp Leu Asn Asn Leu Val Ile
        275                 280                 285

Asp Gly Arg Lys Leu Asp Glu Gln Glu Lys Cys Gln Ile Val Asp Ala
    290                 295                 300

Val Lys His Ala Lys Thr Val Asn Met Lys Asn Ile Ile Ala Lys Val
305                 310                 315                 320
```

-continued

```
Ile Gly Thr Lys Ala Asn Ser Met Asn Met Thr Gly Ala Arg Ile Asp
                325                 330                 335

Lys Asn Glu Lys Glu Ile Phe His Ser Phe Glu Ala Tyr Asn Lys Leu
            340                 345                 350

Arg Lys Ala Leu Glu Glu Ile Asp Phe Asp Ile Glu Thr Leu Ser Thr
        355                 360                 365

Asp Glu Leu Asp Ala Ile Gly Glu Val Leu Thr Leu Asn Thr Asp Arg
    370                 375                 380

Lys Ser Ile Gln Asn Gly Leu Gln Glu Lys Arg Ile Val Val Pro Asp
385                 390                 395                 400

Glu Val Arg Asp Val Leu Ile Ala Thr Arg Lys Arg Asn Gly Ser Leu
                405                 410                 415

Phe Ser Lys Trp Gln Ser Phe Gly Ile Arg Ile Met Lys Glu Leu Ile
            420                 425                 430

Pro Glu Leu Tyr Ala Gln Pro Lys Asn Gln Met Gln Leu Leu Thr Asp
        435                 440                 445

Met Gly Val Phe Lys Thr Lys Asp Glu Arg Phe Val Glu Tyr Asp Lys
    450                 455                 460

Ile Pro Ser Asp Leu Ile Thr Glu Glu Ile Tyr Asn Pro Val Val Ala
465                 470                 475                 480

Lys Thr Val Arg Ile Thr Val Arg Val Leu Asn Ala Leu Ile Lys Lys
                485                 490                 495

Tyr Gly Tyr Pro Asp Arg Val Val Ile Glu Met Pro Arg Asp Lys Asn
            500                 505                 510

Ser Glu Glu Glu Lys Lys Arg Ile Ala Asp Phe Gln Lys Asn Asn Glu
        515                 520                 525

Asn Glu Leu Gly Gly Ile Ile Lys Lys Val Lys Ser Glu Tyr Gly Ile
    530                 535                 540

Glu Ile Thr Asp Ala Asp Phe Lys Asn His Ser Lys Leu Gly Leu Lys
545                 550                 555                 560

Leu Arg Leu Trp Asn Glu Gln Asn Glu Thr Cys Pro Tyr Ser Gly Lys
                565                 570                 575

His Ile Lys Ile Asp Asp Leu Leu Asn Asn Pro Asn Met Phe Glu Val
            580                 585                 590

Asp His Ile Ile Pro Leu Ser Ile Ser Phe Asp Asp Ser Arg Ala Asn
        595                 600                 605

Lys Val Leu Val Tyr Ala Ala Glu Asn Gln Asn Lys Gly Asn Arg Thr
    610                 615                 620

Pro Met Ala Tyr Leu Ser Asn Val Asn Arg Glu Trp Asp Phe His Glu
625                 630                 635                 640

Tyr Met Ser Phe Val Leu Ser Asn Tyr Lys Gly Thr Ile Tyr Gly Lys
                645                 650                 655

Lys Arg Asp Asn Leu Leu Phe Ser Glu Asp Ile Tyr Lys Ile Asp Val
            660                 665                 670

Leu Gln Gly Phe Ile Ser Arg Asn Ile Asn Asp Thr Arg Tyr Ala Ser
        675                 680                 685

Lys Val Ile Leu Asn Ser Leu Gln Ser Phe Phe Gly Ser Lys Glu Cys
    690                 695                 700

Asp Thr Lys Val Lys Val Val Arg Gly Thr Phe Thr His Gln Met Arg
705                 710                 715                 720

Met Asn Leu Lys Ile Glu Lys Asn Arg Glu Glu Ser Tyr Val His His
                725                 730                 735
```

-continued

```
Ala Val Asp Ala Met Leu Ile Ala Phe Ser Gln Met Gly Tyr Asp Ala
            740                 745                 750

Tyr His Lys Leu Thr Glu Lys Tyr Ile Asp Tyr Glu His Gly Glu Phe
        755                 760                 765

Val Asp Gln Lys Gly Tyr Glu Lys Leu Ile Glu Asn Asp Val Ala Tyr
    770                 775                 780

Arg Glu Thr Thr Tyr Gln Asn Lys Trp Met Thr Ile Lys Lys Asn Ile
785                 790                 795                 800

Glu Ile Ala Ala Glu Lys Asn Lys Tyr Trp Tyr Gln Val Asn Arg Lys
                805                 810                 815

Ser Asn Arg Gly Leu Cys Asn Gln Thr Ile Tyr Gly Thr Arg Asn Leu
            820                 825                 830

Asp Gly Lys Thr Val Lys Ile Ser Lys Leu Asp Ile Arg Thr Asp Asp
        835                 840                 845

Gly Ile Lys Lys Phe Lys Gly Ile Val Glu Lys Gly Lys Leu Glu Arg
    850                 855                 860

Phe Leu Met Tyr Arg Asn Asp Pro Lys Thr Phe Glu Trp Leu Leu Gln
865                 870                 875                 880

Ile Tyr Lys Asp Tyr Ser Asp Ser Lys Asn Pro Phe Val Gln Tyr Glu
                885                 890                 895

Ser Glu Thr Gly Asp Val Ile Lys Lys Val Ser Lys Thr Asn Asn Gly
            900                 905                 910

Pro Lys Val Cys Glu Leu Arg Tyr Glu Asp Gly Glu Val Gly Ser Cys
        915                 920                 925

Ile Asp Ile Ser His Lys Tyr Gly Tyr Lys Lys Gly Ser Lys Lys Val
    930                 935                 940

Ile Leu Asp Ser Leu Asn Pro Tyr Arg Met Asp Val Tyr Tyr Asn Thr
945                 950                 955                 960

Lys Asp Asn Arg Tyr Tyr Phe Val Gly Val Lys Tyr Ser Asp Ile Lys
                965                 970                 975

Cys Gln Gly Asp Ser Tyr Val Ile Asp Glu Asp Lys Tyr Ala Ala Ala
            980                 985                 990

Leu Val Gln Glu Lys Ile Val Pro  Glu Gly Lys Gly Arg  Ser Asp Leu
        995                 1000                1005

Thr Glu  Leu Gly Tyr Glu Phe  Lys Leu Ser Phe Tyr  Lys Asn Glu
    1010                1015                1020

Ile Ile  Glu Tyr Glu Lys Asp  Gly Glu Ile Tyr Val  Glu Arg Phe
    1025                1030                1035

Leu Ser  Arg Thr Met Pro Lys  Val Ser Asn Tyr Ile  Glu Thr Lys
    1040                1045                1050

Pro Leu  Glu Ala Ala Lys Phe  Glu Lys Arg Asn Leu  Val Gly Leu
    1055                1060                1065

Ala Lys  Thr Ser Arg Ile Arg  Lys Ile Arg Val Asp  Ile Leu Gly
    1070                1075                1080

Asn Arg  Tyr Leu Asn Ser Met  Glu Asn Phe Asp Phe  Val Val Gly
    1085                1090                1095

His Lys
    1100


<210> SEQ ID NO 2
<211> LENGTH: 1104
<212> TYPE: PRT
<213> ORGANISM: bacterium LF-3

<400> SEQUENCE: 2
```

-continued

```
Met Ser Arg Tyr Val Leu Gly Leu Asp Ile Gly Ile Thr Ser Val Gly
1               5                   10                  15

Tyr Gly Val Ile Asp Ile Asp Asn Asn Leu Phe Val Asp Tyr Gly Val
            20                  25                  30

Arg Leu Phe Lys Glu Gly Thr Ala Ala Glu Asn Glu Thr Arg Arg Thr
        35                  40                  45

Lys Arg Gly Ser Arg Arg Leu Lys Arg Arg Lys Ser Asn Arg Leu Asn
    50                  55                  60

Asp Met Lys Asn Leu Leu Lys Glu Asn Asp Leu Tyr Phe Glu Asp Tyr
65                  70                  75                  80

Arg Asn Tyr Asn Pro Tyr Glu Ile Arg Ala Lys Gly Leu Lys Glu Lys
                85                  90                  95

Leu Leu Pro Glu Glu Leu Cys Thr Ala Ile Met His Ile Thr Lys Ser
            100                 105                 110

Arg Gly Thr Thr Leu Glu Ala Leu Ala Asp Glu Ser Gln Asp Asp Glu
        115                 120                 125

Gly Thr Lys Ala Thr Leu Ser Lys Asn Ala Lys Glu Leu Asn Asp Gly
    130                 135                 140

Lys Tyr Ile Cys Glu Val Gln Leu Asp Arg Leu Asn Lys Asp His Lys
145                 150                 155                 160

Val Arg Gly Thr Glu Asn Asn Phe Lys Thr Glu Asp Tyr Val Lys Glu
                165                 170                 175

Leu Lys Glu Ile Leu Lys His Gln Asp Leu Asn Glu Glu Leu Cys Asp
            180                 185                 190

Gln Ile Ile Glu Met Val Ser Arg Arg Arg Arg Tyr Asp Gln Gly Pro
        195                 200                 205

Gly Ser Glu Lys Ser Pro Thr Pro Tyr Gly Ser Tyr Arg Met Val Asp
    210                 215                 220

Gly Val Leu Lys His Val Asn Leu Ile Asp Glu Met Arg Gly Arg Cys
225                 230                 235                 240

Ser Val Tyr Pro Asp Glu Phe Arg Ala Pro Lys Gln Ser Tyr Thr Ala
                245                 250                 255

Glu Leu Phe Asn Leu Leu Asn Asp Leu Asn Asn Leu Thr Ile Lys Gly
            260                 265                 270

Glu Lys Ile Thr Val Glu Glu Lys Glu Lys Val Val Ala Phe Val Asn
        275                 280                 285

Glu Lys Gly Ser Ile Thr Val Lys Gln Leu Leu Lys Leu Leu Asp Ala
    290                 295                 300

Gln Glu Asp Glu Val Thr Gly Phe Arg Ile Asp Lys Asn Asp Lys Pro
305                 310                 315                 320

Leu Ile Thr Glu Phe Lys Gly Tyr Ser Lys Val Leu Lys Val Phe Lys
                325                 330                 335

Lys Tyr Asn Gln Gln Glu Leu Leu Glu Asp Lys Leu Ile Val Asp Gln
            340                 345                 350

Val Ile Asp Ile Cys Thr Lys Ser Lys Gly Ile Asp Glu Arg Lys Lys
        355                 360                 365

Asp Ile Lys Glu Leu Tyr Pro Glu Phe Asp Asn Glu Leu Ile Glu Glu
    370                 375                 380

Leu Ala Ser Val Lys Gly Val Ser Ala Tyr His Ser Leu Ser Phe Lys
385                 390                 395                 400

Ala Met His Ile Ile Asn Lys Glu Met Leu Thr Thr Glu Met Asn Gln
                405                 410                 415
```

-continued

```
Ile Gln Val Leu His Glu Ile Glu Met Phe Asp Lys Asn Arg Lys Ser
            420                 425                 430

Leu Lys Gly Lys Lys Asn Ile Glu Pro Asp Glu Glu Ala Ile Leu Ser
        435                 440                 445

Pro Val Ala Lys Arg Ala His Arg Glu Thr Phe Lys Val Ile Asn Ala
    450                 455                 460

Leu Arg Lys Gln Tyr Gly Glu Phe Asp Ser Ile Val Ile Glu Met Thr
465                 470                 475                 480

Arg Asp Lys Asn Ser Lys Glu Gln Val Lys Arg Ile Asn Asp Ser Gln
                485                 490                 495

Lys Arg Phe Lys Ser Glu Asn Asp Arg Val Asp Gly Ile Ile Lys Asn
            500                 505                 510

Ser Gly Ile Asp Pro Glu Arg Val Asn Gly Lys Thr Lys Thr Lys Ile
        515                 520                 525

Arg Leu Tyr Leu Gln Gln Asp Cys Lys Thr Ala Tyr Thr Gln Gln Asp
    530                 535                 540

Ile Asp Leu His Thr Leu Ile Phe Asp Asp Lys Ala Tyr Glu Ile Asp
545                 550                 555                 560

His Ile Ile Pro Ile Ser Val Ser Leu Asp Asp Ser Leu Thr Asn Lys
                565                 570                 575

Val Leu Ala Ser Arg Leu Glu Asn Gln Gln Lys Gly Asn Leu Thr Pro
            580                 585                 590

Met Met Ala Tyr Leu Lys Gly Lys Phe Thr Gly Gly Asn Leu Glu Lys
        595                 600                 605

Tyr Lys Leu Phe Val Ser Ser Asn Lys Asn Phe Asn Gly Lys Lys Arg
    610                 615                 620

Asn Asn Leu Leu Thr Glu Gln Asp Ile Thr Lys Glu Asp Val Ala Arg
625                 630                 635                 640

Lys Phe Ile Asn Arg Asn Leu Val Asp Thr Ser Tyr Ala Cys Arg Thr
                645                 650                 655

Val Leu Asn Thr Leu Gln Arg Tyr Phe Lys Asp Asn Glu Ile Asp Thr
            660                 665                 670

Lys Val His Thr Ile Arg Gly Gln Ser Thr Asn Ile Phe Arg Lys Arg
        675                 680                 685

Ile Asn Leu Gln Lys Asp Arg Glu Gln Asp Tyr Phe His His Ala Ile
    690                 695                 700

Asp Ala Leu Ile Val Ala Ser Leu Lys Lys Met Asn Ile Val Asn Ser
705                 710                 715                 720

Tyr Leu Met His Tyr Asn Tyr Ser Asp Leu Tyr Asp Glu Glu Thr Gly
                725                 730                 735

Glu Val Phe Asp Val Leu Pro Asp Lys Gln Phe Ile Asp Gln Arg Tyr
            740                 745                 750

Ile Ser Phe Ile Ser Asp Leu Lys Asn Ile Tyr Gln Glu Ser Asn Gln
        755                 760                 765

Tyr Asn Leu Gly Tyr Ile Thr Gln Glu Gln Met His Tyr Pro Leu Ile
    770                 775                 780

Lys Val Ser His Lys Ile Asp Thr Lys Pro Asn Arg Lys Ile Ala Asp
785                 790                 795                 800

Glu Thr Ile Tyr Ser Thr Arg Asn Ile Glu Gly Gln Asp Met Leu Val
                805                 810                 815

Glu Lys Ile Lys Asn Ile Tyr Asp Pro Lys Glu Lys Lys Ala Ile Glu
            820                 825                 830

Leu Val Asn Asn Ile Ile Asn Asp Asp Thr Asp Lys Tyr Ile Met Lys
```

```
        835                 840                 845

His Lys Asp Pro Gln Thr Phe Glu Lys Ile Lys Glu Val Val Leu Asn
    850                 855                 860

His Phe Asn Asp Tyr Lys Asp Ser Lys Glu Tyr Tyr Val Ile Asp Lys
865                 870                 875                 880

Lys Gly Lys Tyr Ser Leu Lys Glu Glu Ser Pro Leu Thr Ser Tyr Tyr
                885                 890                 895

Asn Glu Asn Gly Ala Ile Thr Lys Tyr Ser Lys Lys Asn Asn Gly Pro
            900                 905                 910

Ala Ile Thr Ser Met Lys Phe Tyr Ser Glu Lys Leu Gly Asn His Leu
        915                 920                 925

Ala Ile Thr Ser Asn Tyr Asn Thr Asn Asn Lys Lys Val Ile Leu Lys
    930                 935                 940

Gln Ile Ser Pro Tyr Arg Thr Asp Phe Tyr Val Ser Pro Glu Gly Lys
945                 950                 955                 960

Tyr Lys Phe Val Thr Val Arg Tyr Lys Asp Val Phe Tyr Lys Glu Thr
                965                 970                 975

Ile His Lys Phe Val Ile Asp Glu Asn Trp Tyr His Glu Glu Lys Ile
            980                 985                 990

Lys Lys Gly Ile Leu Glu Asp Trp  Lys Phe Val Cys Ser  Met His Arg
        995                 1000                1005

Asp Glu  Leu Ile Gly Leu Ile  Lys Pro Glu Gly Lys  Lys Phe Val
    1010                1015                1020

Tyr Asp  Ala Ser Ile Asn Gly  Gly Gln Thr Gln Tyr  His Asp Gly
    1025                1030                1035

Lys His  Tyr Glu Ile Leu Lys  Phe Thr Ala Thr Asn  Asp Glu Lys
    1040                1045                1050

Lys Arg  Thr Phe Glu Val Lys  Pro Ile Asn Thr Asn  Cys Ser Lys
    1055                1060                1065

Arg Leu  Met Pro Ser Val Gly  Pro Phe Ile Lys Ile  Gln Lys Phe
    1070                1075                1080

Ala Thr  Asp Val Leu Gly Asn  Ile Tyr Glu Val Lys  Asp Asn Arg
    1085                1090                1095

Leu Lys  Leu Glu Phe Asp
    1100
```

<210> SEQ ID NO 3
<211> LENGTH: 1370
<212> TYPE: PRT
<213> ORGANISM: Ezakiella peruensis strain M6.X2

<400> SEQUENCE: 3

```
Met Thr Lys Val Lys Asp Tyr Tyr Ile Gly Leu Asp Ile Gly Thr Ser
1               5                   10                  15

Ser Val Gly Trp Ala Val Thr Asp Glu Ala Tyr Asn Val Leu Lys Phe
            20                  25                  30

Asn Ser Lys Lys Met Trp Gly Val Arg Leu Phe Asp Asp Ala Lys Thr
        35                  40                  45

Ala Glu Glu Arg Arg Gly Gln Arg Gly Ala Arg Arg Arg Leu Asp Arg
    50                  55                  60

Lys Lys Glu Arg Leu Ser Leu Leu Gln Asp Phe Phe Ala Glu Glu Val
65                  70                  75                  80

Ala Lys Val Asp Pro Asn Phe Phe Leu Arg Leu Asp Asn Ser Asp Leu
                85                  90                  95
```

-continued

```
Tyr Met Glu Asp Lys Asp Gln Lys Leu Lys Ser Lys Tyr Thr Leu Phe
            100                 105                 110

Asn Asp Lys Asp Phe Lys Asp Lys Asn Phe His Lys Lys Tyr Pro Thr
        115                 120                 125

Ile His His Leu Leu Met Asp Leu Ile Glu Asp Asp Ser Lys Lys Asp
    130                 135                 140

Ile Arg Leu Val Tyr Leu Ala Cys His Tyr Leu Leu Lys Asn Arg Gly
145                 150                 155                 160

His Phe Ile Phe Glu Gly Gln Lys Phe Asp Thr Lys Ser Ser Phe Glu
                165                 170                 175

Asn Ser Leu Asn Glu Leu Lys Val His Leu Asn Asp Glu Tyr Gly Leu
            180                 185                 190

Asp Leu Glu Phe Asp Asn Glu Asn Leu Ile Asn Ile Leu Thr Asp Pro
        195                 200                 205

Lys Leu Asn Lys Thr Ala Lys Lys Lys Glu Leu Lys Ser Val Ile Gly
    210                 215                 220

Asp Thr Lys Phe Leu Lys Ala Val Ser Ala Ile Met Ile Gly Ser Ser
225                 230                 235                 240

Gln Lys Leu Val Asp Leu Phe Glu Asn Pro Glu Asp Phe Asp Asp Ser
                245                 250                 255

Ala Ile Lys Ser Val Asp Phe Ser Thr Thr Ser Phe Asp Asp Lys Tyr
            260                 265                 270

Ser Asp Tyr Glu Leu Ala Leu Gly Asp Lys Ile Ala Leu Val Asn Ile
        275                 280                 285

Leu Lys Glu Ile Tyr Asp Ser Ser Ile Leu Glu Asn Leu Leu Lys Glu
    290                 295                 300

Ala Asp Lys Ser Lys Asp Gly Asn Lys Tyr Ile Ser Asn Ala Phe Val
305                 310                 315                 320

Lys Lys Tyr Asn Lys His Gly Gln Asp Leu Lys Glu Phe Lys Arg Leu
                325                 330                 335

Val Arg Gln Tyr His Lys Ser Ala Tyr Phe Asp Ile Phe Arg Ser Glu
            340                 345                 350

Lys Val Asn Asp Asn Tyr Val Ser Tyr Thr Lys Ser Ser Ile Ser Asn
        355                 360                 365

Asn Lys Arg Val Lys Ala Asn Lys Phe Thr Asp Gln Glu Ala Phe Tyr
    370                 375                 380

Lys Phe Ala Lys Lys His Leu Glu Thr Ile Lys Tyr Lys Ile Asn Lys
385                 390                 395                 400

Val Asn Gly Ser Lys Ala Asp Leu Glu Leu Ile Asp Gly Met Leu Arg
                405                 410                 415

Asp Met Glu Phe Lys Asn Phe Met Pro Lys Ile Lys Ser Ser Asp Asn
            420                 425                 430

Gly Val Ile Pro Tyr Gln Leu Lys Leu Met Glu Leu Asn Lys Ile Leu
        435                 440                 445

Glu Asn Gln Ser Lys His His Glu Phe Leu Asn Val Ser Asp Glu Tyr
    450                 455                 460

Gly Ser Val Cys Asp Lys Ile Ala Ser Ile Met Glu Phe Arg Ile Pro
465                 470                 475                 480

Tyr Tyr Val Gly Pro Leu Asn Pro Asn Ser Lys Tyr Ala Trp Ile Lys
                485                 490                 495

Lys Gln Lys Asp Ser Glu Ile Thr Pro Trp Asn Phe Lys Asp Val Val
            500                 505                 510

Asp Leu Asp Ser Ser Arg Glu Glu Phe Ile Asp Ser Leu Ile Gly Arg
```

-continued

```
        515                 520                 525

Cys Thr Tyr Leu Lys Asp Glu Lys Val Leu Pro Lys Ala Ser Leu Leu
    530                 535                 540

Tyr Asn Glu Tyr Met Val Leu Asn Glu Leu Asn Asn Leu Lys Leu Asn
545                 550                 555                 560

Asp Leu Pro Ile Thr Glu Glu Met Lys Lys Lys Ile Phe Asp Gln Leu
                565                 570                 575

Phe Lys Thr Arg Lys Lys Val Thr Leu Lys Ala Val Ala Asn Leu Leu
            580                 585                 590

Lys Lys Glu Phe Asn Ile Asn Gly Glu Ile Leu Leu Ser Gly Thr Asp
        595                 600                 605

Gly Asp Phe Lys Gln Gly Leu Asn Ser Tyr Asn Asp Phe Lys Ala Ile
    610                 615                 620

Val Gly Asp Lys Val Asp Ser Asp Asp Tyr Arg Asp Lys Ile Glu Glu
625                 630                 635                 640

Ile Ile Lys Leu Ile Val Leu Tyr Gly Asp Asp Lys Ser Tyr Leu Gln
                645                 650                 655

Lys Lys Ile Lys Ala Gly Tyr Gly Lys Tyr Phe Thr Asp Ser Glu Ile
            660                 665                 670

Lys Lys Met Ala Gly Leu Asn Tyr Lys Asp Trp Gly Arg Leu Ser Lys
        675                 680                 685

Lys Leu Leu Thr Gly Leu Glu Gly Ala Asn Lys Ile Thr Gly Glu Arg
    690                 695                 700

Gly Ser Ile Ile His Phe Met Arg Glu Tyr Asn Leu Asn Leu Met Glu
705                 710                 715                 720

Leu Met Ser Ala Ser Phe Thr Phe Thr Glu Glu Ile Gln Lys Leu Asn
                725                 730                 735

Pro Val Asp Asp Arg Lys Leu Ser Tyr Glu Met Val Asp Glu Leu Tyr
            740                 745                 750

Leu Ser Pro Ser Val Lys Arg Met Leu Trp Gln Ser Leu Arg Ile Val
        755                 760                 765

Asp Glu Ile Lys Asn Ile Met Gly Thr Asp Ser Lys Lys Ile Phe Ile
    770                 775                 780

Glu Met Ala Arg Gly Lys Glu Glu Val Lys Ala Arg Lys Glu Ser Arg
785                 790                 795                 800

Lys Asn Gln Leu Leu Lys Phe Tyr Lys Asp Gly Lys Lys Ala Phe Ile
                805                 810                 815

Ser Glu Ile Gly Glu Glu Arg Tyr Ser Tyr Leu Leu Ser Glu Ile Glu
            820                 825                 830

Gly Glu Glu Glu Asn Lys Phe Arg Trp Asp Asn Leu Tyr Leu Tyr Tyr
        835                 840                 845

Thr Gln Leu Gly Arg Cys Met Tyr Ser Leu Glu Pro Ile Asp Ile Ser
    850                 855                 860

Glu Leu Ser Ser Lys Asn Ile Tyr Asp Gln Asp His Ile Tyr Pro Lys
865                 870                 875                 880

Ser Lys Ile Tyr Asp Asp Ser Ile Glu Asn Arg Val Leu Val Lys Lys
                885                 890                 895

Asp Leu Asn Ser Lys Lys Gly Asn Ser Tyr Pro Ile Pro Asp Glu Ile
            900                 905                 910

Leu Asn Lys Asn Cys Tyr Ala Tyr Trp Lys Ile Leu Tyr Asp Lys Gly
        915                 920                 925

Leu Ile Gly Gln Lys Lys Tyr Thr Arg Leu Thr Arg Arg Thr Gly Phe
    930                 935                 940
```

```
Thr Asp Asp Glu Leu Val Gln Phe Ile Ser Arg Gln Ile Val Glu Thr
945                 950                 955                 960

Arg Gln Ala Thr Lys Glu Thr Ala Asn Leu Leu Lys Thr Ile Cys Lys
                965                 970                 975

Asn Ser Glu Ile Val Tyr Ser Lys Ala Glu Asn Ala Ser Arg Phe Arg
            980                 985                 990

Gln Glu Phe Asp Ile Val Lys Cys  Arg Ala Val Asn Asp  Leu His His
        995                 1000                1005

Met His  Asp Ala Tyr Ile Asn  Ile Ile Val Gly Asn  Val Tyr Asn
    1010                1015                1020

Thr Lys  Phe Thr Lys Asp Pro  Met Asn Phe Val Lys  Lys Gln Glu
    1025                1030                1035

Lys Ala  Arg Ser Tyr Asn Leu  Glu Asn Met Phe Lys  Tyr Asp Val
    1040                1045                1050

Lys Arg  Gly Gly Tyr Thr Ala  Trp Ile Ala Asp Asp  Glu Lys Gly
    1055                1060                1065

Thr Val  Lys Asn Ala Ser Ile  Lys Arg Ile Arg Lys  Glu Leu Glu
    1070                1075                1080

Gly Thr  Asn Tyr Arg Phe Thr  Arg Met Asn Tyr Ile  Glu Ser Gly
    1085                1090                1095

Ala Leu  Phe Asn Ala Thr Leu  Gln Arg Lys Asn Lys  Gly Ser Arg
    1100                1105                1110

Pro Leu  Lys Asp Lys Gly Pro  Lys Ser Ser Ile Glu  Lys Tyr Gly
    1115                1120                1125

Gly Tyr  Thr Asn Ile Asn Lys  Ala Cys Phe Ala Val  Leu Asp Ile
    1130                1135                1140

Lys Ser  Lys Asn Lys Ile Glu  Arg Lys Leu Met Pro  Val Glu Arg
    1145                1150                1155

Glu Ile  Tyr Ala Lys Gln Lys  Asn Asp Lys Lys Leu  Ser Asp Glu
    1160                1165                1170

Ile Phe  Ser Lys Tyr Leu Lys  Asp Arg Phe Gly Ile  Glu Asp Tyr
    1175                1180                1185

Arg Val  Val Tyr Pro Val Val  Lys Met Arg Thr Leu  Leu Lys Ile
    1190                1195                1200

Asp Gly  Ser Tyr Tyr Phe Ile  Thr Gly Gly Ser Asp  Lys Thr Leu
    1205                1210                1215

Glu Leu  Arg Ser Ala Leu Gln  Leu Ile Leu Pro Lys  Lys Asn Glu
    1220                1225                1230

Trp Ala  Ile Lys Gln Ile Asp  Lys Ser Ser Glu Asn  Asp Tyr Leu
    1235                1240                1245

Thr Ile  Glu Arg Ile Gln Asp  Leu Thr Glu Glu Leu  Val Tyr Asn
    1250                1255                1260

Thr Phe  Asp Ile Ile Val Asn  Lys Phe Lys Thr Ser  Val Phe Lys
    1265                1270                1275

Lys Ser  Phe Leu Asn Leu Phe  Gln Asp Asp Lys Ile  Glu Asn Ile
    1280                1285                1290

Asp Phe  Lys Phe Lys Ser Met  Asp Phe Lys Glu Lys  Cys Lys Thr
    1295                1300                1305

Leu Leu  Met Leu Val Lys Ala  Ile Arg Ala Ser Gly  Val Arg Gln
    1310                1315                1320

Asp Leu  Lys Ser Ile Asp Leu  Lys Ser Asp Tyr Gly  Arg Leu Ser
    1325                1330                1335
```

-continued

```
Ser Lys  Thr Asn Asn Ile Gly  Asn Tyr Gln Glu Phe  Lys Ile Ile
    1340                 1345                 1350

Asn Gln  Ser Ile Thr Gly Leu  Phe Glu Asn Glu Val  Asp Leu Leu
    1355                 1360                 1365

Lys Leu
    1370


<210> SEQ ID NO 4
<211> LENGTH: 1369
<212> TYPE: PRT
<213> ORGANISM: Clostridium sp. AF02-29

<400> SEQUENCE: 4

Met Lys Glu Lys Met Glu Tyr Tyr Leu Gly Leu Asp Met Gly Thr Asn
1               5                   10                  15

Ser Val Gly Trp Ala Val Thr Asp Lys Glu Tyr Arg Leu Met Arg Ala
            20                  25                  30

Lys Gly Lys Asp Leu Trp Gly Val Arg Leu Phe Glu Arg Ala Asn Thr
        35                  40                  45

Ala Glu Glu Arg Arg Ala Tyr Arg Ile Asn Arg Arg Arg Arg Gln Arg
    50                  55                  60

Glu Val Ala Arg Ile Gly Ile Leu Lys Glu Leu Phe Ala Asp Glu Ile
65                  70                  75                  80

Ala Lys Val Asp Ala Asn Phe Phe Ala Arg Leu Asp Asp Ser Lys Tyr
                85                  90                  95

Tyr Leu Asp Asp Arg Gln Glu Asn Asn Lys Gln Lys Tyr Ala Ile Phe
            100                 105                 110

Ala Asp Lys Asp Tyr Thr Asp Lys Glu Tyr Phe Ser Gln Tyr Gln Thr
        115                 120                 125

Ile Phe His Leu Arg Lys Glu Leu Ile Leu Ser Asp Gln Pro His Asp
    130                 135                 140

Val Arg Leu Ile Tyr Leu Ala Leu Leu Asn Met Phe Lys His Arg Gly
145                 150                 155                 160

His Phe Leu Asn Lys Thr Leu Gly Thr Ser Glu Ser Leu Glu Ser Phe
                165                 170                 175

Phe Asp Met Tyr Gln Arg Leu Ala Val Cys Ala Asp Gly Glu Gly Ile
            180                 185                 190

Lys Leu Pro Glu Thr Val Asp Leu Lys Lys Leu Glu Gln Ile Leu Gly
        195                 200                 205

Ala Arg Gly Cys Ser Arg Lys Ala Thr Leu Glu His Ile Ser Glu Ile
    210                 215                 220

Met Gly Ile Asn Lys Lys Asn Lys Pro Val Tyr Ser Leu Met Gln Met
225                 230                 235                 240

Ile Cys Gly Leu Asp Thr Lys Met Ile Asp Leu Phe Gly Gln Lys Ile
                245                 250                 255

Asp Glu Glu His Lys Lys Ile Ser Leu Ser Phe Arg Thr Ser Asn Tyr
            260                 265                 270

Glu Glu Met Ala Glu Glu Val Arg Asn Thr Ile Gly Asp Asp Ala Phe
        275                 280                 285

Glu Leu Ile Leu Thr Ala Lys Glu Met His Asp Phe Gly Leu Leu Ala
    290                 295                 300

Glu Ile Met Lys Gly Tyr Ser Tyr Leu Ser Glu Ala Arg Val Ala Val
305                 310                 315                 320

Tyr Glu Glu His Arg Lys Asp Leu Ala Lys Leu Lys Ala Val Phe Lys
                325                 330                 335
```

-continued

```
Gln Tyr Asp His Lys Ala Tyr Asp Glu Met Phe Arg Ile Met Lys Asn
            340                 345                 350

Gly Thr Tyr Ser Ala Tyr Val Gly Ser Val Asn Ser Phe Gly Lys Ile
        355                 360                 365

Glu Arg Arg Thr Val Lys Thr Ser Arg Glu Glu Leu Leu Lys Asn Ile
    370                 375                 380

Lys Lys Ile Leu Thr Gly Phe Pro Glu Asp Asp Ala Thr Val Gln Glu
385                 390                 395                 400

Phe Leu Gly Lys Ile Asp Ser Asp Thr Leu Leu Gln Lys Gln Leu Thr
                405                 410                 415

Ala Ser Asn Gly Val Ile Pro Asn Gln Val His Ala Lys Glu Met Lys
            420                 425                 430

Val Ile Leu Lys Asn Ala Glu Lys Tyr Leu Pro Phe Leu Ser Glu Arg
        435                 440                 445

Asp Glu Thr Gly Leu Ser Val Ser Glu Lys Ile Ile Ala Leu Phe Thr
    450                 455                 460

Phe Thr Ile Pro Tyr Tyr Val Gly Pro Leu Gly Gln Gln His Leu Gly
465                 470                 475                 480

Lys Glu Cys Ala His Gly Trp Val Glu Arg Lys Glu Lys Gly Thr Val
                485                 490                 495

Tyr Pro Trp Asn Phe Glu Gln Lys Val Asp Leu Lys Ala Ser Ala Glu
            500                 505                 510

His Phe Ile Glu Arg Met Val Lys His Cys Thr Tyr Leu Ser Asp Glu
        515                 520                 525

Gln Ala Leu Pro Lys Gln Ser Leu Leu Tyr Glu Lys Phe Gln Val Leu
    530                 535                 540

Asn Glu Leu Asn Asn Leu Lys Ile Arg Gly Glu Lys Ile Ser Val Glu
545                 550                 555                 560

Leu Lys Gln Gln Ile Tyr Arg Asp Val Phe Glu His Thr Gly Lys Lys
                565                 570                 575

Val Ser Met Lys Gln Leu Glu Asn Tyr Leu Lys Leu Asn Gly Leu Leu
            580                 585                 590

Glu Lys Asp Glu Lys Asp Ala Val Thr Gly Ile Asp Gly Gly Phe His
        595                 600                 605

Ser Tyr Leu Ser Ser Leu Gly Lys Phe Ile Gly Ile Leu Gly Glu Glu
    610                 615                 620

Ala His Tyr Gly Lys Asn Gln Asn Met Met Glu Lys Ile Val Phe Trp
625                 630                 635                 640

Gly Thr Val Tyr Gly Gln Asp Lys Lys Phe Leu Arg Glu Arg Leu Ser
                645                 650                 655

Glu Val Tyr Gly Asp Arg Leu Ser Lys Glu Gln Ile Arg Arg Ile Thr
            660                 665                 670

Gly Met Lys Phe Glu Gly Trp Gly Arg Leu Ser Lys Glu Phe Leu Leu
        675                 680                 685

Leu Glu Gly Ala Ser Arg Glu Glu Gly Glu Ile Arg Thr Leu Ile Arg
    690                 695                 700

Ser Leu Trp Glu Thr Asn Glu Asn Leu Met Gly Leu Leu Ser Glu Arg
705                 710                 715                 720

Tyr Thr Tyr Ser Glu Glu Val Arg Glu Lys Thr Leu Glu Cys Glu Lys
                725                 730                 735

Ser Leu Ser Glu Trp Thr Ile Glu Asp Leu Glu Gly Met Tyr Leu Ser
            740                 745                 750
```

-continued

```
Ala Pro Val Lys Arg Met Val Trp Gln Thr Leu Leu Ile Val Lys Glu
        755                 760                 765

Leu Glu Lys Val Leu Gly Cys Ala Pro Arg Arg Ile Phe Val Glu Met
    770                 775                 780

Ala Arg Glu Asp Ala Glu Lys Gly Arg Arg Thr Glu Ser Arg Lys Gln
785                 790                 795                 800

Lys Leu Gln Asn Leu Tyr Lys Ala Ile Lys Lys Glu Glu Ile Asp Trp
                805                 810                 815

Lys Lys Glu Ile Asp Glu Lys Thr Glu Gln Ala Phe Arg Ser Lys Lys
            820                 825                 830

Leu Tyr Leu Tyr Tyr Leu Gln Lys Gly Arg Cys Met Tyr Thr Gly Glu
        835                 840                 845

Ser Ile Arg Phe Glu Asp Leu Met Asn Asp Asn Leu Tyr Asp Ile Asp
    850                 855                 860

His Ile Tyr Pro Arg His Phe Val Lys Asp Asp Ser Leu Glu Gln Asn
865                 870                 875                 880

Leu Val Leu Val Lys Lys Glu Lys Asn Ala His Lys Ser Asp Val Phe
                885                 890                 895

Pro Ile Glu Ala Asp Ile Gln Lys Lys Met Ser Pro Phe Trp Lys Glu
            900                 905                 910

Leu Lys Glu Arg Gly Phe Ile Ser Glu Glu Lys Tyr Met Arg Leu Thr
        915                 920                 925

Arg Arg Tyr Gly Phe Ser Glu Glu Glu Lys Ala Gly Phe Ile Asn Arg
    930                 935                 940

Gln Leu Val Glu Thr Arg Gln Gly Thr Lys Ser Ile Thr Glu Ile Leu
945                 950                 955                 960

Gly Gln Ala Phe Pro Asp Val Asp Ile Ile Phe Ser Lys Ala Ser Asn
                965                 970                 975

Val Ser Glu Phe Arg His Ile Tyr Gly Leu Tyr Lys Val Arg Ser Ile
            980                 985                 990

Asn Asp Phe His His Ala His Asp  Ala Tyr Leu Asn Ile  Val Val Gly
        995                 1000                1005

Asn Thr  Tyr His Val Lys Phe  Thr Lys Asn Pro Leu  Asn Phe Ile
    1010                1015                1020

Arg Glu  Ala Glu Lys Asn Pro  Gln Asn Ala Glu Asn  Lys Tyr Asn
    1025                1030                1035

Met Asn  Arg Met Phe Asp Trp  Thr Val Lys Arg Gly  Asn Glu Thr
    1040                1045                1050

Ala Trp  Ile Ala Ser Ser Asp  Lys Glu Ala Gly Ser  Ile Lys Ile
    1055                1060                1065

Val Lys  Ala Ile Leu Ala Lys  Asn Thr Pro Leu Val  Thr Lys Arg
    1070                1075                1080

Cys Ala  Glu Ala His Gly Gly  Ile Thr Arg Lys Ala  Thr Ile Trp
    1085                1090                1095

Asn Lys  Asn Lys Ala Ala Gly  Ser Gly Tyr Ile Pro  Val Lys Met
    1100                1105                1110

Asn Asp  Ala Arg Leu Leu Asp  Val Thr Lys Tyr Gly  Gly Leu Thr
    1115                1120                1125

Ser Val  Ser Ala Ser Gly Tyr  Thr Leu Leu Glu Tyr  Asp Val Lys
    1130                1135                1140

Gly Lys  Lys Ile Arg Ser Leu  Glu Ala Ile Pro Ile  Tyr Leu Gly
    1145                1150                1155

Arg Val  Ser Glu Leu Thr Asn  Glu Ala Ile Leu Lys  Tyr Phe Glu
```

```
    1160                1165                1170

Lys Val  Leu Ile Glu Glu Asn  Lys Gly Lys Glu Ile  Thr Glu Leu
    1175                1180                1185

Arg Ile  Cys Lys Lys Phe Ile  Pro Arg Glu Ser Leu  Val Arg Tyr
    1190                1195                1200

Asn Gly  Tyr Tyr Tyr Tyr Leu  Gly Gly Lys Ser Val  Glu Gln Ile
    1205                1210                1215

Val Leu  Lys Asn Ala Thr Gln  Met Ala Tyr Ser Glu  Glu Glu Thr
    1220                1225                1230

Cys Tyr  Ile Lys Lys Ile Glu  Lys Ala Ile Glu Lys  Thr Tyr Tyr
    1235                1240                1245

Glu Glu  Val Asp Lys Asn Lys  Asn Val Ile Leu Thr  Lys Thr Arg
    1250                1255                1260

Asn Asn  Ala Met Tyr Asp Lys  Phe Ile Ile Lys Tyr  Gln Asn Ser
    1265                1270                1275

Ile Tyr  Gln Asn Gln Ser Gly  Ala Met Lys Asn Ser  Ile Ile Gly
    1280                1285                1290

Lys Arg  Asn Glu Phe Leu Thr  Leu Ser Leu Glu Lys  Gln Cys Arg
    1295                1300                1305

Ile Leu  Lys Ala Leu Val Glu  Tyr Phe Arg Thr Gly  Asp Ile Ile
    1310                1315                1320

Asp Leu  Arg Glu Leu Gly Gly  Ser Ser Gln Ala Gly  Lys Val Ala
    1325                1330                1335

Met Asn  Lys Lys Ile Met Gly  Ala Ser Glu Leu Val  Leu Ile Ser
    1340                1345                1350

Gln Ser  Pro Thr Gly Leu Phe  Gln Gln Glu Ile Asp  Leu Leu Lys
    1355                1360                1365

Ile
```

<210> SEQ ID NO 5
<211> LENGTH: 3303
<212> TYPE: DNA
<213> ORGANISM: Butyrivibrio sp. AC2005

<400> SEQUENCE: 5

```
atgggatata caataggact tgatcttggt gtggcttcat taggatgggc tgtagtcaat      60

gatgaatatg aggtattaga atcatgctca aatatttttc ctgcagcaga atctgcaaat     120

aatgttgaaa gacgaggctt taggcaggga agaaggttgt caaggcgtcg caggaccaga     180

attagtgatt tcagaaaact gtgggagaag agtggtttcg aggttccttc aaatgaattg     240

aacgaggtgc ttcagtatag gattaaaggc atgaatgata aattatcaga agatgagctt     300

tatcatgttc ttttaaatag cctgaaacat aggggaattt cgtatttgga tgatgcagat     360

gatgaaaatg catctgggga ttatgctgca agcattgctt ataacgaaaa tcaattaaag     420

acaaaattgc cttgtgagat tcagtgggag cgctataaga aatatggtgc ttataggggg     480

aatattacta tccaagaagg tggggaaccg cttactctta gaaatgtatt cacaacaagt     540

gcgtatgaaa aagaaattca gaagctatta gacgtacaat ctatgtcaaa tgagaaagta     600

acaaaaaagt ttattgatga atacttaaaa atcttttcaa gaaaaagaga atattatatt     660

gggccgggta acaaaaaatc cagaacagat tatggtgtat acactacaca aaaaaatgaa     720

gatggtactt atcatactga gcagaatctt tttgataaat tgattggaaa gtgtagtgta     780

tatcctgatg agagaagagc tgccggggct acttatactg cacaggaatt taatctttta     840
```

-continued

```
aatgatctga ataatcttgt aattgatgga agaaaactag atgagcagga aaaatgtcag    900
attgttgatg ctgttaaaca tgctaaaacc gtcaatatga agaacattat tgcaaaagtc    960
attggaacaa aagcaaactc aatgaatatg accggcgcaa gaatagataa gaatgaaaaa   1020
gaaatttttc attcttttga ggcttataac aagttaagaa aagcactgga agaaatagat   1080
tttgatatag agactttgtc tacggatgag ttggatgcta taggagaagt gttgactctt   1140
aatactgacc gaaaatcaat tcaaaacgga cttcaagaga aaagaatagt agttcctgat   1200
gaagtcaggg atgtgcttat cgcaaccagg aaaagaaatg gctcattatt tagcaaatgg   1260
cagtcatttg gtataagaat catgaaggaa ttgattcctg aattatatgc gcagcctaag   1320
aatcagatgc aactgcttac tgatatggga gtatttaaaa ctaaggatga gagatttgtt   1380
gagtatgata agattccgtc tgatctaata acagaagaaa tctataatcc tgtggttgct   1440
aaaactgtaa ggattactgt cagagttttg aatgctctta ttaagaaata tggctatccg   1500
gatagagttg ttatagagat gccaagagat aaaaactcag aagaagagaa aaagcgcata   1560
gcagattttc aaaagaacaa tgagaatgag cttggtggaa taataaaaaa agtaaagtca   1620
gaatatggta ttgaaataac tgatgcggat tttaagaacc atagtaaact tggacttaaa   1680
cttaggttgt ggaatgaaca gaatgaaaca tgtccttact cagggaaaca tataaagatt   1740
gatgaccttt taaataatcc taatatgttt gaggtggatc atattatccc attatccatt   1800
tcatttgatg atagtagagc caataaagtg ttggtatacg ctgctgaaaa tcagaataag   1860
ggtaacagaa cgccaatggc atacctgtcc aatgttaata gagaatggga tttccatgaa   1920
tacatgagtt ttgttcttag taattataag ggaacaatat atggtaagaa gagagataat   1980
cttttattct cagaggacat atataaaatt gatgttttac agggatttat tagcagaaat   2040
ataaatgata caagatatgc ttcaaaggta atacttaatt cattacagtc tttctttggt   2100
tcaaaagagt gcgacacgaa ggtgaaggtt gttagaggaa cctttacaca tcagatgcga   2160
atgaatctaa agatagaaaa gaatagagag gagtcatatg tgcatcatgc tgttgatgct   2220
atgcttatag ctttttctca aatggggtat gatgcatatc ataaacttac agagaagtat   2280
attgattatg aacatggcga atttgtagat cagaaaggct atgagaagct tattgaaaat   2340
gatgtagcat atcgtgaaac cacttatcaa aataagtgga tgactataaa gaaaaatata   2400
gaaatagcag ctgaaaagaa taaatactgg tatcaggtaa ataggaaaag caatagaggg   2460
ctttgcaacc agactattta tggtaccaga aatctggatg gcaagacagt aaagatcagc   2520
aaacttgata ttcggacaga tgatgggata aagaaattta aagggatcgt agaaaaaggt   2580
aaactagaac gctttttgat gtataggaat gatccaaaaa catttgaatg gctgcttcag   2640
atttataagg attattcaga ctccaaaaac ccatttgtcc aatatgaatc agagactggt   2700
gatgttatta agaaagtttc aaaaacgaat aatggaccaa aggtatgtga acttcgctat   2760
gaagatggtg aggttggtag ctgtatcgat atttctcata agtatggata taaaaagggt   2820
agtaaaaagg taattctcga ttctttaaac ccttacagaa tggatgtata ttataacact   2880
aaggacaata ggtattattt tgttggtgta aagtattcag acattaagtg ccaaggtgat   2940
agctatgtaa tcgatgagga taaatacgca gcagcactcg ttcaggaaaa aatagtgccg   3000
gaaggaaaag gaagaagtga cttaacagag cttggttatg aatttaagct atcattttat   3060
aaaaatgaga taatagagta tgaaaaagat ggcgaaatat atgtagaaag atttttatcg   3120
cgaacaatgc caaaagtgag caattatatt gaaactaagc cattggaagc tgcaaaattt   3180
gaaaaacgaa atttagtggg gttagctaag actagcagaa taagaaaaat acgagtggat   3240
```

-continued atacttggga atcgttattt aaatagtatg gaaaatttcg attttgttgt gggacataaa 3300
taa 3303

<210> SEQ ID NO 6
<211> LENGTH: 3297
<212> TYPE: DNA
<213> ORGANISM: Artificial Sequence
<220> FEATURE:
<223> OTHER INFORMATION: Synthetic

<400> SEQUENCE: 6
gggtacacca ttggcttgga tttgggagtg gcttcattgg gttgggcagt cgtgaacgac 60
gagtacgaag tgctcgagtc ttgtagcaac atcttccccg ccgccgagtc cgctaacaac 120
gtcgagcgaa gagggttccg ccaaggcagg cggttgtctc ggcgcaggcg cactcgtata 180
agcgattttc gtaagctttg ggaaaagagc ggatttgaag tgcccagtaa cgagctgaat 240
gaagttctcc aataccggat caaggggatg aacgacaagc tgagtgagga cgaattgtac 300
cacgtgctgt tgaactcatt gaagcaccgg ggtatcagct acctggacga cgccgacgac 360
gagaacgcct caggtgacta cgccgcctct atcgcgtaca atgagaacca gttgaaaacc 420
aagctcccct gcgaaatcca atgggaaagg tacaagaagt acggggcgta ccgcggtaac 480
atcaccatac aggagggagg cgagccactg actctccgaa acgtgtttac gacgtctgct 540
tacgagaagg agatccagaa actcttggat gtgcagagta tgagtaacga aaaggtcacg 600
aagaaattca tcgacgagta tctgaagatt ttcagtcgca agagggagta ctacataggt 660
ccaggcaata agaagtcacg aaccgactac ggcgtttata ccactcagaa gaacgaggac 720
ggcacctacc acacagaaca aaacctgttc gacaagctta tcggtaaatg ctccgtttac 780
cccgacgaaa ggcgcgcagc gggtgccaca tacacagccc aagagttcaa cttgctgaac 840
gacttgaaca acctcgttat cgacggcagg aagctggacg aacaagagaa gtgccaaatc 900
gtcgacgcgg tgaagcacgc caagacggtt aacatgaaga atatcatcgc caaggtaatc 960
ggtactaagg cgaatagtat gaacatgaca ggggctagga ttgacaagaa cgagaaggag 1020
atcttccaca gtttcgaagc gtacaataaa ctgaggaagg ctctcgagga gattgacttc 1080
gacattgaaa ccctcagtac cgacgaactt gacgccatcg ggaagtcct gacactgaac 1140 accgatagaa agagcatcca gaatgggttg caggaaaagc ggatcgtggt ccccgacgag 1200
gtaagagatg tactgattgc cactcgtaag cgtaacggga gcctgttctc caagtggcaa 1260
tctttcggaa tccgtattat gaaagagctc atcccggagc tgtacgccca accaaagaac 1320
caaatgcagt tgctgaccga catgggcgtc ttcaagacca aagacgaacg gttcgtggaa 1380
tacgacaaaa tccccagtga cctcatcacg gaagagatat acaaccccgt tgtcgccaag 1440
accgtccgca tcaccgttcg cgtccttaac gcgctcatca agaagtacgg gtatcccgac 1500
agggtggtga tcgaaatgcc tcgtgacaag aatagtgagg aagaaaagaa aaggattgct 1560
gacttccaga agaataacga aaacgaactg ggcggcatca tcaagaaggt caaaagtgag 1620
tacggcatcg agatcaccga cgcagacttc aagaatcaca gcaagttggg tctcaagctg 1680
cgactctgga acgagcaaaa cgagacttgt ccctatagcg gcaagcacat taaaatcgac 1740
gatctgttga acaacccgaa catgttcgaa gtagaccaca tcattcccct ctcaatctcc 1800
ttcgacgact ctcgcgctaa caaggtcctg gtgtatgcag cagagaacca aaacaaagga 1860
aataggactc ccatggctta tttgagtaac gtcaaccgcg agtgggactt tcacgagtat 1920

-continued atgtctttcg tgctgtcaaa ctacaaaggc actatctacg ggaagaaacg ggacaacctc 1980
ttgttttccg aagatatcta caagatagac gtgctgcaag ggttcatctc ccggaacatc 2040
aacgacaccc gatacgcgag taaagtgatt ctgaacagcc tgcaaagttt cttcgggtct 2100
aaggaatgtg ataccaaagt caaagtggta cggggcactt tcacgcacca aatgagaatg 2160
aacttgaaaa ttgagaagaa ccgggaagaa agttacgtcc accacgcagt cgacgcaatg 2220
ctgattgcct tcagccagat gggctacgac gcctaccaca agctcaccga gaaatacata 2280
gactacgagc acggagagtt cgtggaccaa aagggatacg aaaagctgat cgagaacgac 2340
gtcgcctaca gggaaacgac ctaccagaac aaatggatga caatcaagaa gaacattgag 2400
atcgctgccg agaagaacaa gtattggtat caagtgaacc ggaagtcaaa caggggactg 2460
tgtaatcaaa ccatctacgg cactcgtaac cttgacggga aaaccgtgaa aatttctaag 2520
ctcgacatcc gcactgacga cggaatcaag aagttcaagg gtattgttga gaagggcaag 2580
cttgagagat tccttatgta ccgtaacgac cctaagacct tcgagtggct cctgcaaatc 2640
tacaaagact actctgatag caagaatccc ttcgtgcagt acgagtccga aacaggtgac 2700
gtgataaaga aggtaagcaa gacaaacaac ggccccaaag tctgcgagct gcgatacgag 2760
gacggggaag tgggaagttg cattgacata tcccacaaat acgggtacaa gaaaggcagc 2820
aagaaagtga tcctggacag cctgaatccc tatcgcatgg acgtgtacta caataccaaa 2880
gataacagat actacttcgt gggcgttaaa tactctgata tcaaatgtca gggagactct 2940
tacgtgattg acgaagacaa gtatgctgct gccctggtac aagagaagat cgtacctgag 3000
gggaaggggc gcagcgatct cactgaactg ggctacgagt tcaaactgtc tttctacaag 3060
aacgaaatta ttgaatacga gaaggacggg gagatctacg tcgagcgctt cctgtcaagg 3120
accatgccca aggtctccaa ctacatcgag acaaaacccc ttgaggccgc taagttcgag 3180
aagcggaacc tggtaggatt ggccaaaaca tcaaggattc gaaagattag agtcgacatt 3240
ctcggcaaca ggtatctgaa ctcaatggag aactttgact tcgtcgttgg tcacaag 3297

<210> SEQ ID NO 7
<211> LENGTH: 3300
<212> TYPE: DNA
<213> ORGANISM: Artificial Sequence
<220> FEATURE:
<223> OTHER INFORMATION: Synthetic

<400> SEQUENCE: 7
atggggtaca ccattggctt ggatttggga gtggcttcat tgggttgggc agtcgtgaac 60
gacgagtacg aagtgctcga gtcttgtagc aacatcttcc ccgccgccga gtccgctaac 120
aacgtcgagc gaagagggtt ccgccaaggc aggcggttgt ctcggcgcag gcgcactcgt 180
ataagcgatt ttcgtaagct ttgggaaaag agcggatttg aagtgcccag taacgagctg 240
aatgaagttc tccaataccg gatcaagggg atgaacgaca agctgagtga ggacgaattg 300
taccacgtgc tgttgaactc attgaagcac cggggtatca gctacctgga cgacgccgac 360
gacgagaacg cctcaggtga ctacgccgcc tctatcgcgt acaatgagaa ccagttgaaa 420
accaagctcc cctgcgaaat ccaatgggaa aggtacaaga agtacggggc gtaccgcggt 480
aacatcacca tacaggaggg aggcgagcca ctgactctcc gaaacgtgtt tacgacgtct 540
gcttacgaga aggagatcca gaaactcttg gatgtgcaga gtatgagtaa cgaaaaggtc 600
acgaagaaat tcatcgacga gtatctgaag attttcagtc gcaagaggga gtactacata 660
ggtccaggca ataagaagtc acgaaccgac tacggcgttt ataccactca gaagaacgag 720

-continued

```
gacggcacct accacacaga acaaaacctg ttcgacaagc ttatcggtaa atgctccgtt    780
taccccgacg aaaggcgcgc agcgggtgcc acatacacag cccaagagtt caacttgctg    840
aacgacttga acaacctcgt tatcgacggc aggaagctgg acgaacaaga gaagtgccaa    900
atcgtcgacg cggtgaagca cgccaagacg gttaacatga agaatatcat cgccaaggta    960
atcggtacta aggcgaatag tatgaacatg acaggggcta ggattgacaa gaacgagaag   1020
gagatcttcc acagtttcga agcgtacaat aaactgagga aggctctcga ggagattgac   1080
ttcgacattg aaaccctcag taccgacgaa cttgacgcca tcggggaagt cctgacactg   1140
aacaccgata gaaagagcat ccagaatggg ttgcaggaaa agcggatcgt ggtccccgac   1200
gaggtaagag atgtactgat tgccactcgt aagcgtaacg ggagcctgtt ctccaagtgg   1260
caatctttcg gaatccgtat tatgaaagag ctcatcccgg agctgtacgc ccaaccaaag   1320
aaccaaatgc agttgctgac cgacatgggc gtcttcaaga ccaaagacga acggttcgtg   1380
gaatacgaca aaatccccag tgacctcatc acggaagaga tatacaaccc cgttgtcgcc   1440
aagaccgtcc gcatcaccgt tcgcgtcctt aacgcgctca tcaagaagta cgggtatccc   1500
gacagggtgg tgatcgaaat gcctcgtgac aagaatagtg aggaagaaaa gaaaaggatt   1560
gctgacttcc agaagaataa cgaaaacgaa ctgggcggca tcatcaagaa ggtcaaaagt   1620
gagtacggca tcgagatcac cgacgcagac ttcaagaatc acagcaagtt gggtctcaag   1680
ctgcgactct ggaacgagca aaacgagact tgtccctata gcggcaagca cattaaaatc   1740
gacgatctgt tgaacaaccc gaacatgttc gaagtagacc acatcattcc cctctcaatc   1800
tccttcgacg actctcgcgc taacaaggtc ctggtgtatg cagcagagaa ccaaaacaaa   1860
ggaaatagga ctcccatggc ttatttgagt aacgtcaacc gcgagtggga ctttcacgag   1920
tatatgtctt tcgtgctgtc aaactacaaa ggcactatct acgggaagaa acgggacaac   1980
ctcttgtttt ccgaagatat ctacaagata gacgtgctgc aagggttcat ctcccggaac   2040
atcaacgaca cccgatacgc gagtaaagtg attctgaaca gcctgcaaag tttcttcggg   2100
tctaaggaat gtgataccaa agtcaaagtg gtacggggca ctttcacgca ccaaatgaga   2160
atgaacttga aaattgagaa gaaccgggaa gaaagttacg tccaccacgc agtcgacgca   2220
atgctgattg ccttcagcca gatgggctac gacgcctacc acaagctcac cgagaaatac   2280
atagactacg agcacggaga gttcgtggac caaaagggat acgaaaagct gatcgagaac   2340
gacgtcgcct acagggaaac gacctaccag aacaaatgga tgacaatcaa gaagaacatt   2400
gagatcgctg ccgagaagaa caagtattgg tatcaagtga accggaagtc aaacagggga   2460
ctgtgtaatc aaaccatcta cggcactcgt aaccttgacg ggaaaaccgt gaaaatttct   2520
aagctcgaca tccgcactga cgacggaatc aagaagttca agggtattgt tgagaagggc   2580
aagcttgaga gattccttat gtaccgtaac gaccctaaga ccttcgagtg gctcctgcaa   2640
atctacaaag actactctga tagcaagaat cccttcgtgc agtacgagtc cgaaacaggt   2700
gacgtgataa agaaggtaag caagacaaac aacggcccca aagtctgcga gctgcgatac   2760
gaggacgggg aagtgggaag ttgcattgac atatcccaca aatacgggta caagaaaggc   2820
agcaagaaag tgatcctgga cagcctgaat ccctatcgca tggacgtgta ctacaatacc   2880
aaagataaca gatactactt cgtgggcgtt aaatactctg atatcaaatg tcagggagac   2940
tcttacgtga ttgacgaaga caagtatgct gctgccctgg tacaagagaa gatcgtacct   3000
gaggggaagg ggcgcagcga tctcactgaa ctgggctacg agttcaaact gtctttctac   3060
```

aagaacgaaa ttattgaata cgagaaggac ggggagatct acgtcgagcg cttcctgtca 3120
aggaccatgc ccaaggtctc caactacatc gagacaaaac cccttgaggc cgctaagttc 3180
gagaagcgga acctggtagg attggccaaa acatcaagga ttcgaaagat tagagtcgac 3240
attctcggca acaggtatct gaactcaatg gagaactttg acttcgtcgt tggtcacaag 3300

<210> SEQ ID NO 8
<211> LENGTH: 3315
<212> TYPE: DNA
<213> ORGANISM: bacterium LF-3

<400> SEQUENCE: 8
atgagcagat atgtattagg attagatata ggaattactt ctgtagggta tggtgtaata 60
gatattgata ataatttatt tgtggattat ggtgtaaggc ttttcaaaga aggaactgct 120
gcagaaaatg aaacgcgaag aactaaaagg ggttcaagac gtttaaaaag aagaaaatct 180
aatcgtttaa atgatatgaa aaatctttta aaggaaaatg acttatattt tgaagattat 240
cgaaattata atccttatga gataagggct aaaggattaa aagaaaagtt attgcctgaa 300
gaactatgta cagcaattat gcatataaca aaatcaagag gaacaacttt agaagcactt 360
gctgatgaaa gtcaagatga tgaaggaaca aaagctacac tttcaaaaaa tgctaaagaa 420
ttaaatgatg gaaaatatat ttgtgaagtt caattggata gattaaataa ggatcataaa 480
gtaagaggaa cggaaaataa tttcaaaaca gaagattatg tcaaagaact caaagaaata 540
ttaaaacacc aagatttaaa tgaagaattg tgtgatcaaa ttattgaaat ggtttcaaga 600
agaagacgtt atgatcaagg cccaggtagt gaaaaatcac caactcctta tggaagttat 660
cgaatggtgg atggtgtttt aaaacatgtt aatttgattg atgaaatgcg tggaagatgt 720
agtgtctatc cagatgaatt tagagcgcct aaacaatctt atacagcaga attatttaat 780
ttgttaaatg atttaaataa tttaacaatt aaaggtgaga aaataacagt tgaagaaaaa 840
gaaaaggttg ttgcatttgt taatgaaaaa ggaagtatta cagtaaaaca attacttaaa 900
ttattagatg ctcaagaaga tgaagttaca ggatttagaa ttgataaaaa tgataaacca 960
ttaattacag aatttaaggg ttatagtaaa gttttaaaag tctttaaaaa atataaccaa 1020
caagaattac tagaagataa attgattgtt gatcaagtta ttgacatatg tacaaaatca 1080
aaaggtattg atgaaagaaa aaaagatatt aaagaattat atcctgaatt tgataatgag 1140
ttaattgaag aattagcttc agttaaaggt gtttctgctt atcattcatt atcttttaaa 1200
gcaatgcata taatcaataa agaaatgctt acaacagaaa tgaatcaaat acaagttctt 1260
catgaaatag aaatgtttga taaaaataga aaatcattaa agggtaagaa aaatattgaa 1320
cctgatgaag aagctattct atctccagtt gctaaaagag cgcatcgaga aacatttaaa 1380
gtcattaatg cgttaagaaa acaatatggc gaatttgata gtattgttat tgaaatgaca 1440
agagataaaa attcaaagga acaagtaaag cgaataaatg atagtcaaaa aagatttaaa 1500
agcgaaaatg atcgagttga tggaattatt aaaaattcag gtattgatcc agaaagagtt 1560
aatggaaaaa caaaaacgaa aattcgtctt tatttacaac aagattgtaa gacggcctat 1620
acacaacaag atattgattt acatacattg atttttgatg ataaagctta tgaaatagat 1680
catattattc caatatctgt ttcattggat gattctctta ctaataaagt attagcttct 1740
cgtttagaaa accaacaaaa aggtaatcta acaccaatga tggcttattt aaagggaaaa 1800
tttacgggtg gtaatttaga aaaatataaa ttatttgtaa gtagtaataa aaattttaat 1860
ggtaaaaaaa gaaataattt acttactgaa caagatatta caaaagaaga tgtagcaaga 1920

```
aagtttatca atcgtaattt agtagataca agctatgctt gtcgtacagt attaaatact   1980
ttgcaacgct attttaaaga taatgaaata gatacaaaag ttcatactat tagaggacaa   2040
tcaaccaata tttttagaaa acgaataaat ttacaaaaag atagagagca agattatttt   2100
catcatgcaa tcgatgcatt gattgttgct tcgttaaaga aaatgaatat tgtcaattca   2160
tatttaatgc attacaacta tagtgattta tatgatgaag aaacagggga agtatttgat   2220
gttttacctg ataaacaatt tattgatcaa agatatattt catttatctc tgatttaaaa   2280
aatatttatc aagaatcgaa tcaatataac ttaggttata ttacccaaga acaaatgcat   2340
tatccactta tcaaggtatc tcataaaata gatacaaaac caaataggaa aattgcggat   2400
gaaacaatat atagtacaag aaatattgaa ggacaagata tgctagttga aaaaataaaa   2460
aatatctatg atcctaaaga aaagaaagca attgaacttg ttaataatat tattaatgat   2520
gatactgata agtacattat gaaacataaa gatccacaaa cttttgaaaa aataaaagaa   2580
gtggtattaa atcattttaa tgattataaa gattcaaaag aatattatgt aattgacaaa   2640
aaaggtaagt attctttaaa agaagaaagt cctttaacat catattataa tgaaaatgga   2700
gctattacta aatattctaa gaaaaataat ggaccagcaa ttacatcaat gaaattttac   2760
tctgaaaaac taggaaatca tttagcaatt acaagtaatt ataatacaaa taataaaaag   2820
gtaattttaa aacaaataag cccatatcga acagactttt atgtatctcc tgaaggaaaa   2880
tataaatttg ttacagttag atataaagat gtttttttata aagaaacaat tcataaattt   2940
gtcatagatg aaaattggta tcatgaagaa aaaattaaaa aaggaattct agaagattgg   3000
aaatttgtat gttcaatgca tcgagatgaa cttattggac ttatcaaacc tgaaggtaaa   3060
aagtttgttt atgatgcttc aattaatggt ggtcaaacac aatatcatga tggtaaacat   3120
tatgaaatct tgaagtttac agcaacgaat gatgaaaaga aaagaacttt tgaagtaaaa   3180
ccgattaaca ctaactgctc aaaacgatta atgccatctg taggaccttt tattaaaatt   3240
caaaaatttg ctacggatgt tttaggaaat atatatgaag ttaaagataa tagattgaaa   3300
ttagagttcg attag                                                    3315
```

<210> SEQ ID NO 9
<211> LENGTH: 3309
<212> TYPE: DNA
<213> ORGANISM: Artificial Sequence
<220> FEATURE:
<223> OTHER INFORMATION: Synthetic

<400> SEQUENCE: 9

```
tctaggtacg tgttgggact ggacatcggc ataacttccg tgggctacgg ggttatcgac     60
atcgacaaca acctgttcgt cgactacggg gtgagactgt ttaaggaagg cacagccgcg    120
gagaacgaga ccagacggac caagagaggg tcccgacgcc ttaagcgcag gaagagtaac    180
cgccttaacg acatgaagaa cctgctgaaa gagaacgatc tgtacttcga ggactacaga    240
aactacaacc cgtacgaaat tcgagccaag gggttgaagg agaaacttct cccagaggag    300
ctgtgcaccg ctatcatgca catcactaag agtcgtggga ctaccctgga agccttggcc    360
gacgagtctc aggacgacga gggcaccaag gccaccctca gcaagaacgc gaaggagctt    420
aacgacggta agtacatctg cgaggtgcag ctggacaggt tgaacaaaga ccacaaggtc    480
cggggcactg agaacaactt taagaccgag gactacgtta aggaactgaa ggagatcctc    540
aagcatcagg acctgaacga ggagctctgc gaccagatca tcgagatggt atctcgtcgc    600
```

```
aggcggtacg accagggacc cggctctgag aagtccccca caccctacgg ttcttaccgg    660
atggtcgacg ggtgttgaa gcacgtgaac ctgatcgacg agatgagggg ccgatgctcc     720
gtgtacccgg acgagttccg cgctccgaag cagagttaca ccgctgagct tttcaacctg    780
ctgaacgacc tcaacaacct cactatcaag ggagaaaaga ttacggtcga ggagaaggag    840
aaagtggtcg ccttcgtgaa cgagaagggg tctatcactg ttaagcagct tctcaagctc    900
cttgacgcac aagaggacga ggtgaccggt ttccgcatcg acaagaacga caagcctctg    960
atcaccgagt tcaaaggata ctcaaaggtg cttaaggtgt tcaagaagta caatcagcag   1020
gagcttctgg aagacaagct tatcgtggac caggtcatcg atatctgcac taagagcaag   1080
ggcatcgacg agaggaagaa ggacatcaag gagttgtacc cagagttcga caacgaactg   1140
atcgaggagt tggcaagcgt caagggcgtg tcagcatacc acagtctgag cttcaaggct   1200
atgcacatca ttaacaagga gatgctgacc accgagatga accagattca ggtcctgcac   1260
gagatcgaga tgttcgacaa gaaccgcaag agcttgaaag ggaagaagaa catcgagccc   1320
gacgaagagg ccatcctgtc ccccgtagcc aagcgggcac accgcgagac cttcaaggtg   1380
atcaacgccc ttcgtaagca gtacggggag ttcgactcaa tcgtgatcga gatgacccgc   1440
gacaagaact ccaaagagca ggtgaaacgg atcaacgact ctcagaagcg tttcaagtca   1500
gagaacgaca gagtggacgg tatcatcaag aactctggaa tagaccccga gcgtgtcaac   1560
ggcaagacca agacaaagat acgcctctac ctgcagcagg actgcaaaac tgcgtacacc   1620
cagcaggaca tcgacctgca cactcttata ttcgacgaca aggcgtacga gatcgaccac   1680
ataatcccta tcagcgtcag tcttgacgac agtctgacca acaaggttct ggcctcaagg   1740
ctcgagaatc agcagaaggg gaacctcacc cctatgatgg cctacctcaa aggtaagttc   1800
actggcggaa acctggagaa gtacaagctg ttcgtgtcat ccaacaagaa cttcaacggc   1860
aagaagcgca acaacctgct gaccgagcag gacataacta aggaagacgt ggctcgaaaa   1920
ttcattaaca gaaacctggt ggacacatcc tacgcctgca gaaccgtctt gaacacactg   1980
cagaggtact tcaaggacaa cgagattgac actaaggtac acacaatccg aggccagagc   2040
acaaacatct tccgcaagcg cattaacctg cagaaggacc gcgaacagga ctacttccac   2100
cacgccattg acgccctgat cgtggccagt ctgaagaaga tgaacatcgt gaacagctac   2160
ctgatgcact ataattacag cgacttgtac gacgaggaga ctggcgaggt cttcgacgtg   2220
ctgcccgaca agcagttcat cgaccagcgg tacatctcct tcatttccga cctgaagaac   2280
atctaccagg agtccaacca gtacaatctg ggatacataa ctcaggagca gatgcactac   2340
ccgctgatta aagtcagcca caagattgac accaagccca accggaagat agctgacgag   2400
actatctaca gcacccgcaa catcgagggc caggacatgt tggtggagaa gattaagaac   2460
atttacgacc ccaaggagaa gaaggccatc gagctggtga acaacataat caacgacgac   2520
accgacaaat atatcatgaa gcacaaggac ccccagacct tcgagaagat caaagaggtc   2580
gtcctgaacc acttcaacga ctacaaggac tctaaagagt actacgtcat cgataagaag   2640
gggaaataca gcctgaaaga ggagagcccc ctgactagct actacaacga gaacggggcc   2700
ataacgaagt acagcaagaa gaacaacggg cccgctataa catccatgaa gttctatagc   2760
gagaagctcg gcaaccacct ggctatcact agcaactaca acacgaacaa caagaaagtg   2820
atcctcaagc agatttcacc ctaccgtact gatttctacg tgagtccaga gggcaagtac   2880
aagttcgtga ccgtccggta caaggacgtg ttctacaagg agaccatcca caagttcgtt   2940
atcgacgaga actggtatca cgaggagaag ataaagaagg gtatcctgga agactggaag   3000
```

ttcgtttgct ctatgcaccg ggacgagctg atcgggctga ttaagccaga gggcaagaaa 3060
ttcgtgtacg acgcgtccat caacggcgga cagactcagt accacgacgg caagcactac 3120
gagattctta aattcaccgc caccaacgac gagaagaaga ggaccttcga ggtgaagccc 3180
atcaatacaa attgtagtaa gaggttgatg ccttccgtcg gccccttcat caagatccag 3240
aagttcgcca ccgacgtcct ggggaacatc tacgaggtga aggacaacag gcttaagctg 3300
gaatttgac 3309

<210> SEQ ID NO 10
<211> LENGTH: 3312
<212> TYPE: DNA
<213> ORGANISM: Artificial Sequence
<220> FEATURE:
<223> OTHER INFORMATION: Synthetic

<400> SEQUENCE: 10
atgtctaggt acgtgttggg actggacatc ggcataactt ccgtgggcta cggggttatc 60
gacatcgaca acaacctgtt cgtcgactac ggggtgagac tgtttaagga aggcacagcc 120
gcggagaacg agaccagacg gaccaagaga gggtcccgac gccttaagcg caggaagagt 180
aaccgcctta acgacatgaa gaacctgctg aaagagaacg atctgtactt cgaggactac 240
agaaactaca acccgtacga aattcgagcc aaggggttga aggagaaact tctcccagag 300
gagctgtgca ccgctatcat gcacatcact aagagtcgtg ggactaccct ggaagccttg 360
gccgacgagt ctcaggacga cgagggcacc aaggccaccc tcagcaagaa cgcgaaggag 420
cttaacgacg gtaagtacat ctgcgaggtg cagctggaca ggttgaacaa agaccacaag 480
gtccggggca ctgagaacaa ctttaagacc gaggactacg ttaaggaact gaaggagatc 540
ctcaagcatc aggacctgaa cgaggagctc tgcgaccaga tcatcgagat ggtatctcgt 600
cgcaggcggt acgaccaggg acccggctct gagaagtccc ccacacccta cggttcttac 660
cggatggtcg acggggtgtt gaagcacgtg aacctgatcg acgagatgag ggccgatgc 720 tccgtgtacc cggacgagtt ccgcgctccg aagcagagtt acaccgctga gcttttcaac 780
ctgctgaacg acctcaacaa cctcactatc aagggagaaa agattacggt cgaggagaag 840
gagaaagtgg tcgccttcgt gaacgagaag gggtctatca ctgttaagca gcttctcaag 900
ctccttgacg cacaagagga cgaggtgacc ggtttccgca tcgacaagaa cgacaagcct 960
ctgatcaccg agttcaaagg atactcaaag gtgcttaagg tgttcaagaa gtacaatcag 1020
caggagcttc tggaagacaa gcttatcgtg gaccaggtca tcgatatctg cactaagagc 1080
aagggcatcg acgagaggaa gaaggacatc aaggagttgt acccagagtt cgacaacgaa 1140
ctgatcgagg agttggcaag cgtcaagggc gtgtcagcat accacagtct gagcttcaag 1200
gctatgcaca tcattaacaa ggagatgctg accaccgaga tgaaccagat tcaggtcctg 1260
cacgagatcg agatgttcga caagaaccgc aagagcttga aagggaagaa gaacatcgag 1320
cccgacgaag aggccatcct gtcccccgta gccaagcggg cacaccgcga gaccttcaag 1380
gtgatcaacg ccccttcgtaa gcagtacggg gagttcgact caatcgtgat cgagatgacc 1440
cgcgacaaga actccaaaga gcaggtgaaa cggatcaacg actctcagaa gcgtttcaag 1500
tcagagaacg acagagtgga cggtatcatc aagaactctg gaatagaccc cgagcgtgtc 1560
aacggcaaga ccaagacaaa gatacgcctc tacctgcagc aggactgcaa aactgcgtac 1620
acccagcagg acatcgacct gcacactctt atattcgacg acaaggcgta cgagatcgac 1680

-continued

```
cacataatcc ctatcagcgt cagtcttgac gacagtctga ccaacaaggt tctggcctca   1740
aggctcgaga atcagcagaa ggggaacctc accccctatga tggcctacct caaaggtaag   1800
ttcactggcg gaaacctgga gaagtacaag ctgttcgtgt catccaacaa gaacttcaac   1860
ggcaagaagc gcaacaacct gctgaccgag caggacataa ctaaggaaga cgtggctcga   1920
aaattcatta acagaaacct ggtggacaca tcctacgcct gcagaaccgt cttgaacaca   1980
ctgcagaggt acttcaagga caacgagatt gacactaagg tacacacaat ccgaggccag   2040
agcacaaaca tcttccgcaa gcgcattaac ctgcagaagg accgcgaaca ggactacttc   2100
caccacgcca ttgacgccct gatcgtggcc agtctgaaga agatgaacat cgtgaacagc   2160
tacctgatgc actataatta cagcgacttg tacgacgagg agactggcga ggtcttcgac   2220
gtgctgcccg acaagcagtt catcgaccag cggtacatct ccttcatttc cgacctgaag   2280
aacatctacc aggagtccaa ccagtacaat ctgggataca taactcagga gcagatgcac   2340
tacccgctga ttaaagtcag ccacaagatt gacaccaagc ccaaccggaa gatagctgac   2400
gagactatct acagcacccg caacatcgag ggccaggaca tgttggtgga gaagattaag   2460
aacatttacg accccaagga gaagaaggcc atcgagctgg tgaacaacat aatcaacgac   2520
gacaccgaca aatatatcat gaagcacaag gacccccaga ccttcgagaa gatcaaagag   2580
gtcgtcctga accacttcaa cgactacaag gactctaaag agtactacgt catcgataag   2640
aaggggaaat acagcctgaa agaggagagc cccctgacta gctactacaa cgagaacggg   2700
gccataacga agtacagcaa gaagaacaac gggcccgcta taacatccat gaagttctat   2760
agcgagaagc tcggcaacca cctggctatc actagcaact acaacacgaa caacaagaaa   2820
gtgatcctca agcagatttc accctaccgt actgatttct acgtgagtcc agagggcaag   2880
tacaagttcg tgaccgtccg gtacaaggac gtgttctaca aggagaccat ccacaagttc   2940
gttatcgacg agaactggta tcacgaggag aagataaaga agggtatcct ggaagactgg   3000
aagttcgttt gctctatgca ccgggacgag ctgatcgggc tgattaagcc agagggcaag   3060
aaattcgtgt acgacgcgtc catcaacggc ggacagactc agtaccacga cggcaagcac   3120
tacgagattc ttaaattcac cgccaccaac gacgagaaga agaggacctt cgaggtgaag   3180
cccatcaata caaattgtag taagaggttg atgccttccg tcggcccctt catcaagatc   3240
cagaagttcg ccaccgacgt cctggggaac atctacgagg tgaaggacaa caggcttaag   3300
ctggaatttg ac                                                       3312
```

<210> SEQ ID NO 11
<211> LENGTH: 4113
<212> TYPE: DNA
<213> ORGANISM: Ezakiella peruensis strain M6.X2

<400> SEQUENCE: 11

```
atgacaaaag taaaagatta ttatatcgga cttgatatag gtacatcatc agttggctgg     60
gcagtaacag acgaggctta caatgttcta aaattcaact ccaagaagat gtggggagtt    120
cgtctttttg atgatgccaa aactgctgaa gaaagacgag ggcaaagagg ggccaggaga    180
agacttgacc gcaaaaaaga acgcttaagt ctcttgcaag atttttttgc agaggaagtt    240
gctaaagtag atccaaattt ctttttgcgt ctagataaca gcgaccttta tatggaggac    300
aaagatcaaa agttaaagtc caagtacact ttatttaatg ataaagattt taaagacaag    360
aacttccaca aaaaatatcc gactatccac catctcctta tggacttgat tgaagatgat    420
agcaaaaaag atattagact ggtttattta gcttgccatt acttacttaa aaatcgtggc    480
```

```
cactttattt ttgaaggaca aaaatttgat acaaagagct cctttgaaaa ttctctaaat    540
gaattaaagg tccacttaaa tgatgaatac ggtcttgatc ttgagtttga taatgaaaat    600
ttgataaata tacttacaga tcctaagtta aacaagaccg caaaaaagaa agaacttaaa    660
agtgttattg gagatacaaa atttctaaag gcagtatctg ctattatgat tggtagctct    720
caaaagctag tagatctatt tgaaaatcct gaagactttg atgattcggc aatcaaatca    780
gtggattttt ctacgacgag ttttgatgat aaatatagcg attacgagtt agcccttggg    840
gataaaattg cccttgtaaa tatattaaaa gaaatctatg actcatctat acttgaaaat    900
ttattaaaag aagccgataa atcaaaagat ggcaataagt acatttctaa cgcctttgta    960
aaaaaatata acaagcatgg ccaggacctc aaggaattta agcgcctagt tagacagtac   1020
cataaatcag cctacttcga catctttagg agtgaaaaag taaacgataa ctatgtttca   1080
tataccaagt caagtatatc caataacaag agagtgaagg cgaataagtt tacagaccaa   1140
gaagcttttt ataagtttgc taaaaagcac ctagaaacta taaaatacaa aattaataaa   1200
gttaatggta gcaaagctga ccttgaacta atagatggaa tgctaaggga tatggaattt   1260
aaaaatttca tgccaaagat aaaatcttct gataatggag ttataccttta tcaattgaaa   1320
cttatggagc taaataagat ccttgaaaac caatccaaac accatgaatt tttaaacgta   1380
tccgatgaat atggaagcgt ttgcgacaag attgcttcga ttatggaatt taggattcca   1440
tattatgttg ggcctttaaa tcctaactca aaatatgctt ggattaagaa gcaaaaggac   1500
agcgaaatca cgccatggaa ttttaaagat gtagttgatt tggattcttc aagggaagag   1560
tttatagata gcttaattgg caggtgcaca tatttaaaag atgaaaaagt tctaccaaag   1620
gcctcgcttc tctacaatga gtatatggtt ttaaatgaac tcaacaattt aaaattaaat   1680
gatcttccta ttactgaaga aatgaagaag aaaatcttcg atcaactctt taagaccagg   1740
aaaaaagtaa cattaaaggc tgtcgctaat cttctcaaaa aagaatttaa tataaatgga   1800
gaaatcctat tgtccggcac agatggggat tttaaacaag ggctaaactc ttataacgat   1860
tttaaggcca ttgttgggga caaggttgac agcgacgact atagggataa aatcgaagaa   1920
attatcaagc taatcgtcct ctatggagat gacaaatctt acttgcaaaa gaaaataaag   1980
gcgggatacg gcaagtattt tacagattca gaaatcaaaa agatggctgg cctaaattat   2040
aaagactggg gcagattaag taaaaaacta ctcacaggtt tagaaggcgc caataaaatt   2100
acaggcgaaa gaggatctat aatccatttt atgcgtgagt acaatttaaa cttaatggaa   2160
ttaatgagcg ccagcttcac ttttacagag gaaattcaaa agttaaatcc agttgacgat   2220
agaaaactct cctatgagat ggttgatgag ctttatttat caccttcagt taagagaatg   2280
ttatggcaaa gtctaagaat agttgatgaa attaaaaata taatgggcac tgattccaag   2340
aaaatcttta ttgaaatggc caggggcaaa gaagaagtca aggctagaaa agaatctaga   2400
aaaaatcagc tcttaaaatt ttacaaggat ggcaaaaaag cctttatatc agaaatcggc   2460
gaagaaagat atagctatct tttaagtgaa atcgaaggag aagaggaaaa caaattcaga   2520
tgggacaatc tttatctcta ctacacccag cttggcaggt gtatgtatag tcttgagcca   2580
attgatattt cagaactctc atcgaaaaac atctatgacc aagaccacat ttatccaaag   2640
tcaaaaatct atgatgattc aattgaaaac agagttttgg ttaagaaaga tttaaatagc   2700
aagaaaggca attcataccc aataccggat gagattttaa ataaaaattg ctatgcttat   2760
tggaaaattc tatatgacaa gggactaatt ggtcaaaaga aatataccag acttacacgt   2820
```

```
aggacaggat ttactgatga tgaacttgtc caatttatat ccaggcaaat agttgagacc   2880
aggcaggcta ccaaagaaac agcaaatctc ttaaaaacca tttgcaaaaa ttcagaaata   2940
gtttactcta aggcagaaaa tgctagcaga ttcagacagg aatttgatat agtaaaatgc   3000
cgtgcagtca atgacctcca ccacatgcat gacgcttata taaatataat cgttggcaat   3060
gtctacaata caaaatttac caaagacccc atgaactttg tcaaaaaaca agagaaagct   3120
agaagttata acttggaaaa catgtttaaa tatgacgtaa agcgcggggg ctatacagca   3180
tggatagcag acgatgaaaa aggcactgtt aaaaatgcta gcatcaagag aataagaaaa   3240
gaactagagg ggaccaacta cagatttact cgcatgaatt atatagaaag tggtgcacta   3300
tttaatgcta ccctgcaaag aaaaaacaaa ggaagtcgcc ctctaaaaga taaggggcct   3360
aagagctcaa tagaaaaata tggtggatat actaatataa acaaggcttg ctttgcagtg   3420
ttggatatta aatcaaaaaa taaaatagaa agaaaattaa tgccagttga aagagaaata   3480
tacgctaagc aaaagaatga taaaaaattg agtgatgaaa tatttagcaa atatttgaaa   3540
gatagattcg gaattgaaga ttatagagta gtatatcctg tagtaaagat gagaactttg   3600
ttaaaaatag atggatctta ttattttata actggtggaa gtgacaaaac attggaatta   3660
aggagtgcac ttcaattaat attaccaaag aaaaatgaat gggcaataaa gcaaattgat   3720
aaatccagtg agaatgatta cctaacaatt gaaaggatac aagatttaac ggaagaactt   3780
gtatacaata cgtttgatat aatagtgaat aaatttaaaa catctgtatt taaaaaatca   3840
tttttgaatt tattccaaga tgataaaatc gaaaatatag attttaaatt caaatcaatg   3900
gattttaaag aaaagtgtaa aactctattg atgctagtaa aagccatcag agcttctggt   3960
gtacgccaag acttaaaatc tatagattta aaatcagact atggtagatt gagctccaag   4020
actaataata taggaaacta tcaagaattt aaaatcataa accaatcaat tacaggcctc   4080
tttgaaaacg aagtggactt gttaaaatta tga                                4113
```

<210> SEQ ID NO 12
<211> LENGTH: 4107
<212> TYPE: DNA
<213> ORGANISM: Artificial Sequence
<220> FEATURE:
<223> OTHER INFORMATION: Synthetic

<400> SEQUENCE: 12

```
accaaggtga aggactacta cataggcttg gacatcggca cctctagcgt cgggtgggcc     60
gtcaccgatg aagcctataa cgtgcttaag tttaatagca agaaaatgtg ggcgtgcgg    120
ctgttcgacg acgctaagac ggcagaggag cgtaggggcc agcgaggagc aagacgacgt    180
ctggatcgga agaaggagag actcagcctg ctgcaggact tcttcgccga agaggtagca    240
aaggtcgacc ccaacttctt cctcaggctg gacaattccg atctgtacat ggaagataag    300
gaccagaaac tgaaaagcaa atatacactg ttcaacgaca aggacttcaa ggataagaat    360
tttcataaga agtaccccac aatacatcac ctgctgatgg atctgatcga ggacgacagt    420
aagaaggaca tccggctcgt ctacctggcc tgtcactatt tgctcaagaa caggggtcat    480
ttcatcttcg agggccagaa gttcgacact aaatcaagct tcgagaacag tttgaacgag    540
ctcaaagttc atttgaacga cgagtatgga ctggacctcg aatttgacaa cgagaacctg    600
attaacatct tgactgaccc aaaactcaat aaaacggcca agaagaagga gctgaagtcc    660
gtaatcggcg acaccaagtt cctcaaagcc gtttccgcga taatgatcgg ctctagccag    720
aaactcgtcg acttgttcga gaaccccgag gatttcgacg actctgcgat aaagtccgtt    780
```

```
gacttctcaa ctacctcttt cgacgacaag tactctgact atgaactcgc tctgggtgac    840
aagatcgctc tggtcaacat ccttaaggaa atttacgata gctccatcct cgagaacctg    900
ctcaaagagg cagacaagtc taaggacggt aacaaatata tcagtaatgc attcgtgaag    960
aagtacaata aacacggaca agatctgaaa gagttcaaac gtctggtacg acaatatcac   1020
aagagtgcgt attttgatat tttcagatcc gagaaggtga atgacaatta cgtcagctac   1080
actaaaagct caattagcaa caataaacgc gtcaaagcaa acaagttcac tgatcaagag   1140
gccttctaca aattcgccaa gaaacatctg gagacaatca agtataagat caacaaggta   1200
aacggctcca aggcagatct ggagctgatt gacgggatgc tgcgggacat ggagttcaag   1260
aactttatgc ccaaaattaa gtccagtgac aacggggtga ttccatacca gctcaagctg   1320
atggaattga acaaaatact cgagaatcag tcaaagcatc acgagttcct caatgtcagc   1380
gacgagtacg gctccgtgtg tgataaaatc gcatctatca tggagttccg tatcccctac   1440
tacgtgggac ccctgaaccc caatagcaag tacgcctgga tcaagaagca gaaagatagt   1500
gagattactc cctggaactt caaggacgtc gtggaccttg actccagcag agaggagttc   1560
attgactcac tgatcggacg ctgtacttac cttaaggacg agaaggtcct tcccaaagct   1620
tctttgctgt ataacgaata catggtgctg aacgagctga ataacctgaa gttgaacgac   1680
cttcccatca ccgaggagat gaagaagaag atatttgacc agttgttcaa aacaagaaag   1740
aaggtcaccc ttaaagcggt ggcaaacctg ctgaagaagg agttcaacat caacggcgag   1800
attctgctct ctgggaccga cggtgacttc aagcagggct tgaactcata caatgacttc   1860
aaagctatcg tgggcgataa agtcgattcc gatgattacc gggacaagat tgaggagatc   1920
attaaactga tagttcttta cggtgacgat aagagttacc ttcagaagaa gattaaagct   1980
gggtatggaa aatacttcac cgacagtgag attaagaaaa tggcggggct gaactacaag   2040
gattggggaa ggctctcaaa gaagctgctg acgggactcg agggtgcaaa caagatcact   2100
ggagagcggg gctccattat tcacttcatg agggaatata accttaatct gatggagctt   2160
atgtcagctt catttacgtt caccgaagag atacagaaac ttaaccccgt ggatgaccgc   2220
aagctgtcat acgaaatggt ggacgaactg tacctttctc ccagtgtgaa acggatgctc   2280
tggcagtccc tgcgcatcgt cgacgagata aagaacatca tgggaaccga cagtaagaag   2340
attttcatcg agatggctcg gggtaaggaa gaggtgaaag cccgcaagga gtcaaggaag   2400
aaccaactgc tgaagttcta taaagacgga aagaaggcat tcatcagcga gattggcgag   2460
gagaggtact cttacttgct ttctgagata gagggtgagg aagagaataa gtttcgatgg   2520
gataacctgt acctttatta tactcaactg ggtcgctgca tgtactcttt ggaacctatc   2580
gacatatctg agctgtcttc aaagaatatt tacgatcagg atcatatcta ccccaaaagc   2640
aagatttacg acgacagtat cgagaatagg gtgctggtga agaaggacct taactccaag   2700
aagggtaaca gctatcctat cccagacgaa atcctgaaca agaactgtta cgcctactgg   2760
aagatcctgt acgataaagg tcttatcggg cagaagaagt acactcggct gacccggaga   2820
actggcttca cggacgacga gctcgttcag ttcatctcaa gacagatcgt ggaaactaga   2880
caagcaacaa aggagactgc taacctgctc aagacaatat gtaagaactc cgagatcgtg   2940
tattccaaag ccgagaacgc aagtcggttt aggcaagagt tcgacatcgt gaagtgtagg   3000
gcggtgaacg atcttcatca tatgcacgat gcctacatca acatcatagt ggggaacgtg   3060
tataacacca agttcacgaa ggaccctatg aatttcgtaa agaagcagga aaaggcgcgg   3120
```

agctacaatc tcgagaatat gttcaagtac gatgtgaaac gtggcggata caccgcttgg 3180
atcgccgatg acgagaaggg caccgtgaag aacgcgagta ttaaacgtat ccggaaggag 3240
ctggaaggca caaattatag gttcacaaga atgaactaca ttgagtctgg agcgcttttc 3300
aacgccactc tccagcggaa gaataagggc tccagacccc tgaaggacaa aggcccgaaa 3360
tcttccatcg agaagtacgg cggctacaca aacatcaata aagcctgttt cgctgttctt 3420
gacatcaagt ctaagaacaa gattgagagg aagctgatgc ccgtcgagcg tgagatctat 3480
gccaaacaga agaacgacaa gaagctgtcc gacgagattt tctcaaagta cctcaaggac 3540
cgatttggca tcgaggacta cagggttgtc tacccagtgg tgaaaatgcg cacactgctc 3600
aagatcgacg gcagctacta cttcatcaca ggcggttctg ataagaccct ggagttgcga 3660
tctgctctgc agctgattct ccctaagaag aacgagtggg cgatcaaaca gatcgacaag 3720
tcttccgaaa acgactatct gacgatcgag cgtatccagg acctgaccga ggagctggtg 3780
tataacactt tcgacatcat cgtcaacaag ttcaagacca gtgtcttcaa gaagtctttc 3840
cttaacttgt ttcaggacga caagattgag aacattgact tcaagtttaa gtccatggac 3900
ttcaaggaga aatgcaagac acttctcatg ctggtcaagg cgattcgggc atccggcgtg 3960
aggcaggatc tcaagtccat cgacctcaag tctgattacg gacggctcag ttcaaagacc 4020
aacaacatcg gcaattacca ggagttcaag attattaatc agtccatcac tggactgttc 4080
gagaatgagg tcgatctcct gaagctg 4107

<210> SEQ ID NO 13
<211> LENGTH: 4110
<212> TYPE: DNA
<213> ORGANISM: Artificial Sequence
<220> FEATURE:
<223> OTHER INFORMATION: Synthetic

<400> SEQUENCE: 13
atgaccaagg tgaaggacta ctacataggc ttggacatcg gcacctctag cgtcgggtgg 60
gccgtcaccg atgaagccta taacgtgctt aagtttaata gcaagaaaat gtggggcgtg 120
cggctgttcg acgacgctaa gacggcagag gagcgtaggg gccagcgagg agcaagacga 180
cgtctggatc ggaagaagga gagactcagc ctgctgcagg acttcttcgc cgaagaggta 240
gcaaaggtcg accccaactt cttcctcagg ctggacaatt ccgatctgta catggaagat 300
aaggaccaga aactgaaaag caaatataca ctgttcaacg acaaggactt caaggataag 360
aattttcata agaagtaccc cacaatacat cacctgctga tggatctgat cgaggacgac 420
agtaagaagg acatccggct cgtctacctg gcctgtcact atttgctcaa gaacaggggt 480
catttcatct tcgagggcca gaagttcgac actaaatcaa gcttcgagaa cagtttgaac 540
gagctcaaag ttcatttgaa cgacgagtat ggactggacc tcgaatttga caacgagaac 600
ctgattaaca tcttgactga cccaaaactc aataaaacgg ccaagaagaa ggagctgaag 660
tccgtaatcg gcgacaccaa gttcctcaaa gccgtttccg cgataatgat cggctctagc 720
cagaaactcg tcgacttgtt cgagaacccc gaggatttcg acgactctgc gataaagtcc 780
gttgacttct caactacctc tttcgacgac aagtactctg actatgaact cgctctgggt 840
gacaagatcg ctctggtcaa catccttaag gaaatttacg atagctccat cctcgagaac 900
ctgctcaaag aggcagacaa gtctaaggac ggtaacaaat atatcagtaa tgcattcgtg 960
aagaagtaca ataaacacgg acaagatctg aaagagttca aacgtctggt acgacaatat 1020
cacaagagtg cgtattttga tattttcaga tccgagaagg tgaatgacaa ttacgtcagc 1080

-continued

```
tacactaaaa gctcaattag caacaataaa cgcgtcaaag caaacaagtt cactgatcaa   1140
gaggccttct acaaattcgc caagaaacat ctggagacaa tcaagtataa gatcaacaag   1200
gtaaacggct ccaaggcaga tctggagctg attgacggga tgctgcggga catggagttc   1260
aagaacttta tgcccaaaat taagtccagt gacaacgggg tgattccata ccagctcaag   1320
ctgatggaat tgaacaaaat actcgagaat cagtcaaagc atcacgagtt cctcaatgtc   1380
agcgacgagt acggctccgt gtgtgataaa atcgcatcta tcatggagtt ccgtatcccc   1440
tactacgtgg gacccctgaa ccccaatagc aagtacgcct ggatcaagaa gcagaaagat   1500
agtgagatta ctccctggaa cttcaaggac gtcgtggacc ttgactccag cagagaggag   1560
ttcattgact cactgatcgg acgctgtact taccttaagg acgagaaggt ccttcccaaa   1620
gcttctttgc tgtataacga atacatggtg ctgaacgagc tgaataacct gaagttgaac   1680
gaccttccca tcaccgagga gatgaagaag aagatatttg accagttgtt caaaacaaga   1740
aagaaggtca cccttaaagc ggtggcaaac ctgctgaaga aggagttcaa catcaacggc   1800
gagattctgc tctctgggac cgacggtgac ttcaagcagg gcttgaactc atacaatgac   1860
ttcaaagcta tcgtgggcga taaagtcgat tccgatgatt accgggacaa gattgaggag   1920
atcattaaac tgatagttct ttacggtgac gataagagtt accttcagaa gaagattaaa   1980
gctgggtatg gaaaatactt caccgacagt gagattaaga aaatggcggg gctgaactac   2040
aaggattggg gaaggctctc aaagaagctg ctgacgggac tcgagggtgc aaacaagatc   2100
actggagagc ggggctccat tattcacttc atgagggaat ataaccttaa tctgatggag   2160
cttatgtcag cttcatttac gttcaccgaa gagatacaga aacttaaccc cgtggatgac   2220
cgcaagctgt catacgaaat ggtggacgaa ctgtaccttt ctcccagtgt gaaacggatg   2280
ctctggcagt ccctgcgcat cgtcgacgag ataaagaaca tcatgggaac cgacagtaag   2340
aagattttca tcgagatggc tcggggtaag gaagaggtga aagcccgcaa ggagtcaagg   2400
aagaaccaac tgctgaagtt ctataaagac ggaaagaagg cattcatcag cgagattggc   2460
gaggagaggt actcttactt gctttctgag atagagggtg aggaagagaa taagtttcga   2520
tgggataacc tgtaccttta ttatactcaa ctgggtcgct gcatgtactc tttggaacct   2580
atcgacatat ctgagctgtc ttcaaagaat atttacgatc aggatcatat ctaccccaaa   2640
agcaagattt acgacgacag tatcgagaat agggtgctgg tgaagaagga ccttaactcc   2700
aagaagggta acagctatcc tatcccagac gaaatcctga acaagaactg ttacgcctac   2760
tggaagatcc tgtacgataa aggtcttatc gggcagaaga agtacactcg gctgacccgg   2820
agaactggct tcacggacga cgagctcgtt cagttcatct caagacagat cgtggaaact   2880
agacaagcaa caaaggagac tgctaacctg ctcaagacaa tatgtaagaa ctccgagatc   2940
gtgtattcca aagccgagaa cgcaagtcgg tttaggcaag agttcgacat cgtgaagtgt   3000
agggcggtga acgatcttca tcatatgcac gatgcctaca tcaacatcat agtggggaac   3060
gtgtataaca ccaagttcac gaaggaccct atgaatttcg taaagaagca ggaaaaggcg   3120
cggagctaca atctcgagaa tatgttcaag tacgatgtga aacgtggcgg atacaccgct   3180
tggatcgccg atgacgagaa gggcaccgtg aagaacgcga gtattaaacg tatccggaag   3240
gagctggaag gcacaaatta taggttcaca agaatgaact acattgagtc tggagcgctt   3300
ttcaacgcca ctctccagcg gaagaataag ggctccagac ccctgaagga caaaggcccg   3360
aaatcttcca tcgagaagta cggcggctac acaaacatca ataaagcctg tttcgctgtt   3420
```

```
cttgacatca agtctaagaa caagattgag aggaagctga tgcccgtcga gcgtgagatc   3480

tatgccaaac agaagaacga caagaagctg tccgacgaga ttttctcaaa gtacctcaag   3540

gaccgatttg gcatcgagga ctacagggtt gtctacccag tggtgaaaat gcgcacactg   3600

ctcaagatcg acggcagcta ctacttcatc acaggcggtt ctgataagac cctggagttg   3660

cgatctgctc tgcagctgat tctccctaag aagaacgagt gggcgatcaa acagatcgac   3720

aagtcttccg aaaacgacta tctgacgatc gagcgtatcc aggacctgac cgaggagctg   3780

gtgtataaca ctttcgacat catcgtcaac aagttcaaga ccagtgtctt caagaagtct   3840

ttccttaact tgtttcagga cgacaagatt gagaacattg acttcaagtt taagtccatg   3900

gacttcaagg agaaatgcaa gacacttctc atgctggtca aggcgattcg ggcatccggc   3960

gtgaggcagg atctcaagtc catcgacctc aagtctgatt acggacggct cagttcaaag   4020

accaacaaca tcggcaatta ccaggagttc aagattatta atcagtccat cactggactg   4080

ttcgagaatg aggtcgatct cctgaagctg                                     4110
```

<210> SEQ ID NO 14
<211> LENGTH: 4110
<212> TYPE: DNA
<213> ORGANISM: Clostridium sp. AF02-29

<400> SEQUENCE: 14

```
atgaaagaga aaatggaata ctatttaggt cttgacatgg gaaccaattc agtcggatgg     60

gctgtaacag ataaagaata tcgtttgatg cgggcgaagg gaaaagattt gtggggagtt    120

cgtttgttcg aacgtgctaa tacagctgaa gaacggcggg catataggat taaccgaaga    180

agacgtcagc gggaagtagc tagaattgga attttaaaag aattatttgc cgatgaaatt    240

gcaaaagttg atgctaattt ttttgcacgc ctggacgaca gtaaatatta tcttgatgat    300

agacaggaaa ataataaaca gaagtatgcg atatttgctg ataaagatta cacggacaaa    360

gagtatttta gccaatatca gacaattttt catctgagaa aagaactgat cctgtcagat    420

caacctcatg atgttcgtct tatttatctg gcgctgttaa atatgtttaa acatagaggc    480

cattttttaa ataaaacgtt gggaacctcg gaatcattag aatcgttttt tgatatgtat    540

caaagattag ctgtatgtgc ggatggagag ggaatcaaac ttccagaaac ggtggattta    600

aagaaattag aacagatact tggagcacgt ggatgctcta gaaaggcaac attggaacat    660

atatctgaaa taatggggat taataaaaag aataaaccag tttatagcct catgcagatg    720

atatgtggac ttgatactaa aatgatagac ctttttgggc agaagattga tgaagaacac    780

aaaaaaatct ctctttcatt tcgaacgtcc aattatgaag aaatggcaga ggaagtccgt    840

aatacgatag gggatgatgc atttgaactt atattgacag caaaagaaat gcatgatttt    900

ggcttgctgg cggagattat gaaaggatat tcatatttgt cagaagcgcg ggtggctgtc    960

tatgaagagc atcgaaagga tttggctaaa ctgaaagccg tctttaaaca atatgaccat   1020

aaggcatatg atgaaatgtt tcgaatcatg aagaatggta cttatagtgc ctatgttgga   1080

agtgtaaata gtttcggtaa aatagagaga aggacagtaa aaacttccag agaagaattg   1140

ttaaaaaata taaagaaaat tttaacaggg tttccagagg atgatgctac agtacaggaa   1200

tttttgggta agatagattc ggatacactt ctccaaaaac aactgacagc ttctaatgga   1260

gtgattccaa atcaggtaca tgcaaaagaa atgaaggtca ttttgaaaaa tgcagaaaaa   1320

taccttccat ttttaagtga aagagatgaa acaggattaa gtgtatcaga aaaaaataata   1380

gctctgttta catttacgat cccgtactat gttggtcctc ttgggcagca acatttagga   1440
```

aaggaatgtg cacatggctg ggtagagcga aaagaaaaag gtactgtgta tccatggaat 1500
tttgaacaaa aggttgattt aaaggcaagt gcagaacatt ttatagaaag aatggtaaaa 1560
cattgcacgt atttatctga tgagcaggca ttgccaaaac aatcattgtt gtatgaaaaa 1620
tttcaggtat tgaatgaatt aaacaattta aaaattcgag gagaaaaaat atcggtagaa 1680
ttaaaacagc agatatatcg ggatgtcttt gaacatactg ggaaaaaagt atcgatgaag 1740
cagttggaaa actatctgaa gttgaacggc ctgcttgaaa aagacgaaaa ggacgcagtt 1800
acaggaatag atggtggttt ccatagttat ttgtcctctt taggaaaatt tataggaatt 1860
ttgggagaag aagctcatta tggtaaaaac cagaatatga tggaaaaaat tgtattttgg 1920
gggacagtat atggacagga taaaaaattc cttcgcgaac ggttaagtga agtttatgga 1980
gatagattgt caaaagagca gattcgtcgt attactggta tgaaatttga aggatgggga 2040
cgactttcta aagaatttct tttactggag ggggcttcta gagaagaagg ggagattcgg 2100
acattgattc gttcattatg ggagacaaat gaaaatttga tggggctttt aagtgaacga 2160
tatacatata gcgaagaagt acgagaaaaa acgctagagt gtgagaagag cctttctgaa 2220
tggacgattg aagatttgga aggaatgtat ctgtcagcac cggttaagcg catggtatgg 2280
cagactttgt taattgtaaa agagcttgaa aaggtgctgg gatgtgctcc acgacgtatt 2340
tttgtggaga tggcacgcga agatgcggag aaaggaagga gaacagaatc acgaaagcag 2400
aaattgcaga atctttataa agcaattaaa aaagaggaga tagactggaa aaaagagatt 2460
gatgaaaaaa cagagcaggc attccgcagt aaaaaattat atttgtatta cctgcagaag 2520
gggcgctgta tgtatacggg cgagtctatt cgatttgaag atttgatgaa tgataattta 2580
tatgatatcg atcatattta tccgagacat tttgtgaagg atgatagttt agagcagaat 2640
ctggtgctgg taaagaagga aaaaaatgca cataaaagtg atgtatttcc gattgaggcg 2700
gatattcaga aaaagatgag tccgttctgg aaagaactga aagaaagagg ttttatatca 2760
gaagaaaagt atatgcgttt aacgaggagg tatggctttt cggaagagga aaaagcaggt 2820
tttatcaatc ggcaattggt ggaaacaaga cagggaacaa agagtattac agagatattg 2880
ggacaagctt ttccagatgt ggatatcata ttttcaaaag cgtcgaatgt gtcggagttc 2940
agacatattt atggattgta taaggttcgc agtataaatg attttcatca tgcacatgac 3000
gcatacttaa atatagtggt tggaaatacg tatcatgtga aatttacgaa aaatccgttg 3060
aattttattc gggaagcaga aaaaaatccg cagaatgcag aaaataaata caatatgaac 3120
cggatgttcg attggacagt aaaaagagga aatgaaacgg catggatagc aagttccgat 3180
aaagaagcag gtagtattaa aattgtaaag gctatattgg caaaaaatac accattagtt 3240
actaagaggt gtgcggaggc acatggagga ataaccagga aagcaactat ctggaataaa 3300
aacaaagctg ctggcagcgg atatattccg gttaagatga atgatgcaag acttttggat 3360
gttacaaaat atggcggttt gacatctgta tcagcttcgg ggtacacttt gctggaatat 3420
gatgtaaaag gtaaaaaaat aagaagtctt gaggcgattc caatttactt gggacgagtg 3480
tctgaattga caaatgaggc gattttgaaa tattttgaaa aagtgctgat agaggaaaat 3540
aagggaaaag aaataacaga acttcgcatt tgtaagaagt ttattccgag agagtcgtta 3600
gtgagatata atgggtatta ctattatctc ggaggaaaat cagtggaaca gattgtattg 3660
aaaaatgcga cacagatggc atattcagaa gaagaaacat gttatataaa aaagatagaa 3720
aaagctatag aaaaaacata ttatgaagaa gtggacaaaa ataaaaatgt gattttgaca 3780

```
aaaactagaa acaatgcaat gtatgataaa tttattataa aatatcagaa ttcaatttat   3840

cagaatcaaa gtggtgcaat gaaaaattct attattggaa aaagaaatga atttttaaca   3900

ttatcattgg aaaagcagtg tagaatattg aaggcactag tagaatattt taggacagga   3960

gatattattg atttgagaga attaggaggt agttcacagg caggaaaagt ggctatgaac   4020

aagaaaatta tgggagcaag tgaattagtg ctaataagtc aatctccaac aggtttattc   4080

caacaagaga ttgatttact aaaaatatga                                    4110
```

<210> SEQ ID NO 15
<211> LENGTH: 4104
<212> TYPE: DNA
<213> ORGANISM: Artificial Sequence
<220> FEATURE:
<223> OTHER INFORMATION: Synthetic

<400> SEQUENCE: 15

```
aaggaaaaga tggagtatta cctggggctg gatatgggca ctaacagcgt gggttgggcg     60

gtgaccgaca aggagtaccg gctgatgagg gcaaaaggga aggacctgtg ggcgtacgg     120

ctgtttgaga gagcgaacac tgcggaagag aggcgcgcct acagaatcaa tagacgacgg    180

cggcaacgag aggttgcaag gatcggtatc cttaaggaac tcttcgctga cgagatcgcc    240

aaggtggacg caaacttctt cgccagactt gatgattcaa agtactacct ggacgaccgg    300

caagagaaca acaagcagaa atacgctatt ttcgccgaca aggactatac tgataaggaa    360

tacttctccc agtaccaaac tatcttccat ctccggaagg agcttatact cagtgaccag    420

ccacacgacg tgagactgat ctaccttgct cttctgaaca tgttcaagca ccggggacac    480

ttcttgaaca agactctggg gacttccgag agtttggagt ctttcttcga catgtaccag    540

cgactggcag tgtgcgcaga cggggaaggc attaagttgc ccgagaccgt agaccttaag    600

aagctcgagc aaatcctggg cgcccgggga tgtagcagga aagccaccct tgagcacatc    660

agcgagatta tgggaatcaa caagaagaac aagcccgtct actccctgat gcaaatgatt    720

tgcggtctgg acaccaagat gatcgatctg ttcggacaaa agatcgacga ggagcataag    780

aagataagcc tgtccttcag aactagcaac tacgaggaga tggccgaaga ggttagaaac    840

acaattggcg acgacgcctt cgagctgatt ctcactgcca aggagatgca cgacttcggg    900

ctgttggctg aaatcatgaa ggggtactcc tacctgagcg aggctcgcgt tgccgtgtac    960

gaggaacacc ggaaagacct ggccaagctc aaggcagtgt tcaagcagta cgatcacaaa   1020

gcttacgacg agatgttcag gattatgaag aacgggacat actcagctta cgtagggtcc   1080

gtgaactcct ttggcaagat cgaacgcaga accgtgaaga cctctcgcga ggagcttctt   1140

aagaacatta agaagatcct gaccggtttc cccgaagacg acgcaactgt gcaagagttc   1200

ctcgggaaaa ttgactctga cacgctgctt cagaagcagt tgactgccag caacggcgta   1260

atccctaacc aagtccacgc gaaggagatg aaagtaatcc tgaagaacgc cgagaagtat   1320

ctgcctttcc tgtccgagag ggacgagact gggctctcag tctccgagaa gatcattgca   1380

ttgttcacgt tcactattcc ttattacgtg ggacccctgg gtcaacagca cttggggaaa   1440

gagtgcgccc acggttgggt ggaaagaaag gagaagggga ccgtttaccc ctggaacttc   1500

gagcagaaag tcgaccttaa agcttccgct gagcacttca ttgagcgcat ggtgaagcac   1560

tgtacatacc tgtccgacga acaagctctg cccaagcaga gtctgctcta cgagaagttc   1620

caagtgctta acgagctcaa taacttgaag atcaggggcg agaagatcag tgtggagctg   1680

aagcaacaaa tttaccggga cgttttcgag cacaccggaa agaaggtttc aatgaaacaa   1740
```

```
ctggagaatt acttgaaact gaatgggctt ctggagaagg atgagaaaga tgccgtgacc   1800
gggatcgacg gcggatttca ctcatacctt tcttccctgg gcaagttcat cggcatcctc   1860
ggggaagagg cacactacgg aaagaatcaa aacatgatgg agaagatcgt gttctggggt   1920
acggtgtacg ggcaagacaa gaagtttctg cgggagcgtc tgtccgaggt gtacggcgac   1980
cggctgagca aggaacaaat cagaaggata acaggaatga agttcgaggg ctggggccgg   2040
ctctccaagg agttcctgct gctcgaagga gcaagtcggg aagagggcga aatccgcacc   2100
ctcatacgga gcctgtggga aacgaacgag aacctgatgg gactgctgtc agagagatac   2160
acttactcag aagaggtccg cgagaagact ctcgaatgcg agaaatctct gtcagagtgg   2220
accatcgagg acctcgaggg catgtacctt tccgcccctg taaaacggat ggtctggcaa   2280
accctcttga tagtgaagga actggagaaa gtcctcggct gcgcccctcg aaggatcttc   2340
gttgaaatgg ctagagagga cgcagaaaag ggtcgccgga ccgagtcccg caaacaaaag   2400
ctgcaaaacc tgtacaaggc tatcaagaag gaagaaattg attggaagaa ggaaatcgac   2460
gagaagaccg aacaagcctt taggagcaag aagctgtacc tgtactatct ccagaaagga   2520
cgatgcatgt acaccggaga aagcatccgc ttcgaggacc tcatgaacga caacttgtac   2580
gacatagacc acatctaccc ccggcacttc gttaaagacg actcccttga acaaaacctc   2640
gttttggtta agaaggagaa gaacgctcac aagagcgacg tgttcccaat cgaagccgac   2700
atacaaaaga aaatgtctcc cttttggaag gagctcaagg agaggggatt catctctgag   2760
gagaaataca tgagactcac tcgaagatac gggttcagtg aggaagagaa ggctggattc   2820
attaacagac agctggtaga gacccgtcaa ggcacgaaat ctatcactga aatcctgggc   2880
caggccttcc ccgacgttga cataattttc tccaaggctt caaacgtttc agaatttcgg   2940
cacatctacg gcctctacaa agtgaggtct attaacgact tccaccacgc gcacgatgct   3000
tatctgaaca tcgtcgtagg caacacttac cacgttaagt tcacaaagaa ccccctgaac   3060
ttcatccgcg aggccgagaa gaacccacaa aacgccgaga acaagtataa catgaatcgc   3120
atgtttgact ggaccgtgaa gaggggcaac gagactgcct ggatcgccag cagtgacaaa   3180
gaggccggat ctatcaagat agtcaaagcg attcttgcca agaacacccc tcttgtgacc   3240
aaacggtgcg cagaagctca cggcggcatt actcgcaagg cgacaatttg gaacaagaat   3300
aaggccgcgg gttctggcta catcccagtg aaaatgaacg acgcccggct cctggacgtg   3360
accaagtacg gcggactgac ctcagtgagt gcgtccggct ataccctgct tgagtacgac   3420
gtgaagggga agaagattcg atccctggaa gctatcccca tctatcttgg gagagtcagt   3480
gagctcacta acgaagccat cctcaagtac ttcgagaagg ttcttatcga agagaacaaa   3540
gggaaggaga ttaccgagct ccgtatctgc aagaagttca taccccgtga aagcctcgtt   3600
cggtacaacg gatactatta ctacctgggc ggcaagtctg ttgagcaaat agtcctgaag   3660
aacgccaccc aaatggctta ctccgaggaa gagacttgct acatcaagaa aattgagaag   3720
gcaattgaga agacctacta cgaagaggtc gataagaaca agaacgtaat actgactaag   3780
acccgcaata acgcgatgta cgacaagttc atcattaagt accaaaacag tatataccaa   3840
aaccagagcg gagccatgaa gaactcaatc atagggaaga ggaacgagtt cctgactctc   3900
agtctcgaga aacaatgccg catcctcaaa gctctggtcg agtacttccg gaccggggac   3960
atcatagacc tgcgggagct cggcggatca agccaagcgg gcaaggtcgc gatgaataag   4020
aagatcatgg gcgcgagcga gctggtcctg atttcacagt cccccaccgg gttgtttcag   4080
```

caggaaatcg acctgctgaa gatt 4104

<210> SEQ ID NO 16
<211> LENGTH: 4107
<212> TYPE: DNA
<213> ORGANISM: Artificial Sequence
<220> FEATURE:
<223> OTHER INFORMATION: Synthetic

<400> SEQUENCE: 16
atgaaggaaa agatggagta ttacctgggg ctggatatgg gcactaacag cgtgggttgg 60
gcggtgaccg acaaggagta ccggctgatg agggcaaaag ggaaggacct gtggggcgta 120
cggctgtttg agagagcgaa cactgcggaa gagaggcgcg cctacagaat caatagacga 180
cggcggcaac gagaggttgc aaggatcggt atccttaagg aactcttcgc tgacgagatc 240
gccaaggtgg acgcaaactt cttcgccaga cttgatgatt caaagtacta cctggacgac 300
cggcaagaga acaacaagca gaaatacgct attttcgccg acaaggacta tactgataag 360
gaatacttct cccagtacca aactatcttc catctccgga aggagcttat actcagtgac 420
cagccacacg acgtgagact gatctacctt gctcttctga acatgttcaa gcaccgggga 480
cacttcttga acaagactct ggggacttcc gagagtttgg agtctttctt cgacatgtac 540
cagcgactgg cagtgtgcgc agacggggaa ggcattaagt tgcccgagac cgtagacctt 600
aagaagctcg agcaaatcct gggcgcccgg ggatgtagca ggaaagccac ccttgagcac 660
atcagcgaga ttatgggaat caacaagaag aacaagcccg tctactccct gatgcaaatg 720
atttgcggtc tggacaccaa gatgatcgat ctgttcggac aaaagatcga cgaggagcat 780
aagaagataa gcctgtcctt cagaactagc aactacgagg agatggccga agaggttaga 840
aacacaattg gcgacgacgc cttcgagctg attctcactg ccaaggagat gcacgacttc 900
gggctgttgg ctgaaatcat gaaggggtac tcctacctga gcgaggctcg cgttgccgtg 960
tacgaggaac accggaaaga cctggccaag ctcaaggcag tgttcaagca gtacgatcac 1020
aaagcttacg acgagatgtt caggattatg aagaacggga catactcagc ttacgtaggg 1080
tccgtgaact cctttggcaa gatcgaacgc agaaccgtga agacctctcg cgaggagctt 1140
cttaagaaca ttaagaagat cctgaccggt ttccccgaag acgacgcaac tgtgcaagag 1200
ttcctcggga aaattgactc tgacacgctg cttcagaagc agttgactgc cagcaacggc 1260
gtaatcccta accaagtcca cgcgaaggag atgaaagtaa tcctgaagaa cgccgagaag 1320
tatctgcctt tcctgtccga gagggacgag actgggctct cagtctccga gaagatcatt 1380
gcattgttca cgttcactat tccttattac gtgggacccc tgggtcaaca gcacttgggg 1440
aaagagtgcg cccacggttg ggtggaaaga aaggagaagg ggaccgttta cccctggaac 1500
ttcgagcaga aagtcgacct taaagcttcc gctgagcact tcattgagcg catggtgaag 1560
cactgtacat acctgtccga cgaacaagct ctgcccaagc agagtctgct ctacgagaag 1620
ttccaagtgc ttaacgagct caataacttg aagatcaggg gcgagaagat cagtgtggag 1680
ctgaagcaac aaatttaccg ggacgttttc gagcacaccg gaaagaaggt ttcaatgaaa 1740
caactggaga attacttgaa actgaatggg cttctggaga aggatgagaa agatgccgtg 1800
accgggatcg acggcggatt tcactcatac ctttcttccc tgggcaagtt catcggcatc 1860
ctcggggaag aggcacacta cggaaagaat caaaacatga tggagaagat cgtgttctgg 1920
ggtacggtgt acgggcaaga caagaagttt ctgcgggagc gtctgtccga ggtgtacggc 1980
gaccggctga gcaaggaaca aatcagaagg ataacaggaa tgaagttcga gggctggggc 2040

-continued

```
cggctctcca aggagttcct gctgctcgaa ggagcaagtc gggaagaggg cgaaatccgc   2100
accctcatac ggagcctgtg ggaaacgaac gagaacctga tgggactgct gtcagagaga   2160
tacacttact cagaagaggt ccgcgagaag actctcgaat gcgagaaatc tctgtcagag   2220
tggaccatcg aggacctcga gggcatgtac ctttccgccc ctgtaaaacg gatggtctgg   2280
caaaccctct tgatagtgaa ggaactggag aaagtcctcg gctgcgcccc tcgaaggatc   2340
ttcgttgaaa tggctagaga ggacgcagaa aagggtcgcc ggaccgagtc ccgcaaacaa   2400
aagctgcaaa acctgtacaa ggctatcaag aaggaagaaa ttgattggaa gaaggaaatc   2460
gacgagaaga ccgaacaagc ctttaggagc aagaagctgt acctgtacta tctccagaaa   2520
ggacgatgca tgtacaccgg agaaagcatc cgcttcgagg acctcatgaa cgacaacttg   2580
tacgacatag accacatcta cccccggcac ttcgttaaag acgactccct tgaacaaaac   2640
ctcgttttgg ttaagaagga gaagaacgct cacaagagcg acgtgttccc aatcgaagcc   2700
gacatacaaa agaaaatgtc tcccttttgg aaggagctca aggagagggg attcatctct   2760
gaggagaaat acatgagact cactcgaaga tacgggttca gtgaggaaga gaaggctgga   2820
ttcattaaca gacagctggt agagacccgt caaggcacga aatctatcac tgaaatcctg   2880
ggccaggcct tccccgacgt tgacataatt ttctccaagg cttcaaacgt ttcagaattt   2940
cggcacatct acggcctcta caaagtgagg tctattaacg acttccacca cgcgcacgat   3000
gcttatctga acatcgtcgt aggcaacact taccacgtta agttcacaaa gaaccccctg   3060
aacttcatcc gcgaggccga gaagaaccca caaaacgccg agaacaagta taacatgaat   3120
cgcatgtttg actggaccgt gaagaggggc aacgagactg cctggatcgc cagcagtgac   3180
aaagaggccg gatctatcaa gatagtcaaa gcgattcttg ccaagaacac ccctcttgtg   3240
accaaacggt gcgcagaagc tcacggcggc attactcgca aggcgacaat ttggaacaag   3300
aataaggccg cgggttctgg ctacatccca gtgaaaatga acgacgcccg gctcctggac   3360
gtgaccaagt acggcggact gacctcagtg agtgcgtccg gctataccct gcttgagtac   3420
gacgtgaagg ggaagaagat tcgatccctg gaagctatcc ccatctatct tgggagagtc   3480
agtgagctca ctaacgaagc catcctcaag tacttcgaga aggttcttat cgaagagaac   3540
aaagggaagg agattaccga gctccgtatc tgcaagaagt tcatacccccg tgaaagcctc   3600
gttcggtaca acggatacta ttactacctg ggcggcaagt ctgttgagca aatagtcctg   3660
aagaacgcca cccaaatggc ttactccgag gaagagactt gctacatcaa gaaaattgag   3720
aaggcaattg agaagaccta ctacgaagag gtcgataaga acaagaacgt aatactgact   3780
aagacccgca ataacgcgat gtacgacaag ttcatcatta agtaccaaaa cagtatatac   3840
caaaaccaga gcggagccat gaagaactca atcataggga agaggaacga gttcctgact   3900
ctcagtctcg agaaacaatg ccgcatcctc aaagctctgg tcgagtactt ccggaccggg   3960
gacatcatag acctgcggga gctcggcgga tcaagccaag cgggcaaggt cgcgatgaat   4020
aagaagatca tgggcgcgag cgagctggtc ctgatttcac agtcccccac cgggttgttt   4080
cagcaggaaa tcgacctgct gaagatt                                       4107
```

<210> SEQ ID NO 17
<211> LENGTH: 16
<212> TYPE: RNA
<213> ORGANISM: Artificial Sequence
<220> FEATURE:
<223> OTHER INFORMATION: Synthetic

<400> SEQUENCE: 17
guuuuaguac cuagag 16

<210> SEQ ID NO 18
<211> LENGTH: 18
<212> TYPE: RNA
<213> ORGANISM: Artificial Sequence
<220> FEATURE:
<223> OTHER INFORMATION: Synthetic

<400> SEQUENCE: 18
cuuuagaccu acuaaaau 18

<210> SEQ ID NO 19
<211> LENGTH: 19
<212> TYPE: RNA
<213> ORGANISM: Artificial Sequence
<220> FEATURE:
<223> OTHER INFORMATION: Synthetic

<400> SEQUENCE: 19
guuuuaguac cuagagaaa 19

<210> SEQ ID NO 20
<211> LENGTH: 21
<212> TYPE: RNA
<213> ORGANISM: Artificial Sequence
<220> FEATURE:
<223> OTHER INFORMATION: Synthetic

<400> SEQUENCE: 20
uuucuuuaga ccuacuaaaa u 21

<210> SEQ ID NO 21
<211> LENGTH: 46
<212> TYPE: RNA
<213> ORGANISM: Artificial Sequence
<220> FEATURE:
<223> OTHER INFORMATION: Synthetic

<400> SEQUENCE: 21
aaggcuuuau gccgagauua aaggaugccg acgggcaucc uuuuuu 46

<210> SEQ ID NO 22
<211> LENGTH: 11
<212> TYPE: RNA
<213> ORGANISM: Artificial Sequence
<220> FEATURE:
<223> OTHER INFORMATION: Synthetic

<400> SEQUENCE: 22
ggcuuuaugc c 11

<210> SEQ ID NO 23
<211> LENGTH: 23
<212> TYPE: RNA
<213> ORGANISM: Artificial Sequence
<220> FEATURE:
<223> OTHER INFORMATION: Synthetic

<400> SEQUENCE: 23
aaggaugccg acgggcaucc uuu 23

<210> SEQ ID NO 24
<211> LENGTH: 84

<212> TYPE: RNA
<213> ORGANISM: Artificial Sequence
<220> FEATURE:
<223> OTHER INFORMATION: Synthetic

<400> SEQUENCE: 24
guuuuaguac cuagaggaaa cuuuagaccu acuaaaauaa ggcuuuaugc cgagauuaaa 60
ggaugccgac gggcauccuu uuuu 84

<210> SEQ ID NO 25
<211> LENGTH: 90
<212> TYPE: RNA
<213> ORGANISM: Artificial Sequence
<220> FEATURE:
<223> OTHER INFORMATION: Synthetic

<400> SEQUENCE: 25
guuuuaguac cuagagaaag aaauuucuuu agaccuacua aaauaaggcu uuaugccgag 60
auuaaaggau gccgacgggc auccuuuuuu 90

<210> SEQ ID NO 26
<211> LENGTH: 90
<212> TYPE: RNA
<213> ORGANISM: Artificial Sequence
<220> FEATURE:
<223> OTHER INFORMATION: Synthetic

<400> SEQUENCE: 26
guuuaaguac cuagagaaag aaauuucuuu agaccuacuu aaauaaggcu uuaugccgag 60
auuaaaggau gccgacgggc auccuuuuuu 90

<210> SEQ ID NO 27
<211> LENGTH: 16
<212> TYPE: RNA
<213> ORGANISM: Artificial Sequence
<220> FEATURE:
<223> OTHER INFORMATION: Synthetic

<400> SEQUENCE: 27
guuuuguuac cauaug 16

<210> SEQ ID NO 28
<211> LENGTH: 18
<212> TYPE: RNA
<213> ORGANISM: Artificial Sequence
<220> FEATURE:
<223> OTHER INFORMATION: Synthetic

<400> SEQUENCE: 28
uauaugaccu aacaaaac 18

<210> SEQ ID NO 29
<211> LENGTH: 19
<212> TYPE: RNA
<213> ORGANISM: Artificial Sequence
<220> FEATURE:
<223> OTHER INFORMATION: Synthetic

<400> SEQUENCE: 29
guuuuguuac cauaugauu 19

<210> SEQ ID NO 30
<211> LENGTH: 21
<212> TYPE: RNA

<213> ORGANISM: Artificial Sequence
<220> FEATURE:
<223> OTHER INFORMATION: Synthetic

<400> SEQUENCE: 30
auuuauauga ccuaacaaaa c 21

<210> SEQ ID NO 31
<211> LENGTH: 38
<212> TYPE: RNA
<213> ORGANISM: Artificial Sequence
<220> FEATURE:
<223> OTHER INFORMATION: Synthetic

<400> SEQUENCE: 31
aaggguuuau cccggacucg gcucuucgga gccuuuuu 38

<210> SEQ ID NO 32
<211> LENGTH: 11
<212> TYPE: RNA
<213> ORGANISM: Artificial Sequence
<220> FEATURE:
<223> OTHER INFORMATION: Synthetic

<400> SEQUENCE: 32
ggguuuaucc c 11

<210> SEQ ID NO 33
<211> LENGTH: 14
<212> TYPE: RNA
<213> ORGANISM: Artificial Sequence
<220> FEATURE:
<223> OTHER INFORMATION: Synthetic

<400> SEQUENCE: 33
ggcucuucgg agcc 14

<210> SEQ ID NO 34
<211> LENGTH: 76
<212> TYPE: RNA
<213> ORGANISM: Artificial Sequence
<220> FEATURE:
<223> OTHER INFORMATION: Synthetic

<400> SEQUENCE: 34
guuuuguuac cauauggaaa uauaugaccu aacaaaacaa ggguuuaucc cggacucggc 60
ucuucggagc cuuuuu 76

<210> SEQ ID NO 35
<211> LENGTH: 82
<212> TYPE: RNA
<213> ORGANISM: Artificial Sequence
<220> FEATURE:
<223> OTHER INFORMATION: Synthetic

<400> SEQUENCE: 35
guuuuguuac cauaugauug aaaauuuaua ugaccuaaca aaacaagggu uuaucccgga 60
cucggcucuu cggagccuuu uu 82

<210> SEQ ID NO 36
<211> LENGTH: 82
<212> TYPE: RNA
<213> ORGANISM: Artificial Sequence
<220> FEATURE:
<223> OTHER INFORMATION: Synthetic

<400> SEQUENCE: 36
guuuaguuac cauaugauug aaaauuuaua ugaccuaacu aaacaagggu uuaucccgga 60
cucggcucuu cggagccuuu uu 82

<210> SEQ ID NO 37
<211> LENGTH: 14
<212> TYPE: RNA
<213> ORGANISM: Artificial Sequence
<220> FEATURE:
<223> OTHER INFORMATION: Synthetic

<400> SEQUENCE: 37
guuugagagu uaug 14

<210> SEQ ID NO 38
<211> LENGTH: 16
<212> TYPE: RNA
<213> ORGANISM: Artificial Sequence
<220> FEATURE:
<223> OTHER INFORMATION: Synthetic

<400> SEQUENCE: 38
caugacgagu ucaaau 16

<210> SEQ ID NO 39
<211> LENGTH: 17
<212> TYPE: RNA
<213> ORGANISM: Artificial Sequence
<220> FEATURE:
<223> OTHER INFORMATION: Synthetic

<400> SEQUENCE: 39
guuugagagu uauguaa 17

<210> SEQ ID NO 40
<211> LENGTH: 19
<212> TYPE: RNA
<213> ORGANISM: Artificial Sequence
<220> FEATURE:
<223> OTHER INFORMATION: Synthetic

<400> SEQUENCE: 40
uuacaugacg aguucaaau 19

<210> SEQ ID NO 41
<211> LENGTH: 72
<212> TYPE: RNA
<213> ORGANISM: Artificial Sequence
<220> FEATURE:
<223> OTHER INFORMATION: Synthetic

<400> SEQUENCE: 41
aaaaauuuau ucaaaccgcc uauuuauagg ccgcagaugu ucugcauuau gcuugcuauu 60
gcaagcuuuu uu 72

<210> SEQ ID NO 42
<211> LENGTH: 14
<212> TYPE: RNA
<213> ORGANISM: Artificial Sequence
<220> FEATURE:
<223> OTHER INFORMATION: Synthetic

<400> SEQUENCE: 42

-continued gccuauuuau aggc 14

<210> SEQ ID NO 43
<211> LENGTH: 34
<212> TYPE: RNA
<213> ORGANISM: Artificial Sequence
<220> FEATURE:
<223> OTHER INFORMATION: Synthetic

<400> SEQUENCE: 43
gcagauguuc ugcauuaugc uugcuauugc aagc 34

<210> SEQ ID NO 44
<211> LENGTH: 106
<212> TYPE: RNA
<213> ORGANISM: Artificial Sequence
<220> FEATURE:
<223> OTHER INFORMATION: Synthetic

<400> SEQUENCE: 44
guuugagagu uauggaaaca ugacgaguuc aaauaaaaau uuauucaaac cgccuauuua 60
uaggccgcag auguucugca uuaugcuugc uauugcaagc uuuuuu 106

<210> SEQ ID NO 45
<211> LENGTH: 112
<212> TYPE: RNA
<213> ORGANISM: Artificial Sequence
<220> FEATURE:
<223> OTHER INFORMATION: Synthetic

<400> SEQUENCE: 45
guuugagagu uauguaagaa auuacaugac gaguucaaau aaaaauuuau ucaaaccgcc 60
uauuuauagg ccgcagaugu ucugcauuau gcuugcuauu gcaagcuuuu uu 112

<210> SEQ ID NO 46
<211> LENGTH: 14
<212> TYPE: RNA
<213> ORGANISM: Artificial Sequence
<220> FEATURE:
<223> OTHER INFORMATION: Synthetic

<400> SEQUENCE: 46
guuugagaac caug 14

<210> SEQ ID NO 47
<211> LENGTH: 16
<212> TYPE: RNA
<213> ORGANISM: Artificial Sequence
<220> FEATURE:
<223> OTHER INFORMATION: Synthetic

<400> SEQUENCE: 47
cauggugagu gcaaau 16

<210> SEQ ID NO 48
<211> LENGTH: 17
<212> TYPE: RNA
<213> ORGANISM: Artificial Sequence
<220> FEATURE:
<223> OTHER INFORMATION: Synthetic

<400> SEQUENCE: 48
guuugagaac cauguaa 17

-continued

<210> SEQ ID NO 49
<211> LENGTH: 19
<212> TYPE: RNA
<213> ORGANISM: Artificial Sequence
<220> FEATURE:
<223> OTHER INFORMATION: Synthetic

<400> SEQUENCE: 49
uuacauggug agugcaaau 19

<210> SEQ ID NO 50
<211> LENGTH: 64
<212> TYPE: RNA
<213> ORGANISM: Artificial Sequence
<220> FEATURE:
<223> OTHER INFORMATION: Synthetic

<400> SEQUENCE: 50
aaggauuauc cgaaauugua ugcccgcauu gugcggcaau aaaaaggcuc gaaagagucu 60
uuuu 64

<210> SEQ ID NO 51
<211> LENGTH: 64
<212> TYPE: RNA
<213> ORGANISM: Artificial Sequence
<220> FEATURE:
<223> OTHER INFORMATION: Synthetic

<400> SEQUENCE: 51
aaggauuauc cgaaauugua ugcccgcauu gugcggcaau aaaaaggcuc gaaagagucu 60
uuuu 64

<210> SEQ ID NO 52
<211> LENGTH: 46
<212> TYPE: RNA
<213> ORGANISM: Artificial Sequence
<220> FEATURE:
<223> OTHER INFORMATION: Synthetic

<400> SEQUENCE: 52
uguaugcccg cauugugcgg caauaaaaag gcucgaaaga gucuuu 46

<210> SEQ ID NO 53
<211> LENGTH: 98
<212> TYPE: RNA
<213> ORGANISM: Artificial Sequence
<220> FEATURE:
<223> OTHER INFORMATION: Synthetic

<400> SEQUENCE: 53
guuugagaac cauggaaaca uggugagugc aaauaaggau uauccgaaau uguaugcccg 60
cauugugcgg caauaaaaag gcucgaaaga gucuuuuu 98

<210> SEQ ID NO 54
<211> LENGTH: 104
<212> TYPE: RNA
<213> ORGANISM: Artificial Sequence
<220> FEATURE:
<223> OTHER INFORMATION: Synthetic

<400> SEQUENCE: 54
guuugagaac cauguaagaa auuacauggu gagugcaaau aaggauuauc cgaaauugua 60
ugcccgcauu gugcggcaau aaaaaggcuc gaaagagucu uuuu 104

<210> SEQ ID NO 55
<211> LENGTH: 22
<212> TYPE: DNA
<213> ORGANISM: Artificial Sequence
<220> FEATURE:
<223> OTHER INFORMATION: Synthetic

<400> SEQUENCE: 55
ggtgcggttc accagggtgt cg 22

<210> SEQ ID NO 56
<211> LENGTH: 22
<212> TYPE: DNA
<213> ORGANISM: Artificial Sequence
<220> FEATURE:
<223> OTHER INFORMATION: Synthetic

<400> SEQUENCE: 56
ggaagagcag agccttggtc tc 22

<210> SEQ ID NO 57
<211> LENGTH: 6670
<212> TYPE: DNA
<213> ORGANISM: Artificial Sequence
<220> FEATURE:
<223> OTHER INFORMATION: Synthetic

<400> SEQUENCE: 57
gttgtgccac gcggttggga atgtaattca gctccgccat cgccgcttcc actttttccc 60
gcgttttcgc agaaacgtgg ctggcctggt tcaccacgcg ggaaacggtc tgataagaga 120
caccggcata ctctgcgaca tcgtataacg ttactggttt cacattcacc accctgaatt 180
gactctcttc cgggcgctat catgccatac cgcgaaaggt tttgcgccat tcgatggtgt 240
cgggatctcg acgctaaatt aatacgactc actatagggg aattgtgagc ggataacaat 300
tcccctgtag aaataatttt gtttaactaa agaggagaaa tttcatatgt acccatacga 360
tgtgccagat tacgctggca ccgagctcgg taccggctat acaattggcc tggatctggg 420
cgttgcctct cttggctggg ccgtcgtgaa tgatgagtac gaggtgctgg aaagctgcag 480
caacatcttt cctgccgccg agagcgccaa caacgtggaa agaagaggct tccggcaagg 540
cagacggctg agcagaagaa gaaggacccg gatcagcgac ttcagaaagc tgtgggagaa 600
gtccggcttc gaggtgccca gcaatgagct gaatgaggtg ctgcagtacc ggatcaaggg 660
catgaacgac aagctgagcg aggacgagct gtaccacgtg ctgctgaaca gcctgaagca 720
cagaggcatc agctacctgg acgacgccga tgatgagaac gcctctggcg attatgccgc 780
ctctatcgcc tacaacgaga accagctgaa aacaaagctg ccctgcgaga tccagtggga 840
gagatacaag aagtacggcg cctaccgggg caacatcaca atccaagaag gcggcgagcc 900
cctgacactg agaaatgtgt ttaccaccag cgcctacgag aaagagatcc agaaactgct 960
ggacgtgcag agcatgagca acgagaaagt gaccaagaag ttcatcgacg agtacctcaa 1020
gatcttcagc cggaagagag agtactacat cggccctggc aacaagaagt ccagaaccga 1080
ctacggcgtg tacaccacac agaagaacga ggacggcacc taccacaccg agcagaacct 1140
gttcgataag ctgatcggca agtgcagcgt gtaccctgat gagcgtagag ccgctggcgc 1200
cacatacaca gcccaagagt tcaacctgct gaacgatctg aacaacctgg tcatcgacgg 1260
ccggaagctg gacgagcaag agaagtgtca gatcgtggat gccgtgaagc acgccaagac 1320
cgtgaacatg aagaacatca ttgccaaagt gatcggcacc aaggccaaca gcatgaacat 1380

-continued

```
gaccggcgcc agaatcgaca agaatgagaa agaaatcttc cacagcttcg aggcctacaa   1440
caagctgcgg aaggccctgg aagagatcga cttcgacatc gagacactga gcaccgacga   1500
gctggatgcc attggagagg tgctgaccct gaacaccgac cggaagtcta tccagaacgg   1560
cctgcaagag aaacggatcg tggtgcccga tgaagtgcgg gatgtgctga tcgccaccag   1620
aaagagaaat ggcagcctgt tctccaagtg gcagagcttc ggcatccgga tcatgaagga   1680
actgatccca gagctgtacg cccagcctaa gaaccagatg cagctgctga ccgacatggg   1740
cgtgttcaag accaaggacg agagattcgt ggaatacgac aagatcccca gcgacctgat   1800
caccgaagag atctacaacc ccgtggtggc caagacagtg cggatcaccg ttagagtgct   1860
gaacgccctg atcaagaagt atggctaccc cgaccgggtc gtgatcgaga tgcccagaga   1920
taagaactcc gaggaagaga agaagcggat cgccgacttc cagaagaaca acgaaaacga   1980
gcttggcggc atcatcaaga aagtgaagtc cgagtacggc atcgagatca ccgacgccga   2040
ctttaagaac cacagcaagc tgggcctgaa gctgagactg tggaacgagc agaatgagac   2100
atgcccctac agcggcaagc acatcaagat cgacgacctg ctcaacaacc ccaacatgtt   2160
cgaggtggac cacatcatcc ctctgagcat cagcttcgac gacagcagag ccaacaaggt   2220
gctggtgtac gccgccgaaa accagaacaa gggcaacaga acccctatgg cctacctgag   2280
caacgtgaac agagagtggg acttccacga gtacatgagc ttcgtgctga gcaactacaa   2340
gggcaccatc tacggcaaga agcgggacaa tctgctgttc tccgaggaca tctacaagat   2400
cgatgtgctg cagggcttca tctcccggaa catcaacgac accagatacg cctctaaagt   2460
gatcctgaac tccctgcaga gctttttcgg cagcaaagaa tgcgacacca aagtgaaggt   2520
cgtgcggggc accttcacac accagatgcg gatgaacctg aagatcgaga agaaccggga   2580
agagtcctac gtgcaccacg ccgtggatgc tatgctgatt gccttcagcc agatgggcta   2640
cgacgcctac cacaaactga ccgagaagta tatcgactac gagcacggcg agttcgtgga   2700
ccagaaggga tacgagaagc tgattgagaa cgacgtggcc tacagagaga caacctatca   2760
gaacaagtgg atgaccatca agaagaatat cgagatcgcc gctgagaaaa acaagtactg   2820
gtatcaagtg aatcggaagt ccaaccgggg cctgtgcaac cagaccatct atggcaccag   2880
aaacctggac ggcaaaaccg tgaagatctc caagctggac atccggaccg acgacggcat   2940
caaaaagttt aagggcatcg tggaaaaggg caagctggaa cggttcctga tgtaccggaa   3000
cgaccccaag accttcgagt ggctgctgca gatctataag gactacagcg acagcaagaa   3060
ccccttcgtg cagtacgagt ctgagacagg cgacgtgatc aaaaaggtgt ccaagacaaa   3120
caacggcccc aaagtgtgcg agctgagata cgaggatggc gaagtgggct cctgcatcga   3180
catcagccac aaatacggct acaagaaggg cagcaagaaa gtcatcctgg attctctgaa   3240
cccctaccgg atggacgtgt actacaacac caaggacaac cggtactact tcgtgggcgt   3300
gaagtactcc gacatcaagt gccagggcga cagctacgtg atcgacgagg ataagtatgc   3360
cgccgctctg gtgcaagaaa agatcgtgcc agaaggcaag ggcagatccg atctgaccga   3420
gctgggctat gagttcaagc tgtccttcta caagaacgag atcatcgagt acgagaagga   3480
cggggagatc tacgtcgagc ggttcctgtc cagaacaatg cctaaagtgt ccaactatat   3540
cgagacaaag cccctggaag ccgccaagtt cgagaagaga aacctcgtgg gcctcgccaa   3600
gacaagccgg atcagaaaga tcagagtgga catcctgggg aaccgctacc tgaacagcat   3660
ggaaaacttc gacttcgtcg tgggccacaa gggatcctaa gcggccgcct agcataaccc   3720
```

-continued

```
cttggggcct ctaaacgggt cttgaggggt tttttgacct aggctagggg atatattccg   3780
cttcctcgct cactgactcg ctacgctcgg tcgttcgact gcggcgagcg gaaatggctt   3840
acgaacgggg cggagatttc ctggaagatg ccaggaagat acttaacagg gaagtgagag   3900
ggccgcggca aagccgtttt tccataggct ccgcccccct gacaagcatc acgaaatctg   3960
acgctcaaat cagtggtggc gaaacccgac aggactataa agataccagg cgtttccccc   4020
tggcggctcc ctcgtgcgct ctcctgttcc tgcctttcgg tttaccggtg tcattccgct   4080
gttatggccg cgtttgtctc attccacgcc tgacactcag ttccgggtag gcagttcgct   4140
ccaagctgga ctgtatgcac gaaccccccg ttcagtccga ccgctgcgcc ttatccggta   4200
actatcgtct tgagtccaac ccggaaagac atgcaaaagc accactggca gcagccactg   4260
gtaattgatt tagaggagtt agtcttgaag tcatgcgccg gttaaggcta aactgaaagg   4320
acaagttttg gtgactgcgc tcctccaagc cagttacctc ggttcaaaga gttggtagct   4380
cagagaacct tcgaaaaacc gccctgcaag gcggtttttt cgttttcaga gcaagagatt   4440
acgcgcagac caaaacgatc tcaagaagat catcttatta atcagataaa atatttctag   4500
atttcagtgc aatttatctc ttcaaatgta gcacctgaag tcagccccat acgatataag   4560
ttgttactag tgcttggatt ctcaccaata aaaaacgccc ggcggcaacc gagcgttctg   4620
aacaaatcca gatggagttc tgaggtcatt actggatcta tcaacaggag tccaagcgag   4680
ctcgtaaact tggtctgaca gttaccaatg cttaatcagt gaggcaccta tctcagcgat   4740
ctgtctattt cgttcatcca tagttgcctg actccccgtc gtgtagataa ctacgatacg   4800
ggagggctta ccatctggcc ccagtgctgc aatgataccg cgggagccac gctcaccggc   4860
tccagattta tcagcaataa accagccagc cggaagggcc gagcgcagaa gtggtcctgc   4920
aactttatcc gcctccatcc agtctattaa ttgttgccgg gaagctagag taagtagttc   4980
gccagttaat agtttgcgca acgttgttgc cattgctaca ggcatcgtgg tgtcacgctc   5040
gtcgtttggt atggcttcat tcagctccgg ttcccaacga tcaaggcgag ttacatgatc   5100
ccccatgttg tgcaaaaaag cggttagctc cttcggtcct ccgatcgttg tcagaagtaa   5160
gttggccgca gtgttatcac tcatggttat ggcagcactg cataattctc ttactgtcat   5220
gccatccgta agatgctttt ctgtgactgg tgagtactca accaagtcat tctgagaata   5280
gtgtatgcgg cgaccgagtt gctcttgccc ggcgtcaata cgggataata ccgcgccaca   5340
tagcagaact ttaaaagtgc tcatcattgg aaaacgttct tcggggcgaa aactctcaag   5400
gatcttaccg ctgttgagat ccagttcgat gtaacccact cgtgcaccca actgatcttc   5460
agcatctttt actttcacca gcgtttctgg gtgagcaaaa acaggaaggc aaaatgccgc   5520
aaaaaaggga ataagggcga cacggaaatg ttgaatactc atactcttcc tttttcaata   5580
ttattgaagc atttatcagg gttattgtct catgagcgga tacatatttg aatgtattta   5640
gaaaaataaa caaatagggg ttccgcgcac atttccccga aaagtgccac ctgacgtcct   5700
cgagtcccgg tgcctaatga gtgagctaac ttacattaat tgcgttgcgc tcactgcccg   5760
ctttccagtc gggaaacctg tcgtgccagc tgcattaatg aatcggccaa cgcgcgggga   5820
gaggcggttt gcgtattggg cgccagggtg gtttttcttt tcaccagtga cacgggcaac   5880
agctgattgc ccttcaccgc ctggccctga gagagttgca gcaagcggtc cacgctggtt   5940
tgccccagca ggcgaaaatc ctgtttgatg gtggttaacg gcgggatata acatgagctg   6000
tcttcggtat cgtcgtatcc cactaccgag atgtccgcac caacgcgcag cccggactcg   6060
gtaatggcgc gcattgcgcc cagcgccatc tgatcgttgg caaccagcat cgcagtggga   6120
```

-continued

```
acgatgccct cattcagcat ttgcatggtt tgttgaaaac cggacatggc actccagtcg   6180

ccttcccgtt ccgctatcgg ctgaatttga ttgcgagtga gatatttatg ccagccagcc   6240

agacgcagac gcgccgagac agaacttaat gggcccgcta acagcgcgat ttgctggtga   6300

cccaatgcga ccagatgctc cacgcccagt cgcgtaccgt cttcatggga gaaaataata   6360

ctgttgatgg gtgtctggtc agagacatca agaaataacg ccggaacatt agtgcaggca   6420

gcttccacag caatggcatc ctggtcatcc agcggatagt taatgatcag cccactgacg   6480

cgttgcgcga gaagattgtg caccgccgct ttacaggctt cgacgccgct tcgttctacc   6540

atcgacacca ccacgctggc acccagttga tcggcgcgag atttaatcgc cgcgacaatt   6600

tgcgacggcg cgtgcagggc cagactggag gtggcaacgc caatcagcaa cgactgtttg   6660

cccgccagtt                                                          6670
```

<210> SEQ ID NO 58
<211> LENGTH: 2567
<212> TYPE: DNA
<213> ORGANISM: Artificial Sequence
<220> FEATURE:
<223> OTHER INFORMATION: Synthetic

<400> SEQUENCE: 58

```
gcataaccaa gcctatgcct acagcatcca gggtgacggt gccgaggatg acgatgagcg     60

cattgttaga tttcatacac ggtgcctgac tgcgttagca atttaactgt gataaactac    120

cgcattaaag cttatcgatg ataagctgtc aacacatttc cccgaaaagt gccacctgac    180

gtcctcgagt cccgcataat cgaaatttga cagctagctc agtcctaggt ataatactag    240

tggaagagca gagccttggt ctcgttttag tacctagaga aagaaatttc tttagaccta    300

ctaaaataag gctttatgcc gagattaaag gatgccgacg ggcatccttt tttgaattct    360

caaataaaac gaaaggctca gtcgaaagac tgggcctttc gttttatctg ttgtttgtcg    420

gtgaacgctc tcctgagtag gacaaatggt accccgcttc ctcgctcact gactcgctac    480

gctcggtcgt tcgactgcgg cgagcggaaa tggcttacga acggggcgga gatttcctgg    540

aagatgccag gaagatactt aacagggaag tgagagggcc gcggcaaagc cgtttttcca    600

taggctccgc ccccctgaca agcatcacga aatctgacgc tcaaatcagt ggtggcgaaa    660

cccgacagga ctataaagat accaggcgtt tccccctggc ggctccctcg tgcgctctcc    720

tgttcctgcc tttcggttta ccggtgtcat tccgctgtta tggccgcgtt tgtctcattc    780

cacgcctgac actcagttcc gggtaggcag ttcgctccaa gctggactgt atgcacgaac    840

cccccgttca gtccgaccgc tgcgccttat ccggtaacta tcgtcttgag tccaacccgg    900

aaagacatgc aaaagcacca ctggcagcag ccactggtaa ttgatttaga ggagttagtc    960

ttgaagtcat gcgccggtta aggctaaact gaaaggacaa gttttggtga ctgcgctcct   1020

ccaagccagt tacctcggtt caaagagttg gtagctcaga gaaccttcga aaaaccgccc   1080

tgcaaggcgg tttttttcgtt ttcagagcaa gagattacgc gcagaccaaa acgatctcaa   1140

gaagatcatc ttattaatca gataaaatat ttctagattt cagtgcaatt tatctcttca   1200

aatgtagcac ctgaagtcag ccccatacga tataagttgt tactagtgct tggattctca   1260

ccaataaaaa acgcccggcg gcaaccgagc gttctgaaca aatccagatg gagttctgag   1320

gtcattactg gatctatcaa caggagtcca agcgagaagg gttggtttgc gcattcacag   1380

ttctccgcaa gaattgattg gctccaattc ttggagtggt gaatccgtta gcgaggtgcc   1440
```

gccggcttcc attcaggtcg aggtggcccg gctccatgca ccgcgacgca acgcggggag 1500
gcagacaagg tatagggcgg cgcctacaat ccatgccaac ccgttccatg tgctcgccga 1560
ggcggcataa atcgccgtga cgatcagcgg tccaatgatc gaagttaggc tggtaagagc 1620
cgcgagcgat ccttgaagct gtccctgatg gtcgtcatct acctgcctgg acagcatggc 1680
ctgcaacgcg ggcatcccga tgccgccgga agcgagaaga atcataatgg ggaaggccat 1740
ccagcctcgc gtcgcgaacg ccagcaagac gtagcccagc gcgtcggccg ccatgccggc 1800
gataatggcc tgcttctcgc cgaaacgttt ggtggcggga ccagtgacga aggcttgagc 1860
gagggcgtgc aagattccga ataccgcaag cgacaggccg atcatcgtcg cgctccagcg 1920
aaagcggtcc tcgccgaaaa tgacccagag cgctgccggc acctgtccta cgagttgcat 1980
gataaagaag acagtcataa gtgcggcgac gatagtcatg ccccgcgccc accggaagga 2040
gctgactggg ttgaaggctc tcaagggcat cggtcgacgc tctcccttat gcgactcctg 2100
cattaggaag cagcccagta gtaggttgag gccgttgagc accgccgccg caaggaatgg 2160
tgcatgcaag gagatggcgc ccaacagtcc cccggccacg gggcctgcca ccatacccac 2220
gccgaaacaa gcgctcatga gcccgaagtg gcgagcccga tcttccccat cggtgatgtc 2280
ggcgatatag gcgccagcaa ccgcacctgt ggcgccggtg atgccggcca cgatgcgtcc 2340
ggcgtagagg atccacagga cgggtgtggt cgccatgatc gcgtagtcga tagtggctcc 2400
aagtagcgaa gcgagcagga ctgggcggcg gccaaagcgg tcggacagtg ctccgagaac 2460
gggtgcgcat agaaattgca tcaacgcata tagcgctagc agcacgccat agtgactggc 2520
gatgctgtcg gaatggacga tatcccgcaa gaggcccggc agtaccg 2567

<210> SEQ ID NO 59
<211> LENGTH: 5009
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3040)..(3047)
<223> OTHER INFORMATION: n is a, c, g, or t

<400> SEQUENCE: 59
tcgagtcttt acactttatg cttccggctc gtatgttgtg tggaattgtg agcggataac 60
aatttcacac atgattacgg attcaacgtc gtgactggta aaacccgggc gttacccaac 120
ttaatcgcct tgcagcacat ccccctttcg ccagcaggcg taataaggaa aggattcatg 180
tactatttga aaaacacaaa cttttggatg ttcggtttat tctttttctt ttactttttt 240
atcatgggag cctacttccc gtttttcccg atttggctac atgatatcaa ccatatcagc 300
aaaagtgata cgggtattat ttttgccgct atttctctgt tctcgctatt attccaaccg 360
ctgtttggtc tgctttctga caaactcggt ctacgcaaat acctgctgtg gattattacc 420
ggcatgttag tgatgtttgc gccgttcttt atttttatct tcgggccact gctgcagtac 480
aacattttag tagggtcgat tgttggtggt atttatctag gctttagttt taacgccggt 540
gcgccagcag tagaggcatt tattgagaaa gtcagccggc gcagtaattt cgaatttggt 600
cgcgcgcgga tgtttggcag tgttggctgg gcgctggttg cctcgattgt cgggatcatg 660
ttcaccatta ataatcagtt tgttttctgg ctgggctctg gcagttgtct catcctcgcc 720
gttttactct ttttcgccaa aacggacgcg ccctcaagtg ccacggttgc caatgcggta 780
ggtgccaacc attcggcatt tagccttaag ctggcactgg aactgttcag acagccaaaa 840
ctgtggtttt tgtcactgta tgttattggc gtttcctcca cctacgatgt tttgaccaa 900 cagtttgcta atttctttac ttcgttcttt gctaccggtg aacagggtac ccgcgtattt 960
ggctacgtaa cgacaatggg cgaattactt aacgcctcga ttatgttctt tgcgccactg 1020
atcattaatc gcatcggtgg gaagaatgcc ctgctgctgg ctggcactat tatgtctgta 1080
cgtattattg gctcatcgtt cgccacctca gcgctggaag tggttattct gaaaacgctg 1140
catatgtttg aagtaccgtt cctgctggtg ggctccttta aatatattac tagtcagttt 1200
gaagtgcgtt tttcagcgac gatttatctg gtcagtttca gcttctttaa gcaactggcg 1260 atgatttta tgtctgtact ggcgggcaat atgtatgaaa gcataggttt ccaaggcgct 1320
tatctggtgc tgggtctggt ggcgctgggc ttcaccttaa tttccgtgtt cacgcttagc 1380
ggcccgggcc cgctttccct gctgcgtcgt caggtgaatg aagtcgctta aaggcctcga 1440
tgcagctagc atgctaatct gattcgttac caattatgac aacttgacgg ctacatcatt 1500
cactttttct tcacaaccgg cacggaactc gctcgggctg gccccggtgc attttttaaa 1560
tacccgcgag aaatagagtt gatcgtcaaa accaacattg cgaccgacgg tggcgatagg 1620
catccgggtg gtgctcaaaa gcagcttcgc ctggctgata cgttggtcct cgcgccagct 1680
taagacgcta atccctaact gctggcggaa aagatgtgac agacgcgacg gcgacaagca 1740
aacatgctgt gcgacgctgg cgatatcaaa attgctgtct gccaggtgat cgctgatgta 1800
ctgacaagcc tcgcgtaccc gattatccat cggtggatgg agcgactcgt taatcgcttc 1860
catgcgccgc agtaacaatt gctcaagcag atttatcgcc agcagctccg aatagcgccc 1920
ttccccttgc ccggcgttaa tgatttgccc aaacaggtcg ctgaaatgcg gctggtgcgc 1980
ttcatccggg cgaaagaacc ccgtattggc aaatattgac ggccagttaa gccattcatg 2040
ccagtaggcg cgcggacgaa agtaaaccca ctggtgatac cattcgcgag cctccggatg 2100
acgaccgtag tgatgaatct ctcctggcgg gaacagcaaa atatcacccg gtcggcaaac 2160
aaattctcgt ccctgatttt tcaccacccc ctgaccgcga atggtgagat tgagaatata 2220
acctttcatt cccagcggtc ggtcgataaa aaaatcgaga taaccgttgg cctcaatcgg 2280
cgttaaaccc gccaccagat gggcattaaa cgagtatccc ggcagcaggg gatcattttg 2340
cgcttcagcc atacttttca tactcccgcc attcagagaa gaaaccaatt gtccatattg 2400
catcagacat tgccgtcact gcgtctttta ctggctcttc tcgctaacca aaccggtaac 2460
cccgcttatt aaaagcattc tgtaacaaag cgggaccaaa gccatgacaa aaacgcgtaa 2520
caaaagtgtc tataatcacg gcagaaaagt ccacattgat tatttgcacg gcgtcacact 2580
ttgctatgcc atagcatttt tatccataag attagcggat cctacctgac gctttttatc 2640
gcaactctct actgtttctc catacccgtt tttttggggt agcgattgaa aacgatgcag 2700
tttaaggttt acacctataa aagagagagc cgttatcgtc tgtttgtgga tgtacagagt 2760
gatattattg acacgcccgg gcgacggatg gtgatccccc tggccagtgc acgtctgctg 2820
tcagataaag tctcccgtga actttacccg gtggtgcata tcggggatga aagctggcgc 2880
atgatgacca ccgatatggc cagtgtgccg gtctccgtta tcggggaaga agtggctgat 2940
ctcagccacc gcgaaaatga catcaaaaac gccattaacc tgatgttttg gggaatataa 3000
tcttctagac atacaatgga agagcagagc cttggtctcn nnnnnnnaag cttgatatcg 3060
aattcctgca gcccggggga tcccatggta cgcgtgctag aggcatcaaa taaaacgaaa 3120
ggctcagtcg aaagactggg cctttcgttt tatctgttgt ttgtcggtga acgctctcct 3180

```
gagtaggaca aatccgccgc cctagaccta ggcgttcggc tgcggcgagc ggtatcagct   3240
cactcaaagg cggtaatacg gttatccaca gaatcagggg ataacgcagg aaagaacatg   3300
tgagcaaaag gccagcaaaa ggccaggaac cgtaaaaagg ccgcgttgct ggcgtttttc   3360
cataggctcc gcccccctga cgagcatcac aaaaatcgac gctcaagtca gaggtggcga   3420
aacccgacag gactataaag ataccaggcg tttccccctg gaagctccct cgtgcgctct   3480
cctgttccga ccctgccgct taccggatac ctgtccgcct ttctcccttc gggaagcgtg   3540
gcgctttctc aatgctcacg ctgtaggtat ctcagttcgg tgtaggtcgt tcgctccaag   3600
ctgggctgtg tgcacgaacc ccccgttcag cccgaccgct gcgccttatc cggtaactat   3660
cgtcttgagt ccaacccggt aagacacgac ttatcgccac tggcagcagc cactggtaac   3720
aggattagca gagcgaggta tgtaggcggt gctacagagt tcttgaagtg gtggcctaac   3780
tacggctaca ctagaaggac agtatttggt atctgcgctc tgctgaagcc agttaccttc   3840
ggaaaaagag ttggtagctc ttgatccggc aaacaaacca ccgctggtag cggtggtttt   3900
tttgtttgca agcagcagat tacgcgcaga aaaaaaggat ctcaagaaga tcctttgatc   3960
ttttctacgg ggtctgacgc tcagtggaac gaaaactcac gttaagggat tttggtcatg   4020
actagtgctt ggattctcac caataaaaaa cgcccggcgg caaccgagcg ttctgaacaa   4080
atccagatgg agttctgagg tcattactgg atctatcaac aggagtccaa gcgagctcga   4140
tatcaaatta cgccccgccc tgccactcat cgcagtactg ttgtaattca ttaagcattc   4200
tgccgacatg gaagccatca cagacggcat gatgaacctg aatcgccagc ggcatcagca   4260
ccttgtcgcc ttgcgtataa tatttgccca tggtgaaaac gggggcgaag aagttgtcca   4320
tattggccac gtttaaatca aaactggtga aactcaccca gggattggct gagacgaaaa   4380
acatattctc aataaaccct ttagggaaat aggccaggtt ttcaccgtaa cacgccacat   4440
cttgcgaata tatgtgtaga aactgccgga aatcgtcgtg gtattcactc cagagcgatg   4500
aaaacgtttc agtttgctca tggaaaacgg tgtaacaagg gtgaacacta tcccatatca   4560
ccagctcacc gtctttcatt gccatacgga attccggatg agcattcatc aggcgggcaa   4620
gaatgtgaat aaaggccgga taaaacttgt gcttattttt ctttacggtc tttaaaaagg   4680
ccgtaatatc cagctgaacg gtctggttat aggtacattg agcaactgac tgaaatgcct   4740
caaaatgttc tttacgatgc cattgggata tatcaacggt ggtatatcca gtgatttttt   4800
tctccatttt agcttcctta gctcctgaaa atctcgataa ctcaaaaaat acgcccggta   4860
gtgatcttat ttcattatgg tgaaagttgg aacctcttac gtgccgatca acgtctcatt   4920
ttcgccagat atcgacgtct aagaaaccat tattatcatg acattaacct ataaaaatag   4980
gcgtatcacg aggccctttc gtcttcacc                                      5009
```

<210> SEQ ID NO 60
<211> LENGTH: 6439
<212> TYPE: DNA
<213> ORGANISM: Artificial Sequence
<220> FEATURE:
<223> OTHER INFORMATION: Synthetic

<400> SEQUENCE: 60

```
taatacgact cactataggg agaccacaac ggtttccctc tagagagaca ataaccctga     60
taatgcttca ataatattga aaaaggaaga gtatgcctaa gaagaagaga aaggtgggta    120
ccaccaaggt gaaggactac tacataggct tggacatcgg cacctctagc gtcgggtggg    180
ccgtcaccga tgaagcctat aacgtgctta agtttaatag caagaaaatg tggggcgtgc    240
```

```
ggctgttcga cgacgctaag acggcagagg agcgtagggg ccagcgagga gcaagacgac    300
gtctggatcg gaagaaggag agactcagcc tgctgcagga cttcttcgcc gaagaggtag    360
caaaggtcga ccccaacttc ttcctcaggc tggacaattc cgatctgtac atggaagata    420
aggaccagaa actgaaaagc aaatatacac tgttcaacga caaggacttc aaggataaga    480
attttcataa gaagtacccc acaatacatc acctgctgat ggatctgatc gaggacgaca    540
gtaagaagga catccggctc gtctacctgg cctgtcacta tttgctcaag aacaggggtc    600
atttcatctt cgagggccag aagttcgaca ctaaatcaag cttcgagaac agtttgaacg    660
agctcaaagt tcatttgaac gacgagtatg gactggacct cgaatttgac aacgagaacc    720
tgattaacat cttgactgac ccaaaactca ataaaacggc caagaagaag gagctgaagt    780
ccgtaatcgg cgacaccaag ttcctcaaag ccgtttccgc gataatgatc ggctctagcc    840
agaaactcgt cgacttgttc gagaaccccg aggatttcga cgactctgcg ataaagtccg    900
ttgacttctc aactacctct ttcgacgaca agtactctga ctatgaactc gctctgggtg    960
acaagatcgc tctggtcaac atccttaagg aaatttacga tagctccatc ctcgagaacc   1020
tgctcaaaga ggcagacaag tctaaggacg gtaacaaata tatcagtaat gcattcgtga   1080
agaagtacaa taaacacgga caagatctga aagagttcaa acgtctggta cgacaatatc   1140
acaagagtgc gtattttgat attttcagat ccgagaaggt gaatgacaat tacgtcagct   1200
acactaaaag ctcaattagc aacaataaac gcgtcaaagc aaacaagttc actgatcaag   1260
aggccttcta caaattcgcc aagaaacatc tggagacaat caagtataag atcaacaagg   1320
taaacggctc caaggcagat ctggagctga ttgacgggat gctgcgggac atggagttca   1380
agaactttat gcccaaaatt aagtccagtg acaacggggt gattccatac cagctcaagc   1440
tgatggaatt gaacaaaata ctcgagaatc agtcaaagca tcacgagttc ctcaatgtca   1500
gcgacgagta cggctccgtg tgtgataaaa tcgcatctat catggagttc cgtatcccct   1560
actacgtggg acccctgaac cccaatagca agtacgcctg gatcaagaag cagaaagata   1620
gtgagattac tccctggaac ttcaaggacg tcgtggacct cgactccagc agagaggagt   1680
tcattgactc actgatcgga cgctgtactt accttaagga cgagaaggtc cttcccaaag   1740
cttctttgct gtataacgaa tacatggtgc tgaacgagct gaataacctg aagttgaacg   1800
accttcccat caccgaggag atgaagaaga agatatttga ccagttgttc aaaacaagaa   1860
agaaggtcac ccttaaagcg gtggcaaacc tgctgaagaa ggagttcaac atcaacggcg   1920
agattctgct ctctgggacc gacggtgact tcaagcaggg cttgaactca tacaatgact   1980
tcaaagctat cgtgggcgat aaagtcgatt ccgatgatta ccgggacaag attgaggaga   2040
tcattaaact gatagttctt tacggtgacg ataagagtta ccttcagaag aagattaaag   2100
ctgggtatgg aaaatacttc accgacagtg agattaagaa aatggcgggg ctgaactaca   2160
aggattgggg aaggctctca aagaagctgc tgacgggact cgagggtgca aacaagatca   2220
ctggagagcg gggctccatt attcacttca tgagggaata taaccttaat ctgatggagc   2280
ttatgtcagc ttcatttacg ttcaccgaag agatacagaa acttaacccc gtggatgacc   2340
gcaagctgtc atacgaaatg gtggacgaac tgtacctttc tcccagtgtg aaacggatgc   2400
tctggcagtc cctgcgcatc gtcgacgaga taaagaacat catgggaacc gacagtaaga   2460
agattttcat cgagatggct cggggtaagg aagaggtgaa agcccgcaag gagtcaagga   2520
agaaccaact gctgaagttc tataaagacg gaaagaaggc attcatcagc gagattggcg   2580
```

-continued

```
aggagaggta ctcttacttg ctttctgaga tagagggtga ggaagagaat aagtttcgat   2640
gggataacct gtacctttat tatactcaac tgggtcgctg catgtactct ttggaaccta   2700
tcgacatatc tgagctgtct tcaaagaata tttacgatca ggatcatatc taccccaaaa   2760
gcaagattta cgacgacagt atcgagaata gggtgctggt gaagaaggac cttaactcca   2820
agaagggtaa cagctatcct atcccagacg aaatcctgaa caagaactgt tacgcctact   2880
ggaagatcct gtacgataaa ggtcttatcg ggcagaagaa gtacactcgg ctgacccgga   2940
gaactggctt cacggacgac gagctcgttc agttcatctc aagacagatc gtggaaacta   3000
gacaagcaac aaaggagact gctaacctgc tcaagacaat atgtaagaac tccgagatcg   3060
tgtattccaa agccgagaac gcaagtcggt ttaggcaaga gttcgacatc gtgaagtgta   3120
gggcggtgaa cgatcttcat catatgcacg atgcctacat caacatcata gtggggaacg   3180
tgtataacac caagttcacg aaggacccta tgaatttcgt aaagaagcag gaaaaggcgc   3240
ggagctacaa tctcgagaat atgttcaagt acgatgtgaa acgtggcgga tacaccgctt   3300
ggatcgccga tgacgagaag ggcaccgtga agaacgcgag tattaaacgt atccggaagg   3360
agctggaagg cacaaattat aggttcacaa gaatgaacta cattgagtct ggagcgcttt   3420
tcaacgccac tctccagcgg aagaataagg gctccagacc cctgaaggac aaaggcccga   3480
aatcttccat cgagaagtac ggcggctaca caaacatcaa taaagcctgt ttcgctgttc   3540
ttgacatcaa gtctaagaac aagattgaga ggaagctgat gcccgtcgag cgtgagatct   3600
atgccaaaca gaagaacgac aagaagctgt ccgacgagat tttctcaaag tacctcaagg   3660
accgatttgg catcgaggac tacagggttg tctacccagt ggtgaaaatg cgcacactgc   3720
tcaagatcga cggcagctac tacttcatca caggcggttc tgataagacc ctggagttgc   3780
gatctgctct gcagctgatt ctccctaaga agaacgagtg ggcgatcaaa cagatcgaca   3840
agtcttccga aaacgactat ctgacgatcg agcgtatcca ggacctgacc gaggagctgg   3900
tgtataacac tttcgacatc atcgtcaaca agttcaagac cagtgtcttc aagaagtctt   3960
tccttaactt gtttcaggac gacaagattg agaacattga cttcaagttt aagtccatgg   4020
acttcaagga gaaatgcaag acacttctca tgctggtcaa ggcgattcgg gcatccggcg   4080
tgaggcagga tctcaagtcc atcgacctca agtctgatta cggacggctc agttcaaaga   4140
ccaacaacat cggcaattac caggagttca agattattaa tcagtccatc actggactgt   4200
tcgagaatga ggtcgatctc ctgaagctgg gatcctaccc atacgatgtt ccagattacg   4260
cggccgctcc aaaaaagaaa agaaaagttg cggctagcca tcatcaccat caccatcatc   4320
attaaggctg ctaacaaagc ccgaaaggaa gctgagttgg ctgctgccac cgctgagcaa   4380
taactagcat aaccccttgg ggcctctaaa cgggtcttga ggggtttttt gctgaaagga   4440
ggaactatat ccggatatcc acaggacggg tgtggtcgcc atgatcgcgt agtcgatagt   4500
ggctccaagt agcgaagcga gcaggactgg gcggcggcca aagcggtcgg acagtgctcc   4560
gagaacgggt gcgcatagaa attgcatcaa cgcatatagc gctagcagca cgccatagtg   4620
actggcgatg ctgtcggaat ggacgatatc ccgcaagagg cccggcagta ccggcataac   4680
caagcctatg cctacagcat ccagggtgac ggtgccgagg atgacgatga gcgcattgtt   4740
agatttcata cacggtgcct gactgcgtta gcaatttaac tgtgataaac taccgcatta   4800
aagcttatcg atgataagct gtcaaacatg agaattctta gaaaaactca tcgagcatca   4860
aatgaaactg caatttattc atatcaggat tatcaatacc atatttttga aaaagccgtt   4920
tctgtaatga aggagaaaac tcaccgaggc agttccatag gatggcaaga tcctggtatc   4980
```

ggtctgcgat tccgactcgt ccaacatcaa tacaacctat taatttcccc tcgtcaaaaa 5040
taaggttatc aagtgagaaa tcaccatgag tgacgactga atccggtgag aatggcaaaa 5100
gcttatgcat ttctttccag acttgttcaa caggccagcc attacgctcg tcatcaaaat 5160
cactcgcatc aaccaaaccg ttattcattc gtgattgcgc ctgagcgaga cgaaatacgc 5220
gatcgctgtt aaaaggacaa ttacaaacag gaatcgaatg caaccggcgc aggaacactg 5280
ccagcgcatc aacaatattt tcacctgaat caggatattc ttctaatacc tggaatgctg 5340
ttttcccggg gatcgcagtg gtgagtaacc atgcatcatc aggagtacgg ataaaatgct 5400
tgatggtcgg aagaggcata aattccgtca gccagtttag tctgaccatc tcatctgtaa 5460
catcattggc aacgctacct ttgccatgtt tcagaaacaa ctctggcgca tcgggcttcc 5520
catacaatcg atagattgtc gcacctgatt gcccgacatt atcgcgagcc catttatacc 5580
catataaatc agcatccatg ttggaattta atcgcggcct cgagcaagac gtttcccgtt 5640
gaatatggct cataacaccc cttgtattac tgtttatgta agcagacagt tttattgttc 5700
atgaccaaaa tcccttaacg tgagttttcg ttccactgag cgtcagaccc cgtagaaaag 5760
atcaaaggat cttcttgaga tccttttttt ctgcgcgtaa tctgctgctt gcaaacaaaa 5820
aaaccaccgc taccagcggt ggtttgtttg ccggatcaag agctaccaac tctttttccg 5880
aaggtaactg gcttcagcag agcgcagata ccaaatactg tccttctagt gtagccgtag 5940
ttaggccacc acttcaagaa ctctgtagca ccgcctacat acctcgctct gctaatcctg 6000
ttaccagtgg ctgctgccag tggcgataag tcgtgtctta ccgggttgga ctcaagacga 6060
tagttaccgg ataaggcgca gcggtcgggc tgaacggggg gttcgtgcac acagcccagc 6120
ttggagcgaa cgacctacac cgaactgaga tacctacagc gtgagctatg agaaagcgcc 6180
acgcttcccg aagggagaaa ggcggacagg tatccggtaa gcggcagggt cggaacagga 6240
gagcgcacga gggagcttcc agggggaaac gcctggtatc tttatagtcc tgtcgggttt 6300
cgccacctct gacttgagcg tcgatttttg tgatgctcgt caggggggcg gagcctatgg 6360
aaaaacgcca gcaacgcggc ctttttacgg ttcctggcct tttgctggcc ttttgctcac 6420
atgttcgatc ccgcgaaat 6439

<210> SEQ ID NO 61
<211> LENGTH: 9542
<212> TYPE: DNA
<213> ORGANISM: Artificial Sequence
<220> FEATURE:
<223> OTHER INFORMATION: Synthetic

<400> SEQUENCE: 61
ggtcgctgag tagtgcgcga gcaaaattta agctacaaca aggcaaggct tgaccgacaa 60
ttgcatgaag aatctgctta gggttaggcg ttttgcgctg cttcgcgatg tacgggccag 120
atatacgcgt tgacattgat tattgactag ttattaatag taatcaatta cggggtcatt 180
agttcatagc ccatatatgg agttccgcgt tacataactt acggtaaatg gcccgcctgg 240
ctgaccgccc aacgaccccc gcccattgac gtcaataatg acgtatgttc ccatagtaac 300
gccaataggg actttccatt gacgtcaatg ggtggagtat ttacggtaaa ctgcccactt 360
ggcagtacat caagtgtatc atatgccaag tacgccccct attgacgtca atgacggtaa 420
atggcccgcc tggcattatg cccagtacat gaccttatgg gactttccta cttggcagta 480
catctacgta ttagtcatcg ctattaccat ggtgatgcgg ttttggcagt acatcaatgg 540

-continued

```
gcgtggatag cggtttgact cacggggatt tccaagtctc caccccattg acgtcaatgg    600
gagtttgttt tggcaccaaa atcaacggga ctttccaaaa tgtcgtaaca actccgcccc    660
attgacgcaa atgggcggta ggcgtgtacg gtgggaggtc tatataagca gagctctctg    720
gctaactaga gaacccactg cttactggct tatcgaaatt aatacgactc actataggga    780
gacccaagct ggctagcgtt taaacttaag cttgccacca tgcctaagaa gaagagaaag    840
gtgggtaccg gctatacaat tggcctggat ctgggcgttg cctctcttgg ctgggccgtc    900
gtgaatgatg agtacgaggt gctggaaagc tgcagcaaca tctttcctgc cgccgagagc    960
gccaacaacg tggaaagaag aggcttccgg caaggcagac ggctgagcag aagaagaagg   1020
acccggatca gcgacttcag aaagctgtgg gagaagtccg gcttcgaggt gcccagcaat   1080
gagctgaatg aggtgctgca gtaccggatc aagggcatga acgacaagct gagcgaggac   1140
gagctgtacc acgtgctgct gaacagcctg aagcacagag gcatcagcta cctggacgac   1200
gccgatgatg agaacgcctc tggcgattat gccgcctcta tcgcctacaa cgagaaccag   1260
ctgaaaacaa agctgccctg cgagatccag tgggagagat acaagaagta cggcgcctac   1320
cggggcaaca tcacaatcca agaaggcggc gagcccctga cactgagaaa tgtgtttacc   1380
accagcgcct acgagaaaga gatccagaaa ctgctggacg tgcagagcat gagcaacgag   1440
aaagtgacca agaagttcat cgacgagtac ctcaagatct tcagccggaa gagagagtac   1500
tacatcggcc ctggcaacaa gaagtccaga accgactacg gcgtgtacac cacacagaag   1560
aacgaggacg gcacctacca caccgagcag aacctgttcg ataagctgat cggcaagtgc   1620
agcgtgtacc ctgatgagcg tagagccgct ggcgccacat acacagccca agagttcaac   1680
ctgctgaacg atctgaacaa cctggtcatc gacggccgga agctggacga gcaagagaag   1740
tgtcagatcg tggatgccgt gaagcacgcc aagaccgtga acatgaagaa catcattgcc   1800
aaagtgatcg gcaccaaggc caacagcatg aacatgaccg gcgccagaat cgacaagaat   1860
gagaaagaaa tcttccacag cttcgaggcc tacaacaagc tgcggaaggc cctggaagag   1920
atcgacttcg acatcgagac actgagcacc gacgagctgg atgccattgg agaggtgctg   1980
accctgaaca ccgaccggaa gtctatccag aacggcctgc aagagaaacg gatcgtggtg   2040
cccgatgaag tgcgggatgt gctgatcgcc accagaaaga gaaatggcag cctgttctcc   2100
aagtggcaga gcttcggcat ccggatcatg aaggaactga tcccagagct gtacgcccag   2160
cctaagaacc agatgcagct gctgaccgac atgggcgtgt tcaagaccaa ggacgagaga   2220
ttcgtggaat acgacaagat ccccagcgac ctgatcaccg aagagatcta caaccccgtg   2280
gtggccaaga cagtgcggat caccgttaga gtgctgaacg ccctgatcaa gaagtatggc   2340
taccccgacc gggtcgtgat cgagatgccc agagataaga actccgagga agagaagaag   2400
cggatcgccg acttccagaa gaacaacgaa aacgagcttg gcggcatcat caagaaagtg   2460
aagtccgagt acggcatcga gatcaccgac gccgacttta agaaccacag caagctgggc   2520
ctgaagctga gactgtggaa cgagcagaat gagacatgcc cctacagcgg caagcacatc   2580
aagatcgacg acctgctcaa caaccccaac atgttcgagg tggaccacat catccctctg   2640
agcatcagct tcgacgacag cagagccaac aaggtgctgg tgtacgccgc cgaaaaccag   2700
aacaagggca acagaacccc tatggcctac ctgagcaacg tgaacagaga gtgggacttc   2760
cacgagtaca tgagcttcgt gctgagcaac tacaagggca ccatctacgg caagaagcgg   2820
gacaatctgc tgttctccga ggacatctac aagatcgatg tgctgcaggg cttcatctcc   2880
cggaacatca acgacaccag atacgcctct aaagtgatcc tgaactccct gcagagcttt   2940
```

ttcggcagca aagaatgcga caccaaagtg aaggtcgtgc ggggcacctt cacacaccag 3000
atgcggatga acctgaagat cgagaagaac cgggaagagt cctacgtgca ccacgccgtg 3060
gatgctatgc tgattgcctt cagccagatg ggctacgacg cctaccacaa actgaccgag 3120
aagtatatcg actacgagca cggcgagttc gtggaccaga agggatacga gaagctgatt 3180
gagaacgacg tggcctacag agagacaacc tatcagaaca agtggatgac catcaagaag 3240
aatatcgaga tcgccgctga gaaaaacaag tactggtatc aagtgaatcg gaagtccaac 3300
cggggcctgt gcaaccagac catctatggc accagaaacc tggacggcaa aaccgtgaag 3360
atctccaagc tggacatccg gaccgacgac ggcatcaaaa agtttaaggg catcgtggaa 3420
aagggcaagc tggaacggtt cctgatgtac cggaacgacc ccaagacctt cgagtggctg 3480
ctgcagatct ataaggacta cagcgacagc aagaacccct tcgtgcagta cgagtctgag 3540
acaggcgacg tgatcaaaaa ggtgtccaag acaaacaacg gccccaaagt gtgcgagctg 3600
agatacgagg atggcgaagt gggctcctgc atcgacatca gccacaaata cggctacaag 3660
aagggcagca agaaagtcat cctggattct ctgaacccct accggatgga cgtgtactac 3720
aacaccaagg acaaccggta ctacttcgtg ggcgtgaagt actccgacat caagtgccag 3780
ggcgacagct acgtgatcga cgaggataag tatgccgccg ctctggtgca agaaaagatc 3840
gtgccagaag gcaagggcag atccgatctg accgagctgg gctatgagtt caagctgtcc 3900
ttctacaaga acgagatcat cgagtacgag aaggacgggg agatctacgt cgagcggttc 3960
ctgtccagaa caatgcctaa agtgtccaac tatatcgaga caaagcccct ggaagccgcc 4020
aagttcgaga agagaaacct cgtgggcctc gccaagacaa gccggatcag aaagatcaga 4080
gtggacatcc tggggaaccg ctacctgaac agcatggaaa acttcgactt cgtcgtgggc 4140
cacaagggat cctacccata cgatgttcca gattacgcgg ccgctccaaa aaagaaaaga 4200
aaagttgaat tcggcggcag cggcgccacc aacttcagcc tgctgaagca ggccggcgac 4260
gtggaggaga accccggccc catggtgagc aagggcgagg aggataacat ggccatcatc 4320
aaggagttca tgcgcttcaa ggtgcacatg gagggctccg tgaacggcca cgagttcgag 4380
atcgagggcg agggcgaggg ccgcccctac gagggcaccc agaccgccaa gctgaaggtg 4440
accaagggtg gccccctgcc cttcgcctgg gacatcctgt cccctcagtt catgtacggc 4500
tccaaggcct acgtgaagca ccccgccgac atccccgact acttgaagct gtccttcccc 4560
gagggcttca agtgggagcg cgtgatgaac ttcgaggacg gcggcgtggt gaccgtgacc 4620
caggactcct ccctgcagga cggcgagttc atctacaagg tgaagctgcg cggcaccaac 4680
ttcccctccg acggccccgt aatgcagaag aagaccatgg gctgggaggc ctcctccgag 4740
cggatgtacc ccgaggacgg cgccctgaag ggcgagatca agcagaggct gaagctgaag 4800
gacggcggcc actacgacgc tgaggtcaag accacctaca aggccaagaa gcccgtgcag 4860
ctgcccggcg cctacaacgt caacatcaag ttggacatca cctcccacaa cgaggactac 4920
accatcgtgg aacagtacga acgcgccgag ggccgccact ccaccggcgg catggacgag 4980
ctgtacaagt agctcgagtc tagagggccc gtttaaaccc gctgatcagc ctcgactgtg 5040
ccttctagtt gccagccatc tgttgtttgc ccctcccccg tgccttcctt gaccctggaa 5100
ggtgccactc ccactgtcct ttcctaataa aatgaggaaa ttgcatcgca ttgtctgagt 5160
aggtgtcatt ctattctggg gggtggggtg gggcaggaca gcaaggggga ggattgggaa 5220
gacaatagca ggcatgctgg ggatgcggtg ggctctatgg cttctgaggc ggaaagaacc 5280
agctggggct ctagggggta tccccacgcg ccctgtagcg gcgcattaag cgcggcgggt 5340
gtggtggtta cgcgcagcgt gaccgctaca cttgccagcg ccctagcgcc cgctcctttc 5400
gctttcttcc cttcctttct cgccacgttc gccggctttc cccgtcaagc tctaaatcgg 5460
gggctccctt tagggttccg atttagtgct ttacggcacc tcgaccccaa aaaacttgat 5520
tagggtgatg gttcacgtag tgggccatcg ccctgataga cggtttttcg ccctttgacg 5580
ttggagtcca cgttctttaa tagtggactc ttgttccaaa ctggaacaac actcaaccct 5640
atctcggtct attcttttga tttataaggg attttgccga tttcggccta ttggttaaaa 5700
aatgagctga tttaacaaaa atttaacgcg aattaattct gtggaatgtg tgtcagttag 5760
ggtgtggaaa gtccccaggc tccccagcag gcagaagtat gcaaagcatg catctcaatt 5820
agtcagcaac caggtgtgga aagtccccag gctccccagc aggcagaagt atgcaaagca 5880
tgcatctcaa ttagtcagca accatagtcc cgcccctaac tccgcccatc ccgcccctaa 5940
ctccgcccag ttccgcccat tctccgcccc atggctgact aattttttt atttatgcag 6000 aggccgaggc cgcctctgcc tctgagctat tccagaagta gtgaggaggc ttttttggag 6060
gcctaggctt ttgcaaaaag ctcccgggag cttgtatatc cattttcgga tctgatcaag 6120
agacaggatg aggatcgttt cgcatgattg aacaagatgg attgcacgca ggttctccgg 6180
ccgcttgggt ggagaggcta ttcggctatg actgggcaca acagacaatc ggctgctctg 6240
atgccgccgt gttccggctg tcagcgcagg ggcgcccggt tctttttgtc aagaccgacc 6300
tgtccggtgc cctgaatgaa ctgcaggacg aggcagcgcg gctatcgtgg ctggccacga 6360
cgggcgttcc ttgcgcagct gtgctcgacg ttgtcactga agcgggaagg gactggctgc 6420
tattgggcga agtgccgggg caggatctcc tgtcatctca ccttgctcct gccgagaaag 6480
tatccatcat ggctgatgca atgcggcggc tgcatacgct tgatccggct acctgcccat 6540
tcgaccacca agcgaaacat cgcatcgagc gagcacgtac tcggatggaa gccggtcttg 6600
tcgatcagga tgatctggac gaagagcatc aggggctcgc gccagccgaa ctgttcgcca 6660
ggctcaaggc gcgcatgccc gacggcgagg atctcgtcgt gacccatggc gatgcctgct 6720
tgccgaatat catggtggaa aatggccgct tttctggatt catcgactgt ggccggctgg 6780
gtgtggcgga ccgctatcag gacatagcgt tggctacccg tgatattgct gaagagcttg 6840
gcggcgaatg ggctgaccgc ttcctcgtgc tttacggtat cgccgctccc gattcgcagc 6900
gcatcgcctt ctatcgcctt cttgacgagt tcttctgagc gggactctgg ggttcgaaat 6960
gaccgaccaa gcgacgccca acctgccatc acgagatttc gattccaccg ccgccttcta 7020
tgaaaggttg ggcttcggaa tcgttttccg ggacgccggc tggatgatcc tccagcgcgg 7080
ggatctcatg ctggagttct tcgcccaccc caacttgttt attgcagctt ataatggtta 7140
caaataaagc aatagcatca caaatttcac aaataaagca tttttttcac tgcattctag 7200
ttgtggtttg tccaaactca tcaatgtatc ttatcatgtc tgtataccgt cgacctctag 7260
ctagagcttg gcgtaatcat ggtcatagct gtttcctgtg tgaaattgtt atccgctcac 7320
aattccacac aacatacgag ccggaagcat aaagtgtaaa gcctggggtg cctaatgagt 7380
gagctaactc acattaattg cgttgcgctc actgcccgct ttccagtcgg gaaacctgtc 7440
gtgccagctg cattaatgaa tcggccaacg cgcggggaga ggcggtttgc gtattgggcg 7500
ctcttccgct tcctcgctca ctgactcgct gcgctcggtc gttcggctgc ggcgagcggt 7560
atcagctcac tcaaaggcgg taatacggtt atccacagaa tcaggggata acgcaggaaa 7620
gaacatgtga gcaaaaggcc agcaaaaggc caggaaccgt aaaaaggccg cgttgctggc 7680

-continued

```
gtttttccat aggctccgcc cccctgacga gcatcacaaa aatcgacgct caagtcagag   7740

gtggcgaaac ccgacaggac tataaagata ccaggcgttt ccccctggaa gctccctcgt   7800

gcgctctcct gttccgaccc tgccgcttac cggatacctg tccgcctttc tcccttcggg   7860

aagcgtggcg ctttctcata gctcacgctg taggtatctc agttcggtgt aggtcgttcg   7920

ctccaagctg ggctgtgtgc acgaaccccc cgttcagccc gaccgctgcg ccttatccgg   7980

taactatcgt cttgagtcca acccggtaag acacgactta tcgccactgg cagcagccac   8040

tggtaacagg attagcagag cgaggtatgt aggcggtgct acagagttct tgaagtggtg   8100

gcctaactac ggctacacta gaagaacagt atttggtatc tgcgctctgc tgaagccagt   8160

taccttcgga aaaagagttg gtagctcttg atccggcaaa caaaccaccg ctggtagcgg   8220

tggttttttt gtttgcaagc agcagattac gcgcagaaaa aaaggatctc aagaagatcc   8280

tttgatcttt tctacggggt ctgacgctca gtggaacgaa aactcacgtt aagggatttt   8340

ggtcatgaga ttatcaaaaa ggatcttcac ctagatcctt ttaaattaaa aatgaagttt   8400

taaatcaatc taaagtatat atgagtaaac ttggtctgac agttaccaat gcttaatcag   8460

tgaggcacct atctcagcga tctgtctatt tcgttcatcc atagttgcct gactccccgt   8520

cgtgtagata actacgatac gggagggctt accatctggc cccagtgctg caatgatacc   8580

gcgagaccca cgctcaccgg ctccagattt atcagcaata aaccagccag ccggaagggc   8640

cgagcgcaga agtggtcctg caactttatc cgcctccatc cagtctatta attgttgccg   8700

ggaagctaga gtaagtagtt cgccagttaa tagtttgcgc aacgttgttg ccattgctac   8760

aggcatcgtg gtgtcacgct cgtcgtttgg tatggcttca ttcagctccg gttcccaacg   8820

atcaaggcga gttacatgat cccccatgtt gtgcaaaaaa gcggttagct ccttcggtcc   8880

tccgatcgtt gtcagaagta agttggccgc agtgttatca ctcatggtta tggcagcact   8940

gcataattct cttactgtca tgccatccgt aagatgcttt tctgtgactg gtgagtactc   9000

aaccaagtca ttctgagaat agtgtatgcg gcgaccgagt tgctcttgcc cggcgtcaat   9060

acgggataat accgcgccac atagcagaac tttaaaagtg ctcatcattg gaaaacgttc   9120

ttcggggcga aaactctcaa ggatcttacc gctgttgaga tccagttcga tgtaacccac   9180

tcgtgcaccc aactgatctt cagcatcttt tactttcacc agcgtttctg ggtgagcaaa   9240

aacaggaagg caaaatgccg caaaaaaggg aataagggcg acacggaaat gttgaatact   9300

catactcttc ctttttcaat attattgaag catttatcag ggttattgtc tcatgagcgg   9360

atacatattt gaatgtattt agaaaaataa acaaataggg gttccgcgca catttccccg   9420

aaaagtgcca cctgacgtcg acggatcggg agatctcccg atcccctatg gtgcactctc   9480

agtacaatct gctctgatgc cgcatagtta agccagtatc tgctccctgc ttgtgtgttg   9540

ga                                                                  9542
```

<210> SEQ ID NO 62
<211> LENGTH: 2726
<212> TYPE: DNA
<213> ORGANISM: Artificial Sequence
<220> FEATURE:
<223> OTHER INFORMATION: Synthetic

<400> SEQUENCE: 62

```
gagggcctat ttcccatgat tccttcatat ttgcatatac gatacaaggc tgttagagag     60

ataattagaa ttaatttgac tgtaaacaca aagatattag tacaaaatac gtgacgtaga    120
```

```
aagtaataat ttcttgggta gtttgcagtt ttaaaattat gttttaaaat ggactatcat    180
atgcttaccg taacttgaaa gtatttcgat ttcttggctt tatatatctt gtggaaagga    240
cgaaacaccg ccaagtgata aacacgagga gtttaagtac ctagagaaag aaatttcttt    300
agacctactt aaataaggct ttatgccgag attaaaggat gccgacgggc atcctttttt    360
gaattctcaa ataaaacgaa aggctcagtc gaaagactgg gcctttcgtt ttatctgttg    420
tttgtcggtg aacgctctcc tgagtaggac aaatggtacc ccgcttcctc gctcactgac    480
tcgctacgct cggtcgttcg actgcggcga gcggaaatgg cttacgaacg gggcggagat    540
ttcctggaag atgccaggaa gatacttaac agggaagtga gagggccgcg gcaaagccgt    600
ttttccatag gctccgcccc cctgacaagc atcacgaaat ctgacgctca aatcagtggt    660
ggcgaaaccc gacaggacta taaagatacc aggcgtttcc ccctggcggc tccctcgtgc    720
gctctcctgt tcctgccttt cggtttaccg gtgtcattcc gctgttatgg ccgcgtttgt    780
ctcattccac gcctgacact cagttccggg taggcagttc gctccaagct ggactgtatg    840
cacgaacccc ccgttcagtc cgaccgctgc gccttatccg gtaactatcg tcttgagtcc    900
aacccggaaa gacatgcaaa agcaccactg gcagcagcca ctggtaattg atttagagga    960
gttagtcttg aagtcatgcg ccggttaagg ctaaactgaa aggacaagtt ttggtgactg   1020
cgctcctcca agccagttac ctcggttcaa agagttggta gctcagagaa ccttcgaaaa   1080
accgccctgc aaggcggttt tttcgttttc agagcaagag attacgcgca gaccaaaacg   1140
atctcaagaa gatcatctta ttaatcagat aaaatatttc tagatttcag tgcaatttat   1200
ctcttcaaat gtagcacctg aagtcagccc catacgatat aagttgttac tagtgcttgg   1260
attctcacca ataaaaaacg cccggcggca accgagcgtt ctgaacaaat ccagatggag   1320
ttctgaggtc attactggat ctatcaacag gagtccaagc gagaagggtt ggtttgcgca   1380
ttcacagttc tccgcaagaa ttgattggct ccaattcttg gagtggtgaa tccgttagcg   1440
aggtgccgcc ggcttccatt caggtcgagg tggcccggct ccatgcaccg cgacgcaacg   1500
cggggaggca gacaaggtat agggcggcgc ctacaatcca tgccaacccg ttccatgtgc   1560
tcgccgaggc ggcataaatc gccgtgacga tcagcggtcc aatgatcgaa gttaggctgg   1620
taagagccgc gagcgatcct tgaagctgtc cctgatggtc gtcatctacc tgcctggaca   1680
gcatggcctg caacgcgggc atcccgatgc cgccggaagc gagaagaatc ataatgggga   1740
aggccatcca gcctcgcgtc gcgaacgcca gcaagacgta gcccagcgcg tcggccgcca   1800
tgccggcgat aatggcctgc ttctcgccga aacgtttggt ggcgggacca gtgacgaagg   1860
cttgagcgag ggcgtgcaag attccgaata ccgcaagcga caggccgatc atcgtcgcgc   1920
tccagcgaaa gcggtcctcg ccgaaaatga cccagagcgc tgccggcacc tgtcctacga   1980
gttgcatgat aaagaagaca gtcataagtg cggcgacgat agtcatgccc cgcgcccacc   2040
ggaaggagct gactgggttg aaggctctca agggcatcgg tcgacgctct cccttatgcg   2100
actcctgcat taggaagcag cccagtagta ggttgaggcc gttgagcacc gccgccgcaa   2160
ggaatggtgc atgcaaggag atggcgccca acagtccccc ggccacgggg cctgccacca   2220
tacccacgcc gaaacaagcg ctcatgagcc cgaagtggcg agcccgatct tccccatcgg   2280
tgatgtcggc gatataggcg ccagcaaccg cacctgtggc gccggtgatg ccggccacga   2340
tgcgtccggc gtagaggatc cacaggacgg gtgtggtcgc catgatcgcg tagtcgatag   2400
tggctccaag tagcgaagcg agcaggactg ggcggcggcc aaagcggtcg gacagtgctc   2460
cgagaacggg tgcgcataga aattgcatca acgcatatag cgctagcagc acgccatagt   2520
```

gactggcgat gctgtcggaa tggacgatat cccgcaagag gcccggcagt accggcataa 2580
ccaagcctat gcctacagca tccagggtga cggtgccgag gatgacgatg agcgcattgt 2640
tagatttcat acacggtgcc tgactgcgtt agcaatttaa ctgtgataaa ctaccgcatt 2700
aaagcttatc gatgataagc tgtcaa 2726

<210> SEQ ID NO 63
<211> LENGTH: 9
<212> TYPE: PRT
<213> ORGANISM: Artificial Sequence
<220> FEATURE:
<223> OTHER INFORMATION: Synthetic

<400> SEQUENCE: 63

Tyr Pro Tyr Asp Val Pro Asp Tyr Ala
1 5

<210> SEQ ID NO 64
<211> LENGTH: 27
<212> TYPE: DNA
<213> ORGANISM: Artificial Sequence
<220> FEATURE:
<223> OTHER INFORMATION: Synthetic

<400> SEQUENCE: 64
tacccatacg atgttccaga ttacgct 27

<210> SEQ ID NO 65
<211> LENGTH: 7
<212> TYPE: PRT
<213> ORGANISM: Artificial Sequence
<220> FEATURE:
<223> OTHER INFORMATION: Synthetic

<400> SEQUENCE: 65

Pro Lys Lys Lys Arg Lys Val
1 5

<210> SEQ ID NO 66
<211> LENGTH: 21
<212> TYPE: DNA
<213> ORGANISM: Artificial Sequence
<220> FEATURE:
<223> OTHER INFORMATION: Synthetic

<400> SEQUENCE: 66
ccaaaaaaga aaagaaaagt t 21

<210> SEQ ID NO 67
<211> LENGTH: 236
<212> TYPE: PRT
<213> ORGANISM: Artificial Sequence
<220> FEATURE:
<223> OTHER INFORMATION: Synthetic

<400> SEQUENCE: 67

Met Val Ser Lys Gly Glu Glu Asp Asn Met Ala Ile Ile Lys Glu Phe
1 5 10 15

Met Arg Phe Lys Val His Met Glu Gly Ser Val Asn Gly His Glu Phe
20 25 30

Glu Ile Glu Gly Glu Gly Glu Gly Arg Pro Tyr Glu Gly Thr Gln Thr
35 40 45

Ala Lys Leu Lys Val Thr Lys Gly Gly Pro Leu Pro Phe Ala Trp Asp

-continued

```
    50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys
225                 230                 235


<210> SEQ ID NO 68
<211> LENGTH: 711
<212> TYPE: DNA
<213> ORGANISM: Artificial Sequence
<220> FEATURE:
<223> OTHER INFORMATION: Synthetic

<400> SEQUENCE: 68

atggtgagca agggcgagga ggataacatg gccatcatca aggagttcat gcgcttcaag     60

gtgcacatgg agggctccgt gaacggccac gagttcgaga tcgagggcga gggcgagggc    120

cgcccctacg agggcaccca gaccgccaag ctgaaggtga ccaagggtgg cccccctgccc    180

ttcgcctggg acatcctgtc ccctcagttc atgtacggct ccaaggccta cgtgaagcac    240

cccgccgaca tccccgacta cttgaagctg tccttccccg agggcttcaa gtgggagcgc    300

gtgatgaact tcgaggacgg cggcgtggtg accgtgaccc aggactcctc cctgcaggac    360

ggcgagttca tctacaaggt gaagctgcgc ggcaccaact tcccctccga cggccccgta    420

atgcagaaga agaccatggg ctgggaggcc tcctccgagc ggatgtaccc cgaggacggc    480

gccctgaagg gcgagatcaa gcagaggctg aagctgaagg acggcggcca ctacgacgct    540

gaggtcaaga ccacctacaa ggccaagaag cccgtgcagc tgcccggcgc ctacaacgtc    600

aacatcaagt tggacatcac ctcccacaac gaggactaca ccatcgtgga acagtacgaa    660

cgcgccgagg gccgccactc caccggcggc atggacgagc tgtacaagta g             711


<210> SEQ ID NO 69
<211> LENGTH: 7
<212> TYPE: PRT
<213> ORGANISM: Simian virus 40

<400> SEQUENCE: 69

Pro Lys Lys Lys Arg Lys Val
1               5
```

<210> SEQ ID NO 70
<211> LENGTH: 16
<212> TYPE: PRT
<213> ORGANISM: Unknown
<220> FEATURE:
<223> OTHER INFORMATION: Synthetic

<400> SEQUENCE: 70

```
Lys Arg Pro Ala Ala Thr Lys Lys Ala Gly Gln Ala Lys Lys Lys Lys
1               5                   10                  15
```

<210> SEQ ID NO 71
<211> LENGTH: 7
<212> TYPE: PRT
<213> ORGANISM: Unknown
<220> FEATURE:
<223> OTHER INFORMATION: Synthetic

<400> SEQUENCE: 71

```
Pro Ala Ala Arg Val Leu Asp
1               5
```

<210> SEQ ID NO 72
<211> LENGTH: 11
<212> TYPE: PRT
<213> ORGANISM: Unknown
<220> FEATURE:
<223> OTHER INFORMATION: Synthetic

<400> SEQUENCE: 72

```
Arg Gln Arg Arg Asn Glu Leu Lys Arg Ser Pro
1               5                   10
```

<210> SEQ ID NO 73
<211> LENGTH: 37
<212> TYPE: PRT
<213> ORGANISM: Homo sapiens

<400> SEQUENCE: 73

```
Asn Gln Ser Ser Asn Phe Gly Pro Met Gly Gly Asn Phe Gly Gly Arg
1               5                   10                  15

Ser Ser Gly Pro Tyr Gly Gly Gly Gly Gln Tyr Phe Ala Lys Pro Arg
            20                  25                  30

Asn Gln Gly Gly Tyr
        35
```

<210> SEQ ID NO 74
<211> LENGTH: 42
<212> TYPE: PRT
<213> ORGANISM: Unknown
<220> FEATURE:
<223> OTHER INFORMATION: Synthetic

<400> SEQUENCE: 74

```
Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40
```

<210> SEQ ID NO 75
<211> LENGTH: 8

```
<212> TYPE: PRT
<213> ORGANISM: Unknown
<220> FEATURE:
<223> OTHER INFORMATION: Synthetic

<400> SEQUENCE: 75

Val Ser Arg Lys Arg Pro Arg Pro
1               5


<210> SEQ ID NO 76
<211> LENGTH: 8
<212> TYPE: PRT
<213> ORGANISM: Unknown
<220> FEATURE:
<223> OTHER INFORMATION: Synthetic

<400> SEQUENCE: 76

Pro Pro Lys Lys Ala Arg Glu Asp
1               5


<210> SEQ ID NO 77
<211> LENGTH: 7
<212> TYPE: PRT
<213> ORGANISM: Homo sapiens

<400> SEQUENCE: 77

Pro Gln Pro Lys Lys Pro Leu
1               5


<210> SEQ ID NO 78
<211> LENGTH: 9
<212> TYPE: PRT
<213> ORGANISM: Mus musculus

<400> SEQUENCE: 78

Ser Ala Ile Ile Lys Lys Lys Lys Met
1               5


<210> SEQ ID NO 79
<211> LENGTH: 5
<212> TYPE: PRT
<213> ORGANISM: Influenza virus

<400> SEQUENCE: 79

Asp Arg Leu Arg Arg
1               5


<210> SEQ ID NO 80
<211> LENGTH: 7
<212> TYPE: PRT
<213> ORGANISM: Influenza virus

<400> SEQUENCE: 80

Pro Lys Gln Lys Lys Arg Lys
1               5


<210> SEQ ID NO 81
<211> LENGTH: 10
<212> TYPE: PRT
<213> ORGANISM: Hepatitis delta virus

<400> SEQUENCE: 81

Arg Lys Leu Lys Lys Lys Ile Lys Lys Leu
1               5                   10
```

<210> SEQ ID NO 82
<211> LENGTH: 10
<212> TYPE: PRT
<213> ORGANISM: Mus musculus

<400> SEQUENCE: 82

Arg Glu Lys Lys Lys Phe Leu Lys Arg Arg
1 5 10

<210> SEQ ID NO 83
<211> LENGTH: 19
<212> TYPE: PRT
<213> ORGANISM: Homo sapiens

<400> SEQUENCE: 83

Lys Arg Gly Asp Glu Val Asp Gly Val Asp Glu Val Ala Lys Lys Lys
1 5 10 15

Ser Lys Lys

<210> SEQ ID NO 84
<211> LENGTH: 17
<212> TYPE: PRT
<213> ORGANISM: Homo sapiens

<400> SEQUENCE: 84

Arg Lys Cys Leu Gln Ala Gly Met Asn Leu Glu Ala Arg Lys Thr Lys
1 5 10 15

Lys

<210> SEQ ID NO 85
<211> LENGTH: 19
<212> TYPE: PRT
<213> ORGANISM: Artificial Sequence
<220> FEATURE:
<223> OTHER INFORMATION: Synthetic

<400> SEQUENCE: 85

Ala Thr Asn Phe Ser Leu Leu Lys Gln Ala Gly Asp Val Glu Glu Asn
1 5 10 15

Pro Gly Pro

<210> SEQ ID NO 86
<211> LENGTH: 57
<212> TYPE: DNA
<213> ORGANISM: Artificial Sequence
<220> FEATURE:
<223> OTHER INFORMATION: Synthetic

<400> SEQUENCE: 86
gccaccaact tcagcctgct gaagcaggcc ggcgacgtgg aggagaaccc cggcccc 57

<210> SEQ ID NO 87
<211> LENGTH: 108
<212> TYPE: RNA
<213> ORGANISM: Artificial Sequence
<220> FEATURE:
<223> OTHER INFORMATION: Synthetic

<400> SEQUENCE: 87
guuugagagu uaugugaaaa caugacgagu ucaaauaaaa auuuauucaa accgccuauu 60
uauaggccgc agauguucug cauuaugcuu gcuauugcaa gcuuuuuu 108

<210> SEQ ID NO 88

```
<211> LENGTH: 110
<212> TYPE: RNA
<213> ORGANISM: Artificial Sequence
<220> FEATURE:
<223> OTHER INFORMATION: Synthetic

<400> SEQUENCE: 88

guuugagagu uauguagaaa uacaugacga guucaaauaa aaauuuauuc aaaccgccua     60

uuuauaggcc gcagauguuc ugcauuaugc uugcuauugc aagcuuuuuu               110


<210> SEQ ID NO 89
<211> LENGTH: 20
<212> TYPE: RNA
<213> ORGANISM: Artificial Sequence
<220> FEATURE:
<223> OTHER INFORMATION: Synthetic

<400> SEQUENCE: 89

ccaagugaua aacacgagga                                                 20


<210> SEQ ID NO 90
<211> LENGTH: 21
<212> TYPE: RNA
<213> ORGANISM: Artificial Sequence
<220> FEATURE:
<223> OTHER INFORMATION: Synthetic

<400> SEQUENCE: 90

gucaccucca augacuaggg u                                               21


<210> SEQ ID NO 91
<211> LENGTH: 20
<212> TYPE: RNA
<213> ORGANISM: Artificial Sequence
<220> FEATURE:
<223> OTHER INFORMATION: Synthetic

<400> SEQUENCE: 91

gccgccauug acagagggac                                                 20


<210> SEQ ID NO 92
<211> LENGTH: 20
<212> TYPE: RNA
<213> ORGANISM: Artificial Sequence
<220> FEATURE:
<223> OTHER INFORMATION: Synthetic

<400> SEQUENCE: 92

aacugguacc gcaugagccc                                                 20


<210> SEQ ID NO 93
<211> LENGTH: 20
<212> TYPE: RNA
<213> ORGANISM: Artificial Sequence
<220> FEATURE:
<223> OTHER INFORMATION: Synthetic

<400> SEQUENCE: 93

caucaggcuc ucagcucagc                                                 20


<210> SEQ ID NO 94
<211> LENGTH: 20
<212> TYPE: RNA
<213> ORGANISM: Artificial Sequence
<220> FEATURE:
<223> OTHER INFORMATION: Synthetic
```

<400> SEQUENCE: 94
aggugccguu uguucauuuu 20

<210> SEQ ID NO 95
<211> LENGTH: 20
<212> TYPE: RNA
<213> ORGANISM: Artificial Sequence
<220> FEATURE:
<223> OTHER INFORMATION: Synthetic

<400> SEQUENCE: 95
ccaguuguag caccgcccag 20

<210> SEQ ID NO 96
<211> LENGTH: 20
<212> TYPE: RNA
<213> ORGANISM: Artificial Sequence
<220> FEATURE:
<223> OTHER INFORMATION: Synthetic

<400> SEQUENCE: 96
ucuccccagc ccugcucgug 20

<210> SEQ ID NO 97
<211> LENGTH: 20
<212> TYPE: RNA
<213> ORGANISM: Artificial Sequence
<220> FEATURE:
<223> OTHER INFORMATION: Synthetic

<400> SEQUENCE: 97
ucugugaaug uuagacccau 20

<210> SEQ ID NO 98
<211> LENGTH: 20
<212> TYPE: RNA
<213> ORGANISM: Artificial Sequence
<220> FEATURE:
<223> OTHER INFORMATION: Synthetic

<400> SEQUENCE: 98
ccaugggagc agcuggucag 20

<210> SEQ ID NO 99
<211> LENGTH: 20
<212> TYPE: RNA
<213> ORGANISM: Artificial Sequence
<220> FEATURE:
<223> OTHER INFORMATION: Synthetic

<400> SEQUENCE: 99
gcaagagacc cacacaccgg 20

<210> SEQ ID NO 100
<211> LENGTH: 20
<212> TYPE: RNA
<213> ORGANISM: Artificial Sequence
<220> FEATURE:
<223> OTHER INFORMATION: Synthetic

<400> SEQUENCE: 100
acaccggagg agcgcccgcu 20

<210> SEQ ID NO 101

<211> LENGTH: 20
<212> TYPE: RNA
<213> ORGANISM: Artificial Sequence
<220> FEATURE:
<223> OTHER INFORMATION: Synthetic

<400> SEQUENCE: 101
cgucugggcg gugcuacaac 20

<210> SEQ ID NO 102
<211> LENGTH: 20
<212> TYPE: RNA
<213> ORGANISM: Artificial Sequence
<220> FEATURE:
<223> OTHER INFORMATION: Synthetic

<400> SEQUENCE: 102
cuacaacugg gcuggcggcc 20

<210> SEQ ID NO 103
<211> LENGTH: 20
<212> TYPE: RNA
<213> ORGANISM: Artificial Sequence
<220> FEATURE:
<223> OTHER INFORMATION: Synthetic

<400> SEQUENCE: 103
aguccgggcu gggagcgggu 20

<210> SEQ ID NO 104
<211> LENGTH: 20
<212> TYPE: RNA
<213> ORGANISM: Artificial Sequence
<220> FEATURE:
<223> OTHER INFORMATION: Synthetic

<400> SEQUENCE: 104
gcugcgggaa agggauuccc 20

<210> SEQ ID NO 105
<211> LENGTH: 20
<212> TYPE: RNA
<213> ORGANISM: Artificial Sequence
<220> FEATURE:
<223> OTHER INFORMATION: Synthetic

<400> SEQUENCE: 105
acagcgggug uagacuccga 20

<210> SEQ ID NO 106
<211> LENGTH: 20
<212> TYPE: RNA
<213> ORGANISM: Artificial Sequence
<220> FEATURE:
<223> OTHER INFORMATION: Synthetic

<400> SEQUENCE: 106
cagcgggugu agacuccgag 20

<210> SEQ ID NO 107
<211> LENGTH: 20
<212> TYPE: RNA
<213> ORGANISM: Artificial Sequence
<220> FEATURE:
<223> OTHER INFORMATION: Synthetic

<400> SEQUENCE: 107
gucaagcccc agaggccaca 20

<210> SEQ ID NO 108
<211> LENGTH: 20
<212> TYPE: RNA
<213> ORGANISM: Artificial Sequence
<220> FEATURE:
<223> OTHER INFORMATION: Synthetic

<400> SEQUENCE: 108
gccuggggcc ccuaacccua 20

<210> SEQ ID NO 109
<211> LENGTH: 20
<212> TYPE: RNA
<213> ORGANISM: Artificial Sequence
<220> FEATURE:
<223> OTHER INFORMATION: Synthetic

<400> SEQUENCE: 109
auuuucugac acucccgccc 20

<210> SEQ ID NO 110
<211> LENGTH: 20
<212> TYPE: RNA
<213> ORGANISM: Artificial Sequence
<220> FEATURE:
<223> OTHER INFORMATION: Synthetic

<400> SEQUENCE: 110
auccuggccg ccagcccagu 20

<210> SEQ ID NO 111
<211> LENGTH: 20
<212> TYPE: RNA
<213> ORGANISM: Artificial Sequence
<220> FEATURE:
<223> OTHER INFORMATION: Synthetic

<400> SEQUENCE: 111
ggagagcuuc gugcuaaacu 20

<210> SEQ ID NO 112
<211> LENGTH: 23
<212> TYPE: RNA
<213> ORGANISM: Artificial Sequence
<220> FEATURE:
<223> OTHER INFORMATION: Synthetic

<400> SEQUENCE: 112
ugcaguccgg gcugggagcg ggu 23

<210> SEQ ID NO 113
<211> LENGTH: 135
<212> TYPE: RNA
<213> ORGANISM: Artificial Sequence
<220> FEATURE:
<223> OTHER INFORMATION: Synthetic

<400> SEQUENCE: 113
ugcaguccgg gcugggagcg gguguuugag aguuauguaa gaaauuacau gacgaguuca 60
aauaaaaauu uauucaaacc gccuauuuau aggccgcaga uguucugcau uaugcuugcu 120
auugcaagcu uuuuu 135

<210> SEQ ID NO 114
<211> LENGTH: 43
<212> TYPE: DNA
<213> ORGANISM: Artificial Sequence
<220> FEATURE:
<223> OTHER INFORMATION: Synthetic

<400> SEQUENCE: 114
ctgttgctgc agtccgggct gggagcgggt ggggagcaga ggg 43

<210> SEQ ID NO 115
<211> LENGTH: 43
<212> TYPE: DNA
<213> ORGANISM: Artificial Sequence
<220> FEATURE:
<223> OTHER INFORMATION: Synthetic

<400> SEQUENCE: 115
gttaagagac agtccaggct gggagcaggt ggggagagga ggg 43

<210> SEQ ID NO 116
<211> LENGTH: 22
<212> TYPE: RNA
<213> ORGANISM: Artificial Sequence
<220> FEATURE:
<223> OTHER INFORMATION: Synthetic

<400> SEQUENCE: 116
gcaguccggg cugggagcgg gu 22

<210> SEQ ID NO 117
<211> LENGTH: 134
<212> TYPE: RNA
<213> ORGANISM: Artificial Sequence
<220> FEATURE:
<223> OTHER INFORMATION: Synthetic

<400> SEQUENCE: 117
gcaguccggg cugggagcgg guguuugaga guuauguaag aaauuacaug acgaguucaa 60
auaaaaauuu auucaaaccg ccuauuuaua ggccgcagau guucugcauu augcuugcua 120
uugcaagcuu uuuu 134

<210> SEQ ID NO 118
<211> LENGTH: 21
<212> TYPE: RNA
<213> ORGANISM: Artificial Sequence
<220> FEATURE:
<223> OTHER INFORMATION: Synthetic

<400> SEQUENCE: 118
caguccgggc ugggagcggg u 21

<210> SEQ ID NO 119
<211> LENGTH: 133
<212> TYPE: RNA
<213> ORGANISM: Artificial Sequence
<220> FEATURE:
<223> OTHER INFORMATION: Synthetic

<400> SEQUENCE: 119
caguccgggc ugggagcggg uguuugagag uuauguaaga aauuacauga cgaguucaaa 60
uaaaaauuua uucaaaccgc cuauuuauag gccgcagaug uucugcauua ugcuugcuau 120
ugcaagcuuu uuu 133

<210> SEQ ID NO 120
<211> LENGTH: 20
<212> TYPE: RNA
<213> ORGANISM: Artificial Sequence
<220> FEATURE:
<223> OTHER INFORMATION: Synthetic

<400> SEQUENCE: 120
aguccgggcu gggagcgggu 20

<210> SEQ ID NO 121
<211> LENGTH: 132
<212> TYPE: RNA
<213> ORGANISM: Artificial Sequence
<220> FEATURE:
<223> OTHER INFORMATION: Synthetic

<400> SEQUENCE: 121
aguccgggcu gggagcgggu guuugagagu uauguaagaa auuacaugac gaguucaaau 60
aaaaauuuau ucaaaccgcc uauuuauagg ccgcagaugu ucugcauuau gcuugcuauu 120
gcaagcuuuu uu 132

<210> SEQ ID NO 122
<211> LENGTH: 19
<212> TYPE: RNA
<213> ORGANISM: Artificial Sequence
<220> FEATURE:
<223> OTHER INFORMATION: Synthetic

<400> SEQUENCE: 122
guccgggcug ggagcgggu 19

<210> SEQ ID NO 123
<211> LENGTH: 131
<212> TYPE: RNA
<213> ORGANISM: Artificial Sequence
<220> FEATURE:
<223> OTHER INFORMATION: Synthetic

<400> SEQUENCE: 123
guccgggcug ggagcgggug uuugagaguu auguaagaaa uuacaugacg aguucaaaua 60
aaaauuuauu caaaccgccu auuuauaggc cgcagauguu cugcauuaug cuugcuauug 120
caagcuuuuu u 131

<210> SEQ ID NO 124
<211> LENGTH: 18
<212> TYPE: RNA
<213> ORGANISM: Artificial Sequence
<220> FEATURE:
<223> OTHER INFORMATION: Synthetic

<400> SEQUENCE: 124
uccgggcugg gagcgggu 18

<210> SEQ ID NO 125
<211> LENGTH: 130
<212> TYPE: RNA
<213> ORGANISM: Artificial Sequence
<220> FEATURE:
<223> OTHER INFORMATION: Synthetic

<400> SEQUENCE: 125
uccgggcugg gagcgggugu uugagaguua uguaagaaau uacaugacga guucaaauaa 60
aaauuuauuc aaaccgccua uuuauaggcc gcagauguuc ugcauuaugc uugcuauugc 120
aagcuuuuuu 130

<210> SEQ ID NO 126
<211> LENGTH: 17
<212> TYPE: RNA
<213> ORGANISM: Artificial Sequence
<220> FEATURE:
<223> OTHER INFORMATION: Synthetic

<400> SEQUENCE: 126
ccgggcuggg agcgggu 17

<210> SEQ ID NO 127
<211> LENGTH: 129
<212> TYPE: RNA
<213> ORGANISM: Artificial Sequence
<220> FEATURE:
<223> OTHER INFORMATION: Synthetic

<400> SEQUENCE: 127
ccgggcuggg agcggguguu ugagaguuau guaagaaauu acaugacgag uucaaauaaa 60
aauuuauuca aaccgccuau uuauaggccg cagauguucu gcauuaugcu ugcuauugca 120
agcuuuuuu 129

<210> SEQ ID NO 128
<211> LENGTH: 128
<212> TYPE: RNA
<213> ORGANISM: Artificial Sequence
<220> FEATURE:
<223> OTHER INFORMATION: Synthetic

<400> SEQUENCE: 128
aguccgggcu gggagcgggu guuugagagu uaugugaaaa caugacgagu ucaaauaaaa 60
auuuauucaa accgccuauu uauaggccgc agauguucug cauuaugcuu gcuauugcaa 120
gcuuuuuu 128

<210> SEQ ID NO 129
<211> LENGTH: 130
<212> TYPE: RNA
<213> ORGANISM: Artificial Sequence
<220> FEATURE:
<223> OTHER INFORMATION: Synthetic

<400> SEQUENCE: 129
aguccgggcu gggagcgggu guuugagagu uauguagaaa uacaugacga guucaaauaa 60
aaauuuauuc aaaccgccua uuuauaggcc gcagauguuc ugcauuaugc uugcuauugc 120
aagcuuuuuu 130

<210> SEQ ID NO 130
<211> LENGTH: 28
<212> TYPE: DNA
<213> ORGANISM: Artificial Sequence
<220> FEATURE:
<223> OTHER INFORMATION: Synthetic

<400> SEQUENCE: 130
agtccgggct gggagcgggt ggggagca 28

<210> SEQ ID NO 131
<211> LENGTH: 28
<212> TYPE: DNA
<213> ORGANISM: Artificial Sequence
<220> FEATURE:
<223> OTHER INFORMATION: Synthetic

<400> SEQUENCE: 131
gtcaagcccc agaggccaca gggacaga 28

<210> SEQ ID NO 132
<211> LENGTH: 28
<212> TYPE: DNA
<213> ORGANISM: Artificial Sequence
<220> FEATURE:
<223> OTHER INFORMATION: Synthetic

<400> SEQUENCE: 132
agtcctggct gggagcaggt ggggagag 28

<210> SEQ ID NO 133
<211> LENGTH: 28
<212> TYPE: DNA
<213> ORGANISM: Artificial Sequence
<220> FEATURE:
<223> OTHER INFORMATION: Synthetic

<400> SEQUENCE: 133
gccaagcctc agaggccaca gggcagca 28

<210> SEQ ID NO 134
<211> LENGTH: 28
<212> TYPE: DNA
<213> ORGANISM: Artificial Sequence
<220> FEATURE:
<223> OTHER INFORMATION: Synthetic

<400> SEQUENCE: 134
ccaagtgata aacacgagga tggcaaga 28

<210> SEQ ID NO 135
<211> LENGTH: 28
<212> TYPE: DNA
<213> ORGANISM: Artificial Sequence
<220> FEATURE:
<223> OTHER INFORMATION: Synthetic

<400> SEQUENCE: 135
aactggtacc gcatgagccc cagcaacc 28

<210> SEQ ID NO 136
<211> LENGTH: 28
<212> TYPE: DNA
<213> ORGANISM: Artificial Sequence
<220> FEATURE:
<223> OTHER INFORMATION: Synthetic

<400> SEQUENCE: 136
catcaggctc tcagctcagc ctgagtgt 28

<210> SEQ ID NO 137
<211> LENGTH: 28
<212> TYPE: DNA
<213> ORGANISM: Artificial Sequence
<220> FEATURE:
<223> OTHER INFORMATION: Synthetic

<400> SEQUENCE: 137
aggtgccgtt tgttcatttt ctgacact 28

<210> SEQ ID NO 138
<211> LENGTH: 28
<212> TYPE: DNA
<213> ORGANISM: Artificial Sequence
<220> FEATURE:
<223> OTHER INFORMATION: Synthetic

<400> SEQUENCE: 138
ccagttgtag caccgcccag acgactgg 28

<210> SEQ ID NO 139
<211> LENGTH: 28
<212> TYPE: DNA
<213> ORGANISM: Artificial Sequence
<220> FEATURE:
<223> OTHER INFORMATION: Synthetic

<400> SEQUENCE: 139
tctccccagc cctgctcgtg gtgaccga 28

<210> SEQ ID NO 140
<211> LENGTH: 28
<212> TYPE: DNA
<213> ORGANISM: Artificial Sequence
<220> FEATURE:
<223> OTHER INFORMATION: Synthetic

<400> SEQUENCE: 140
tctgtgaatg ttagacccat gggagcag 28

<210> SEQ ID NO 141
<211> LENGTH: 28
<212> TYPE: DNA
<213> ORGANISM: Artificial Sequence
<220> FEATURE:
<223> OTHER INFORMATION: Synthetic

<400> SEQUENCE: 141
gcaagagacc cacacaccgg aggagcgc 28

<210> SEQ ID NO 142
<211> LENGTH: 28
<212> TYPE: DNA
<213> ORGANISM: Artificial Sequence
<220> FEATURE:
<223> OTHER INFORMATION: Synthetic

<400> SEQUENCE: 142
acaccggagg agcgcccgct tgggggag 28

<210> SEQ ID NO 143
<211> LENGTH: 28
<212> TYPE: DNA
<213> ORGANISM: Artificial Sequence
<220> FEATURE:
<223> OTHER INFORMATION: Synthetic

<400> SEQUENCE: 143
cgtctgggcg gtgctacaac tgggctgg 28

<210> SEQ ID NO 144
<211> LENGTH: 28

<212> TYPE: DNA
<213> ORGANISM: Artificial Sequence
<220> FEATURE:
<223> OTHER INFORMATION: Synthetic

<400> SEQUENCE: 144
gctgcgggaa agggattccc tgggactc 28

<210> SEQ ID NO 145
<211> LENGTH: 28
<212> TYPE: DNA
<213> ORGANISM: Artificial Sequence
<220> FEATURE:
<223> OTHER INFORMATION: Synthetic

<400> SEQUENCE: 145
gcctggggcc cctaacccta tgtagcct 28

<210> SEQ ID NO 146
<211> LENGTH: 28
<212> TYPE: DNA
<213> ORGANISM: Artificial Sequence
<220> FEATURE:
<223> OTHER INFORMATION: Synthetic

<400> SEQUENCE: 146
attttctgac actcccgccc aatatacc 28

<210> SEQ ID NO 147
<211> LENGTH: 28
<212> TYPE: DNA
<213> ORGANISM: Artificial Sequence
<220> FEATURE:
<223> OTHER INFORMATION: Synthetic

<400> SEQUENCE: 147
atcctggccg ccagcccagt tgtagcac 28

<210> SEQ ID NO 148
<211> LENGTH: 28
<212> TYPE: DNA
<213> ORGANISM: Artificial Sequence
<220> FEATURE:
<223> OTHER INFORMATION: Synthetic

<400> SEQUENCE: 148
ggagagcttc gtgctaaact ggtaccgc 28

<210> SEQ ID NO 149
<211> LENGTH: 11
<212> TYPE: RNA
<213> ORGANISM: Artificial Sequence
<220> FEATURE:
<223> OTHER INFORMATION: tracrRNA

<400> SEQUENCE: 149
cgaguucaaa u 11

<210> SEQ ID NO 150
<211> LENGTH: 17
<212> TYPE: RNA
<213> ORGANISM: Artificial Sequence
<220> FEATURE:
<223> OTHER INFORMATION: tracrRNA Portion 1

<400> SEQUENCE: 150
aaaaauuuau ucaaacc 17

<210> SEQ ID NO 151
<211> LENGTH: 14
<212> TYPE: RNA
<213> ORGANISM: Artificial Sequence
<220> FEATURE:
<223> OTHER INFORMATION: tracrRNA Portion 3

<400> SEQUENCE: 151
cgcagauguu cugc 14

<210> SEQ ID NO 152
<211> LENGTH: 27
<212> TYPE: RNA
<213> ORGANISM: Artificial Sequence
<220> FEATURE:
<223> OTHER INFORMATION: tracrRNA Portion 4

<400> SEQUENCE: 152
auuaugcuug cuauugcaag cuuuuuu 27

<210> SEQ ID NO 153
<211> LENGTH: 88
<212> TYPE: RNA
<213> ORGANISM: Artificial Sequence
<220> FEATURE:
<223> OTHER INFORMATION: Full tracrRNA V1

<400> SEQUENCE: 153
caugacgagu ucaaauaaaa auuuauucaa accgccuauu uauaggccgc agauguucug 60
cauuaugcuu gcuauugcaa gcuuuuuu 88

<210> SEQ ID NO 154
<211> LENGTH: 91
<212> TYPE: RNA
<213> ORGANISM: Artificial Sequence
<220> FEATURE:
<223> OTHER INFORMATION: Full tracrRNA V2

<400> SEQUENCE: 154
uuacaugacg aguucaaaua aaaauuuauu caaaccgccu auuuauaggc cgcagauguu 60
cugcauuaug cuugcuauug caagcuuuuu u 91

<210> SEQ ID NO 155
<211> LENGTH: 4194
<212> TYPE: DNA
<213> ORGANISM: Artificial Sequence
<220> FEATURE:
<223> OTHER INFORMATION: pPML3.1
<220> FEATURE:
<221> NAME/KEY: misc_feature
<222> LOCATION: (2256)..(2261)
<223> OTHER INFORMATION: n is a, c, g, or t

<400> SEQUENCE: 155
gggtctctct ggttagacca gatctgagcc tgggagctct ctggctaact agggaaccca 60
ctgcttaagc ctcaataaag cttgccttga gtgcttcaag tagtgtgtgc ccgtctgttg 120
tgtgactctg gtaactagag atccctcaga cccttttagt cagtgtggaa aatctctagc 180
agtggcgccc gaacagggac ttgaaagcga aagggaaacc agaggagctc tctcgacgca 240
ggactcggct tgctgaagcg cgcacggcaa gaggcgaggg gcggcgactg gtgagtacgc 300
caaaaatttt gactagcgga ggctagaagg agagagatgg gtgcgagagc gtcagtatta 360

```
agcgggggag aattagatcg cgatgggaaa aaattcggtt aaggccaggg ggaaagaaaa    420
aatataaatt aaaacatata gtatgggcaa gcagggagct agaacgattc gcagttaatc    480
ctggcctgtt agaaacatca gaaggctgta gacaaatact gggacagcta caaccatccc    540
ttcagacagg atcagaagaa cttagatcat tatataatac agtagcaacc ctctattgtg    600
tgcatcaaag gatagagata aaagacacca aggaagcttt agacaagata gaggaagagc    660
aaaacaaaag taagaccacc gcacagcaag cggccgctga tcttcagacc tggaggagga    720
gatatgaggg acaattggag aagtgaatta tataaatata aagtagtaaa aattgaacca    780
ttaggagtag cacccaccaa ggcaaagaga agagtggtgc agagagaaaa aagagcagtg    840
ggaataggag ctttgttcct tgggttcttg ggagcagcag gaagcactat gggcgcagcg    900
tcaatgacgc tgacggtaca ggccagacaa ttattgtctg gtatagtgca gcagcagaac    960
aatttgctga gggctattga ggcgcaacag catctgttgc aactcacagt ctggggcatc   1020
aagcagctcc aggcaagaat cctggctgtg gaaagatacc taaaggatca acagctcctg   1080
gggatttggg gttgctctgg aaaactcatt tgcaccactg ctgtgccttg gaatgctagt   1140
tggagtaata aatctctgga acagatttgg aatcacacga cctggatgga gtgggacaga   1200
gaaattaaca attacacaag cttaatacac tccttaattg aagaatcgca aaaccagcaa   1260
gaaaagaatg aacaagaatt attggaatta gataaatggg caagtttgtg gaattggttt   1320
aacataacaa attggctgtg gtatataaaa ttattcataa tgatagtagg aggcttggta   1380
ggtttaagaa tagtttttgc tgtactttct atagtgaata gagttaggca gggatattca   1440
ccattatcgt ttcagaccca cctcccaacc ccgaggggac ccgacaggcc cgaaggaata   1500
gaagaagaag gtggagagag agacagagac agatccattc gattagtgaa cggatctcga   1560
cggtatcgat aagcttggga gttccgcgtt acataactta cggtaaatgg cccgcctggc   1620
tgaccgccca acgacccccg cccattgacg tcaataatga cgtatgttcc catagtaacg   1680
ccaataggga ctttccattg acgtcaatgg gtggagtatt tacggtaaac tgcccacttg   1740
gcagtacatc aagtgtatca tatgccaagt acgcccccta ttgacgtcaa tgacggtaaa   1800
tggcccgcct ggcattatgc ccagtacatg accttatggg actttcctac ttggcagtac   1860
atctacgtat tagtcatcgc tattaccatg gtgatgcggt tttggcagta catcaatggg   1920
cgtggatagc ggtttgactc acggggattt ccaagtctcc accccattga cgtcaatggg   1980
agtttgtttt ggcaccaaaa tcaacgggac tttccaaaat gtcgtaacaa ctccgcccca   2040
ttgacgcaaa tgggcggtag gcgtgtacgg tgggaggtct atataagcag agctcgttta   2100
gtgaaccgtc agatcgcctg gagacgccat ccacgctgtt ttgacctcca tagaagacac   2160
cgactctaga ggatccacta gtccagtgtg gtggaattct gcagatatca aagcttgcca   2220
ccatgcatac aatggaagag cagagccttg gtctcnnnnn ngcgggtctg gtggcgctag   2280
cgtgtccaag ggcgaggagc tgttcaccgg cgtggtgccc atcctggtgg agctggacgg   2340
cgacgtgaac ggccacaagt tcagcgtgag cggcgagggc gaaggggacg ctacttacgg   2400
caaactgact ctcaagttta tctgtactac cgggaagctc cctgtccctt ggcctacact   2460
ggtcacaact ctcacatatg ggtccagtg cttcagcaga taccccgacc acatgaagca   2520
gcacgacttc ttcaagagcg ccatgcccga gggctacgtg caggagagaa ccatcttctt   2580
caaggacgac ggcaactaca agaccagagc tgaggtcaag tttgagggtg acaccctggt   2640
gaacagaatc gagctgaagg gcatcgactt caaggaggac ggcaacatcc tgggccacaa   2700
```

-continued

```
gctggagtac aactacaaca gccacaacgt gtacatcatg gctgataaac agaagaatgg   2760

gattaaggtg aacttcaaga tcagacacaa catcgaggac ggcagcgtgc agctggccga   2820

ccactaccag cagaacaccc ccatcggcga cggccccgtg ctgctgcccg acaaccacta   2880

cctgagcacc cagagcgctc tcagtaagga ccctaatgag aagagagacc acatggtgct   2940

gctggagttc gtgaccgccg ccggcatcac cctgggcatg gacgagctgt acaagtgagg   3000

gcctaatgag tttggaatta attctgtgga atgtgtgtca gttagggtgt ggaaagtccc   3060

caggctcccc agcaggcaga agtatgcaaa gcatgcatct caattagtca gcaaccaggt   3120

gtggaaagtc cccaggctcc ccagcaggca gaagtatgca aagcatgcat ctcaattagt   3180

cagcaaccat agtcccgccc ctaactccgc ccatcccgcc cctaactccg cccagttccg   3240

cccattctcc gccccatggc tgactaattt tttttattta tgcagaggcc gaggccgcct   3300

ctgcctctga gctattccag aagtagtgag gaggcttttt tggaggccta ggcttttgca   3360

aaaagctccc gggagcttgt atatccattt tcggatctga tcagcacgtg ttgacaatta   3420

atcatcggca tagtatatcg gcatagtata atacgacaag gtgaggaact aaaccatggc   3480

caagcctttg tctcaagaag aatccaccct cattgaaaga gcaacggcta caatcaacag   3540

catccccatc tctgaagact acagcgtcgc cagcgcagct ctctctagcg acggccgcat   3600

cttcactggt gtcaatgtat atcattttac tgggggacct tgtgcagaac tcgtggtgct   3660

gggcactgct gctgctgcgg cagctggcaa cctgacttgt atcgtcgcga tcggaaatga   3720

gaacaggggc atcttgagcc cctgcggacg gtgccgacag gtgcttctcg atctgcatcc   3780

tgggatcaaa gccatagtga aggacagtga tggacagccg acggcagttg ggattcgtga   3840

attgctgccc tctggttatg tgtgggaggg ctaagcacaa ttcgagctcg gtacctttaa   3900

gaccaatgac ttacaaggca gctgtagatc ttagccactt tttaaaagaa aaggggggac   3960

tggaagggct aattcactcc caacgaagac aagatctgct tttgcttgt actgggtctc   4020

tctggttaga ccagatctga gcctgggagc tctctggcta actagggaac ccactgctta   4080

agcctcaata aagcttgcct tgagtgcttc aagtagtgtg tgcccgtctg ttgtgtgact   4140

ctggtaacta gagatccctc agaccctttt agtcagtgtg gaaaatctct agca         4194
```

<210> SEQ ID NO 156
<211> LENGTH: 21
<212> TYPE: DNA
<213> ORGANISM: Artificial Sequence
<220> FEATURE:
<223> OTHER INFORMATION: TRAC gRNA 1

<400> SEQUENCE: 156

```
tctctcagct ggtacacggc a                                               21
```

<210> SEQ ID NO 157
<211> LENGTH: 21
<212> TYPE: DNA
<213> ORGANISM: Artificial Sequence
<220> FEATURE:
<223> OTHER INFORMATION: TRAC gRNA 2

<400> SEQUENCE: 157

```
gcgtcatgag cagattaaac c                                               21
```

<210> SEQ ID NO 158
<211> LENGTH: 21
<212> TYPE: DNA
<213> ORGANISM: Artificial Sequence
<220> FEATURE:
<223> OTHER INFORMATION: TRAC gRNA 3

<400> SEQUENCE: 158
tctcgaccag cttgacatca c 21

<210> SEQ ID NO 159
<211> LENGTH: 21
<212> TYPE: DNA
<213> ORGANISM: Artificial Sequence
<220> FEATURE:
<223> OTHER INFORMATION: TRAC gRNA 4

<400> SEQUENCE: 159
ttaaacccgg ccactttcag g 21

<210> SEQ ID NO 160
<211> LENGTH: 21
<212> TYPE: DNA
<213> ORGANISM: Artificial Sequence
<220> FEATURE:
<223> OTHER INFORMATION: TRAC gRNA 5

<400> SEQUENCE: 160
ctgtgctaga catgaggtct a 21

<210> SEQ ID NO 161
<211> LENGTH: 21
<212> TYPE: DNA
<213> ORGANISM: Artificial Sequence
<220> FEATURE:
<223> OTHER INFORMATION: TRAC gRNA 8

<400> SEQUENCE: 161
acttcaagag caacagtgct g 21

<210> SEQ ID NO 162
<211> LENGTH: 21
<212> TYPE: DNA
<213> ORGANISM: Artificial Sequence
<220> FEATURE:
<223> OTHER INFORMATION: TRAC gRNA 9

<400> SEQUENCE: 162
aagagcaaca gtgctgtggc c 21

<210> SEQ ID NO 163
<211> LENGTH: 21
<212> TYPE: DNA
<213> ORGANISM: Artificial Sequence
<220> FEATURE:
<223> OTHER INFORMATION: TRAC gRNA 10

<400> SEQUENCE: 163
gctggggaag aaggtgtctt c 21

<210> SEQ ID NO 164
<211> LENGTH: 21
<212> TYPE: DNA
<213> ORGANISM: Artificial Sequence
<220> FEATURE:
<223> OTHER INFORMATION: TRAC gRNA 15

<400> SEQUENCE: 164
ataggcagac agacttgtca c 21

<210> SEQ ID NO 165
<211> LENGTH: 21
<212> TYPE: DNA
<213> ORGANISM: Artificial Sequence
<220> FEATURE:
<223> OTHER INFORMATION: TRAC gRNA 17

<400> SEQUENCE: 165
tagagtctct cagctggtac a 21

<210> SEQ ID NO 166
<211> LENGTH: 21
<212> TYPE: DNA
<213> ORGANISM: Artificial Sequence
<220> FEATURE:
<223> OTHER INFORMATION: TRACR gRNA 18

<400> SEQUENCE: 166
gtctctcagc tggtacacgg c 21

<210> SEQ ID NO 167
<211> LENGTH: 21
<212> TYPE: DNA
<213> ORGANISM: Artificial Sequence
<220> FEATURE:
<223> OTHER INFORMATION: TRAC gRNA 19

<400> SEQUENCE: 167
cagctggtac acggcagggt c 21

<210> SEQ ID NO 168
<211> LENGTH: 21
<212> TYPE: DNA
<213> ORGANISM: Artificial Sequence
<220> FEATURE:
<223> OTHER INFORMATION: TRAC gRNA 20

<400> SEQUENCE: 168
agctggtaca cggcagggtc a 21

<210> SEQ ID NO 169
<211> LENGTH: 21
<212> TYPE: DNA
<213> ORGANISM: Artificial Sequence
<220> FEATURE:
<223> OTHER INFORMATION: TRAC gRNA 21

<400> SEQUENCE: 169
tacacggcag ggtcagggtt c 21

<210> SEQ ID NO 170
<211> LENGTH: 21
<212> TYPE: DNA
<213> ORGANISM: Artificial Sequence
<220> FEATURE:
<223> OTHER INFORMATION: TRAC gRNA 23

<400> SEQUENCE: 170
ctttcaaaac ctgtcagtga t 21

<210> SEQ ID NO 171
<211> LENGTH: 21
<212> TYPE: DNA
<213> ORGANISM: Artificial Sequence
<220> FEATURE:
<223> OTHER INFORMATION: TRAC gRNA 25

<400> SEQUENCE: 171
tccgaatcct cctcctgaaa g 21

<210> SEQ ID NO 172
<211> LENGTH: 21
<212> TYPE: DNA
<213> ORGANISM: Artificial Sequence
<220> FEATURE:
<223> OTHER INFORMATION: TRAC gRNA 26

<400> SEQUENCE: 172
aatcctcctc ctgaaagtgg c 21

<210> SEQ ID NO 173
<211> LENGTH: 21
<212> TYPE: DNA
<213> ORGANISM: Artificial Sequence
<220> FEATURE:
<223> OTHER INFORMATION: TRAC gRNA 27

<400> SEQUENCE: 173
atcctcctcc tgaaagtggc c 21

<210> SEQ ID NO 174
<211> LENGTH: 21
<212> TYPE: DNA
<213> ORGANISM: Artificial Sequence
<220> FEATURE:
<223> OTHER INFORMATION: TRAC gRNA 29

<400> SEQUENCE: 174
ctgctcatga cgctgcggct g 21

<210> SEQ ID NO 175
<211> LENGTH: 21
<212> TYPE: DNA
<213> ORGANISM: Artificial Sequence
<220> FEATURE:
<223> OTHER INFORMATION: TRAC gRNA 30

<400> SEQUENCE: 175
agattaaacc cggccacttt c 21

<210> SEQ ID NO 176
<211> LENGTH: 21
<212> TYPE: DNA
<213> ORGANISM: Artificial Sequence
<220> FEATURE:
<223> OTHER INFORMATION: TRAC gRNA 31

<400> SEQUENCE: 176
aacccggcca ctttcaggag g 21

<210> SEQ ID NO 177
<211> LENGTH: 21
<212> TYPE: DNA
<213> ORGANISM: Artificial Sequence
<220> FEATURE:
<223> OTHER INFORMATION: TRAC gRNA 32

<400> SEQUENCE: 177
gccactttca ggaggaggat t 21

<210> SEQ ID NO 178

<211> LENGTH: 21
<212> TYPE: DNA
<213> ORGANISM: Artificial Sequence
<220> FEATURE:
<223> OTHER INFORMATION: B2M gRNA 1

<400> SEQUENCE: 178
tactctctct ttctggcctg g 21

<210> SEQ ID NO 179
<211> LENGTH: 21
<212> TYPE: DNA
<213> ORGANISM: Artificial Sequence
<220> FEATURE:
<223> OTHER INFORMATION: B2M gRNA 2

<400> SEQUENCE: 179
gcatactcat ctttttcagt g 21

<210> SEQ ID NO 180
<211> LENGTH: 21
<212> TYPE: DNA
<213> ORGANISM: Artificial Sequence
<220> FEATURE:
<223> OTHER INFORMATION: B2M gRNA 3

<400> SEQUENCE: 180
cgctactctc tctttctggc c 21

<210> SEQ ID NO 181
<211> LENGTH: 21
<212> TYPE: DNA
<213> ORGANISM: Artificial Sequence
<220> FEATURE:
<223> OTHER INFORMATION: B2M gRNA 4

<400> SEQUENCE: 181
gcgcgagcac agctaaggcc a 21

<210> SEQ ID NO 182
<211> LENGTH: 21
<212> TYPE: DNA
<213> ORGANISM: Artificial Sequence
<220> FEATURE:
<223> OTHER INFORMATION: B2M gRNA 6

<400> SEQUENCE: 182
gctcgcgcta ctctctcttt c 21

<210> SEQ ID NO 183
<211> LENGTH: 21
<212> TYPE: DNA
<213> ORGANISM: Artificial Sequence
<220> FEATURE:
<223> OTHER INFORMATION: B2M gRNA 7

<400> SEQUENCE: 183
agagtagcgc gagcacagct a 21

<210> SEQ ID NO 184
<211> LENGTH: 21
<212> TYPE: DNA
<213> ORGANISM: Artificial Sequence
<220> FEATURE:
<223> OTHER INFORMATION: B2M gRNA 15

<400> SEQUENCE: 184
tcacagccca agatagttaa g 21

<210> SEQ ID NO 185
<211> LENGTH: 21
<212> TYPE: DNA
<213> ORGANISM: Artificial Sequence
<220> FEATURE:
<223> OTHER INFORMATION: B2M gRNA 16

<400> SEQUENCE: 185
cacagcccaa gatagttaag t 21

<210> SEQ ID NO 186
<211> LENGTH: 21
<212> TYPE: DNA
<213> ORGANISM: Artificial Sequence
<220> FEATURE:
<223> OTHER INFORMATION: B2M gRNA 18

<400> SEQUENCE: 186
gacaaagtca catggttcac a 21

<210> SEQ ID NO 187
<211> LENGTH: 21
<212> TYPE: DNA
<213> ORGANISM: Artificial Sequence
<220> FEATURE:
<223> OTHER INFORMATION: B2M gRNA 19

<400> SEQUENCE: 187
aagtcacatg gttcacacgg c 21

<210> SEQ ID NO 188
<211> LENGTH: 21
<212> TYPE: DNA
<213> ORGANISM: Artificial Sequence
<220> FEATURE:
<223> OTHER INFORMATION: B2M gRNA 20

<400> SEQUENCE: 188
aggcatactc atctttttca g 21

<210> SEQ ID NO 189
<211> LENGTH: 21
<212> TYPE: DNA
<213> ORGANISM: Artificial Sequence
<220> FEATURE:
<223> OTHER INFORMATION: B2M gRNA 21

<400> SEQUENCE: 189
ggcatactca tctttttcag t 21

<210> SEQ ID NO 190
<211> LENGTH: 21
<212> TYPE: DNA
<213> ORGANISM: Artificial Sequence
<220> FEATURE:
<223> OTHER INFORMATION: B2M gRNA 22

<400> SEQUENCE: 190
catactcatc tttttcagtg g 21

<210> SEQ ID NO 191
<211> LENGTH: 21
<212> TYPE: DNA

<213> ORGANISM: Artificial Sequence
<220> FEATURE:
<223> OTHER INFORMATION: B2M gRNA 23

<400> SEQUENCE: 191
tcagtaagtc aacttcaatg t 21

<210> SEQ ID NO 192
<211> LENGTH: 21
<212> TYPE: DNA
<213> ORGANISM: Artificial Sequence
<220> FEATURE:
<223> OTHER INFORMATION: B2M gRNA 26

<400> SEQUENCE: 192
acgtgagtaa acctgaatct t 21

<210> SEQ ID NO 193
<211> LENGTH: 20
<212> TYPE: DNA
<213> ORGANISM: Artificial Sequence
<220> FEATURE:
<223> OTHER INFORMATION: ELANEg35_OMNI-50

<400> SEQUENCE: 193
agtccgggct gggagcgggt 20

<210> SEQ ID NO 194
<211> LENGTH: 20
<212> TYPE: DNA
<213> ORGANISM: Artificial Sequence
<220> FEATURE:
<223> OTHER INFORMATION: ELANEg38_OMNI-50

<400> SEQUENCE: 194
acagcgggtg tagactccga 20

<210> SEQ ID NO 195
<211> LENGTH: 20
<212> TYPE: DNA
<213> ORGANISM: Artificial Sequence
<220> FEATURE:
<223> OTHER INFORMATION: ELANEg39_OMNI-50

<400> SEQUENCE: 195
cagcgggtgt agactccgag 20

<210> SEQ ID NO 196
<211> LENGTH: 20
<212> TYPE: DNA
<213> ORGANISM: Artificial Sequence
<220> FEATURE:
<223> OTHER INFORMATION: ELANEg58_OMNI-50

<400> SEQUENCE: 196
gctgcgggaa agggattccc 20

<210> SEQ ID NO 197
<211> LENGTH: 20
<212> TYPE: DNA

-continued

```
<213> ORGANISM: Artificial Sequence
<220> FEATURE:
<223> OTHER INFORMATION: ELANEg62_OMNI-50

<400> SEQUENCE: 197

gtcaagcccc agaggccaca                                              20
```

CRISPR NUCLEASE

This application claims the benefit of U.S. Provisional Application Nos. 62/991,285 filed Mar. 18, 2020, 62/959,672 filed Jan. 10, 2020, 62/931,630 filed Nov. 6, 2019, 62/897,806 filed Sep. 9, 2019, and 62/841,046 filed Apr. 30, 2019, the contents of which are hereby incorporated by reference.

This application is a § 371 national stage of PCT International Application No. PCT/US2020/030782, filed Apr. 30, 2020, claiming the benefit of U.S. Provisional Application Nos. 62/991,285 filed Mar. 18, 2020, 62/959,672 filed Jan. 10, 2020, 62/931,630 filed Nov. 6, 2019, 62/897,806 filed Sep. 9, 2019, and 62/841,046 filed Apr. 30, 2019, the contents each of which are hereby incorporated by reference into the application.

REFERENCE TO SEQUENCE LISTING

This application incorporates-by-reference nucleotide sequences which are present in the file named "211028_91116-A-PCT-US_Substitute_Sequence_Listing_JMP.txt", which is 186 kilobytes in size, and which was created on Oct. 27, 2021 in the IBM-PC machine format, having an operating system compatibility with MS-Windows, which is contained in the text file filed Oct. 28, 2021 as part of this application.

FIELD OF THE INVENTION

The present invention is directed to, inter alia, composition and methods for genome editing.

BACKGROUND OF THE INVENTION

The Clustered Regularly Interspaced Short Palindromic Repeat (CRISPR) systems of bacterial and archaeal adaptive immunity show extreme diversity of protein composition and genomic loci architecture. The CRISPR systems have become important tools for research and genome engineering. Nevertheless, many details of CRISPR systems have not been determined and the applicability of CRISPR nucleases may be limited by sequence specificity requirements, expression, or delivery challenges. Different CRISPR nucleases have diverse characteristics such as: size, PAM site, on target activity, specificity, cleavage pattern (e.g. blunt, staggered ends), and prominent pattern of indel formation following cleavage. Different sets of characteristics may be useful for different applications. For example, some CRISPR nucleases may be able to target particular genomic loci that other CRISPR nucleases cannot due to limitations of the PAM site. In addition, some CRISPR nucleases currently in use exhibit pre-immunity, which may limit in vivo applicability. See Charlesworth et al., Nature Medicine (2019) and Wagner et al., Nature Medicine (2019). Accordingly, discovery, engineering, and improvement of novel CRISPR nucleases is of importance.

SUMMARY OF THE INVENTION

Disclosed herein are compositions and methods that may be utilized for genomic engineering, epigenomic engineering, genome targeting, genome editing of cells, and/or in vitro diagnostics.

The disclosed compositions may be utilized for modifying genomic DNA sequences. As used herein, genomic DNA refers to linear and/or chromosomal DNA and/or plasmid or other extrachromosomal DNA sequences present in the cell or cells of interest. In some embodiments, the cell of interest is a eukaryotic cell. In some embodiments, the cell of interest is a prokaryotic cell. In some embodiments, the methods produce double-stranded breaks (DSBs) at pre-determined target sites in a genomic DNA sequence, resulting in mutation, insertion, and/or deletion of a DNA sequence at the target site(s) in a genome.

Accordingly, in some embodiments, the compositions comprise a Clustered Regularly Interspaced Short Palindromic Repeat (CRISPR) nucleases. In some embodiments, the CRISPR nuclease is a CRISPR-associated protein.

In some embodiments, the compositions comprise a Clustered Regularly Interspaced Short Palindromic Repeats (CRISPR) nuclease having 100%, 99%, 98%, 97%, 96%, 95%, 94%, 93%, 92%, 91%, 90%, 85% identity to a CRISPR nuclease derived from *Ezakiella peruensis* strain M6.X2. Each possibility represents a separate embodiment.

OMNI-50™ Nuclease

Embodiments of the present invention provide for a CRISPR nuclease designated as an "OMNI-50™" nuclease (i.e. SEQ ID NO: 3), as provided in Table 1.

This invention provides a method of modifying a nucleotide sequence at a target site in the genome of a mammalian cell comprising introducing into the cell (i) a composition comprising a CRISPR nuclease having at least 95% identity to an amino acid sequence of SEQ ID NO: 3 or a nucleic acid molecule comprising a sequence encoding a CRISPR nuclease which sequence has at least 95% identity to the nucleic acid sequence of SEQ ID NOs: 12 or 13 and (ii) a DNA-targeting RNA molecule, or a DNA polynucleotide encoding a DNA-targeting RNA molecule, comprising a nucleotide sequence that is complementary to a sequence in the target DNA.

This invention also provides a non-naturally occurring composition comprising a CRISPR associated system comprising:

a) one or more RNA molecules comprising a guide sequence portion linked to a direct repeat sequence, wherein the guide sequence is capable of hybridizing with a target sequence, or one or more nucleotide sequences encoding the one or more RNA molecules; and
b) a CRISPR nuclease comprising an amino acid sequence having at least 95% identity to the amino acid sequence of SEQ ID NO: 3 or a nucleic acid molecule comprising a sequence encoding the CRISPR nuclease; and wherein the one or more RNA molecules hybridize to the target sequence, wherein the target sequence is 3' of a Protospacer Adjacent Motif (PAM), and the one or more RNA molecules form a complex with the RNA-guided nuclease.

This invention also provides a non-naturally occurring composition comprising:

a) a CRISPR nuclease comprising a sequence having at least 95% identity to the amino acid sequence of SEQ ID NO: 3 or a nucleic acid molecule comprising a sequence encoding the CRISPR nuclease; and
b) one or more RNA molecules, or one or more DNA polynucleotide encoding the one or more RNA molecules, comprising at least one of:
   i) a nuclease-binding RNA nucleotide sequence capable of interacting with/binding to the CRISPR nuclease; and ii) a DNA-targeting RNA nucleotide sequence comprising a sequence complementary to a sequence in a target DNA sequence, wherein the CRISPR nuclease is capable of complexing with the one or more RNA molecules to form a complex capable of hybridizing with the target DNA sequence.

BRIEF DESCRIPTION OF THE DRAWINGS

FIG. 5A: Activity assay of OMNI-50™ RNP with different spacer lengths (17-23 bps) of guide 35 (Table 10). FIG. 5B: Decreasing amounts of RNPs (4 μmol, 2 μmol, 1.2 μmol, 0.6 pmol and 0.2 μmol) with spacer lengths 20-23 nts were incubated with 100 ng DNA target template. FIG. 5C: Activity assay for OMNI-50™ as RNP in U2OS cells: RNPs with spacer lengths 17-23 bps were electroporated into U2OS cell line and editing levels (indels) measured by NGS. FIG. 5D: Activity assay for OMNI-50™ as RNP in U2OS cells: RNPs with ELANE g35 sgRNA V1-V4 were electroporated into U2OS cell line and editing levels (indels) measured by NGS.

DETAILED DESCRIPTION

Figure 1A:
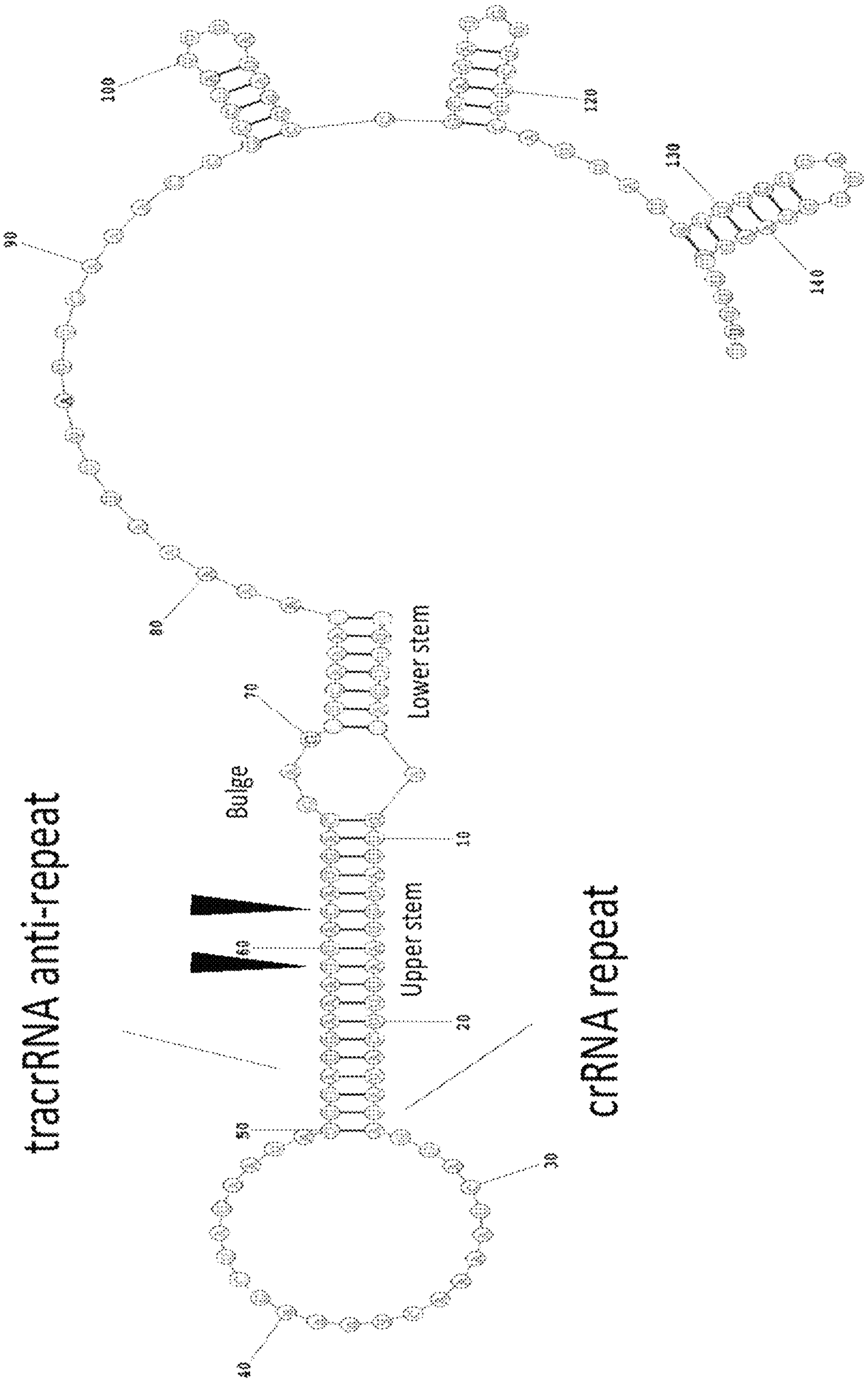
FIG. 1A: An example of the predicted secondary structures of the full duplex RNA elements (crRNA:tracrRNA chimera) used for identification of possible elements in the design of sgRNAs for each nuclease.

According to some aspects of the invention, the disclosed compositions comprise a Clustered Regularly Interspaced Short Palindromic Repeats (CRISPR) nuclease and/or a nucleic acid molecule comprising a sequence encoding the same.

In some embodiments, the CRISPR nuclease comprises an amino acid sequence having at least 100%, 99%, 98%, 97%, 96%, 95%, 94%, 93%, 92%, 91%, 90%, 89%, 88%, 87%, 86%, 85%, 84%, 83%, or 82% amino acid sequence identity to a CRISPR nuclease as set forth as SEQ ID NO: 3. In an embodiment the sequence encoding the CRISPR nuclease has at least 95% identity to a nucleic acid sequence selected from the group consisting of SEQ ID NOs: 11-13.

In some embodiments, the CRISPR nuclease comprises an amino acid sequence having at least 100%, 99%, 98%, 97%, 96%, 95%, 94%, 93%, 92%, 91%, 90%, 89%, 88%, 87%, 86%, 85%, 84%, 83%, 82%, 81%, 80%, 75% amino acid sequence identity to a CRISPR nucleases derived from *Ezakiella peruensis* strain M6.X2. Each possibility represents a separate embodiment.

According to some aspects of the invention, the disclosed compositions comprise DNA constructs or a vector system comprising nucleotide sequences that encode the CRISPR nuclease or variant CRISPR nuclease. In some embodiments, the nucleotide sequence that encode the CRISPR nuclease or variant CRISPR nuclease is operably linked to a promoter that is operable in the cells of interest. In some embodiments, the cell of interest is a eukaryotic cell. In some embodiments the cell of interest is a mammalian cell. In some embodiments, the nucleic acid sequence encoding the engineered CRISPR nuclease is codon optimized for use in cells from a particular organism. In some embodiments, the nucleic acid sequence encoding the nuclease is codon optimized for *E. coli*. In some embodiments, the nucleic acid sequence encoding the nuclease is codon optimized for eukaryotic cells. In some embodiments, the nucleic acid sequence encoding the nuclease is codon optimized for mammalian cells.

In some embodiments, the composition comprises a recombinant nucleic acid, comprising a heterologous promoter operably linked to a polynucleotide encoding a CRISPR enzyme having at least 100%, 99%, 98%, 97%, 96%, 95%, 94%, 93%, 92%, 91%, 90% identity to SEQ ID NO: 3. Each possibility represents a separate embodiment.

In an embodiment of the composition, the CRISPR nuclease has at least 75%, 80%, 85, 90%, 95%, or 97% identity to the amino acid sequence as set forth in SEQ ID NO: 3 or the sequence encoding the CRISPR nuclease has at least a 75%, 80%, 85, 90%, 95%, or 97% sequence identity to a nucleotide sequence selected from the group consisting of SEQ ID NOs: 11, 12, and 13.

According to some embodiments, there is provided an engineered or non-naturally occurring composition comprising a CRISPR nuclease comprising a sequence having at least 100%, 99%, 98%, 97%, 96%, 95%, 94%, 93%, 92%, 91%, 90%, 85%, 80% identity to the amino acid sequence of SEQ ID NO: 3 or a nucleic acid molecule comprising a sequence encoding the CRISPR nuclease. Each possibility represents a separate embodiment.

In an embodiment, the CRISPR nuclease is engineered or non-naturally occurring. The CRISPR nuclease may also be recombinant. Such CRISPR nucleases are produced using laboratory methods (molecular cloning) to bring together genetic material from multiple sources, creating sequences that would not otherwise be found in biological organisms.

In an embodiment, the CRISPR nuclease of the invention exhibits increased specificity to a target site compared to a SpCas9 nuclease when complexed with the one or more RNA molecules.

In an embodiment, the complex of the CRISPR nuclease of the invention and one or more RNA molecules exhibits at least maintained on-target editing activity of the target site and reduced off-target activity compared to SpCas9 nuclease.

In an embodiment, the CRISPR nuclease further comprises an RNA-binding portion capable of interacting with a DNA-targeting RNA molecule (gRNA) and an activity portion that exhibits site-directed enzymatic activity.

In an embodiment, the composition further comprises a DNA-targeting RNA molecule or a DNA polynucleotide encoding a DNA-targeting RNA molecule, wherein the DNA-targeting RNA molecule comprises a nucleotide sequence that is complementary to a sequence in a target region, wherein the DNA-targeting RNA molecule and the CRISPR nuclease do not naturally occur together.

In an embodiment, the DNA-targeting RNA molecule comprises a crRNA repeat sequence which comprises the sequence GUUUGAGAG.

In an embodiment, the DNA-targeting RNA molecule comprises a tracrRNA sequence which comprises one or more sequences selected from SEQ ID NOs: 41-43 and SEQ ID NOs: 149-154.

In an embodiment, the DNA-targeting RNA molecule further comprises a nucleotide sequence that can form a complex with a CRISPR nuclease.

This invention also provides a non-naturally occurring composition comprising a CRISPR associated system comprising:

a) one or more RNA molecules comprising a guide sequence portion linked to a direct repeat sequence, wherein the guide sequence is capable of hybridizing with a target sequence, or one or more nucleotide sequences encoding the one or more RNA molecules; and
b) a CRISPR nuclease comprising an amino acid sequence having at least 95% identity to the amino acid sequence of SEQ ID NO: 3 or a nucleic acid molecule comprising a sequence encoding the CRISPR nuclease;

wherein the one or more RNA molecules hybridize to the target sequence, wherein the target sequence is 3' of a Protospacer Adjacent Motif (PAM), and the one or more RNA molecules form a complex with the RNA-guided nuclease.

In an embodiment, the composition further comprises an RNA molecule comprising a nucleotide sequence that can form a complex with a CRISPR nuclease (tracrRNA) or a DNA polynucleotide comprising a sequence encoding an RNA molecule that can form a complex with the CRISPR nuclease.

In an embodiment, the composition further comprises a donor template for homology directed repair (HDR).

In an embodiment, the composition is capable of editing the target region in the genome of a cell.

In an embodiment of the composition the CRISPR nuclease has at least 100%, 99%, 98%, 97%, 96%, 95%, 94%, 93%, 92%, 91%, 90%, 85%, 80% identity to SEQ ID NO: 3, and the nucleotide sequence that can form a complex with the CRISPR nuclease in the DNA-targeting RNA molecule comprises a sequence selected from SEQ ID NOs: 37-45, 87-88, 149-154, and GUUUGAGAG.

According to some embodiments, there is provided a non-naturally occurring composition comprising:

(a) a CRISPR nuclease, or a polynucleotide encoding the CRISPR nuclease, comprising:
  an RNA-binding portion; and
  an activity portion that exhibits site-directed enzymatic activity, wherein the CRISPR nuclease has at least 100%, 99%, 98%, 97%, 96%, 95%, 94%, 93%, 92%, 91%, 90%, 85%, 80% identity to SEQ ID NO: 3; and
(b) one or more RNA molecules or a DNA polynucleotide encoding the one or more RNA molecules comprising:
  i) a DNA-targeting RNA sequence, comprising a nucleotide sequence that is complementary to a sequence in a target DNA sequence; and
  ii) a protein-binding RNA sequence, capable of interacting with the RNA-binding portion of the CRISPR nuclease, wherein the DNA targeting RNA sequence and the CRISPR nuclease do not naturally occur together. Each possibility represents a separate embodiment.

In some embodiments, there is provided a single RNA molecule comprising the DNA-targeting RNA sequence and the protein-binding RNA sequence, wherein the RNA molecule can form a complex with the CRISPR nuclease and serve as the DNA targeting module. In some embodiments, the RNA molecule has a length of up to 1000 bases, 900 bases, 800 bases, 700 bases, 600 bases, 500 bases, 400 bases, 300 bases, 200 bases, 100 bases, 50 bases. Each possibility represents a separate embodiment. In some embodiments, a first RNA molecule comprising the DNA-targeting RNA sequence and a second RNA molecule comprising the protein-binding RNA sequence interact by base pairing or alternatively fused together to form one or more RNA molecules that complex with the CRISPR nuclease and serve as the DNA targeting module.

In some embodiments, the CRISPR nuclease has at least 100%, 99%, 98%, 97%, 96%, 95%, 94%, 93%, 92%, 91%, 90%, 85%, 80% identity to SEQ ID NO: 3, and the RNA molecule comprises a sequence selected from SEQ ID NOs: 37-45, 87-88, 149-154 and GUUUGAGAG.

This invention also provides a non-naturally occurring composition comprising:

a) a CRISPR nuclease comprising a sequence having at least 95% identity to the amino acid sequence of SEQ ID NO: 3 or a nucleic acid molecule comprising a sequence encoding the CRISPR nuclease; and b) one or more RNA molecules, or one or more DNA polynucleotide encoding the one or more RNA molecules, comprising at least one of:

i) a nuclease-binding RNA nucleotide sequence capable of interacting with/binding to the CRISPR nuclease; and ii) a DNA-targeting RNA nucleotide sequence comprising a sequence complementary to a sequence in a target DNA sequence, wherein the CRISPR nuclease is capable of complexing with the one or more RNA molecules to form a complex capable of hybridizing with the target DNA sequence.

In an embodiment, the CRISPR nuclease and the one or more RNA molecules form a CRISPR complex that is capable of binding to the target DNA sequence to effect cleavage of the target DNA sequence.

In an embodiment, the CRISPR nuclease and at least one of the one or more RNA molecules do not naturally occur together.

In an embodiment:

a) the CRISPR nuclease comprises an RNA-binding portion and an activity portion that exhibits site-directed enzymatic activity;

b) the DNA-targeting RNA nucleotide sequence comprises a nucleotide sequence that is complementary to a sequence in a target DNA sequence; and c) the nuclease-binding RNA nucleotide sequence comprises a sequence that interacts with the RNA-binding portion of the CRISPR nuclease.

In an embodiment, the nuclease-binding RNA nucleotide sequence and the DNA-targeting RNA nucleotide sequence are on a single guide RNA molecule (sgRNA), wherein the sgRNA molecule can form a complex with the CRISPR nuclease and serve as the DNA targeting module.

In an embodiment, the nuclease-binding RNA nucleotide sequence is on a first RNA molecule and the DNA-targeting RNA nucleotide sequence is on a single guide RNA molecule, and wherein the first and second RNA sequence interact by base-pairing or are fused together to form one or more RNA molecules or sgRNA that complex with the CRISPR nuclease and serve as the targeting module.

In an embodiment, the sgRNA has a length of up to 1000 bases, 900 bases, 800 bases, 700 bases, 600 bases, 500 bases, 400 bases, 300 bases, 200 bases, 100 bases, 50 bases.

In an embodiment, the composition further comprises a donor template for homology directed repair (HDR).

In some embodiments, (a) the CRISPR nuclease has at least 100%, 99%, 98%, 97%, 96%, 95%, 94%, 93%, 92%, 91%, 90%, 85%, 80% identity to SEQ ID NO: 3, or (b) the nucleic acid molecule comprising a sequence encoding the CRISPR nuclease comprises a sequence of at least a 95% sequence identity to the nucleic acid sequence as set forth in SEQ ID NO: 11, 12, or 13, and the PAM is NGG. Non-limiting examples of suitable PAM sequences include: GGG, AGG, and TGG. In this embodiment, the nucleotide sequence that can form a complex with the CRISPR nuclease in the DNA-targeting RNA molecule comprises a sequence selected from SEQ ID NOs: 37-45, 87-88, 149-154 and GUUUGAGAG.

In some embodiments, the CRISPR nuclease utilizes a PAM having a sequence of NAG or NGA.

In an embodiment, the CRISPR nuclease comprises 1-10, 10-20, 20-30, 30-40, 40-50, 50-60, 60-70, 70-80, 80-90, 90-100, 100-110, 110-120, 120-130, 130-140, or 140-150 amino acid substitutions, deletions, and/or insertions compared to the amino acid sequence of the wild-type of the CRISPR nuclease.

In an embodiment, the CRISPR nuclease exhibits at least 2%, 5%, 7% 10%, 15%, 20%, 25%, 30%, or 35% increased specificity compared the wild-type of the CRISPR nuclease.

In an embodiment, the CRISPR nuclease exhibits at least 2%, 5%, 7% 10%, 15%, 20%, 25%, 30%, or 35% increased activity compared the wild-type of the CRISPR nuclease.

In an embodiment, the CRISPR nuclease has altered PAM specificity compared to the wild-type of the CRISPR nuclease.

In an embodiment, the CRISPR nuclease is non-naturally occurring.

In an embodiment, the CRISPR nuclease is engineered and comprises unnatural or synthetic amino acids.

In an embodiment, the CRISPR nuclease is engineered and comprises one or more of a nuclear localization sequences (NLS), cell penetrating peptide sequences, and/or affinity tags.

In an embodiment, the CRISPR nuclease comprises one or more nuclear localization sequences of sufficient strength to drive accumulation of a CRISPR complex comprising the CRISPR nuclease in a detectable amount in the nucleus of a eukaryotic cell.

This invention also provides a method of modifying a nucleotide sequence at a target site in a cell-free system or the genome of a cell comprising introducing into the cell any of the compositions of the invention.

In an embodiment, the cell is a eukaryotic cell.

In another embodiment, the cell is a prokaryotic cell.

In some embodiments, the one or more RNA molecules further comprises an RNA sequence comprising a nucleotide molecule that can form a complex with the RNA nuclease (tracrRNA) or a DNA polynucleotide encoding an RNA molecule comprising a nucleotide sequence that can form a complex with the CRISPR nuclease.

In an embodiment, the CRISPR nuclease comprises 1, 2, 3, 4, 5, 6, 7, 8, 9, 10, or more NLSs at or near the amino-terminus, 1, 2, 3, 4, 5, 6, 7, 8, 9, 10, or more NLSs at or near carboxy-terminus, or a combination of 1, 2, 3, 4, 5, 6, 7, 8, 9, 10, or more NLSs at or near the amino-terminus and 1, 2, 3, 4, 5, 6, 7, 8, 9, 10, or more NLSs at or near carboxy-terminus. In an embodiment 1-4 NLSs are fused with the CRISPR nuclease. In an embodiment, an NLS is located within the open-reading frame (ORF) of the CRISPR nuclease.

Methods of fusing an NLS at or near the amino-terminus, at or near carboxy-terminus, or within the ORF of an expressed protein are well known in the art. As an example, to fuse an NLS to the amino-terminus of a CRISPR nuclease, the nucleic acid sequence of the NLS is placed immediately after the start codon of the CRISPR nuclease on the nucleic acid encoding the NLS-fused CRISPR nuclease. Conversely, to fuse an NLS to the carboxy-terminus of a CRISPR nuclease the nucleic acid sequence of the NLS is placed after the codon encoding the last amino acid of the CRISPR nuclease and before the stop codon.

Any combination of NLSs, cell penetrating peptide sequences, and/or affinity tags at any position along the ORF of the CRISPR nuclease is contemplated in this invention.

The amino acid sequences and nucleic acid sequences of the CRISPR nucleases provided herein may include NLS and/or TAGs inserted so as to interrupt the contiguous amino acid or nucleic acid sequences of the CRISPR nucleases.

In an embodiment, the one or more NLSs are in tandem repeats.

In an embodiment, the one or more NLSs are considered in proximity to the N- or C-terminus when the nearest amino acid of the NLS is within about 1, 2, 3, 4, 5, 10, 15, 20, 25, 30, 40, 50, or more amino acids along the polypeptide chain from the N- or C-terminus.

As discussed, the CRISPR nuclease may be engineered to comprise one or more of a nuclear localization sequences (NLS), cell penetrating peptide sequences, and/or affinity tags.

In an embodiment, the CRISPR nuclease exhibits increased specificity to a target site compared to the wild-type of the CRISPR nuclease when complexed with the one or more RNA molecules.

In an embodiment, the complex of the CRISPR nuclease and one or more RNA molecules exhibits at least maintained on-target editing activity of the target site and reduced off-target activity compared to the wild-type of the CRISPR nuclease.

In an embodiment, the composition further comprises a recombinant nucleic acid molecule comprising a heterologous promoter operably linked to the nucleotide acid molecule comprising the sequence encoding the CRISPR nuclease.

In an embodiment, the CRISPR nuclease or nucleic acid molecule comprising a sequence encoding the CRISPR nuclease is non-naturally occurring or engineered.

This invention also provides a non-naturally occurring or engineered composition comprising a vector system comprising the nucleic acid molecule comprising a sequence encoding any of the CRISPR nucleases of the invention.

This invention also provides use of any of the compositions of the invention for the treatment of a subject afflicted with a disease associated with a genomic mutation comprising modifying a nucleotide sequence at a target site in the genome of the subject.

This invention provides a method of modifying a nucleotide sequence at a target site in the genome of a mammalian cell comprising introducing into the cell (i) a composition comprising a CRISPR nuclease having at least 95% identity to the amino acid sequence of SEQ ID NO: 3 or a nucleic acid molecule comprising a sequence encoding a CRISPR nuclease which sequence has at least 95% identity to a nucleic acid sequence selected from the group consisting of SEQ ID NOs: 12 or 13 and (ii) a DNA-targeting RNA molecule, or a DNA polynucleotide encoding a DNA-targeting RNA molecule, comprising a nucleotide sequence that is complementary to a sequence in the target DNA.

In some embodiments, the method is performed ex vivo. In some embodiments, the method is performed in vivo. In some embodiments, some steps of the method are performed ex vivo and some steps are performed in vivo. In some embodiments the mammalian cell is a human cell.

In an embodiment, the method further comprises introducing into the cell: (iii) an RNA molecule comprising a nuclease-binding RNA sequence or a DNA polynucleotide encoding an RNA molecule comprising a nuclease-binding RNA that interacts with the CRISPR nuclease.

In an embodiment, the DNA targeting RNA molecule is a crRNA molecule suitable to form an active complex with the CRISPR nuclease.

In an embodiment, the RNA molecule comprising a nuclease-binding RNA sequence is a tracrRNA molecule suitable to form an active complex with the CRISPR nuclease.

In an embodiment, the DNA-targeting RNA molecule and the RNA molecule comprising a nuclease-biding RNA sequence are fused in the form of a single guide RNA molecule.

In an embodiment, the method further comprises introducing into the cell: (iv) an RNA molecule comprising a sequence complementary to a protospacer sequence.

In an embodiment, the CRISPR nuclease forms a complex with the one or more RNA molecules and effects a double strand break in the 3' of a Protospacer Adjacent Motif (PAM).

In an embodiment, the CRISPR nuclease forms a complex with the one or more RNA molecules and effects a double strand break in the 5' of a Protospacer Adjacent Motif (PAM).

In some embodiments, (a) the CRISPR nuclease has at least 100%, 99%, 98%, 97%, 96%, 95%, 94%, 93%, 92%, 91%, 90%, 85%, 80% identity to SEQ ID NO: 3, or (b) the nucleic acid molecule comprising a sequence encoding the CRISPR nuclease comprises a sequence of at least a 95% sequence identity to the nucleic acid sequence as set forth in SEQ ID NO: 11, 12, or 13, and the PAM is NGG. Non-limiting examples of suitable PAM sequences include: GGG, AGG, and TGG. In this embodiment, the nucleotide sequence that can form a complex with the CRISPR nuclease in the DNA-targeting RNA molecule comprises a sequence selected from SEQ ID NOs: 37-45, 87-88, 149-154 and GUUUGAGAG.

In some embodiments, the CRISPR nuclease utilizes a PAM having a sequence of NAG or NGA.

In an embodiment of any of the methods described herein, the method is for treating a subject afflicted with a disease associated with a genomic mutation comprising modifying a nucleotide sequence at a target site in the genome of the subject.

In an embodiment, the method comprises first selecting a subject afflicted with a disease associated with a genomic mutation and obtaining the cell from the subject.

This invention also provides a modified cell or cells obtained by any of the methods described herein. In an embodiment these modified cell or cells are capable of giving rise to progeny cells. In an embodiment these modified cell or cells are capable of giving rise to progeny cells after engraftment.

This invention also provides a composition comprising these modified cells and a pharmaceutically acceptable carrier. Also provided is an in vitro or ex vivo method of preparing this, comprising mixing the cells with the pharmaceutically acceptable carrier.

DNA-Targeting RNA Molecules

In embodiments of the present invention, the DNA-targeting RNA sequence comprises a guide sequence portion. The "guide sequence portion" of an RNA molecule refers to a nucleotide sequence that is capable of hybridizing to a specific target DNA sequence, e.g., the guide sequence portion has a nucleotide sequence which is fully complementary to the DNA sequence being targeted along the length of the guide sequence portion. In some embodiments, the guide sequence portion is 17, 18, 19, 20, 21, 22, 23, or 24 nucleotides in length, or approximately 17-24, 18-22, 19-22, 18-20, 17-20, or 21-22 nucleotides in length. The entire length of the guide sequence portion is fully complementary to the DNA sequence being targeted along the length of the guide sequence portion. The guide sequence portion may be part of an RNA molecule that can form a complex with a CRISPR nuclease with the guide sequence portion serving as the DNA targeting portion of the CRISPR complex. When the RNA molecule having the guide sequence portion is present contemporaneously with the CRISPR molecule, the RNA molecule is capable of targeting the CRISPR nuclease to the specific target DNA sequence. Each possibility represents a separate embodiment. An RNA molecule can be custom designed to target any desired sequence.

In embodiments of the present invention, the CRISPR nuclease has greater cleavage activity when used with an RNA molecule comprising a guide sequence portion having 21-23 nucleotides, compared to its cleavage activity when used with an RNA molecule comprising a guide sequence portion having 20 or fewer nucleotides, and/or 24 or more nucleotides. In embodiments of the present invention, the CRISPR nuclease has greater cleavage activity when used with an RNA molecule comprising a guide sequence portion having 21-22 nucleotides, compared to its cleavage activity when used with an RNA molecule comprising a guide sequence portion having 20 or fewer nucleotides, and/or 23 or more nucleotides. In an embodiment, the CRISPR nuclease has its greatest cleavage activity when used with an RNA molecule comprising a guide sequence portion having 22 nucleotides.

In an embodiment, such a CRISPR nuclease has at least 95% identity to the amino acid sequence as set forth in SEQ ID NO: 3 or the sequence encoding the CRISPR nuclease has at least a 95% sequence identity to any of SEQ ID NOs: 11-13. In an embodiment, such a CRISPR nuclease has at least 100%, 99.5%, 99%, 98%, 97%, 96%, 95%, 94%, 93%, 92%, 91%, 90%, 89%, 88%, 87%, 86%, 85%, 84%, 83%, or 82% identity to the amino acid sequence as set forth in SEQ ID NO: 3 or the sequence encoding the CRISPR nuclease has at least a 100%, 99%, 98%, 97%, 96%, 95%, 94%, 93%, 92%, 91%, 90%, 89%, 88%, 87%, 86%, 85%, 84%, 83%, or 82% sequence identity to any of SEQ ID NOs: 11-13.

Figure 8:
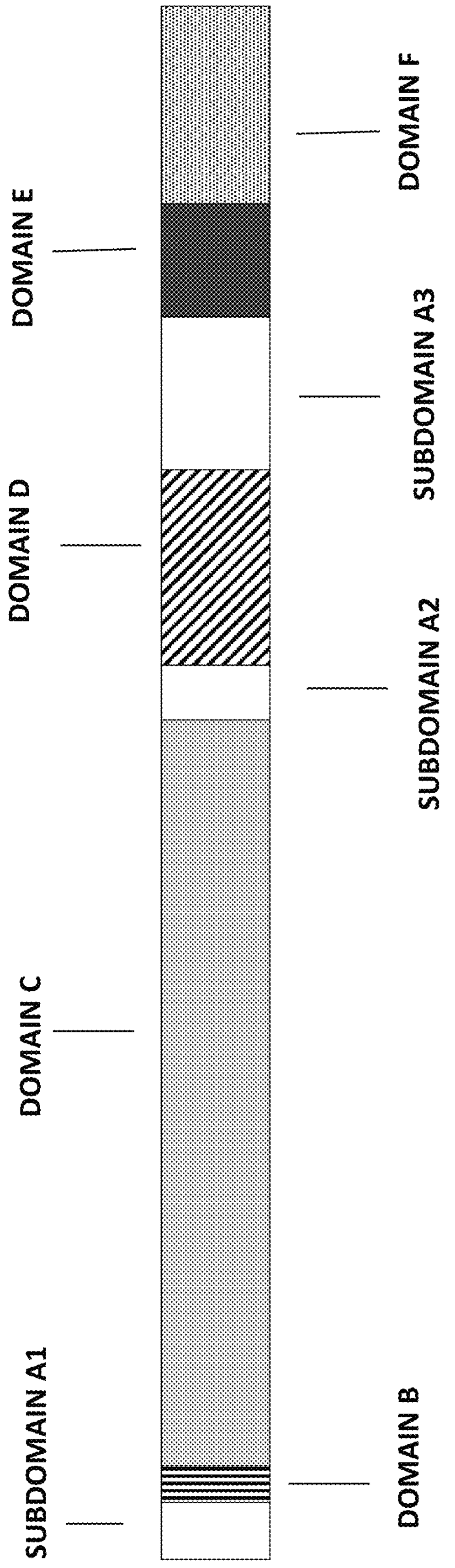
FIG. 8: Schematic representation of the OMNI-50™ nuclease. The OMNI-50™ nuclease comprises several functional domains, represented in the schematic as Domains A-F. Domain A comprises three subdomains, A1, A2, and A3, and is represented in the schematic as white boxes. Domain B is represented in the schematic with horizontal stripes. Domain C comprises three subdomains, C1, C2, and C3, and is represented in the schematic as a lightly shaded box. Domain B is represented in the schematic with diagonal stripes. Domain E is represented in the schematic as a dark shaded box. Domain F is represented in the schematic as a dotted box.

The characteristic targeted nuclease activity of a CRISPR nuclease is imparted by the various functions of its specific domains. In this application the OMNI-50™ domains are defined as Domain A, Domain B, Domain C, Domain D, Domain E, and Domain F as presented in the FIG. 8 OMNI-50™ schematic.

As used herein, Domain A comprises three subdomains: Subdomain A1, Subdomain A2, and Subdomain A3. As used herein, Subdomain A1 begins at an amino acid position within 1-10 and ends at an amino acid position within 45-55 of SEQ ID NO: 3; Subdomain A2 begins at an amino acid position within 736-746 and ends at an amino acid position within 784-794 of SEQ ID NO: 3; and Subdomain A3 begins at an amino acid position within 957-967 and ends at an amino acid position within 1091-1101 of SEQ ID NO: 3. Based on a preferred analysis of a local alignment generated using the Smith-Waterman algorithm, in an embodiment Subdomain A1 has been identified as amino acids 1 to 50 of SEQ ID NO: 3, Subdomain A2 has been identified as amino acids 741 to 789 of SEQ ID NO: 3, and Subdomain A3 has been identified as amino acids 962 to 1096 of SEQ ID NO: 3.

As used herein, Domain B begins at an amino acid position within 46-56 and ends at an amino acid position within 78-88 of SEQ ID NO: 3. Based on a preferred analysis of a local alignment generated using the Smith-Waterman algorithm, in an embodiment Domain B has been identified as amino acids 51 to 83 of SEQ ID NO: 3.

As used herein, Domain C comprises three subdomains: Subdomain C1, Subdomain C2, and Subdomain C3, or alternatively two subdomains: Subdomain Ca and Subdomain Cb. As used herein, Subdomain C1 begins at an amino acid position within 79-89 and ends at an amino acid position within 155-165 of SEQ ID NO: 3; Subdomain C2 begins at an amino acid position within 156-166 and ends at an amino acid position within 294-304 of SEQ ID NO: 3; and Subdomain C3 begins at an amino acid position within 295-305 and ends at an amino acid position within 732-742 of SEQ ID NO: 3. Based on a preferred analysis of a local alignment generated using the Smith-Waterman algorithm, in an embodiment Subdomain C1 has been identified as amino acids 84-160 of SEQ ID NO: 3, Subdomain C2 has been identified as amino acids 161-299 of SEQ ID NO: 3, and Subdomain C3 has been identified as amino acids 300-737 of SEQ ID NO: 3. As used herein, Subdomain Ca begins at an amino acid position within 79-89 and ends at an amino acid position within 473-483 of SEQ ID NO: 3; and Subdomain Cb begins at an amino acid position within 474-484 and ends at an amino acid position within 732-742 of SEQ ID NO: 3. Based on an analysis of a local alignment generated using the Smith-Waterman algorithm, in an embodiment Subdomain Ca has been identified as amino acids 84-478 of SEQ ID NO: 3 and Subdomain Cb has been identified as amino acids 479-737 of SEQ ID NO: 3.

As used herein, Domain D begins at an amino acid position within 785-795 and ends at an amino acid position within 956-966 of SEQ ID NO: 3. Based on a preferred analysis of a local alignment generated using the Smith-Waterman algorithm, in an embodiment Domain D has been identified as amino acids 790 to 961 of SEQ ID NO: 3.

As used herein, Domain E begins at an amino acid position within 1092-1102 and ends at an amino acid position within 1191-1201 of SEQ ID NO: 3. Based on a preferred analysis of a local alignment generated using the Smith-Waterman algorithm, in an embodiment Domain E has been identified as amino acids 1097 to 1196 of SEQ ID NO: 3.

As used herein, Domain F begins at an amino acid position within 1192-1202 and ends at an amino acid position within 1360-1370 of SEQ ID NO: 3. Based on a preferred analysis of a local alignment generated using the Smith-Waterman algorithm, in an embodiment Domain F has been identified as amino acids 1197 to 1370 of SEQ ID NO: 3.

The activity of each OMNI-50™ nuclease domain is described herein, with each domain activity providing aspects of the advantageous features of the nuclease.

Specifically, OMNI-50™ Domain A and contains a nuclease active site that participates in DNA strand cleavage. Domain A cleaves a DNA strand that a targeting RNA molecule binds at a DNA target site.

Domain B is involved in initiating DNA cleavage activity upon OMNI-50™ binding to a target a DNA site.

Domain C binds a targeting RNA molecule and participates in providing specificity for target site recognition. Domain C comprises Subdomain C1, Subdomain C2, and Subdomain C3, which each participate in specific functional aspects of Domain C activity. For example, C3 is involved in sensing a DNA target site; C2 is involved in regulating the activation of a nuclease domain (e.g. Domain D); and C1 is involved in locking the nuclease domain at the target site. Accordingly, Domain C participates in controlling cleavage of off-target sequences.

Domain D contains a nuclease active site that participates in DNA strand cleavage. Domain D cleaves a DNA strand that is displaced by a targeting RNA molecule binding at a DNA target site.

Domain E is structurally similar to a topoisomerase domain.

Domain F is involved in providing PAM site specificity, including aspects of PAM site interrogation and recognition.

Further description of other CRISPR nuclease domains and their general functions can be found in, inter alia, Mir et al., ACS Chem. Biol. (2019), Palermo et al., Quarterly Reviews of Biophysics (2018), Jiang and Doudna, Annual Review of Biophysics (2017), Nishimasu et al., Cell (2014) and Nishimasu et al., Cell (2015), incorporated herein by reference.

In one aspect of the invention, an amino acid sequence having similarity to an OMNI-50™ domain or subdomain may be utilized in the design and manufacture of a non-naturally occurring peptide, e.g. a CRISPR nuclease, such that the peptide displays the advantageous feature of the OMNI-50™ domain or subdomain activity.

In an embodiment, such a peptide, e.g. a CRISPR nuclease, comprises an amino acid sequence that has at least 100%, 99.5%, 99%, 98%, 97%, 96%, 95%, 94%, 93%, 92%, 91%, 90%, 89%, 88%, 87%, 86%, 85%, 84%, 83%, or 82% identity to the amino acid sequence of at least one of Domain A or any one of its three subdomains, Domain B, Domain C or any one of its three subdomains, Domain D, Domain E, or Domain F of the OMNI-50™ nuclease. In an embodiment, the peptide exhibits extensive amino acid variability relative to the full length OMNI-50™ amino acid sequence (SEQ ID NO: 3) outside of the peptide amino acid sequence having at least 100%, 99.5%, 99%, 98%, 97%, 96%, 95%, 94%, 93%, 92%, 91%, 90%, 89%, 88%, 87%, 86%, 85%, 84%, 83%, or 82% identity to the amino acid sequence of at least one of Domain A or any one of its three subdomains, Domain B, Domain C or any one of its three subdomains, Domain D, Domain E, or Domain F of the OMNI-50™ nuclease. In an embodiment, the peptide comprises an intervening amino acid sequence between two domain sequences. In an embodiment, the intervening amino acid sequence is 1-10, 10-20, 20-40, 40-50 or up to 100 amino acids in length. In an embodiment, the intervening sequence is a linker sequence.

In one aspect of the invention, an amino acid sequence encoding any one of the domains of the OMNI-50™ nuclease described herein in the peptide may comprise one or more amino acid substitutions relative to the original OMNI-50™ domain sequence. The amino acid substitution may be a conservative substitution, i.e. substitution for an amino acid having similar chemical properties as the original amino acid. For example, a positively charged amino acid may be substituted for an alternate positively charged amino acid, e.g. an arginine residue may be substituted for a lysine residue, or a polar amino acid may be substituted for a different polar amino acid. Conservative substitutions are more tolerable, and the amino acid sequence encoding any one of the domains of the OMNI-50™ nuclease may contain as many as 10% of such substitutions. The amino acid substitution may be a radical substitution, i.e. substitution for an amino acid having different chemical properties as the original amino acid. For example, a positively charged amino acid may be substituted for a negatively charged amino acid, e.g. an arginine residue may be substituted for a glutamic acid residue, or a polar amino acid may be substituted for a non-polar amino acid. The amino acid substitution may be a semi-conservative substitution, or the amino acid substitution may be to any other amino acid. The substitution may alter the activity relative to the original OMNI-50™ domain function e.g. reduce catalytic nuclease activity.

According to some aspects of the invention, the disclosed compositions comprise a non-naturally occurring composition comprising a CRISPR nuclease, wherein the CRISPR nuclease comprises an amino acid sequence corresponding to the amino acid sequence of at least one of Domain A, Domain B, Domain C, Domain D, Domain E, or Domain F of the OMNI-50™ nuclease. In some embodiments of the invention, the CRISPR nuclease comprises at least one, at least two, at least three, at least four, or at least five amino acid sequences, wherein each amino acid sequence corresponds to any one of the amino acid sequences of Domain A, Domain B, Domain C, Domain D, Domain E, or Domain F of the OMNI-50™ nuclease. Accordingly, the CRISPR nuclease may include any combination of amino acid sequences that corresponding to any of Domain A, Domain B, Domain C, Domain D, Domain E, or Domain F of the OMNI-50™ nuclease.

In some embodiments, the CRISPR nuclease comprises a Domain A which comprises at least one of a) Subdomain A1 having at least 97% sequence identity to amino acids 1 to 50 of SEQ ID NO: 3;

b) Subdomain A2 having at least 97% sequence identity to amino acids 741 to 789 of SEQ ID NO: 3; or c) Subdomain A3 having at least 97% sequence identity to amino acids 962 to 1096 of SEQ ID NO: 3.

In some embodiments, the CRISPR nuclease comprises a Domain B having at least 97% sequence identity to amino acids 51 to 83 of SEQ ID NO: 3.

In some embodiments, the CRISPR nuclease comprises a Domain C which comprises at least one of a) Subdomain C1 having at least 97% sequence identity to amino acids 84 to 160 of SEQ ID NO: 3;

b) Subdomain C2 having at least 97% sequence identity to amino acids 161 to 299 of SEQ ID NO: 3; or c) Subdomain C3 having at least 97% sequence identity to amino acids 300 to 737 of SEQ ID NO: 3.

In some embodiments, the CRISPR nuclease comprises a Domain C which comprises at least one of a) Subdomain Ca having at least 97% sequence identity to amino acids 84 to 478 of SEQ ID NO: 3; and b) Subdomain Cb having at least 97% sequence identity to amino acids 479 to 737 of SEQ ID NO: 3.

In some embodiments, Domain C has at least 97% sequence identity to amino acids 84 to 737 of SEQ ID NO: 3.

In some embodiments, the CRISPR nuclease comprises a Domain D having at least 97% sequence identity to amino acids 790 to 961 of SEQ ID NO: 3.

In some embodiments, the CRISPR nuclease comprises a Domain E having at least 97% sequence identity to amino acids 1097 to 1196 of SEQ ID NO: 3.

In some embodiments, the CRISPR nuclease comprises a Domain F having at least 97% sequence identity to amino acids 1197 to 1370 of SEQ ID NO: 3.

In some embodiments, the CRISPR nuclease comprises Domain A, Domain B, Domain C, Domain D, Domain E, and Domain F, wherein a) Domain A comprises
   i. Subdomain A1 having at least 97% sequence identity to amino acids 1 to 50 of SEQ ID NO: 3;
   ii. Subdomain A2 having at least 97% sequence identity to amino acids 741 to 789 of SEQ ID NO: 3; and
   iii. Subdomain A3 having at least 97% sequence identity to amino acids 962 to 1096 of SEQ ID NO: 3;
b) Domain B has at least 97% sequence identity to amino acids 51 to 83 of SEQ ID NO: 3;
c) Domain C has at least 97% sequence identity to amino acids 84 to 737 of SEQ ID NO: 3;
d) Domain D has at least 97% sequence identity to amino acids 790 to 961 of SEQ ID NO: 3;
e) Domain E has at least 97% sequence identity to amino acids 1097 to 1196 of SEQ ID NO: 3; and
f) Domain F has at least 97% sequence identity to amino acids 1197 to 1370 of SEQ ID NO: 3.

In some embodiments, the CRISPR nuclease sequence is at least 100-250, 250-500, 500-1000, or 1000-2000 amino acids in length.

According to some aspects of the invention, the disclosed compositions comprise a non-naturally occurring composition comprising a peptide, wherein the peptide comprises an amino acid sequence having at least 97% sequence identity to the amino acid sequence of at least one of Domain A, Domain B, Domain C, Domain D, Domain E, or Domain F of the OMNI-50™ nuclease.

In some embodiments, the amino acid sequence of Domain A comprises an amino acid sequence of at least one of a) Subdomain A1 having at least 97% sequence identity to amino acids 1 to 50 of SEQ ID NO: 3;
b) Subdomain A2 having at least 97% sequence identity to amino acids 741 to 789 of SEQ ID NO: 3; or
c) Subdomain A3 having at least 97% sequence identity to amino acids 962 to 1096 of SEQ ID NO: 3.

In some embodiments, the amino acid sequence of Domain B has at least 97% sequence identity to amino acids 51 to 83 of SEQ ID NO: 3.

In some embodiments, the amino acid sequence of Domain C comprises an amino acid sequence of at least one of a) Subdomain C1 having at least 97% sequence identity to amino acids 84 to 160 of SEQ ID NO: 3;
b) Subdomain C2 having at least 97% sequence identity to amino acids 161 to 299 of SEQ ID NO: 3; or
c) Subdomain C3 having at least 97% sequence identity to amino acids 300 to 737 of SEQ ID NO: 3.

In some embodiments, the amino acid sequence of Domain C comprises an amino acid sequence of at least one of a) Subdomain Ca having at least 97% sequence identity to amino acids 84 to 478 of SEQ ID NO: 3; and
b) Subdomain Cb having at least 97% sequence identity to amino acids 479 to 737 of SEQ ID NO: 3.

In some embodiments, the amino acid sequence of Domain C has at least 97% sequence identity to amino acids 84 to 737 of SEQ ID NO: 3.

In some embodiments, the amino acid sequence of Domain D has at least 97% sequence identity to amino acids 790 to 961 of SEQ ID NO: 3.

In some embodiments, the amino acid sequence of Domain E has at least 97% sequence identity to amino acids 1097 to 1196 of SEQ ID NO: 3.

In some embodiments, the amino acid sequence of Domain F has at least 97% sequence identity to amino acids 1197 to 1370 of SEQ ID NO: 3.

In some embodiments, the amino acid sequence is at least 100-250, 250-500, 500-1000, or 1000-2000 amino acids in length.

According to some aspects of the invention, the disclosed compositions comprise a non-naturally occurring composition comprising a polynucleotide encoding an amino acid sequence having at least 97% sequence identity to the amino acid sequence of at least one of Domain A, Domain B, Domain C, Domain D, Domain E, or Domain F of the OMNI-50™ nuclease.

According to some aspects of the invention, the disclosed compositions comprise a non-naturally occurring amino acid sequence having at least 97% sequence identity to the amino acid sequence of at least one of Domain A, Domain B, Domain C, Domain D, Domain E, or Domain F of the OMNI-50™ nuclease.

According to some aspects of the invention, the disclosed methods comprise a method of modifying a nucleotide sequence at a target site in a cell-free system or the genome of a cell comprising introducing into the cell the composition of any one of the embodiments described herein.

In some embodiments, the cell is a eukaryotic cell, preferably a mammalian cell or a plant cell.

According to some aspects of the invention, the disclosed methods comprise a use of any one of the compositions described herein for the treatment of a subject afflicted with a disease associated with a genomic mutation comprising modifying a nucleotide sequence at a target site in the genome of the subject.

According to some aspects of the invention, the disclosed methods comprise a method of treating subject having a mutation disorder comprising targeting any one of the compositions described herein to an allele associated with the mutation disorder.

In some embodiments, the mutation disorder is related to a disease or disorder selected from any of a neoplasia, age-related macular degeneration, schizophrenia, neurological, neurodegenerative, or movement disorder, Fragile X Syndrome, secretase-related disorders, prion-related disorders, ALS, addiction, autism, Alzheimer's Disease, neutropenia, inflammation-related disorders, Parkinson's Disease, blood and coagulation diseases and disorders, cell dysregulation and oncology diseases and disorders, inflammation and immune-related diseases and disorders, metabolic, liver, kidney and protein diseases and disorders, muscular and skeletal diseases and disorders, dermatological diseases and disorders, neurological and neuronal diseases and disorders, and ocular diseases and disorders.

In some embodiments, the mutation disorder is beta thalassemia or sickle cell anemia.

In some embodiments, the allele associated with the disease is BCL11A.

Diseases and Therapies

Certain embodiments of the invention target a nuclease to a specific genetic locus associated with a disease or disorder as a form of gene editing, method of treatment, or therapy. For example, to induce editing or knockout of a gene, a novel nucleases disclosed herein may be specifically targeted to a pathogenic mutant allele of the gene using a custom designed guide RNA molecule. The guide RNA molecule is preferably designed by first considering the PAM requirement of the nuclease, which as shown herein is also dependent on the system in which the gene editing is being performed. For example, a guide RNA molecule designed to target an OMNI-50™ nuclease to a target site is designed to contain a spacer region complementary to a region neighboring the OMNI-50™ PAM sequence "NGG." The guide RNA molecule is further preferably designed to contain a spacer region (i.e. the region of the guide RNA molecule having complementarity to the target allele) of sufficient and preferably optimal length in order to increase specific activity of the nuclease and reduce off-target effects. For example, a guide RNA molecule designed to target OMNI-50™ nuclease may be designed to contain a 22 nt spacer for high on-target cleavage activity.

As a non-limiting example, the guide RNA molecule may be designed to target the nuclease to a specific region of a mutant allele, e.g. near the start codon, such that upon DNA damage caused by the nuclease a non-homologous end joining (NHEJ) pathway is induced and leads to silencing of the mutant allele by introduction of frameshift mutations. This approach to guide RNA molecule design is particularly useful for altering the effects of dominant negative mutations and thereby treating a subject. As a separate non-limiting example, the guide RNA molecule may be designed to target a specific pathogenic mutation of a mutated allele, such that upon DNA damage caused by the nuclease a homology directed repair (HDR) pathway is induced and leads to template mediated correction of the mutant allele. This approach to guide RNA molecule design is particularly useful for altering haploinsufficiency effects of a mutated allele and thereby treating a subject.

Non-limiting examples of specific genes which may be targeted for alteration to treat a disease or disorder are presented herein below. Specific disease-associated genes and mutations that induce a mutation disorder are described in the literature. Such mutations can be used to design a DNA-targeting RNA molecule to target a CRISPR composition to an allele of the disease associated gene, where the CRISPR composition causes DNA damage and induces a DNA repair pathway to alter the allele and thereby treat the mutation disorder.

Mutations in the ELANE gene are associated with neutropenia. Accordingly, without limitation, embodiments of the invention that target ELANE may be used in methods of treating subjects afflicted with neutropenia.

CXCR4 is a co-receptor for the human immunodeficiency virus type 1 (HIV-1) infection. Accordingly, without limitation, embodiments of the invention that target CXCR4 may be used in methods of treating subjects afflicted with HIV-1 or conferring resistance to HIV-1 infection in a subject.

Programmed cell death protein 1 (PD-1) disruption enhances CAR-T cell mediated killing of tumor cells and PD-1 may be a target in other cancer therapies. Accordingly, without limitation, embodiments of the invention that target PD-1 may be used in methods of treating subjects afflicted with cancer. In an embodiment, the treatment is CAR-T cell therapy with T cells that have been modified according to the invention to be PD-1 deficient.

In addition, BCL11A is a gene that plays a role in the suppression of hemoglobin production. Globin production may be increased to treat diseases such as thalassemia or sickle cell anemia by inhibiting BCL11A. See for example, PCT International Publication No. WO 2017/077394A2; U.S. Publication No. US2011/0182867A1; Humbert et al. Sci. Transl. Med. (2019); and Canver et al. Nature (2015). Accordingly, without limitation, embodiments of the invention that target an enhancer of BCL11A may be used in methods of treating subjects afflicted with beta thalassemia or sickle cell anemia.

Embodiments of the invention may also be used for targeting any disease-associated gene, for studying, altering, or treating any of the diseases or disorders listed in Table A or Table B below. Indeed, any disease-associated with a genetic locus may be studied, altered, or treated by using the nucleases disclosed herein to target the appropriate disease-associated gene, for example, those listed in U.S. Publication No. 2018/0282762A1 and European Patent No. EP3079726B1.

TABLE A

Diseases, Disorders and their associated genes

| DISEASE/DISORDERS | GENE(S) |
|---|---|
| Neoplasia | PTEN; ATM; ATR; EGFR; ERBB2; ERBB3; ERBB4; Notch1; Notch2; Notch3; Notch4; AKT; AKT2; AKT3; HIF; HIF1a; HIF3a; Met; HRG; Bc12; PPAR alpha; PPAR gamma; WT1 (Wilms Tumor); FGF Receptor Family members (5 members: 1, 2, 3, 4, 5); CDKN2a; APC; RB (retinoblastoma); MEN1; VHL; BRCA1; BRCA2; AR (Androgen Receptor); TSG101; IGF; IGF Receptor; Igf1 (4 variants); gf2 (3 variants); Igf 1 Receptor; Igf 2 Receptor; Bax; Bc12; caspases family (9 members: 1, 2, 3, 4, 6, 7, 8, 9, 12); Kras; Apc |
| Age-related Macular Degeneration | Aber; Cc12; Cc2; cp (ceruloplasmin); Timp3; cathepsinD; Vldlr; Ccr2 |
| Schizophrenia | Neuregulinl (Nrg1); Erb4 (receptor for Neuregulin); Complexinl (Cp1x1); Tphl Tryptophan hydroxylase; Tph2 Tryptophan hydroxylase 2; Neurexin 1; GSK3; GSK3a; GSK3b |
| Neurological, Neuro degenerative, and Movement Disorders | 5-HTT (S1c6a4); COMT; DRD (Drd1a); SLC6A3; DAOA; DTNBP1; Dao (Dao 1) |
| Trinucleotide Repeat Disorders | HTT (Huntington's Dx); SBMA/SMAX1/AR (Kennedy's Dx); FXN/X25 (Friedrich's Ataxia); ATX3 (Machado-Joseph's Dx); ATXN1 and ATXN2 (spinocerebellar ataxias); DMPK (myotonic dystrophy); Atrophin-1 and Atnl (DRPLA Dx); CBP (Creb-BP - global instability); VLDLR (Alzheimer's); Atxn7; Atxn10 |

TABLE A-continued

| Diseases, Disorders and their associated genes | |
|---|---|
| DISEASE/DISORDERS | GENE(S) |
| Fragile X Syndrome | FMR2; FXR1; FXR2; mGLUR5 |
| Secretase Related Disorders | APH-1 (alpha and beta); Presenilin (Psenl); nicastrin (Ncstn); PEN-2 |
| Others | Nos1; Parp1; Nat1 ; Nat2 |
| Prion related disorders | Prp |
| ALS | SOD1; ALS2; STEX; FUS; TARDBP; VEGF (VEGF-a; VEGF-b; VEGF-c) |
| Addiction | Prkce (alcohol); Drd2; Drd4; ABAT (alcohol); GRIA2; Grm5; Grin1; Htr1b; Grin2a; Drd3; Pdyn; Gria1 (alcohol) |
| Autism | Mecp2; BZRAP1; MDGA2; Sema5A; Neurexin 1; Fragile X (FMR2 (AFF2); FXR1; FXR2; Mglur5) |
| Alzheimer's Disease | El; CHIP; UCH; UBB; Tau; LRP; PICALM; Clusterin; PS1; SORL1; CR1; Vldlr; Uba1; Uba3; CHIP28 (Aqp1, Aquaporin 1); Uchl1; Uch13; APP |
| Inflammation | IL-10; IL-1 (IL-1a; IL-1b); IL-13; IL-17 (IL-17a (CTLA8); IL-17b; IL-17c; IL-17d; IL-17f); 11-23; Cx3cr1; ptpn22; TNFa; NOD2/CARD15 for IBD; IL-6; IL-12 (IL-12a; IL-12b); CTLA4; Cx3cl1 |
| Parkinson's Disease | x-Synuclein; DJ-1; LRRK2; Parkin; PINK1 |

TABLE B

| Diseases, Disorders and their associated genes | |
|---|---|
| DISEASE CATEGORY | DISEASE AND ASSOCIATED GENES |
| Blood and coagulation diseases and disorders | Anemia (CDAN1, CDA1, RPS19, DBA, PKLR, PK1, NT5C3, UMPH1, PSN1, RHAG, RH50A, NRAMP2, SPTB, ALAS2, ANH1, ASB, ABCB7, ABC7, ASAT); Bare lymphocyte syndrome (TAPBP, TPSN, TAP2, ABCB3, PSF2, RING11, MHC2TA, C2TA, RFX5, RFXAP, RFX5), Bleeding disorders (TBXA2R, P2RX1, P2X1); Factor H and factor H-like 1 (HF1, CFH, HUS); Factor V and factor VIII (MCFD2); Factor VII deficiency (F7); Factor X deficiency (F10); Factor XI deficiency (F11); Factor XII deficiency (F12, HAF); Factor XIIIA deficiency (F13A1, F13A); Factor XIIIB deficiency (F13B); Fanconi anemia (FANCA, FACA, FA1, FA, FAA, FAAP95, FAAP90, F1134064, FANCB, FANCC, FACC, BRCA2, FANCD1, FANCD2, FANCD, FACD, FAD, FANCE, FACE, FANCF, XRCC9, FANCG, BRIP1, BACH1, FANCJ, PHF9, FANCL, FANCM, KIAA1596); Hemophagocytic lymphohistiocytosis disorders (PRF1, HPLH2, UNC13D, DISEASE CATEGORY DISEASE AND ASSOCIATED GENES MUNC13-4, HPLH3, HLH3, FHL3); Hemophilia A (F8, F8C, HEMA); Hemophilia B (F9, HEMB), Hemorrhagic disorders (PI, ATT, F5); Leukocyde deficiencies and disorders (ITGB2, CD18, LCAMB, LAD, EIF2B1, EIF2BA, EIF2B2, EIF2B3, EIF2B5, LVWM, CACH, CLE, EIF2B4); Sickle cell anemia (HBB); Thalassemia (HBA2, HBB, HBD, LCRB, HBA1) |
| Cell dysregulation and oncology diseases and disorders | B-cell non-Hodgkin lymphoma (BCL7A, BCL7); Leukemia (TAL1, TCL5, SCL, TAL2, FLT3, NBS1, NBS, ZNFN1A1, IK1, LYF1, HOXD4, HOX4B, BCR, CML, PHL, ALL, ARNT, KRAS2, RASK2, GMPS, AF10, ARHGEF12, LARG, KIAA0382, CALM, CLTH, CEBPA, CEBP, CHIC2, BTL, FLT3, KIT, PBT, LPP, NPM1, NUP214, D9546E, CAN, CAIN, RUNX1, CBFA2, AML1, WHSC1L1, NSD3, FLT3, AF1Q, NPM1, NUMA1, ZNF145, PLZF, PML, MYL, STAT5B, AF10, CALM, CLTH, ARL11, ARLTS1, P2RX7, P2X7, BCR, CML, PHL, ALL, GRAF, NF1, VRNF, WSS, NFNS, PTPN11, PTP2C, SHP2, NS1, BCL2, CCND1, PRAD1, BCL1, TCRA, GATA1, GF1, ERYF1, NFE1, ABL1, NQO1, DIA4, NMOR1, NUP214, D9546E, CAN, CAIN) |
| Inflammation and immune related diseases and disorders | AIDS (KIR3DL1, NKAT3, NKB1, AMB11, KIR3DS1, IFNG, CXCL12, SDF1); Autoimmune lymphoproliferative syndrome (TNFRSF6, APT1, FAS, CD95, ALPS1A); Combined immunodeficiency, (IL2RG, SCIDX1, SCIDX, IMD4); HIV-1 (CCL5, SCYA5, D175136E, TCP228), HIV susceptibility or infection (IL10, CSIF, CMKBR2, CCR2, CMKBR5, CCCKR5 (CCR5)); Immunodeficiencies (CD3E, CD3G, AICDA, AID, HIGM2, TNFRSF5, CD40, UNG, DGU, HIGM4, TNFSF5, CD40LG, HIGM1, IGM, FOXP3, IPEX, AIID, XPID, PIDX, TNFRSF14B, TACI); Inflammation (IL-10, IL-1 (IL-1a, IL-1b), IL-13, IL-17 (IL-17a (CTLA8), IL-17b, IL-17c, IL- 17d, IL- |

TABLE B-continued

| Diseases, Disorders and their associated genes | |
|---|---|
| DISEASE CATEGORY | DISEASE AND ASSOCIATED GENES |
| | 171), 11-23, Cx3cr1, ptpn22, TNFa, NOD2/CARD15 for IBD, IL-6, IL-12 (IL-12a, IL-12b), CTLA4, Cx3cl1); Severe combined immunodeficiencies (SCIDs)(JAK3, JAKL, DCLRE1C, ARTEMIS, SCIDA, RAG1, RAG2, ADA, PTPRC, CD45, LCA, IL7R, CD3D, T3D, IL2RG, SCIDX1, SCIDX, IMD4) |
| Metabolic, liver, kidney and protein diseases and disorders | Amyloid neuropathy (TTR, PALB); Amyloidosis (APOA1, APP, AAA, CVAP, AD1, GSN, FGA, LYZ, TTR, PALB); Cirrhosis (KRT18, KRT8, CIRH1A, NAIC, TEX292, KIAA1988); Cystic fibrosis (CFTR, ABCC7, CF, MRP7); DISEASE CATEGORY DISEASE AND ASSOCIATED GENES Glycogen storage diseases (SLC2A2, GLUT2, G6PC, G6PT, G6PT1, GAA, LAMP2, LAMPB, AGL, GDE, GBE1, GYS2, PYGL, PFKM); Hepatic adenoma, 142330 (TCF1, HNF1A, MODY3), Hepatic failure, early onset, and neurologic disorder (SCOD1, SCO1), Hepatic lipase deficiency (LIPC), Hepatoblastoma, cancer and carcinomas (CTNNB1, PDGFRL, PDGRL, PRLTS, AXIN1, AXIN, CTNNB1, TP53, P53, LFS1, IGF2R, MPRI, MET, CASP8, MCH5; Medullary cystic kidney disease (UMOD, HNFJ, FJHN, MCKD2, ADMCKD2); Phenylketonuria (PAH, PKU1, QDPR, DHPR, PTS); Polycystic kidney and hepatic disease (FCYT, PKHD1, ARPKD, PKD1, PKD2, PKD4, PKDTS, PRKCSH, G19P1, PCLD, SEC63) |
| Muscular/Skeletal diseases and disorders | Becker muscular dystrophy (DMD, BMD, MYF6), Duchenne Muscular Dystrophy (DMD, BMD); Emery-Dreifuss muscular dystrophy (LMNA, LMN1, EMD2, FPLD, CMD1A, HGPS, LGMD1B, LMNA, LMN1, EMD2, FPLD, CMD1A); Facioscapulohumeral muscular dystrophy (FSHMD1A, FSHD1A); Muscular dystrophy (FKRP, MDC1C, LGMD2I, LAMA2, LAMM, LARGE, KIAA0609, MDC1D, FCMD, TTID, MYOT, CAPN3, CANP3, DYSF, LGMD2B, SGCG, LGMD2C, DMDA1, SCG3, SGCA, ADL, DAG2, LGMD2D, DMDA2, SGCB, LGMD2E, SGCD, SGD, LGMD2F, CMD1L, TCAP, LGMD2G, CMD1N, TRIM32, HT2A, LGMD2H, FKRP, MDC1C, LGMD2I, TTN, CMD1G, TMD, LGMD2J, POMT1, CAV3, LGMD1C, SEPN1, SELN, RSMD1, PLEC1, PLTN, EBS1); Osteopetrosis (LRP5, BMND1, LRP7, LR3, OPPG, VBCH2, CLCN7, CLC7, OPTA2, OSTM1, GL, TCIRG1, TIRC7, OC116, OPTB1); Muscular atrophy (VAPB, VAPC, ALS8, SMN1, SMA1, SMA2, SMA3, SMA4, BSCL2, SPG17, GARS, SMAD1, CMT2D, HEXB, IGHMBP2, SMUBP2, CATF1, SMARD1) |
| Dermatological diseases and disorders | Albinisim (TYR, OCA2, TYRP1, SLC45A2, LYST), Ectodermal dysplasias (EDAR, EDARADD, WNT10A), Ehlers-Danlos syndrome (COL5A1, COL5A2, COL1A1, COL1A2, COL3A1, TNXB, ADAMTS2, PLOD1, FKBP14), Ichthyosis-associated disorders (FLG, STS, TGM1, ALOXE3/ALOX12B, KRT1, KRT10, ABCA12, KRT2, GJB2, TGM1, ABCA12, CYP4F22, ALOXE3, CERS3, NSHDL, EBP, MBTPS2, GJB2, SPINK5, AGHD5, PHYH, PEX7, ALDH3A2, ERCC2, ERCC3, GFT2H5, GBA), Incontinentia pigmenti (IKBKG, NEMO), DISEASE CATEGORY DISEASE AND ASSOCIATED GENES Tuberous sclerosis (TSC1, TSC2), Premature aging syndromes (POLR3A, PYCR1, LMA, POLD1, WRN, DMPK) |
| Neurological and Neuronal diseases and disorders | ALS (SOD1, ALS2, STEX, FUS, TARDBP, VEGF (VEGF-a, VEGF-b, VEGF-c); Alzheimer disease (APP, AAA, CVAP, AD1, APOE, AD2, PSEN2, AD4, STM2, APBB2, FE65L1, NOS3, PLAU, URK, ACE, DCP1, ACE1, MPO, PACIP1, PAXIP1L, PTIP, A2M, BLMH, BMH, PSEN1, AD3); Autism (Mecp2, BZRAP1, MDGA2, Sema5A, Neurexin 1, GLO1, MECP2, RTT, PPMX, MRX16, MRX79, NLGN3, NLGN4, KIAA1260, AUTSX2); Fragile X Syndrome (FMR2, FXR1, FXR2, mGLUR5); Huntington's disease and disease like disorders (HD, IT15, PRNP, PRIP, JPH3, JP3, HDL2, TBP, SCA17); Parkinson disease (NR4A2, NURR1, NOT, TINUR, SNCAIP, TBP, SCA17, SNCA, NACP, PARK1, PARK4, DJ1, PARK7, LRRK2, PARK8, PINK1, PARK6, UCHL1, PARKS, SNCA, NACP, PARK1, PARK4, PRKN, PARK2, PDJ, DBH, NDUFV2); Rett syndrome (MECP2, RTT, PPMX, MRX16, MRX79, CDKL5, STK9, MECP2, RTT, PPMX, MRX16, MRX79, x-Synuclein, DJ-1); Schizophrenia (Neuregulinl (Nrg1), Erb4 (receptor for Neuregulin), Complexinl (Cp1x1), Tphl Tryptophan hydroxylase, Tph2, Tryptophan hydroxylase 2, Neurexin 1, GSK3, GSK3a, GSK3b, 5-HTT (Slc6a4), COMT, DRD (Drdl a), SLC6A3, DAOA, DTNBP1, Dao (Dao1)); |

TABLE B-continued

| Diseases, Disorders and their associated genes | |
|---|---|
| DISEASE CATEGORY | DISEASE AND ASSOCIATED GENES |
| | Secretase Related Disorders (APH-1 (alpha and beta), Presenilin (Psen1), nicastrin, (Ncstn), PEN-2, Nos 1, Parp1, Nat1, Nat2); Trinucleotide Repeat Disorders (HTT (Huntington's Dx), SBMA/SMAX1/AR (Kennedy's Dx), FXN/X25 (Friedrich's Ataxia), ATX3 (Machado-Joseph's Dx), ATXN1 and ATXN2 (spinocerebellar ataxias), DMPK (myotonic dystrophy), Atrophin-1 and Atnl (DRPLA Dx), CBP (Creb-BP - global instability), VLDLR (Alzheimer's), Atxn7, Atxn10) |
| Ocular diseases and disorders | Age-related macular degeneration (Abcr, Cc12, Cc2, cp (ceruloplasmin), Timp3, cathepsinD, Vldlr, Ccr2); Cataract (CRYAA, CRYA1, CRYBB2, CRYB2, PITX3, BFSP2, CP49, CP47, CRYAA, CRYA1, PAX6, AN2, MGDA, CRYBA1, CRYB1, CRYGC, CRYG3, CCL, LIM2, MP19, CRYGD, CRYG4, BFSP2, CP49, CP47, HSF4, CTM, HSF4, CTM, MIP, AQP0, CRYAB, CRYA2, CTPP2, CRYBB1, CRYGD, CRYG4, CRYBB2, CRYB2, CRYGC, CRYG3, CCL, CRYAA, CRYA1, GJA8, CX50, CAE1, GJA3, CX46, CZP3, CAE3, CCM1, CAM, KRIT1); Corneal clouding and dystrophy (AP0A1, TGFBI, CSD2, CDGG1, CSD, BIGH3, CDG2, TACSTD2, TROP2, DISEASE CATEGORY DISEASE AND ASSOCIATED GENES M 1 S 1, VSX1, RINX, PPCD, PPD, KTCN, COL8A2, FECD, PPCD2, PIP5K3, CFD); Cornea plana congenital (KERA, CNA2); Glaucoma (MYOC, TIGR, GLC1A, JOAG, GPOA, OPTN, GLC1E, FIP2, HYPL, NRP, CYP1B1, GLC3A, OPA1, NTG, NPG, CYP1B1, GLC3A); Leber congenital amaurosis (CRB1, RP12, CRX, CORD2, CRD, RPGRIP1, LCA6, CORD9, RPE65, RP20, AIPL1, LCA4, GUCY2D, GUC2D, LCA1, CORD6, RDH12, LCA3); Macular dystrophy (ELOVL4, ADMD, STGD2, STGD3, RDS, RP7, PRPH2, PRPH, AVMD, AOFMD, VMD2) |

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of and any combination of items it conjoins.

It should be understood that the terms "a" and "an" as used above and elsewhere herein refer to "one or more" of the enumerated components. It will be clear to one of ordinary skill in the art that the use of the singular includes the plural unless specifically stated otherwise. Therefore, the terms "a," "an" and "at least one" are used interchangeably in this application.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

It is understood that where a numerical range is recited herein, the present invention contemplates each integer between, and including, the upper and lower limits, unless otherwise stated.

In the description and claims of the present application, each of the verbs, "comprise," "include" and "have" and conjugates thereof, are used to indicate that the object or objects of the verb are not necessarily a complete listing of components, elements or parts of the subject or subjects of the verb. Other terms as used herein are meant to be defined by their well-known meanings in the art.

The terms "polynucleotide", "nucleotide", "nucleotide sequence", "nucleic acid" and "oligonucleotide" are used interchangeably. They refer to a polymeric form of nucleotides of any length, either deoxyribonueleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, in Irons, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers, A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

The term "nucleotide analog" or "modified nucleotide" refers to a nucleotide that contains one or more chemical modifications (e.g., substitutions), in or on the nitrogenous base of the nucleoside (e.g., cytosine (C), thymine (T) or uracil (U), adenine (A) or guanine (G)), in or on the sugar moiety of the nucleoside (e.g., ribose, deoxyribose, modified ribose, modified deoxyribose, six-membered sugar analog, or open-chain sugar analog), or the phosphate. Each of the RNA sequences described herein may comprise one or more nucleotide analogs.

As used herein, the following nucleotide identifiers are used to represent a referenced nucleotide base(s):

| Nucleotide reference | Base(s) represented | | | |
|---|---|---|---|---|
| A | A | | | |
| C | | C | | |
| G | | | G | |
| T | | | | T |
| W | A | | | T |
| S | | C | G | |
| M | A | C | | |
| K | | | G | T |
| R | A | | G | |
| Y | | C | | T |
| B | | C | G | T |
| D | A | | G | T |
| H | A | C | | T |
| V | A | C | G | |
| N | A | C | G | T |

As used herein, the term "targeting sequence" or "targeting molecule" refers a nucleotide sequence or molecule comprising a nucleotide sequence that is capable of hybridizing to a specific target sequence, e.g., the targeting sequence has a nucleotide sequence which is at least partially complementary to the sequence being targeted along the length of the targeting sequence. The targeting sequence or targeting molecule may be part of a targeting RNA molecule that can form a complex with a CRISPR nuclease with the targeting sequence serving as the targeting portion of the CRISPR complex. When the molecule having the targeting sequence is present contemporaneously with the CRISPR molecule, the RNA molecule is capable of targeting the CRISPR nuclease to the specific target sequence. Each possibility represents a separate embodiment. A targeting RNA molecule can be custom designed to target any desired sequence.

The term "targets" as used herein, refers to preferential hybridization of a targeting sequence or a targeting molecule to a nucleic acid having a targeted nucleotide sequence. It is understood that the term "targets" encompasses variable hybridization efficiencies, such that there is preferential targeting of the nucleic acid having the targeted nucleotide sequence, but unintentional off-target hybridization in addition to on-target hybridization might also occur. It is understood that where an RNA molecule targets a sequence, a complex of the RNA molecule and a CRISPR nuclease molecule targets the sequence for nuclease activity.

In the context of targeting a DNA sequence that is present in a plurality of cells, it is understood that the targeting encompasses hybridization of the guide sequence portion of the RNA molecule with the sequence in one or more of the cells, and also encompasses hybridization of the RNA molecule with the target sequence in fewer than all of the cells in the plurality of cells. Accordingly, it is understood that where an RNA molecule targets a sequence in a plurality of cells, a complex of the RNA molecule and a CRISPR nuclease is understood to hybridize with the target sequence in one or more of the cells, and also may hybridize with the target sequence in fewer than all of the cells. Accordingly, it is understood that the complex of the RNA molecule and the CRISPR nuclease introduces a double strand break in relation to hybridization with the target sequence in one or more cells and may also introduce a double strand break in relation to hybridization with the target sequence in fewer than all of the cells. As used herein, the term "modified cells" refers to cells in which a double strand break is affected by a complex of an RNA molecule and the CRISPR nuclease as a result of hybridization with the target sequence, i.e. on-target hybridization.

As used herein the term "wild type" is a term of the art understood by skilled persons and means the typical form of an organism, strain, gene or characteristic as it occurs in nature as distinguished from mutant or variant forms. Accordingly, as used herein, where a sequence of amino acids or nucleotides refers to a wild type sequence, a variant refers to variant of that sequence, e.g., comprising substitutions, deletions, insertions. In embodiments of the present invention, an engineered CRISPR nuclease is a variant CRISPR nuclease comprising at least one amino acid modification (e.g., substitution, deletion, and/or insertion) compared to the CRISPR nuclease of any of the CRISPR nucleases indicated in Table 1.

The terms "non-naturally occurring" or "engineered" are used interchangeably and indicate human manipulation. The terms, when referring to nucleic acid molecules or polypeptides may mean that the nucleic acid molecule or the polypeptide is at least substantially free from at least one other component with which they are naturally associated in nature and as found in nature.

As used herein the term "amino acid" includes natural and/or unnatural or synthetic amino acids, including glycine and both the D or I, optical isomers, and amino acid analogs and peptidomimetics.

As used herein, "genomic DNA" refers to linear and/or chromosomal DNA and/or to plasmid or other extrachromosomal DNA sequences present in the cell or cells of interest. In some embodiments, the cell of interest is a eukaryotic cell. In some embodiments, the cell of interest is a prokaryotic cell. In some embodiments, the methods produce double-stranded breaks (DSBs) at pre-determined target sites in a genomic DNA sequence, resulting in mutation, insertion, and/or deletion of DNA sequences at the target site(s) in a genome.

"Eukaryotic" cells include, but are not limited to, fungal cells (such as yeast), plant cells, animal cells, mammalian cells and human cells.

The term "nuclease" as used herein refers to an enzyme capable of cleaving the phosphodiester bonds between the nucleotide subunits of nucleic acid. A nuclease may be isolated or derived from a natural source. The natural source may be any living organism. Alternatively, a nuclease may be a modified or a synthetic protein which retains the phosphodiester bond cleaving activity.

The term "PAM" as used herein refers to a nucleotide sequence of a target DNA located in proximity to the targeted DNA sequence and recognized by the CRISPR nuclease. The PAM sequence may differ depending on the nuclease identity.

The term "mutation disorder" or "mutation disease" as used herein refers to any disorder or disease that is related to dysfunction of a gene caused by a mutation. A dysfunctional gene manifesting as a mutation disorder contains a mutation in at least one of its alleles and is referred to as a "disease-associated gene." The mutation may be in any portion of the disease-associated gene, for example, in a regulatory, coding, or non-coding portion. The mutation may be any class of mutation, such as a substitution, insertion, or deletion. The mutation of the disease-associated gene may manifest as a disorder or disease according to the mechanism of any type of mutation, such as a recessive, dominant negative, gain-of-function, loss-of-function, or a mutation leading to haploinsufficiency of a gene product.

A skilled artisan will appreciate that embodiments of the present invention disclose RNA molecules capable of complexing with a nuclease, e.g. a CRISPR nuclease, such as to associate with a target genomic DNA sequence of interest next to a protospacer adjacent motif (PAM). The nuclease then mediates cleavage of target DNA to create a double-stranded break within the protospacer.

In embodiments of the present invention, a CRISPR nuclease and a targeting molecule form a CRISPR complex that binds to a target DNA sequence to effect cleavage of the target DNA sequence. A CRISPR nuclease may form a CRISPR complex comprising the CRISPR nuclease and RNA molecule without a further, separate tracrRNA molecule. Alternatively, CRISPR nucleases may form a CRISPR complex between the CRISPR nuclease, an RNA molecule, and a tracrRNA molecule.

The term "protein binding sequence" or "nuclease binding sequence" refers to a sequence capable of binding with a CRISPR nuclease to form a CRISPR complex. A skilled artisan will understand that a tracrRNA capable of binding with a CRISPR nuclease to form a CRISPR complex comprises a protein or nuclease binding sequence.

An "RNA binding portion" of a CRISPR nuclease refers to a portion of the CRISPR nuclease which may bind to an RNA molecule to form a CRISPR complex, e.g. the nuclease binding sequence of a tracrRNA molecule. An "activity portion" or "active portion" of a CRISPR nuclease refers to a portion of the CRISPR nuclease which effects a double strand break in a DNA molecule, for example when in complex with a DNA-targeting RNA molecule.

An RNA molecule may comprise a sequence sufficiently complementary to a tracrRNA molecule so as to hybridize to the tracrRNA via basepairing and promote the formation of a CRISPR complex. (See U.S. Pat. No. 8,906,616). In embodiments of the present invention, the RNA molecule may further comprise a portion having a tracr mate sequence.

In embodiments of the present invention, the targeting molecule may further comprise the sequence of a tracrRNA molecule. Such embodiments may be designed as a synthetic fusion of the guide portion of the RNA molecule (gRNA or crRNA) and the trans-activating crRNA (tracrRNA), together forming a single guide RNA (sgRNA). (See Jinek et al., Science (2012)). Embodiments of the present invention may also form CRISPR complexes utilizing a separate tracrRNA molecule and a separate RNA molecule comprising a guide sequence portion. In such embodiments the tracrRNA molecule may hybridize with the RNA molecule via base pairing and may be advantageous in certain applications of the invention described herein.

In embodiments of the present invention an RNA molecule may comprise a "nexus" region and/or "hairpin" regions which may further define the structure of the RNA molecule. (See Briner et al., Molecular Cell (2014)).

As used herein, the term "direct repeat sequence" refers to two or more repeats of a specific amino acid sequence of nucleotide sequence.

As used herein, an RNA sequence or molecule capable of "interacting with" or "binding" with a CRISPR nuclease refers to the RNA sequence or molecules ability to form a CRISPR complex with the CRISPR nuclease.

As used herein, the term "operably linked" refers to a relationship (i.e. fusion, hybridization) between two sequences or molecules permitting them to function in their intended manner. In embodiments of the present invention, when an RNA molecule is operably linked to a promoter, both the RNA molecule and the promotor are permitted to function in their intended manner.

As used herein, the term "heterologous promoter" refers to a promoter that does not naturally occur together with the molecule or pathway being promoted.

As used herein, a sequence or molecule has an X % "sequence identity" to another sequence or molecule if X % of bases or amino acids between the sequences of molecules are the same and in the same relative position. For example, a first nucleotide sequence having at least a 95% sequence identity with a second nucleotide sequence will have at least 95% of bases, in the same relative position, identical with the other sequence.

Nuclear Localization Sequences

The terms "nuclear localization sequence" and "NLS" are used interchangeably to indicate an amino acid sequence/peptide that directs the transport of a protein with which it is associated from the cytoplasm of a cell across the nuclear envelope barrier. The term "NLS" is intended to encompass not only the nuclear localization sequence of a particular peptide, but also derivatives thereof that are capable of directing translocation of a cytoplasmic polypeptide across the nuclear envelope barrier. NLSs are capable of directing nuclear translocation of a polypeptide when attached to the N-terminus, the C-terminus, or both the N- and C-termini of the polypeptide. In addition, a polypeptide having an NLS coupled by its N- or C-terminus to amino acid side chains located randomly along the amino acid sequence of the polypeptide will be translocated. Typically, an NLS consists of one or more short sequences of positively charged lysines or arginines exposed on the protein surface, but other types of NLS are known. Non-limiting examples of NLSs include an NLS sequence derived from: the SV40 virus large T-antigen, nucleoplasmin, c-myc, the hRNPA1 M9 NLS, the IBB domain from importin-alpha, myoma T protein, human p53, mouse c-abl IV, influenza vims NS1, Hepatitis virus delta antigen, mouse Mx1 protein, human poly(ADP-ribose) polymerase, and the steroid hormone receptors (human) glucocorticoid. Such NLS sequences are listed as SEQ ID NOs: 69-84.

Delivery

The CRISPR nuclease or CRISPR compositions described herein may be delivered as a protein, DNA molecules, RNA molecules, Ribonucleoproteins (RNP), nucleic acid vectors, or any combination thereof. In some embodiments, the RNA molecule comprises a chemical modification. Non-limiting examples of suitable chemical modifications include 2'-O-methyl (M), 2'-O-methyl, 3'phosphorothioate (MS) or 2'-O-methyl, 3' thioPACE (MSP), pseudouridine, and 1-methyl pseudo-uridine. Each possibility represents a separate embodiment of the present invention.

The CRISPR nucleases and/or polynucleotides encoding same described herein, and optionally additional proteins (e.g., ZFPs, TALENs, transcription factors, restriction enzymes) and/or nucleotide molecules such as guide RNA may be delivered to a target cell by any suitable means. The target cell may be any type of cell e.g., eukaryotic or prokaryotic, in any environment e.g., isolated or not, maintained in culture, in vitro, ex vivo, in vivo or in planta.

In some embodiments, the composition to be delivered includes mRNA of the nuclease and RNA of the guide. In some embodiments, the composition to be delivered includes mRNA of the nuclease, RNA of the guide and a donor template. In some embodiments, the composition to be delivered includes the CRISPR nuclease and guide RNA. In some embodiments, the composition to be delivered includes the CRISPR nuclease, guide RNA and a donor template for gene editing via, for example, homology directed repair. In some embodiments, the composition to be delivered includes mRNA of the nuclease, DNA-targeting RNA and the tracrRNA. In some embodiments, the composition to be delivered includes mRNA of the nuclease, DNA-targeting RNA and the tracrRNA and a donor template. In some embodiments, the composition to be delivered includes the CRISPR nuclease DNA-targeting RNA and the tracrRNA. In some embodiments, the composition to be delivered includes the CRISPR nuclease, DNA-targeting RNA and the tracrRNA and a donor template for gene editing via, for example, homology directed repair.

Any suitable viral vector system may be used to deliver RNA compositions. Conventional viral and non-viral based gene transfer methods can be used to introduce nucleic acids and/or CRISPR nuclease in cells (e.g., mammalian cells, plant cells, etc.) and target tissues. Such methods can also be used to administer nucleic acids encoding and/or CRISPR nuclease protein to cells in vitro. In certain embodiments, nucleic acids and/or CRISPR nuclease are administered for in vivo or ex vivo gene therapy uses. Non-viral vector delivery systems include naked nucleic acid, and nucleic acid complexed with a delivery vehicle such as a liposome or poloxamer. For a review of gene therapy procedures, see Anderson, Science (1992); Nabel and Felgner, TIBTECH (1993); Mitani and Caskey, TIBTECH (1993); Dillon, TIBTECH (1993); Miller, Nature (1992); Van Brunt, Biotechnology (1988); Vigne et al., Restorative Neurology and Neuroscience 8:35-36 (1995); Kremer and Perricaudet, British Medical Bulletin (1995); Haddada et al., Current Topics in Microbiology and Immunology (1995); and Yu et al., Gene Therapy 1:13-26 (1994).

Methods of non-viral delivery of nucleic acids and/or proteins include electroporation, lipofection, microinjection, biolistics, particle gun acceleration, virosomes, liposomes, immunoliposomes, polycation or lipid:nucleic acid conjugates, artificial virions, and agent-enhanced uptake of nucleic acids or can be delivered to plant cells by bacteria or viruses (e.g., *Agrobacterium, Rhizobium* sp. NGR234, *Sinorhizoboiummeliloti, Mesorhizobium loti*, tobacco mosaic virus, potato virus X, cauliflower mosaic virus and cassava vein mosaic virus. See, e.g., Chung et al. Trends Plant Sci. (2006). Sonoporation using, e.g., the Sonitron 2000 system (Rich-Mar) can also be used for delivery of nucleic acids. Cationic-lipid mediated delivery of proteins and/or nucleic acids is also contemplated as an in vivo or in vitro delivery method. See Zuris et al., Nat. Biotechnol. (2015), Coelho et al., N. Engl. J. Med. (2013); Judge et al., Mol. Ther. (2006); and Basha et al., Mol. Ther. (2011).

Additional exemplary nucleic acid delivery systems include those provided by Amaxa® Biosystems (Cologne, Germany), Maxcyte, Inc. (Rockville, Md.), BTX Molecular Delivery Systems (Holliston, Mass.) and Copernicus Therapeutics Inc., (see for example U.S. Pat. No. 6,008,336). Lipofection is described in e.g., U.S. Pat. Nos. 5,049,386, 4,946,787; and 4,897,355) and lipofection reagents are sold commercially (e.g., Transfectam™, Lipofectin™ and Lipofectamine™ RNAiMAX). Cationic and neutral lipids that are suitable for efficient receptor-recognition lipofection of polynucleotides include those disclosed in PCT International Publication Nos. WO/1991/017424 and WO/1991/016024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, Science (1995); Blaese et al., Cancer Gene Ther. (1995); Behr et al., Bioconjugate Chem. (1994); Remy et al., Bioconjugate Chem. (1994); Gao and Huang, Gene Therapy (1995); Ahmad and Allen, Cancer Res., (1992); U.S. Pat. Nos. 4,186,183; 4,217,344; 4,235,871; 4,261,975; 4,485,054; 4,501,728; 4,774,085; 4,837,028; and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiamid et al., Nature Biotechnology (2009)).

The use of RNA or DNA viral based systems for the delivery of nucleic acids take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of nucleic acids include, but are not limited to, recombinant retroviral, lentivirus, adenoviral, adeno-associated, vaccinia and herpes simplex virus vectors for gene transfer. However, an RNA virus is preferred for delivery of the RNA compositions described herein. Additionally, high transduction efficiencies have been observed in many different cell types and target tissues. Nucleic acid of the invention may be delivered by non-integrating lentivirus. Optionally, RNA delivery with Lentivirus is utilized. Optionally the lentivirus includes mRNA of the nuclease, RNA of the guide. Optionally the lentivirus includes mRNA of the nuclease, RNA of the guide and a donor template. Optionally, the lentivirus includes the nuclease protein, guide RNA. Optionally, the lentivirus includes the nuclease protein, guide RNA and/or a donor template for gene editing via, for example, homology directed repair. Optionally the lentivirus includes mRNA of the nuclease, DNA-targeting RNA, and the tracrRNA. Optionally the lentivirus includes mRNA of the nuclease, DNA-targeting RNA, and the tracrRNA, and a donor template. Optionally, the lentivirus includes the nuclease protein, DNA-targeting RNA, and the tracrRNA. Optionally, the lentivirus includes the nuclease protein, DNA-targeting RNA, and the tracrRNA, and a donor template for gene editing via, for example, homology directed repair.

As mentioned above, the compositions described herein may be delivered to a target cell using a non-integrating lentiviral particle method, e.g. a LentiFlash® system. Such a method may be used to deliver mRNA or other types of RNAs into the target cell, such that delivery of the RNAs to the target cell results in assembly of the compositions described herein inside of the target cell. See also PCT International Publication Nos. WO2013/014537, WO2014/016690, WO2016185125, WO2017194902, and WO2017194903.

The tropism of a retrovirus can be altered by incorporating foreign envelope proteins, expanding the potential target population of target cells. Lentiviral vectors are retroviral vectors capable of transducing or infecting non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher Panganiban, J. Virol. (1992); Johann et al., J. Virol. (1992); Sommerfelt et al., Virol. (1990); Wilson et al., J. Virol. (1989); Miller et al., J. Virol. (1991); PCT International Publication No. WO/1994/026877A1).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., Blood (1995); Kohn et al., Nat. Med. (1995); Malech et al., PNAS (1997)). PA317/pLASN was the first therapeutic vector used in a gene therapy trial. (Blaese et al., Science (1995)). Transduction efficiencies of 50% or greater have been observed for MFG-S packaged vectors. (Ellem et al., Immunol Immunother. (1997); Dranoff et al., Hum. Gene Ther. (1997).

Packaging cells are used to form virus particles that are capable of infecting a host cell. Such cells include 293 cells, which package adenovirus, AAV, and psi.2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. Additionally, AAV can be produced at clinical scale using baculovirus systems (see U.S. Pat. No. 7,479,554).

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., Proc. Natl. Acad. Sci. USA (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to non-viral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector. In some embodiments, delivery of mRNA in-vivo and ex-vivo, and RNPs delivery may be utilized.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with an RNA composition, and re-infused back into the subject organism (e.g., patient). Various cell types suitable for ex vivo transfection are well known to those of skill in the art (see, e.g., Freshney, "Culture of Animal Cells, A Manual of Basic Technique and Specialized Applications (6th edition, 2010)) and the references cited therein for a discussion of how to isolate and culture cells from patients).

Suitable cells include but not limited to eukaryotic and prokaryotic cells and/or cell lines. Non-limiting examples of such cells or cell lines generated from such cells include COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NSO, 5P2/0-Ag14, HeLa, HEK293 (e.g., HEK293-F, HEK293-H, HEK293-T), and perC6 cells, any plant cell (differentiated or undifferentiated) as well as insect cells such as *Spodoptera fugiperda* (Sf), or fungal cells such as *Saccharomyces, Pichia* and *Schizosaccharomyces*. In certain embodiments, the cell line is a CHO-K1, MDCK or HEK293 cell line. Additionally, primary cells may be isolated and used ex vivo for reintroduction into the subject to be treated following treatment with the nucleases (e.g. ZFNs or TALENs) or nuclease systems (e.g. CRISPR). Suitable primary cells include peripheral blood mononuclear cells (PBMC), and other blood cell subsets such as, but not limited to, CD4+ T cells or CD8+ T cells. Suitable cells also include stem cells such as, by way of example, embryonic stem cells, induced pluripotent stem cells, hematopoietic stem cells (CD34+), neuronal stem cells and mesenchymal stem cells.

In one embodiment, stem cells are used in ex vivo procedures for cell transfection and gene therapy. The advantage to using stem cells is that they can be differentiated into other cell types in-vitro or can be introduced into a mammal (such as the donor of the cells) where they will engraft in the bone marrow. Methods for differentiating CD34+ cells in vitro into clinically important immune cell types using cytokines such a GM-CSF, IFN-gamma. and TNF-alpha are known (as a non-limiting example see, Inaba et al., J. Exp. Med. (1992)).

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+ (panB cells), GR-1 (granulocytes), and Tad (differentiated antigen presenting cells) (as a non-limiting example see Inaba et al., J. Exp. Med. (1992)). Stem cells that have been modified may also be used in some embodiments.

Notably, the CRISPR nuclease described herein may be suitable for genome editing in post-mitotic cells or any cell which is not actively dividing, e.g., arrested cells. Examples of post-mitotic cells which may be edited using a CRISPR nuclease of the present invention include, but are not limited to, myocyte, a cardiomyocyte, a hepatocyte, an osteocyte and a neuron.

Vectors (e.g., retroviruses, liposomes, etc.) containing therapeutic RNA compositions can also be administered directly to an organism for transduction of cells in vivo. Alternatively, naked RNA or mRNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Vectors suitable for introduction of transgenes into immune cells (e.g., T-cells) include non-integrating lentivirus vectors. See, for example, U.S. Patent Publication No. 2009/0117617.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., Remington's Pharmaceutical Sciences, 17th ed., 1989).

DNA Repair by Homologous Recombination

The term "homology-directed repair" or "HDR" refers to a mechanism for repairing DNA damage in cells, for example, during repair of double-stranded and single-stranded breaks in DNA. HDR requires nucleotide sequence homology and uses a "nucleic acid template" (nucleic acid template or donor template used interchangeably herein) to repair the sequence where the double-stranded or single break occurred (e.g., DNA target sequence). This results in the transfer of genetic information from, for example, the nucleic acid template to the DNA target sequence. HDR may result in alteration of the DNA target sequence (e.g., insertion, deletion, mutation) if the nucleic acid template sequence differs from the DNA target sequence and part or all of the nucleic acid template polynucleotide or oligonucleotide is incorporated into the DNA target sequence. In some embodiments, an entire nucleic acid template polynucleotide, a portion of the nucleic acid template polynucleotide, or a copy of the nucleic acid template is integrated at the site of the DNA target sequence.

The terms "nucleic acid template" and "donor", refer to a nucleotide sequence that is inserted or copied into a genome. The nucleic acid template comprises a nucleotide sequence, e.g., of one or more nucleotides, that will be added to or will template a change in the target nucleic acid or may be used to modify the target sequence. A nucleic acid template sequence may be of any length, for example between 2 and 10,000 nucleotides in length (or any integer value there between or there above), preferably between about 100 and 1,000 nucleotides in length (or any integer there between), more preferably between about 200 and 500 nucleotides in length. A nucleic acid template may be a single stranded nucleic acid, a double stranded nucleic acid. In some embodiment, the nucleic acid template comprises a nucleotide sequence, e.g., of one or more nucleotides, that corresponds to wild type sequence of the target nucleic acid, e.g., of the target position. In some embodiment, the nucleic acid template comprises a ribonucleotide sequence, e.g., of one or more ribonucleotides, that corresponds to wild type sequence of the target nucleic acid, e.g., of the target position. In some embodiment, the nucleic acid template comprises modified ribonucleotides.

Insertion of an exogenous sequence (also called a "donor sequence," donor template" or "donor"), for example, for correction of a mutant gene or for increased expression of a wild-type gene can also be carried out. It will be readily apparent that the donor sequence is typically not identical to the genomic sequence where it is placed. A donor sequence can contain a non-homologous sequence flanked by two regions of homology to allow for efficient HDR at the location of interest. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest.

The donor polynucleotide can be DNA or RNA, single-stranded and/or double-stranded and can be introduced into a cell in linear or circular form. See, e.g., U.S. Patent Publication Nos. 2010/0047805; 2011/0281361; 2011/0207221; and 2019/0330620. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang and Wilson, Proc. Natl. Acad. Sci. USA (1987); Nehls et al., Science (1996). Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

Accordingly, embodiments of the present invention using a donor template for repair may use a DNA or RNA, single-stranded and/or double-stranded donor template that can be introduced into a cell in linear or circular form. In embodiments of the present invention a gene-editing composition comprises: (1) an RNA molecule comprising a guide sequence to affect a double strand break in a gene prior to repair and (2) a donor RNA template for repair, the RNA molecule comprising the guide sequence is a first RNA molecule and the donor RNA template is a second RNA molecule. In some embodiments, the guide RNA molecule and template RNA molecule are connected as part of a single molecule.

A donor sequence may also be an oligonucleotide and be used for gene correction or targeted alteration of an endogenous sequence. The oligonucleotide may be introduced to the cell on a vector, may be electroporated into the cell, or may be introduced via other methods known in the art. The oligonucleotide can be used to 'correct' a mutated sequence in an endogenous gene (e.g., the sickle mutation in beta globin), or may be used to insert sequences with a desired purpose into an endogenous locus.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by recombinant viruses (e.g., adenovirus, AAV, herpesvirus, retrovirus, lentivirus and integrase defective lentivirus (IDLV)).

The donor is generally inserted so that its expression is driven by the endogenous promoter at the integration site, namely the promoter that drives expression of the endogenous gene into which the donor is inserted. However, it will be apparent that the donor may comprise a promoter and/or enhancer, for example a constitutive promoter or an inducible or tissue specific promoter.

The donor molecule may be inserted into an endogenous gene such that all, some or none of the endogenous gene is expressed. For example, a transgene as described herein may be inserted into an endogenous locus such that some (N-terminal and/or C-terminal to the transgene) or none of the endogenous sequences are expressed, for example as a fusion with the transgene. In other embodiments, the transgene (e.g., with or without additional coding sequences such as for the endogenous gene) is integrated into any endogenous locus, for example a safe-harbor locus, for example a CCR5 gene, a CXCR4 gene, a PPP1R12c (also known as AAVS1) gene, an albumin gene or a Rosa gene. See, e.g., U.S. Pat. Nos. 7,951,925 and 8,110,379; U.S. Publication Nos. 2008/0159996; 20100/0218264; 2010/0291048; 2012/0017290; 2011/0265198; 2013/0137104; 2013/0122591; 2013/0177983 and 2013/0177960 and U.S. Provisional Application No. 61/823,689).

When endogenous sequences (endogenous or part of the transgene) are expressed with the transgene, the endogenous sequences may be full-length sequences (wild-type or mutant) or partial sequences. Preferably the endogenous sequences are functional. Non-limiting examples of the function of these full length or partial sequences include increasing the serum half-life of the polypeptide expressed by the transgene (e.g., therapeutic gene) and/or acting as a carrier.

Furthermore, although not required for expression, exogenous sequences may also include transcriptional or translational regulatory sequences, for example, promoters, enhancers, insulators, internal ribosome entry sites, sequences encoding 2A peptides and/or polyadenylation signals.

In certain embodiments, the donor molecule comprises a sequence selected from the group consisting of a gene encoding a protein (e.g., a coding sequence encoding a protein that is lacking in the cell or in the individual or an alternate version of a gene encoding a protein), a regulatory sequence and/or a sequence that encodes a structural nucleic acid such as a microRNA or siRNA.

For the foregoing embodiments, each embodiment disclosed herein is contemplated as being applicable to each of the other disclosed embodiment. For example, it is understood that any of the RNA molecules or compositions of the present invention may be utilized in any of the methods of the present invention.

As used herein, all headings are simply for organization and are not intended to limit the disclosure in any manner. The content of any individual section may be equally applicable to all sections.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Generally, the nomenclature used herein, and the laboratory procedures utilized in the present invention include molecular, biochemical, microbiological and recombinant DNA techniques. Such techniques are thoroughly explained in the literature. See, for example, Sambrook et al., "Molecular Cloning: A laboratory Manual" (1989); Ausubel, R. M. (Ed.), "Current Protocols in Molecular Biology" Volumes I-III (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (Eds.), "Genome Analysis: A Laboratory Manual Series", Vols. 1-4, Cold Spring Harbor Laboratory Press, New York (1998); Methodologies as set forth in U.S. Pat. Nos. 4,666,828; 4,683,202; 4,801,531; 5,192,659 and 5,272,057; Cellis, J. E. (Ed.), "Cell Biology: A Laboratory Handbook", Volumes I-III (1994); Freshney, "Culture of Animal Cells—A Manual of Basic Technique" Third Edition, Wiley-Liss, N. Y. (1994); Coligan J. E. (Ed.), "Current Protocols in Immunology" Volumes I-III (1994); Stites et al. (Eds.), "Basic and Clinical Immunology" (8th Edition), Appleton & Lange, Norwalk, Conn. (1994); Mishell and Shiigi (Eds.), "Strategies for Protein Purification and Characterization—A Laboratory Course Manual" CSHL Press (1996); Clokie and Kropinski (Eds.), "Bacteriophage Methods and Protocols", Volume 1: Isolation, Characterization, and Interactions (2009), all of which are incorporated by reference. Other general references are provided throughout this document.

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only.

EXPERIMENTAL DETAILS

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only.

CRISPR repeat (crRNA), transactivating crRNA (tracrRNA), nuclease polypeptide, and PAM sequences were predicted from different metagenomic databases of sequences of environmental samples. The bacterial species/strain from which the CRISPR repeat, tracRNA sequence, and nuclease polypeptide sequence were predicted is provided in Table 1.

Construction of OMNI-50™ nuclease polypeptides

For construction of OMNI-50™ nuclease polypeptides, the open reading frame of the OMNI-50™ nuclease was codon optimized for human cell line expression. The optimized ORF was cloned into the bacterial plasmid pb-NNC and into the mammalian plasmid pmOMNI (Table 4).

Prediction and Construction of sgRNA

For the OMNI-50™ nuclease, the sgRNA was predicted by detection of the CRISPR repeat array sequence (crRNA) and a trans-activating crRNA (tracrRNA) in the bacterial genome in which the nuclease was identified. The native pre-mature crRNA and tracrRNA sequences were connected in-silico with tetra-loop 'gaaa' and the secondary structure elements of the duplex were predicted by using an RNA secondary structure prediction tool.

Figure 1B:
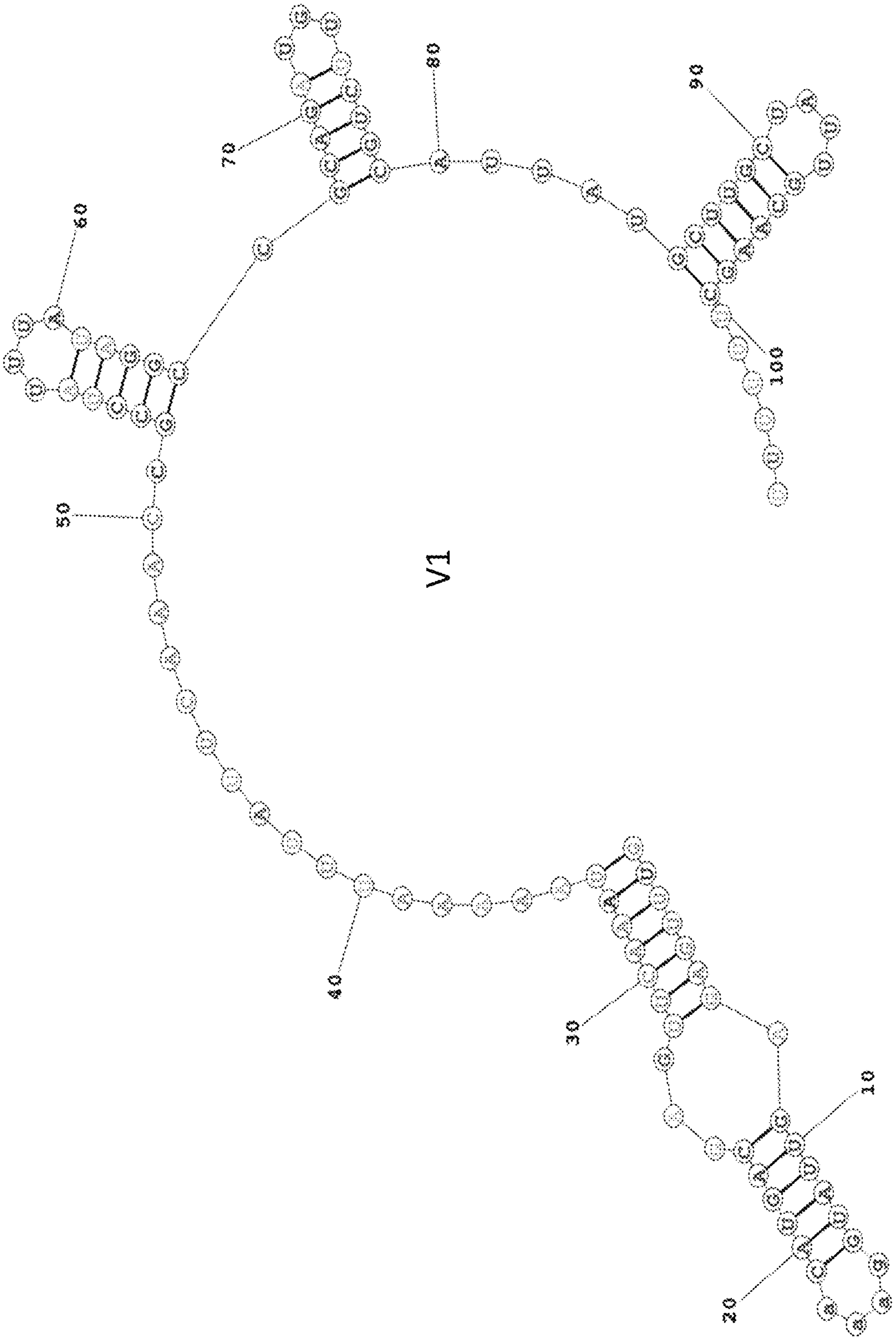
FIGS. 1B-1C: An example of the variation in structure between regions of two different sgRNAs, V1 (FIG. 1B) and V2 (FIG. 1C), designed for use with a single nuclease. By shortening the duplex at the upper stem at different locations, the crRNA and tracrRNA were connected with tetra-loop 'gaaa', generating sgRNA scaffolds.

The predicted secondary structures of the full duplex RNA elements (i.e. crRNA-tracrRNA chimera) was used for identification of possible tracr sequences for the design of a sgRNA having various versions for the OMNI-50™ nuclease (see for example, FIG. 1A). By shortening the duplex at the upper stem at different locations, the crRNA and tracrRNA were connected with tetra-loop 'gaaa', thereby generating possible sgRNA scaffolds (see for example, FIG. 1B; OMNI-50™ sgRNA designs are listed in Table 2). At least two versions of possible designed scaffolds for OMNI-50™ were synthesized and connected downstream to a 22 nt universal unique spacer sequence (T2, SEQ ID NO: 56), and cloned into a bacterial expression plasmid under a constitutive promoter and into a mammalian expression plasmid under a U6 promoter (pbGuide and pmGuide, respectively, Table 4).

Figure 1C:
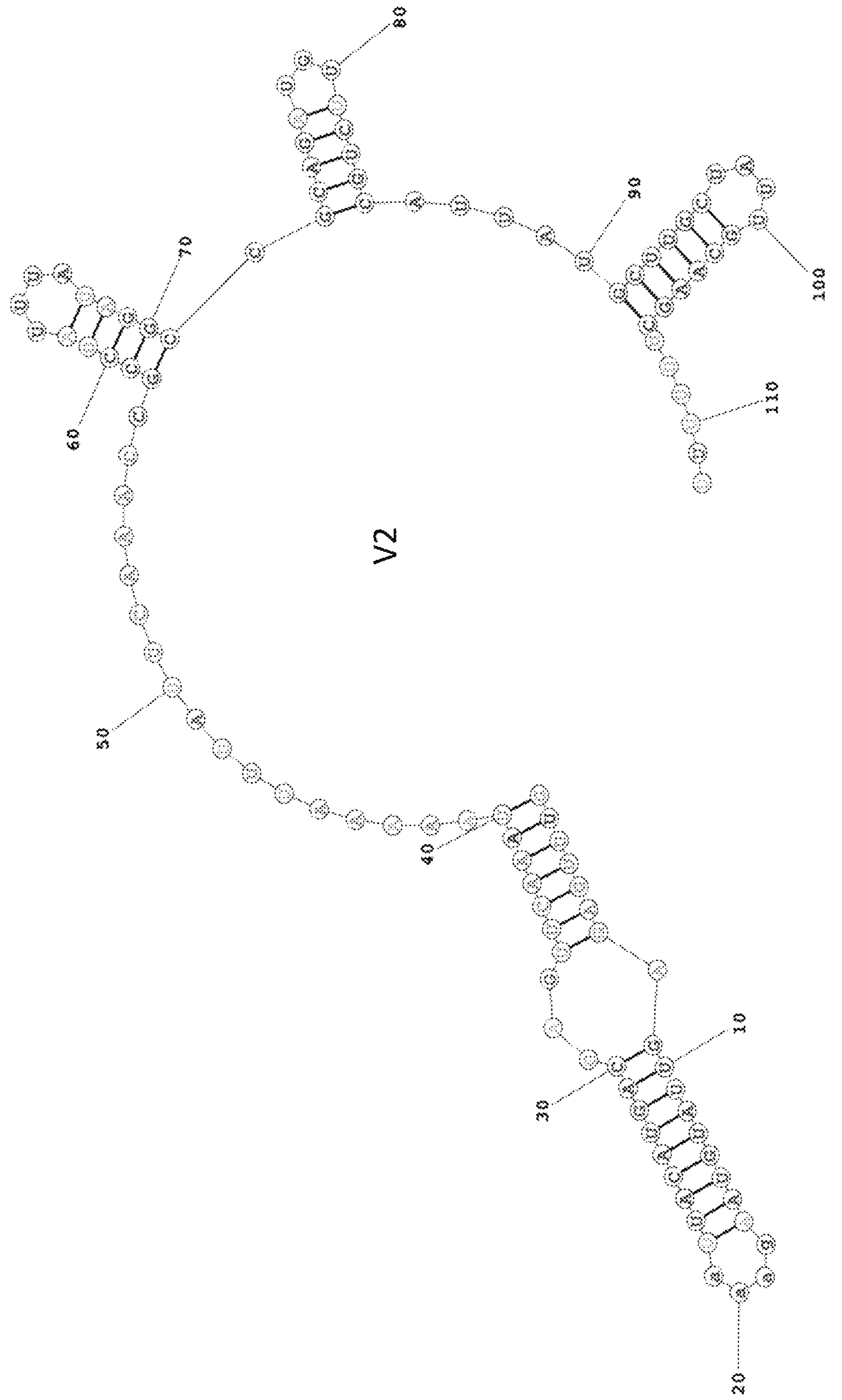

In order to overcome potential transcriptional and structural constraints and to assess the plasticity of the sgRNA scaffold in the human cellular environmental context, several versions of the sgRNA were tested. In each case the modifications represent small variations in the nucleotide sequence of the possible sgRNA (FIG. 1C, Table 2)

```
                                        (SEQ ID NO: 55)
T1 - GGTGCGGTTCACCAGGGTGTCG

                                        (SEQ ID NO: 56)
T2 - GGAAGAGCAGAGCCTTGGTCTC
```

In-Vitro Depletion Assay by TXTL

Figure 2A:
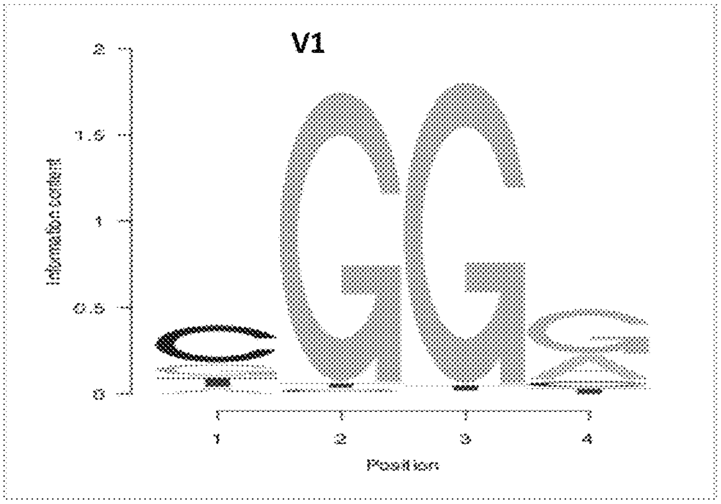
FIG. 2A: A condensed 4N window library of all possible PAM locations along an 8 bp sequence for OMNI-50™ sgRNA V1 in a cell-free in vitro TXTL system. Sequence motifs generated for PAM sites based on depletion assay results. Activity estimated based on the average of the two most depleted sequences and was calculated as: 1—Depletion score.
Figure 2B:
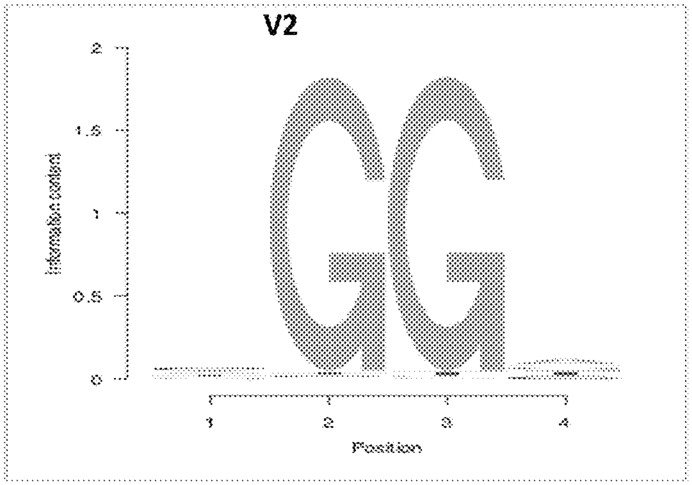
FIG. 2B: The sequence motifs generated for all possible PAM locations along an 8 bp sequence for the OMNI-50™ sgRNA V2.

Depletion of PAM sequences in-vitro was followed by Maxwell et al., Methods (2018). Briefly, linear DNA expressing the OMNI-50™ nuclease and an sgRNA under a T7 promoter were added to a TXTL mix (Arbor Bioscience) together with a linear construct expressing T7 polymerase. RNA expression and protein translation by the TXTL mix result in the formation of the RNP complex. Since linear DNA was used, Chili sequences, a RecBCD inhibitor, were added to protect the DNA from degradation. The sgRNA spacer is designed to target a library of plasmids containing the targeting protospacer (pbPOS T2 library, Table 4) flanked by an 8N randomized set of potential PAM sequences. Depletion of PAM sequences from the library was measured by high-throughput sequencing upon using PCR to add the necessary adapters and indices to both the cleaved library and to a control library expressing a non-targeting gRNA (T1). Following deep sequencing, the in-vitro activity was confirmed by the fraction of the depleted sequences having the same PAM sequence relative to their occurrence in the control by the OMNI nuclease indicating functional DNA cleavage by an in-vitro system (FIG. 2, Table 3). OMNI-50™ was tested with two sgRNA versions (V1 and V2). In both cases, a clear PAM of NGG was deduced from the analysis (FIG. 2). Some activity was also observed with NAG and NGA PAM sequences.

PAM Library in Mammalian System

While a PAM sequence preference is considered as an inherent property of the nuclease, it may be affected, to some extent, by the cellular environment, genomic composition, and genome size. Since the human cellular environment is significantly different from the bacterial environment with respect to each of those properties, a "fine tuning" step has been introduced to address potential differences in PAM preferences in the human cellular context. To this end, a PAM library was constructed in a human cell line. In this assay, The PAM library was introduced to the cells using a viral vector (see Table 4) as a constant target sequence followed by a stretch of 6N. Upon introduction of OMNI-50™ and an sgRNA targeting the library constant target site, NGS analysis was used to identify the edited sequences and the PAM associated with them. The enriched edited sequences were then used to define the PAM consensus. This methodology is applied to determine the optimized PAM requirements of the OMNI-50™ nuclease in mammalian cells (Table 3, "Mammalian refinements"). The OMNI-50™ PAM was found to be identical to the one found in the in-vitro TXTL.

Figure 3:
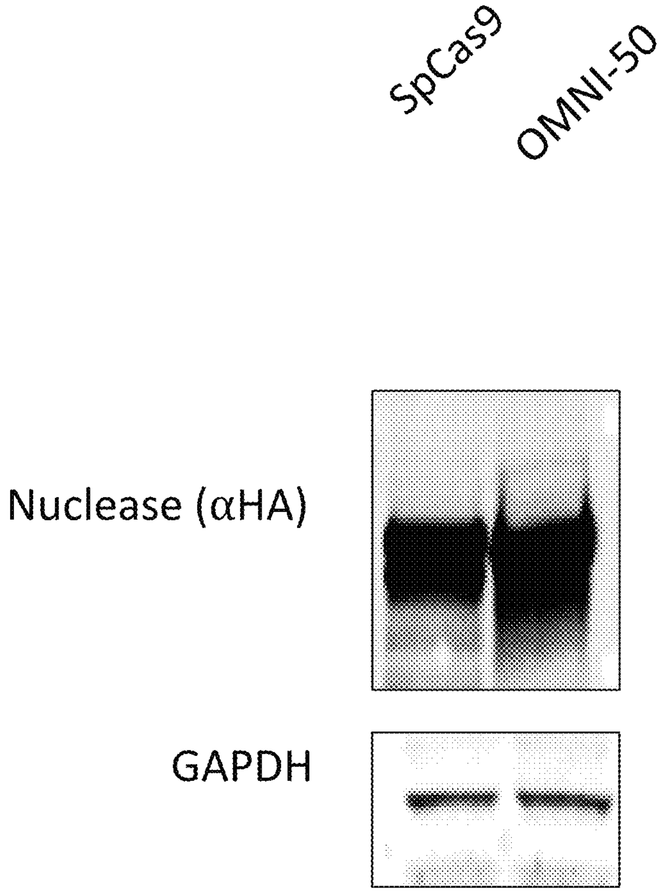
FIG. 3: Expression of OMNI-50™ in mammalian cells. OMNI-50™ or SpCas9 nuclease were transiently transfected in Hek293T cells. Cells were harvested and lysed at 72 h, and the lysates were used to test OMNI-50™ expression in the mammalian cells by western blot using an antibody against the HA-tag. SpCas9-HA was transfected in the same manner served as a positive control. GAPDH was used to normalize loading quantities.

Expression of OMNI-50™ Nuclease Coded by an Optimized DNA Sequence in Mammalian Cells First, expression of each of the optimized DNA sequences encoding OMNI-50™ in mammalian cells was validated. To this end, an expression vector coding for an HA-tagged OMNI-50™ nuclease or *Streptococcus pyogenes* Cas9 (SpCas9) linked to mCherry by a P2A peptide (pmOMNI, Table 4) was introduced into Hek293T cells using the Jet-optimus™ transfection reagent (polyplus-transfection). The P2A peptide is a self-cleaving peptide which can induce the cleaving of the recombinant protein in a cell such that the OMNI nuclease and the mCherry are separated upon expression. The mCherry serves as indicator for transcription efficiency of the OMNI from expression vector. Expression of OMNI-50™ protein was confirmed by a western blot assay using an anti-HA antibody (FIG. 3).

Activity in Human Cells on Endogenous Genomic Targets

OMNI-50™ was also assayed for its ability to promote editing on specific genomic locations in human cells. To this end, an OMNI-P2A-mCherry expression vector (pmOMNI, Table 4) was transfected into HeLa cells together with an sgRNA designed to target a specific location in the human genome (pmGuide, Table 4). At 72h, cells were harvested. Half of the cells were used for quantification of transfection efficiency by FACS using mCherry fluorescence as a marker. The other half of the cells were lysed, and their genomic DNA was used to PCR amplify the corresponding putative genomic targets. Amplicons were subjected to NGS and the resulting sequences were used calculate the percentage of editing events in each target site. Short insertions or deletions (indels) around the cut site are the typical outcome of repair of DNA ends following nuclease-induced DNA cleavage. The calculation of percent editing was deduced from the fraction of indel-containing sequences within each amplicon. All editing values were normalized to the transfection and translation efficacy obtained for each experiment and deduced from the percentage of mCherry expressing cells. The normalized values represent the effective editing levels within the population of cells that expressed the nuclease.

Genomic activity of OMNI-50™ was assessed using a panel of eleven unique sgRNAs each designed to target a different genomic location. The results of these experiments are summarized in Table 6. As can be seen in the table (column 6, "% editing"), OMNI-50™ exhibits high and significant editing levels compared to the negative control (column 9, "% editing in neg control") in all target sites tested. OMNI-50™ exhibits high and significant editing levels in 11/11 sites tested.

Intrinsic Fidelity in Human Cells

Figure 4A:
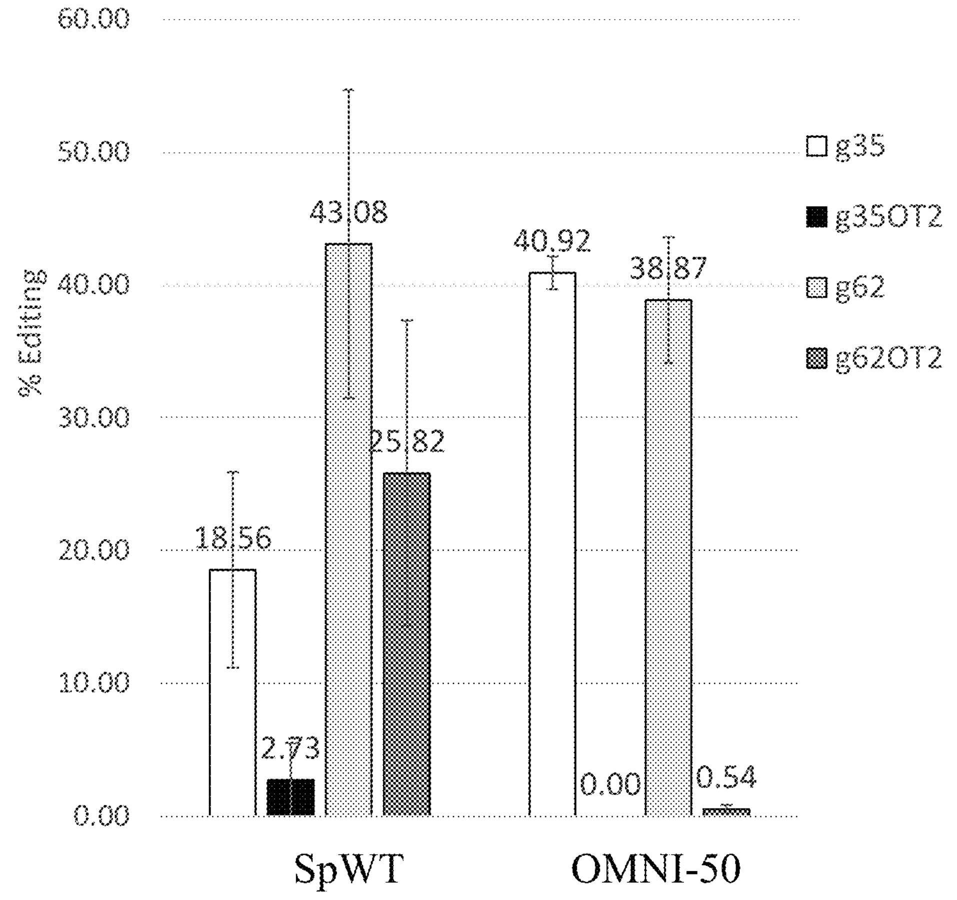
FIG. 4A: Intrinsic fidelity in human cells. OMNI-50™ or SpCas9 nuclease were expressed in mammalian cell system by DNA transfection together with sgRNA expressing plasmid. Cell lysates were used for site specific genomic DNA amplification and NGS. The percentage of Indels was measured and analyzed as described in section vii, target vs off-target editing in HeLa cell line using ELANEg35_OMNI-50 or ELANEg62_OMNI-50. In both cases the genomic On and Off target sequences are noted below the chart, PAM sequence in underline. Each experiment represents 3 independent repeats.
Figure 4B:
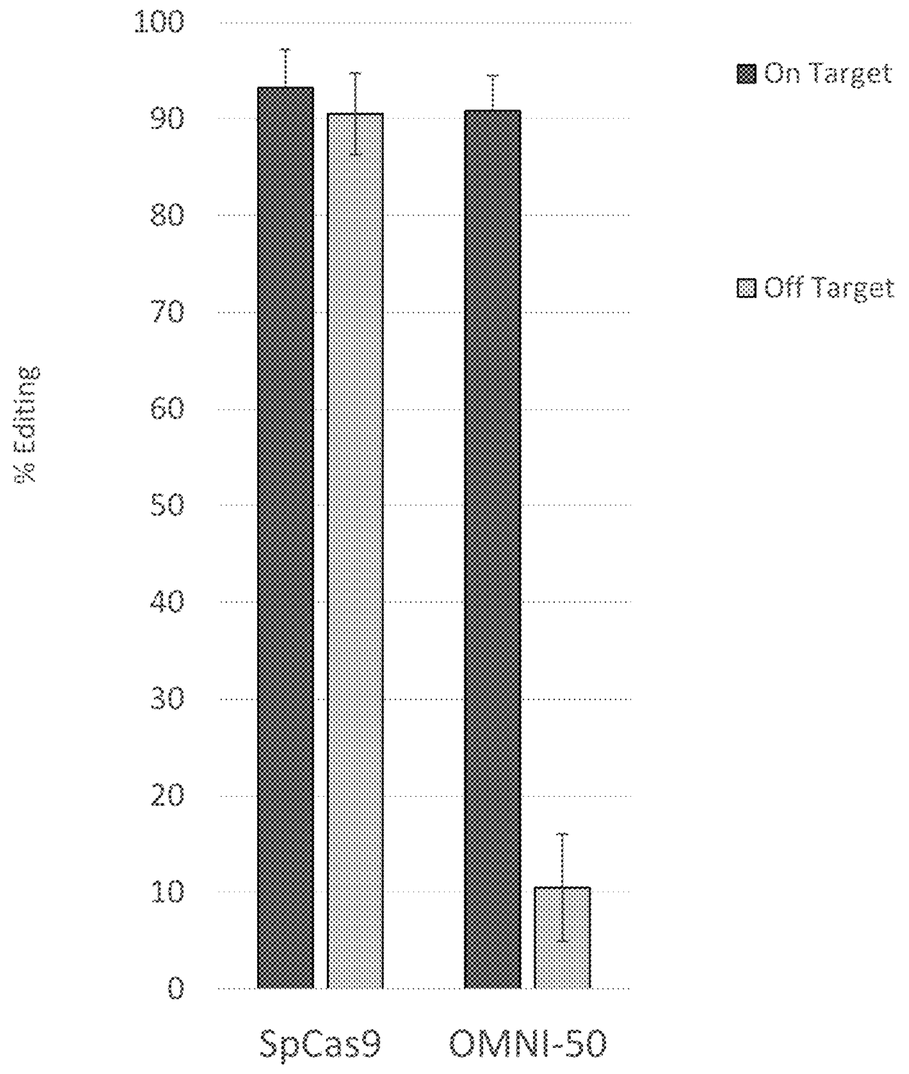
FIG. 4B: RNP introduction of OIVI-50™ or SpCas9 targeting ELANEg35 was followed by lysis, site specific DNA amplification and NGS. Editing level of both On and Off target sequences is shown in a second system.

The intrinsic fidelity of a nuclease is a measure of its cleavage specificity. A high-fidelity nuclease is a nuclease that promotes cleavage on an intended target ("on-target") with minimal or no cleavage of an unintended target ("off-target"). For CRISPR nucleases the target is acquired based on sequence complementarity to the spacer element of the guide RNA. Off-targeting results from similarity between the spacer sequence and an unintended target. The intrinsic fidelity of OMNI-50™ at the genomic level in human cells was measured by conducting an activity assay as described in the section above, following PCR amplification, NGS, and indel analysis for both the on-target region and a pre-validated off-target region. A measurement of intrinsic fidelity for OMNI-50™ is provided in FIG. 4A. In this example, OMNI-50™ fidelity was measured using two guide RNAs independently, in each case a side by side measurement of SpCas9 is provided for reference. The first site was targeted using the ELANE g35 gRNA (Table 6) which has a defined on-target site upstream to the ELANE gene on chr19 and an off-target site on chr15. As can be seen in FIG. 4A, the on/off target editing efficiency ratio obtained by OMNI-50™ was 41:0 while SpCas9 on/off ratio is 6.8:1 (40.9%/0%; 18.6%/2.7%, respectively). The second site was targeted by ELANE g62 gRNA (Table 6). This gRNA spacer sequence has a defined on-target site at the ELANE gene on chr19 and an off-target site on chr1. In this case, the on/off ratio obtained by OMNI-50™ was 72:1 compared to 1.7:1 ratio obtained by SpCas9 (38.9%/0.6%; 43.1%/25.8%, respectively). These results demonstrate that OMNI-50™ has a significantly higher intrinsic fidelity in comparison to SpCas9 using these specific gRNAs. Intrinsic fidelity was later tested in a second system by RNP electroporation into a U2OS cell line (FIG. 4B). For ELANE g35 the on/off target editing efficiency ratio obtained by OMNI-50™ was 9:1 while the SpCas9 on/off ratio is 1:1 (91%/10%; 93%/91%, respectively). In two separate systems OMNI-50™ fidelity was superior to SpCas9.

Evaluating Off-Target Using a Guide-Seq Unbiased Analysis Method

To further evaluate the specificity of OMNI-50™, the number of off-targets were tested across several sites using guide-seq. The off-targets count for SpCas9 varied across sites from several to hundreds, while the OMNI-50™ off-targets count was lower than twenty in all sites tested. Comparing the number of off-targets found for sites having greater than 10 reads using either SpCas9 or OMNI-50™ indicates the high specificity of OMNI-50™. In five out of six sites tested, the number of SpCas9 off-targets was considerably higher compared to OMNI-50™ (double to twenty-fold), while in only one of six sites the off-targets count is comparable between the two nucleases (Table 9).

Purification of OMNI-50™ Protein

The OMNI-50™ open reading frame was cloned into bacterial expression plasmids (T7-NLS-OMNI-NLS-HA-His-tag, pET9a, Table 4) and expressed in C43 cells (Lucigen). Cells were grown in Terrific Broth to mid-log phase and the temperature was then lowered to 18° C. Expression was induced at 0.6 OD with 1 mM IPTG for 16-20 h before harvesting and freezing cells at −80° C. Cell paste was resuspended in lysis buffer (50 mM $NaH_2PO_4$, 300 mM NaCl, 10 mM imidazole pH8.0, 1 mM TCEP) supplemented with EDTA-free complete protease inhibitor cocktail set III (Calbiochem). Cells were lysed using sonication and cleared lysate was incubated with Ni-NTA resin. The resin was loaded onto a gravity column, washed with wash buffer (50 mM $NaH_2PO_4$, 300 mM NaCl, 50 mM imidazole pH8.0, 1 mM TCEP), and OMNI-50™ protein was eluted with wash buffer supplemented with 100-500 mM imidazole. Fractions containing OMNI-50™ protein were pooled, concentrated, loaded onto a centricone (Amicon Ultra 15 ml 100K, Merck), and buffer exchanged to GF buffer (50 mM Tris-HCl pH 7.5, 500 mM NaCl, 10% glycerol, 0.4M Arginine). The concentrated OMNI-50™ protein was further purified by SEC on HiLoad 16/600 Superdex 200 pg-SEC, AKTA Pure (GE Healthcare Life Sciences) with a 50 mM Tris-HCl pH 7.5, 500 mM NaCl, 10% glycerol, 0.4M Arginine. Fractions containing OMNI-50™ protein were pooled, concentrated, and loaded onto a centricone (Amicon Ultra 15 ml 100K, Merck) with a final storage buffer of 10 mM Tris-HCl, pH 7.5, 150 mM NaCl, 10% glycerol and 1 mM TCEP. Purified OMNI-50™ protein was concentrated to 10 mg/ml stocks, flash-frozen in liquid nitrogen, and stored at −80° C.

Guide Optimization by RNP Activity Assay

Figure 5A:
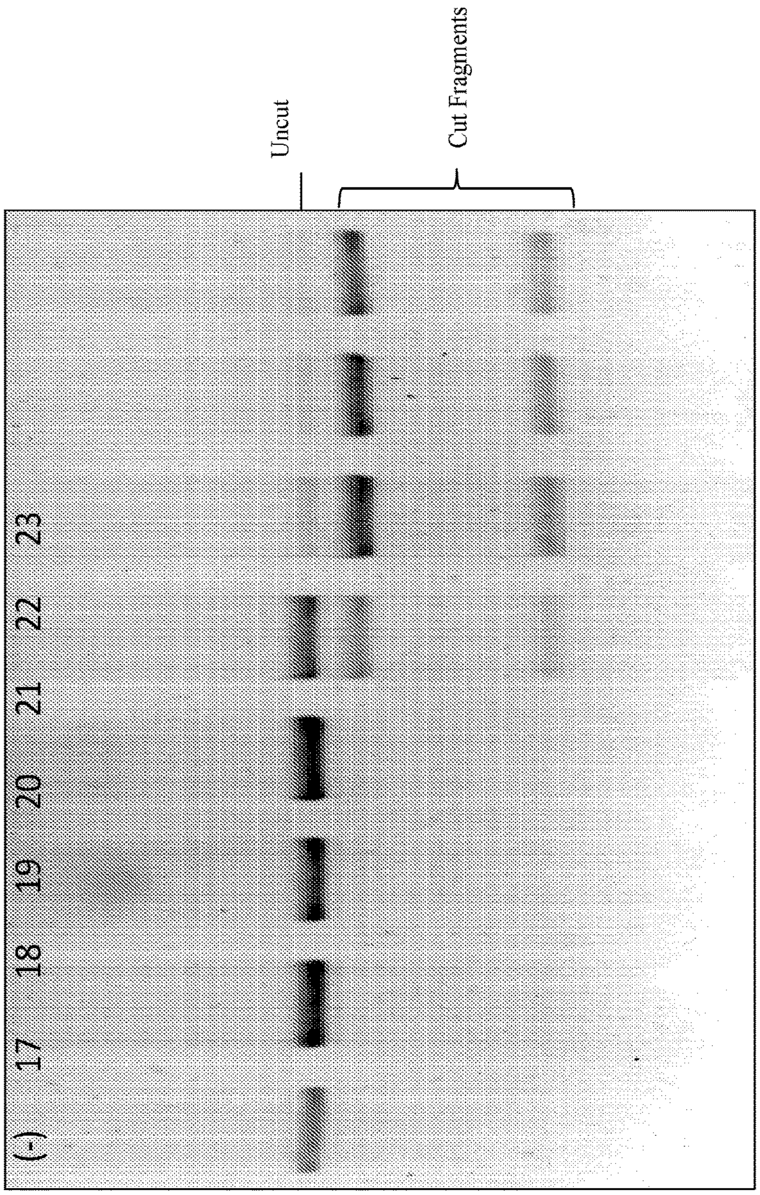
FIG. 5A-FIG. 5D: OMNI-50™ activity Assay as RNP. OMNI-50™ nuclease was over-expressed and purified. The purified protein was complexed with synthetic sgRNA to form RNPs. For the in-vitro assays (FIG. 5A and FIG. 5B) RNPs were incubated with a linear DNA template containing the corresponding target and PAM sequences (listed in Table 5). Activity was verified by cleavage of the linear template. For the in-vivo assays (FIG. 5C and FIG. 5D), U2OS cells were electroporated with RNPs and activity was determined by measurement of indel frequency by NGS.
Figure 5B:
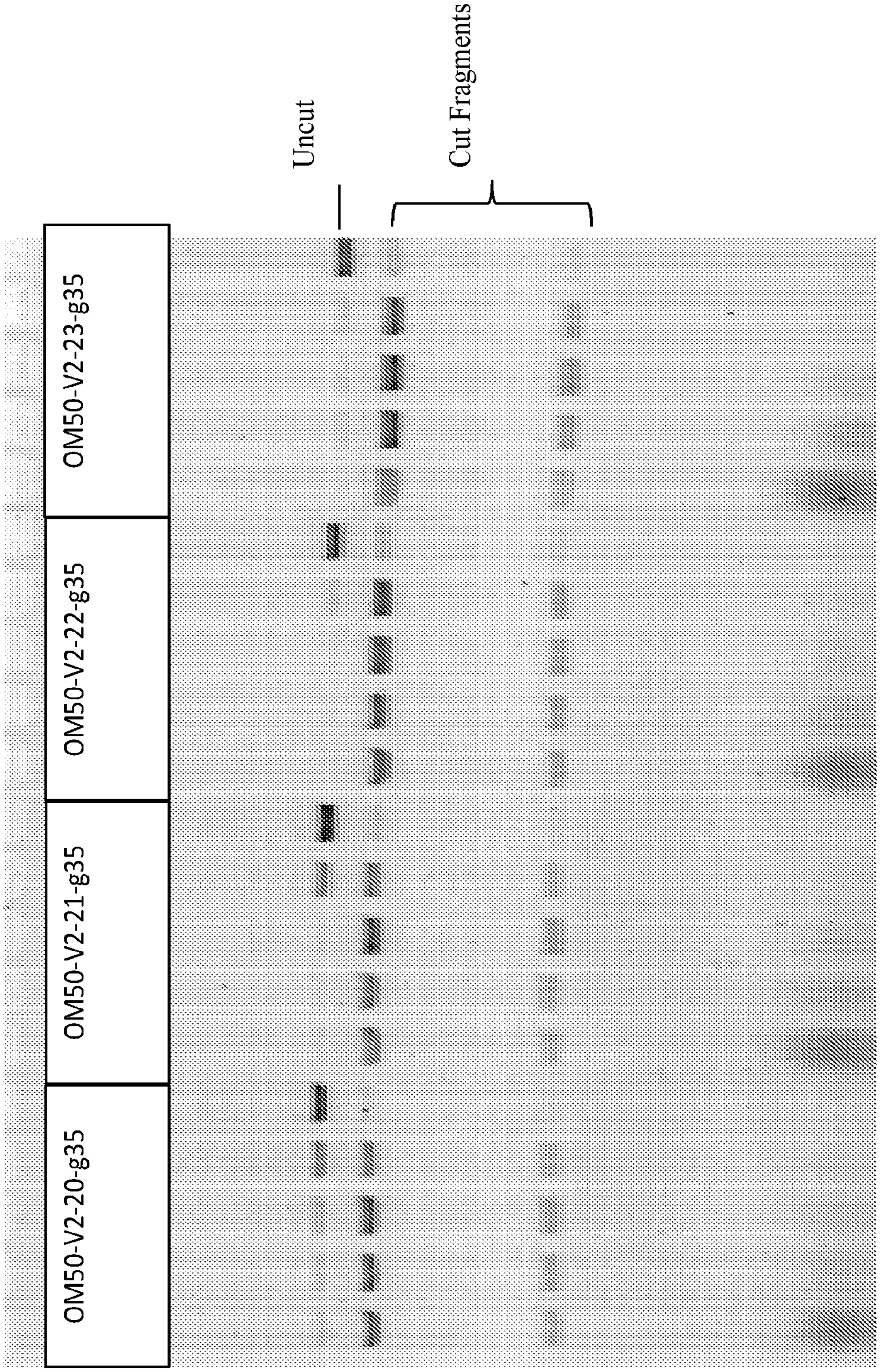

Synthetic sgRNAs of OMNI-50™ were synthesized with three 2'-O-methyl 3'-phosphorothioate at the 3' and 5' ends (Agilent). An activity assay of OMNI-50™ RNPs with different spacer lengths (17-23 nts) of guide 35 is described herein (Table 5, FIG. 5A). Briefly, 4 pmol of OMNI-50™ nuclease was mixed with 6 pmol of synthetic guide. After 10 minutes of incubation at room temperature, the RNP complexes were reacted with 100 ng of on-target template. Only spacer greater than or equal to 22 nts show near full cleavage of the on-target template. When decreasing amounts of RNPs (4, 2, 1.2, 0.6 and 0.2 pmol) having spacer lengths 20-23 nts were reacted with 100 ng of DNA target template (FIG. 5B). Spacer at lengths greater than or equal to 22 nt show better cleavage activity even at lower RNP concentrations.

Figure 5C:
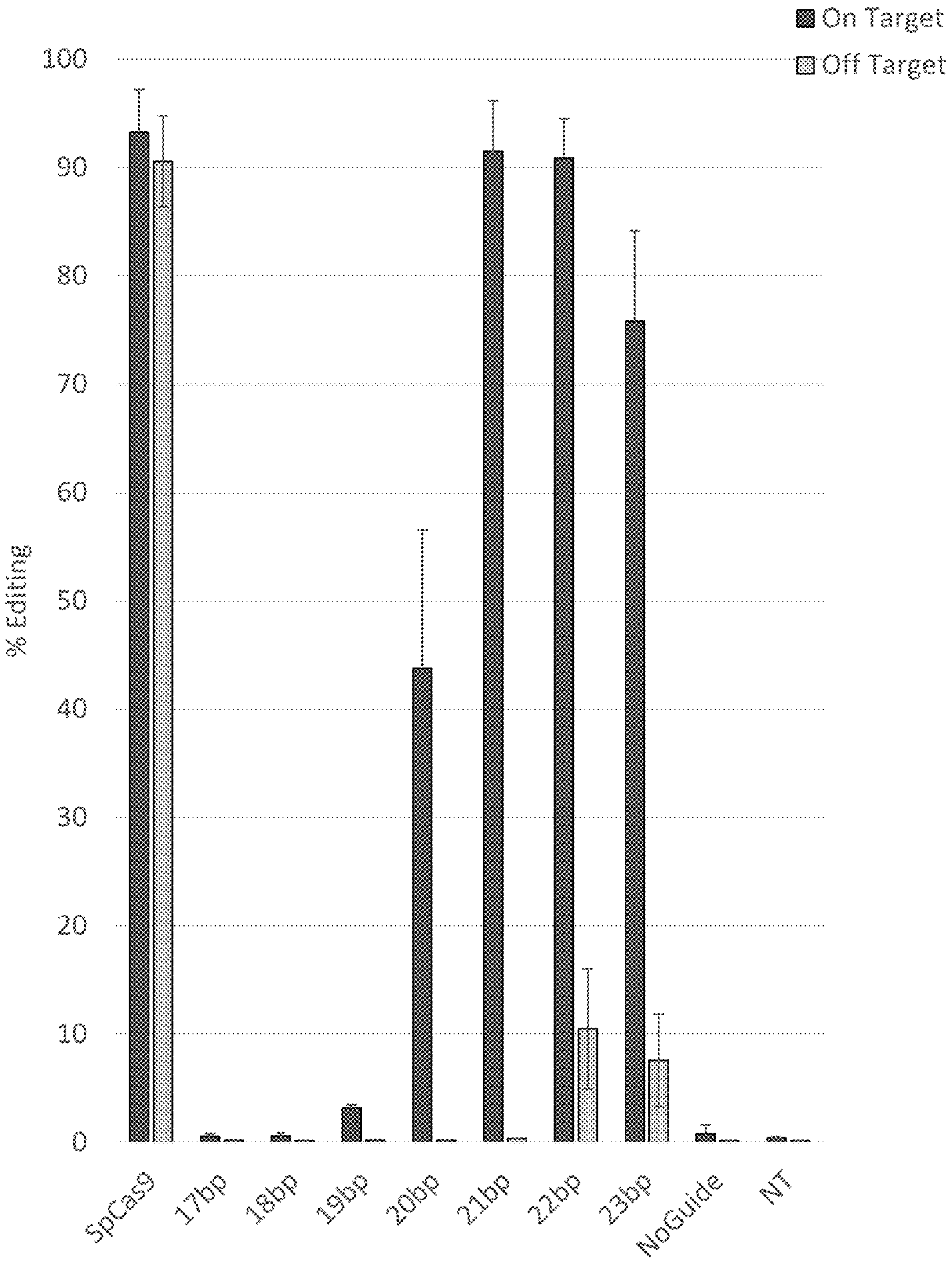
Figure 6:
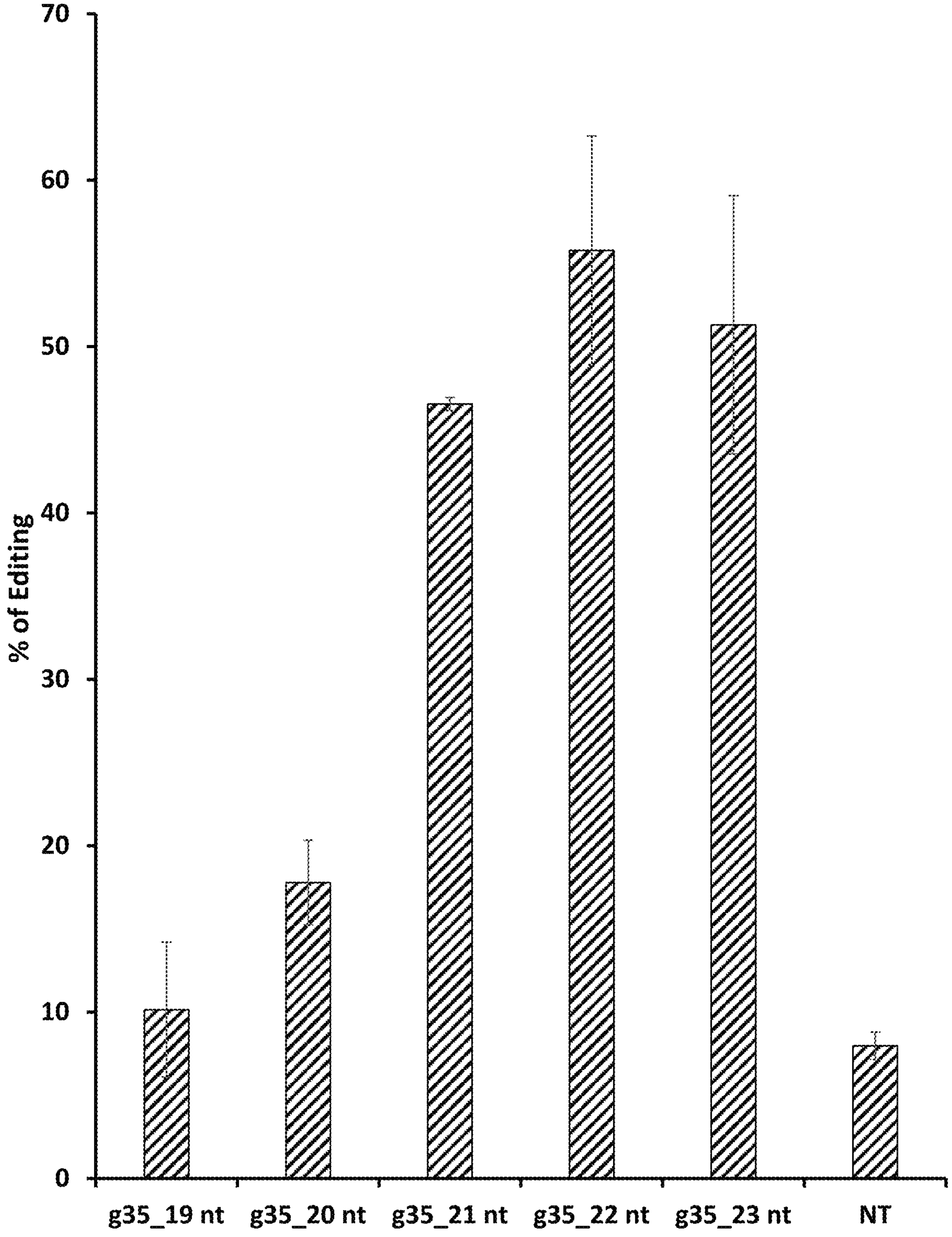
FIG. 6: Activity assay for OMNI-50™ as RNP in iPSCs. RNPs with spacer lengths 17-23 nts (Table 10) were electroporated into an iPSC cell line and editing levels (indels) were measured by NGS.
Figure 7:
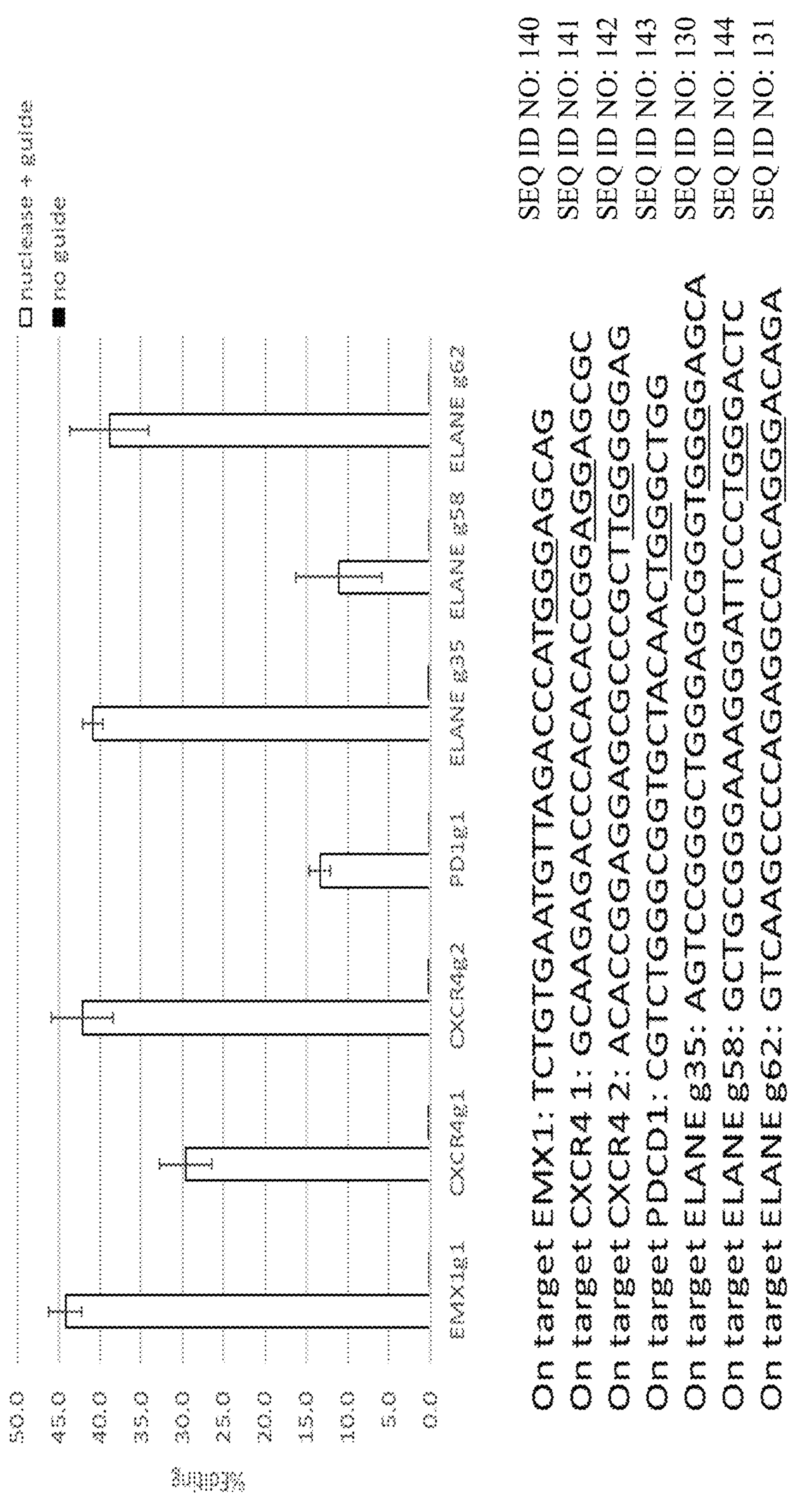
FIG. 7. OMNI-50™ nuclease activity in an endogenous mammalian cellular context. OMNI-50™ nuclease was expressed in mammalian cell system by DNA transfection together with sgRNA expressing plasmid. Cell lysates were used for site specific genomic DNA amplification and NGS. The percentage of indels was measured and analyzed to determine the editing level. Cells transfected with the OMNI-50™ nuclease without a guide RNA served as a negative control for comparison and background determination. Editing levels in different genomic locations are shown.

Spacer length optimization was also performed in a mammalian cell context. RNPs were assembled by mixing 100 uM nuclease with 120 uM of synthetic guide with different spacer lengths (17-23 nt, Table 5) and 100 uM Cas9 electroporation enhancer (IDT). After 10 minutes of incubation at room temperature, the RNP complexes were mixed with 200,000 pre-washed U205, iPSC, or HSC cells and electroporated using Lonza SE or P3 Cell Line 4D-Nucleofector™ X Kit with the DN100 or CA137 program, respectively, according to the manufacture's protocol. At 72h cells were lysed and their genomic DNA was used in a PCR reaction to amplify the corresponding putative genomic targets. Amplicons were subjected to NGS and the resulting sequences were then used to calculate the percentage of editing events. As can be seen in FIG. 5C, FIG. 6, and Table 10, spacers of 17-19 nts show a low editing level, 20 nt spacers show a medium editing level, and spacers of 21-23 nts show the highest editing level.

Figure 5D:
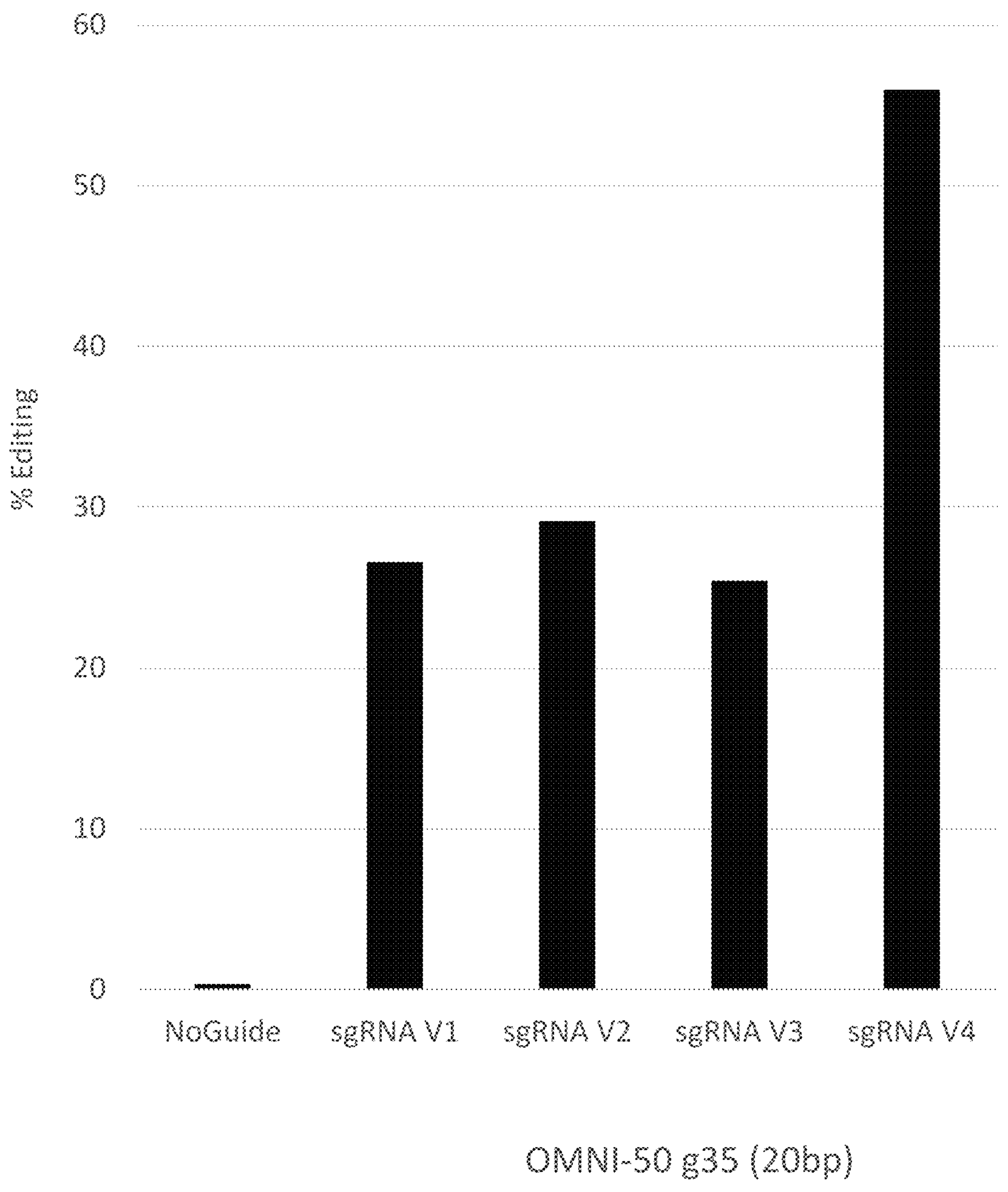

Using the U2OS cell line, different tracer RNA sequence variations were tested (Table 2). The different sgRNA versions were tested with a 20 nt spacer. As can be seen in FIG. 5D, RNP assembly using either sgRNA V1, V2, or V3 results in a similar editing level. However, RNP assembly using sgRNA V4 results in a significantly higher editing level.

Comparing results obtained in HSCs using 21 nt and 22 nt spacers across five genomic sites suggests that a 22 nt spacer is slightly preferred for efficient editing (FIG. 6 and table 10).

Activity of OMNI-50™ as an RNP

Activity of OMNI-50™ protein as RNP in mammalian cells was first tested in the U2OS cell line, and later tested in three primary cell systems: iPSCs, HSCs, and T cells. As can be seen in Table 7, editing was observed in all systems.

OMNI-50™ was tested for editing activity in T-cells on two genes (Appendix Table 7). OMNI-50™ was tested with 34 guides targeting TRAC and 26 guides targeting B2M. 64% (22/34) of the tested TRAC guides were found to be active, with editing levels ranging between 5% to 84%. Similarly, 57% of the B2M guides were active, with editing levels ranging between 5% and 61%. These results are summarized in Appendix Table 7.

High editing was observed in both TRAC and B2M genes in a repertoire of 19 guides each. Considering the potential for multiplexing and further optimization, full knock-out of both genes by OMNI-50™ is possible with the appropriate strategy.

In U2OS cells, iPSCs and HSCs, guides targeting the ELANE gene were tested with OMNI-50™. All five guides tested showed editing above 22% in both U2OS cells and HSCs. In iPSCs only ELANE g35 was tested with editing level of 53%. This result is lower compared with the results obtained with other systems.

Multiplexing

OMNI-50™ was also tested for multiplex editing by mixing two RNP populations and electroporating the mix into primary T cells. gRNA #32 was used for TRAC, and gRNA #15 was used for B2M (spacer sequences are listed in Table 8). At 72h cells were harvested and tested for editing by NGS. The TRAC gene measured 50% editing, and the B2M gene measured 25% editing. These results were similar to editing levels with a single RNP that was performed side-by-side to the multiplex test (Table 8).

TABLE 1

OMNI-50 ™ nuclease sequences

| Source Organism | SEQ ID NO of OMNI-50 ™ Amino Acid Sequence | SEQ ID NO of DNA sequence encoding OMNI-50 ™ | SEQ ID NO of DNA sequence codon optimized for encoding OMNI-50 ™ in human cells |
|---|---|---|---|
| *Ezakiella peruensis* strain M6.X2 | 3 | 11 | 12, 13 |

Table 1. OMNI-50™ nuclease sequences: Table 1 lists the organism from which the OMNI-50™ nuclease was identified, its protein sequence, its DNA sequence, and its human optimized DNA sequence(s).

TABLE 2

OMNI-50 ™ guide sequences

| | | |
|---|---|---|
| Minimal crRNA:tracrRNA duplex | crRNA (Repeat) | GUUUGAGAG |
| | tracrRNA (Antirepeat) | CGAGUUCAAAU (SEQ ID NO: 149) |
| crRNA:tracrRNA duplex V1 | crRNA (Repeat) | GUUUGAGAGUUAUG (SEQ ID NO: 37) |
| | tracrRNA (Antirepeat) | CAUGACGAGUUCAAAU (SEQ ID NO: 38) |
| crRNA:tracrRNA duplex V2 | crRNA (Repeat) | GUUUGAGAGUUAUGUAA (SEQ ID NO: 39) |
| | tracrRNA (Antirepeat) | UUACAUGACGAGUUCAAAU (SEQ ID NO: 40) |
| TracrRNA sequences | TracrRNA Portion 1 | AAAAAUUUAUUCAAACC (SEQ ID NO: 150) |
| | TracrRNA Portion 2 | GCCUAUUUAUAGGC (SEQ ID NO: 42) |
| | TracrRNA Portion 3 | CGCAGAUGUUCUGC (SEQ ID NO: 151) |
| | TracrRNA Portion 4 | AUUAUGCUUGCUAUUGCAAGCUUUUUU (SEQ ID NO: 152) |

TABLE 2-continued

| OMNI-50 ™ guide sequences | | |
|---|---|---|
| | Full tracrRNA V1 | CAUGACGAGUUCAAAUAAAAAUUUAUUCAAACCGCCUAUUUAUAGGCCGCAGAUGUUCUGCAUUAUGCUUGCUAUUGCAAGCUUUUUU (SEQ ID NO: 153) |
| | Full tracrRNA V2 | UUACAUGACGAGUUCAAAUAAAAAUUUAUUCAAACCGCCUAUUUAUAGGCCGCAGAUGUUCUGCAUUAUGCUUGCUAUUGCAAGCUUUUUU (SEQ ID NO: 154) |
| sgRNA Versions | sgRNA V1 | GUUUGAGAGUUAUGgaaaCAUGACGAGUUCAAAUAAAAAUUUAUUCAAACCGCCUAUUUAUAGGCCGCAGAUGUUCUGCAUUAUGCUUGCUAUUGCAAGCUUUUUU (SEQ ID NO: 44) |
| | sgRNA V2 | GUUUGAGAGUUAUGUAAgaaaUUACAUGACGAGUUCAAAUAAAAAUUUAUUCAAACCGCCUAUUUAUAGGCCGCAGAUGUUCUGCAUUAUGCUUGCUAUUGCAAGCUUUUUU (SEQ ID NO: 45) |
| Other sgRNA Optimizations | sgRNA V3 | GUUUGAGAGUUAUGUgaaaACAUGACGAGUUCAAAUAAAAAUUUAUUCAAACCGCCUAUUUAUAGGCCGCAGAUGUUCUGCAUUAUGCUUGCUAUUGCAAGCUUUUUU (SEQ ID NO: 87) |
| | sgRNA V4 | GUUUGAGAGUUAUGUAgaaaUACAUGACGAGUUCAAAUAAAAAUUUAUUCAAACCGCCUAUUUAUAGGCCGCAGAUGUUCUGCAUUAUGCUUGCUAUUGCAAGCUUUUUU (SEQ ID NO: 88) |

TABLE 3

| OMNI-50 ™ PAM sequences | | |
|---|---|---|
| TXTL Depletion | PAM General | NGG |
| | PAM Specific | NGG |
| | Activity (1-Depletion score)* | 0.98 |
| | sgRNA | V1, V2 |
| Mammalian refinements | PAM Mammlian | NGG |

*Depletion score - Average of the ratios from two most depleted sites

TABLE 4

| Plasmids and Constructs | | | |
|---|---|---|---|
| Plasmid | Purpose | Elements | Example |
| pbNNC-2 | Expressing OMNI polypeptide in the bacterial system | T7 promoter HA Tag-Linker-OMNI ORF (Human optimized) - T7 terminator | pbNNC2 OMNI-50 |
| pbGuide T1/T2 | Expressing OMNI sgRNA in the bacterial system | J23119 promoter - T1/T2 spacer sgRNA scaffold - rrnB T1 terminator | pbGuide OMNI-50 T2 sgRNA V2 |
| pbPOS T2 library | Bacterial/TXTL depletion assay | T2 protospacer - 8N PAM library - chloramphenicol acetyltransferase | pbPOS T2 library |
| pET9a | Expression and purification of OMNI proteins | T7 promoter - SV40 NLS - OMNI ORF (human optimized) - HA - SV40 NLS - 8 His-tag - T7 terminator | pET9a OMNI-50-HisTag |
| pmOMNI | Expressing OMNI polypeptide in the mammalian system | CMV promoter - Kozak - SV40 NLS - OMNI ORF (human optimized) - HA - SV40 NLS - P2A - mCherry - Bgh poly(A) signal | pmOMNI OMNI-50 |
| pmGuide Endogenic site | Expressing OMNI sgRNA in the mammalian system | U6 promoter - Endogenic spacer sgRNA scaffold | pmGuide OMNI-50 CXCR4 sgRNA V3 |
| pPM3L3.1 | Viral vector for PAM library in mammalian cells | LTR - HIV-1 Ψ - CMV promoter - T2 - PAM library (6N) - GFP - SV40 promoter - blastocydin S deaminase - LTR | pPM3L3.1 |

TABLE 4

| Appendix - Details of construct elements | | |
|---|---|---|
| Element | Protein Sequence | DNA sequence |
| HA Tag | SEQ ID NO: 63 | SEQ ID NO: 64 |
| NLS | SEQ ID NO: 65 | SEQ ID NO: 66 |

TABLE 4-continued

| Appendix - Details of construct elements | | |
|---|---|---|
| Element | Protein Sequence | DNA sequence |
| P2A | SEQ ID NO: 85 | SEQ ID NO: 86 |
| mCherry | SEQ ID NO: 67 | SEQ ID NO: 68 |

TABLE 5

| Synthetic sgRNA (spacer and scaffold) | | | | | |
|---|---|---|---|---|---|
| Name | O50_ELANE_V2_g35_23 | O50_ELANE_V2_g35_22 | O50_ELANE_V2_g35_21 | O50_ELANE_V2_g35_20 | O50_ELANE_V2_g35_19 |
| Spacer | UgcAGUCCGGGCUGGGAGCGGGU (SEQ ID NO: 112) | gcAGUCCGGGCUGGGAGCGGGU (SEQ ID NO: 116) | cAGUCCGGGCUGGGAGCGGGU (SEQ ID NO: 118) | AGUCCGGGCUGGGAGCGGGU (SEQ ID NO: 120) | GUCCGGGCUGGGAGCGGGU (SEQ ID NO: 122) |
| Scaffold | gUUUGAGAGUUAUGUAAgaaaUUACAUGACGAGUUCAAAUAAAAAUUUAUUCAAACCGCCUAUUUAUAGGCCGCAGAUGUUCUGCAUUAUGCUUGCUAUUGCAAGCUUUUUU (SEQ ID NO: 45) | gUUUGAGAGUUAUGUAAgaaaUUACAUGACGAGUUCAAAUAAAAAUUUAUUCAAACCGCCUAUUUAUAGGCCGCAGAUGUUCUGCAUUAUGCUUGCUAUUGCAAGCUUUUUU (SEQ ID NO: 45) | gUUUGAGAGUUAUGUAAgaaaUUACAUGACGAGUUCAAAUAAAAAUUUAUUCAAACCGCCUAUUUAUAGGCCGCAGAUGUUCUGCAUUAUGCUUGCUAUUGCAAGCUUUUUU (SEQ ID NO: 45) | gUUUGAGAGUUAUGUAAgaaaUUACAUGACGAGUUCAAAUAAAAAUUUAUUCAAACCGCCUAUUUAUAGGCCGCAGAUGUUCUGCAUUAUGCUUGCUAUUGCAAGCUUUUUU (SEQ ID NO: 45) | gUUUGAGAGUUAUGUAAgaaaUUACAUGACGAGUUCAAAUAAAAAUUUAUUCAAACCGCCUAUUUAUAGGCCGCAGAUGUUCUGCAUUAUGCUUGCUAUUGCAAGCUUUUUU (SEQ ID NO: 45) |
| Version | V2 | V2 | V2 | V2 | V2 |
| Full sgRNA sequence | UgcAGUCCGGGCUGGGAGCGGGUgUUUGAGAGUUAUGUAAgaaaUUACAUGACGAGUUCAAAUAAAAAUUUAUUCAAACCGCCUAUUUAUAGGCCGCAGAUGUUCUGCAUUAUGCUUGCUAUUGCAAGCUUUUUU (SEQ ID NO: 113) | gcAGUCCGGGCUGGGAGCGGGUgUUUGAGAGUUAUGUAAgaaaUUACAUGACGAGUUCAAAUAAAAAUUUAUUCAAACCGCCUAUUUAUAGGCCGCAGAUGUUCUGCAUUAUGCUUGCUAUUGCAAGCUUUUUU (SEQ ID NO: 117) | cAGUCCGGGCUGGGAGCGGGUgUUUGAGAGUUAUGUAAgaaaUUACAUGACGAGUUCAAAUAAAAAUUUAUUCAAACCGCCUAUUUAUAGGCCGCAGAUGUUCUGCAUUAUGCUUGCUAUUGCAAGCUUUUU (SEQ ID NO: 119) | AGUCCGGGCUGGGAGCGGGUgUUUGAGAGUUAUGUAAgaaaUUACAUGACGAGUUCAAAUAAAAAUUUAUUCAAACCGCCUAUUUAUAGGCCGCAGAUGUUCUGCAUUAUGCUUGCUAUUGCAAGCUUUUU (SEQ ID NO: 121) | GUCCGGGCUGGGAGCGGGUgUUUGAGAGUUAUGUAAgaaaUUACAUGACGAGUUCAAAUAAAAAUUUAUUCAAACCGCCUAUUUAUAGGCCGCAGAUGUUCUGCAUUAUGCUUGCUAUUGCAAGCUUUUUU (SEQ ID NO: 123) |
| Protospacer (with PAM bolded) - On target | CTGTTGCTGCAGTCCGGGCTGGGAGCGGG**TGGG**GAGCAGAGGG (SEQ ID NO: 114) | CTGTTGCTGCAGTCCGGGCTGGGAGCGGG**TGGG**GAGCAGAGGG (SEQ ID NO: 114) | CTGTTGCTGCAGTCCGGGCTGGGAGCGGG**TGGG**GAGCAGAGGG (SEQ ID NO: 114) | CTGTTGCTGCAGTCCGGGCTGGGAGCGGG**TGGG**GAGCAGAGGG (SEQ ID NO: 114) | CTGTTGCTGCAGTCCGGGCTGGGAGCGGG**TGGG**GAGCAGAGGG (SEQ ID NO: 114) |
| Protospacer (with PAM bolded) - Off target | GTTAAGAgaCAGTCCaGGCTGGGAGCaGGT**GGG**GAGAGGAGGG | GTTAAGAgaCAGTCCaGGCTGGGAGCaGGT**GGG**GAGAGGAGGG | GTTAAGAgaCAGTCCaGGCTGGGAGCaGGT**GGG**GAGAGGAGGG | GTTAAGAgaCAGTCCaGGCTGGGAGCaGGT**GGG**GAGAGGAGGG | sGTTAAGAgaCAGTCCaGGCTGGGAGCaGGT**GGG**GAGAGGAGGG |

TABLE 5-continued

| Synthetic sgRNA (spacer and scaffold) | | | | | |
|---|---|---|---|---|---|
| | (SEQ ID NO: 115) | (SEQ ID NO: 115) | (SEQ ID NO: 115) | (SEQ ID NO: 115) | (SEQ ID NO: 115) |
| Name | O50_ELANE_V2_g35_18 | O50_ELANE_V2_g35_17 | O50_ELANE_V3_g35_20 | O50_ELANE_V4_g35_20 | |
| Spacer | UCCGGGCUGGGAGCGGGU (SEQ ID NO: 124) | CCGGGCUGGGAGCGGGU (SEQ ID NO: 126) | AGUCCGGGCUGGGAGCGGGU (SEQ ID NO: 120) | AGUCCGGGCUGGGAGCGGGU (SEQ ID NO: 120) | |
| Scaffold | gUUUGAGAGUUAUGUAAgaaaUUACAUGACGAGUUCAAAUAAAAAUUUAUUCAAACCGCCUAUUUAUAGGCCGCAGAUGUUCUGCAUUAUGCUUGCUAUUGCAAGCUUUUUU (SEQ ID NO: 45) | gUUUGAGAGUUAUGUAAgaaaUUACAUGACGAGUUCAAAUAAAAAUUUAUUCAAACCGCCUAUUUAUAGGCCGCAGAUGUUCUGCAUUAUGCUUGCUAUUGCAAGCUUUUUU (SEQ ID NO: 45) | gUUUGAGAGUUAUGUgaaaACAUGACGAGUUCAAAUAAAAAUUUAUUCAAACCGCCUAUUUAUAGGCCGCAGAUGUUCUGCAUUAUGCUUGCUAUUGCAAGCUUUUUU (SEQ ID NO: 87) | gUUUGAGAGUUAUGUAgaaaUACAUGACGAGUUCAAAUAAAAAUUUAUUCAAACCGCCUAUUUAUAGGCCGCAGAUGUUCUGCAUUAUGCUUGCUAUUGCAAGCUUUUUU (SEQ ID NO: 88) | |
| Version | V2 | V2 | V3 | V4 | |
| Full sgRNA sequence | UCCGGGCUGGGAGCGGGUgUUUGAGAGUUAUGUAAgaaaUUACAUGACGAGUUCAAAUAAAAAUUUAUUCAAACCGCCUAUUUAUAGGCCGCAGAUGUUCUGCAUUAUGCUUGCUAUUGCAAGCUUUUUU (SEQ ID NO: 125) | CCGGGCUGGGAGCGGGUgUUUGAGAGUUAUGUAAgaaaUUACAUGACGAGUUCAAAUAAAAAUUUAUUCAAACCGCCUAUUUAUAGGCCGCAGAUGUUCUGCAUUAUGCUUGCUAUUGCAAGCUTJUTJUU (SEQ ID NO: 127) | AGUCCGGGCUGGGAGCGGGUgUUUGAGAGUUAUGUgaaaACAUGACGAGUUCAAAUAAAAAUUUAUUCAAACCGCCUAUUUAUAGGCCGCAGAUGUUCUGCAUUAUGCUUGCUAUUGCAAGCUUUUUU (SEQ ID NO: 128) | AGUCCGGGCUGGGAGCGGGUgUUUGAGAGUUAUGUAgaaaUACAUGACGAGUUCAAAUAAAAAUUUAUUCAAACCGCCUAUUUAUAGGCCGCAGAUGUUCUGCAUUAUGCUUGCUAUUGCAAGCUUUUUU (SEQ ID NO: 129) | |
| Protospacer (with PAM bolded) - On target | CTGTTGCTGCAGTCCGGGCTGGGAGCGGG**TGGG**GAGCAGAGGG (SEQ ID NO: 114) | CTGTTGCTGCAGTCCGGGCTGGGAGCGGG**TGGG**GAGCAGAGGG (SEQ ID NO: 114) | CTGTTGCTGCAGTCCGGGCTGGGAGCGGG**TGGG**GAGCAGAGGG (SEQ ID NO: 114) | CTGTTGCTGCAGTCCGGGCTGGGAGCGGG**TGGG**GAGCAGAGGG (SEQ ID NO: 114) | |
| Protospacer (with PAM bolded) - Off target | GTTAAGAgaCAGTCCaGGCTGGGAGCaGGT**GGG**GAGAGGAGGG (SEQ ID NO: 115) | GTTAAGAgaCAGTCCaGGCTGGGAGCaGGT**GGG**GAGAGGAGGG (SEQ ID NO: 115) | GTTAAGAgaCAGTCCaGGCTGGGAGCaGGT**GGG**GAGAGGAGGG (SEQ ID NO: 115) | GTTAAGAgaCAGTCCaGGCTGGGAGCaGGT**GGG**GAGAGGAGGG (SEQ ID NO: 115) | |

TABLE 6

Activity of OMNI-50 ™ in human cells on endogenous genomic targets

| Genomic site | Corresponding Spacer name | Spacer sequence | 3' (PAM containing) genomic seq (PAM Bolded) | % indels | % transfection | Norm. % editing | % editing in neg control | % transfection in neg control | Norm. % editing in neg control |
|---|---|---|---|---|---|---|---|---|---|
| EMX1 site 2 | EMX1g1_OMNI50 | UCUGUGAAUGUUAGACCCAU (SEQ ID NO: 97) | **GGG**AGCAG | 44.18-25.72 | | | 0.02 | | |

TABLE 6-continued

| Activity of OMNI-50 ™ in human cells on endogenous genomic targets | | | | | | | | | |
|---|---|---|---|---|---|---|---|---|---|
| Genomic site | Corre-sponding Spacer name | Spacer sequence | 3' (PAM containing) genomic seq (PAM Bolded) | % indels | % trans-fection | Norm. % editing | % editing in neg control | % trans-fection in neg control | Norm. % editing in neg control |
| EMX1 site 3 | EMX1g2_ OMNI50 | CCAUGG GAGCAG CUGGUC AG (SEQ ID NO: 98) | **AGG**GG ACC | 55.81 | | | | | |
| CXCR4 site 3 | CXCR4g1_ OMNI50 | GCAAGA GACCCA CACACC GG (SEQ ID NO: 99) | **AGG**AG CGC | 29.58- 32.14 | | | 0.18 | | |
| CXCR4 site 4 | CXCR4g2_ OMNI50 | ACACCG GAGGAG CGCCCG CU (SEQ ID NO: 100) | **TGG**GG GAG | 42.13- 49.85 | | | 0.22 | | |
| PDCD1 site 4 | PDCD1g1_ OMNI50 | CGUCUG GGCGGU GCUACA AC (SEQ ID NO: 101) | **TGG**GCT GG | 13.35- 8.7 | | | 0.05 | | |
| PDCD1 site 5 | PDCD1g2_ OMNI50 | CUACAA CUGGGC UGGCGG CC (SEQ ID NO: 102) | **AGG**AT GGT | 17.53 | | | | | |
| ELANE g35 | ELANEg3 5_OMNI50 | AGUCCG GGCUGG GAGCGG GU (SEQ ID NO: 103) | **GGG**GA GCA | 40.92- 55.39 | | | 0.24 | 5.95 | 3.982225429 |
| ELANE g58 | ELANEg5 8_OMNI50 | GCUGCG GGAAAG GGAUUC CC (SEQ ID NO: 104) | **TGG**GA CTC | 11.11 | 20.50 | 54.23 | 0.18 | 5.95 | 2.974553445 |
| ELANE g38 | ELANEg3 8 OMNI50 | ACAGCG GGUGUA GACUCC GA (SEQ ID NO: 105) | **GGG**GG ACG | 9.99 | | | | | |
| ELANE g39 | ELANEg3 9_OMNI50 | CAGCGG GUGUAG ACUCCG AG (SEQ ID NO: 106) | **GGG**GA CGT | 24.87 | | | | | |
| ELANE g62 | ELANEg6 2_OMNI50 | GUCAAG CCCCAG AGGCCA CA (SEQ ID NO: 107) | **GGG**AC AGA | 38.87- 52.74 | | | 0.12 | 5.95 | 2.002503126 |

Table 6. Nuclease activity in endogenous context in mammalian cells: The OMNI-50™ nuclease was expressed in mammalian cell system (HeLa) by DNA transfection together with an sgRNA expressing plasmid. Cell lysates were used for site specific genomic DNA amplification and NGS. The percentage of indels was measured and analyzed to determine editing level. Each sgRNA is composed of the tracrRNA (see Table 2) and the spacer detailed here. The 3' genomic spacer sequence contains the PAM relevant for the OMNI-50™ nuclease. Transfection efficiency (% transfection) was measured by flow cytometry quantification of mCherry signal, as described above. The transfection efficiency was used to normalize the editing level (% indels norm). All tests were performed in triplicate. OMNI nuclease only (i.e. no guide) transfected cells served as a negative control.

TABLE 7

OMNI-50 ™ Activity as an RNP

| System | Genomic site | Corresponding spacer name | Spacer sequence | % indels |
|---|---|---|---|---|
| Primary T cells | TRAC | gRNA 1 | TCTCTCAGCTGGTACACGGCA (SEQ ID NO: 156) | 18% |
| | | gRNA 2 | GCGTCATGAGCAGATTAAACC (SEQ ID NO: 157) | 81% |
| | | gRNA 3 | TCTCGACCAGCTTGACATCAC (SEQ ID NO: 158) | 10% |
| | | gRNA 4 | TTAAACCCGGCCACTTTCAGG (SEQ ID NO: 159) | 46% |
| | | gRNA 5 | CTGTGCTAGACATGAGGTCTA (SEQ ID NO: 160) | 26% |
| | | gRNA 8 | ACTTCAAGAGCAACAGTGCTG (SEQ ID NO: 161) | 3% |
| | | gRNA 9 | AAGAGCAACAGTGCTGTGGCC (SEQ ID NO: 162) | 13% |
| | | gRNA 10 | GCTGGGGAAGAAGGTGTCTTC (SEQ ID NO: 163) | 7% |
| | | gRNA 15 | ATAGGCAGACAGACTTGTCAC (SEQ ID NO: 164) | 16% |
| | | gRNA 17 | TAGAGTCTCTCAGCTGGTACA (SEQ ID NO: 165) | 23% |
| | | gRNA 18 | GTCTCTCAGCTGGTACACGGC (SEQ ID NO: 166) | 5% |
| | | gRNA 19 | CAGCTGGTACACGGCAGGGTC (SEQ ID NO: 167) | 11% |
| | | gRNA 20 | AGCTGGTACACGGCAGGGTCA (SEQ ID NO: 168) | 13% |
| | | gRNA 21 | TACACGGCAGGGTCAGGGTTC (SEQ ID NO: 169) | 19% |
| | | gRNA 23 | CTTTCAAAACCTGTCAGTGAT (SEQ ID NO: 170) | 4% |
| | | gRNA 25 | TCCGAATCCTCCTCCTGAAAG (SEQ ID NO: 171) | 21% |
| | | gRNA 26 | AATCCTCCTCCTGAAAGTGGC (SEQ ID NO: 172) | 11% |
| | | gRNA 27 | ATCCTCCTCCTGAAAGTGGCC (SEQ ID NO: 173) | 9% |
| | | gRNA 29 | CTGCTCATGACGCTGCGGCTG (SEQ ID NO: 174) | 15% |
| | | gRNA 30 | AGATTAAACCCGGCCACTTTC (SEQ ID NO: 175) | 24% |
| | | gRNA 31 | AACCCGGCCACTTTCAGGAGG (SEQ ID NO: 176) | 29% |
| | | gRNA 32 | GCCACTTTCAGGAGGAGGATT (SEQ ID NO: 177) | 29% |
| | B2M | gRNA 1 | TACTCTCTCTTTCTGGCCTGG (SEQ ID NO: 178) | 5% |
| | | gRNA 2 | GCATACTCATCTTTTTCAGTG (SEQ ID NO: 179) | 12% |
| | | gRNA 3 | CGCTACTCTCTCTTTCTGGCC (SEQ ID NO: 180) | 17% |
| | | gRNA 4 | GCGCGAGCACAGCTAAGGCCA (SEQ ID NO: 181) | 64% |
| | | gRNA 6 | GCTCGCGCTACTCTCTCTTTC (SEQ ID NO: 182) | 9% |
| | | gRNA 7 | AGAGTAGCGCGAGCACAGCTA (SEQ ID NO: 183) | 61% |
| | | gRNA 15 | TCACAGCCCAAGATAGTTAAG (SEQ ID NO: 184) | 45% |
| | | gRNA 16 | CACAGCCCAAGATAGTTAAGT (SEQ ID NO: 185) | 42% |
| | | gRNA 18 | GACAAAGTCACATGGTTCACA (SEQ ID NO: 186) | 43% |
| | | gRNA 19 | AAGTCACATGGTTCACACGGC (SEQ ID NO: 187) | 8% |

TABLE 7-continued

| OMNI-50 ™ Activity as an RNP | | | | |
|---|---|---|---|---|
| System | Genomic site | Corresponding spacer name | Spacer sequence | % indels |
| | | gRNA 20 | AGGCATACTCATCTTTTTCAG (SEQ ID NO: 188) | 37% |
| | | gRNA 21 | GGCATACTCATCTTTTTCAGT (SEQ ID NO: 189) | 33% |
| | | gRNA 22 | CATACTCATCTTTTTCAGTGG (SEQ ID NO: 190) | 29% |
| | | gRNA 23 | TCAGTAAGTCAACTTCAATGT (SEQ ID NO: 191) | 41% |
| | | gRNA 26 | ACGTGAGTAAACCTGAATCTT (SEQ ID NO: 192) | 22% |
| | ELANE g35 | ELANEg35_ OMNI-50 | AGTCCGGGCTGGGAGCGGGT (SEQ ID NO: 193) | 49.5% |
| U2OS | ELANE g35 | ELANEg35_ OMNI-50 | AGTCCGGGCTGGGAGCGGGT (SEQ ID NO: 193) | 95% |
| | ELANE g38 | ELANEg38_ OMNI-50 | ACAGCGGGTGTAGACTCCGA (SEQ ID NO: 194) | 35% |
| | ELANE g39 | ELANEg39_ OMNI-50 | CAGCGGGTGTAGACTCCGAG (SEQ ID NO: 195) | 75% |
| | ELANE g58 | ELANEg58_ OMNI-50 | GCTGCGGGAAAGGGATTCCC (SEQ ID NO: 196) | 83% |
| | ELANE g62 | ELANEg62_ OMNI-50 | GTCAAGCCCCAGAGGCCACA (SEQ ID NO: 197) | 86% |
| iPSC | ELANE g35 | ELANEg35_ OMNI-50 | AGTCCGGGCTGGGAGCGGGT (SEQ ID NO: 193) | 53% |
| HSC | ELANE g35 | ELANEg35_ OMNI-50 | AGTCCGGGCTGGGAGCGGGT (SEQ ID NO: 193) | 96% |
| | ELANE g38 | ELANEg38_ OMNI-50 | ACAGCGGGTGTAGACTCCGA (SEQ ID NO: 194) | 44% |
| | ELANE g39 | ELANEg39_ OMNI-50 | CAGCGGGTGTAGACTCCGAG (SEQ ID NO: 195) | 59% |
| | ELANE g58 | ELANEg58_ OMNI-50 | GCTGCGGGAAAGGGATTCCC (SEQ ID NO: 196) | 22% |
| | ELANE g62 | ELANEg62_ OMNI-50 | GTCAAGCCCCAGAGGCCACA (SEQ ID NO: 197) | 59% |

Table 7. OMNI-50™ activity as RNP: OMNI-50™ RNP was assembled with synthetic sgRNA (Agilent) and electroporated into cells. Several cell types were tested with a variety of sgRNAs. Cellular system, gene name, and spacer sequences are indicated next to the editing level as measured by NGS.

TABLE 8

| OMNI-50 ™ Multiplexing | | | | | | |
|---|---|---|---|---|---|---|
| | | | OMNI-50 ™ Editing | | OMNI-50 ™ STD | |
| Gene | Site | Spacer Sequence | Donor 1 | Donor 2 | Donor 1 | Donor 2 |
| TRAC | gRNA 32 | GCCACTTTCAG GAGGAGGATT (SEQ ID NO: 177) | 59.00 | 53.00 | 9.00 | 10.00 |
| B2M | gRNA 15 | TCACAGCCCAA GATAGTTAAG (SEQ ID NO: 184) | 42.00 | 44.00 | 13.00 | 19.00 |
| TRAC + B2M | gRNA 32 + gRNA 15 | Test for TRAC | 55.00 | 44.00 | 5.00 | 1.00 |
| TRAC + B2M | gRNA 32 + gRNA 15 | Test for B2M | 22.00 | 27.00 | 3.00 | 1.00 |

Table 8. OMNI-50™ multiplexing in primary T cells: Multiplexing of OMNI-50™ was performed by electroporation into activated primary T cells, targeting either TRAC or B2M genes, or combined targeting. The first two rows show each gene separately on two donors that were randomly chosen from a five-donor bank. The final two rows show the same analysis for each gene when electroporation was performed as a multiplex. Editing activity was determined by indel count after amplicon based NGS. Standard deviation of duplicates is also shown. Using only TRAC gRNA had no effect on the B2M gene and vice versa (not shown).

TABLE 9

OMNI-50 ™ off-targets

| Guide | SpCas9 #1 | SpCas9 #2 | OMNI-50 ™ #1 | OMNI-50 ™ #2 | SpCas9 on target editing | SpCas9 ODN integration | OMNI-50 ™ on target editing | OMNI-50 ™ ODN integration |
|---|---|---|---|---|---|---|---|---|
| ELANE g35 | 206 | 201 | 11 | 5 | 85%, 90% | 58%, 62% | 97%, 97% | 37%, 38% |
| ELANE g58 | 51 | 92 | 18 | 13 | 86%, 86% | 39%, 42% | 88%, 83% | 37%, 36% |
| ELANE g58_alt | 67 | N.A. | 4 | 9 | 82% | 34% | 88%, 82% | 34%, 39% |
| ELANE g62 | 17 | 12 | 12 | 15 | 88%, 90% | 3%, 27% | 89%, 89% | 22%, 17% |
| ELANE g62_alt | 18 | 13 | 5 | 9 | 1%, 2% | N.A. | 0%, 0% | N.A. |
| TRAC g32 | 10 | 9 | 5 | 5 | 93%, 81% | 14% | 51%, 74% | 31%, 26% |

Table 9. OMNI-50™ off-targets analysis by unbiased biochemical assay (guide seq): Off-target site counts of SpCas9 or OMNI-50™ nucleases is shown in two replicates. For this analysis, only amplified sites with ≥10 reads were analyzed, and sites with a lower number of reads were discarded in order to reduce background noise. The editing level at the on-target site determined by indel count after amplicon based NGS is also indicated, as well as ODN integration.

TABLE 10

OMNI-50 ™ spacer optimization

| | U2OS cell line | | | | HSC | | | | iPSC | | | |
|---|---|---|---|---|---|---|---|---|---|---|---|---|
| | % editing ELANE g35 | % editing g35 Off-target | STD ELANE g35 | STD Off-target | % editing ELANE g35 | % editing g35 Off-target | STD ELANE g35 | STD Off-target | % editing ELANE g35 | % editing g35 Off-target | STD ELANE g35 | STD Off-target |
| 17bp | 0.54 | 0.20 | 0.28 | 0.04 | N.A. | N.A. | N.A. | N.A. | N.A. | N.A. | N.A. | N.A. |
| 18bp | 0.59 | 0.15 | 0.30 | 0.01 | N.A. | N.A. | N.A. | N.A. | N.A. | N.A. | N.A. | N.A. |
| 19bp | 3.20 | 0.21 | 0.29 | 0.07 | 11.54 | 0.00 | 3.24 | 0.00 | 0.41 | 0.00 | 0.19 | 0.00 |
| 20bp | 43.77 | 0.21 | 12.77 | 0.02 | 26.47 | 0.00 | 3.23 | 0.00 | 6.63 | 0.00 | 0.68 | 0.00 |
| 21bp | 91.50 | 0.37 | 4.66 | 0.03 | 74.86 | 0.00 | 1.70 | 0.00 | 48.15 | 0.00 | 0.16 | 0.00 |
| 22bp | 90.87 | 10.50 | 3.63 | 5.55 | 89.10 | 0.10 | 1.14 | 0.11 | 52.80 | 3.60 | 3.77 | 0.27 |
| 23bp | 75.81 | 7.59 | 8.35 | 4.25 | 85.86 | 0.10 | 1.69 | 0.27 | 51.16 | 2.50 | 7.40 | 0.15 |

Table 10. OMNI-50™ spacer optimization. RNP was assembled for OMNI-50™ protein with sgRNA of different lengths. The RNPs were electroporated into U2OS, HSCs, and iPSCs cells, and activity was determined by indel count after amplicon based NGS. OMNI-50™ was tested on ELANE g35 in duplicates (standard deviation is shown). Table 10 Appendix shows a detailed comparison of 21 nt vs 22 nt spacer was done across five different genomic sites in HSCs.

TABLE 10

Appendix - comparison of 21nt vs 22nt spacers in HSCs

| | 21nt % editing | 22nt % editing | 21nt STD | 22nt STD |
|---|---|---|---|---|
| ELANE g35 | 71.04 | 96.32 | 3.23 | 1.43 |
| ELANE g38 | 9.79 | 43.89 | 1.26 | 0.53 |

TABLE 10-continued

Appendix - comparison of 21nt vs 22nt spacers in HSCs

| | 21nt % editing | 22nt % editing | 21nt STD | 22nt STD |
|---|---|---|---|---|
| ELANE g39 | 19.30 | 58.87 | 1.20 | 1.07 |
| ELANE g58 | 11.02 | 21.86 | 2.83 | 0.40 |
| ELANE g62 | 26.86 | 58.70 | 0.23 | 0.70 |

REFERENCES

1. Ahmad and Allen (1992) "Antibody-mediated Specific Binging and Cytotoxicity of Lipsome-entrapped Doxorubicin to Lung Cancer Cells in Vitro", Cancer Research 52:4817-20.
2. Anderson (1992) "Human gene therapy", Science 256: 808-13.
3. Basha et al. (2011) "Influence of Cationic Lipid Composition on Gene Silencing Properties of Lipid Nanoparticle Formulations of siRNA in Antigen-Presenting Cells", Mol. Ther. 19(12):2186-200.
4. Behr (1994) "Gene transfer with synthetic cationic amphiphiles: Prospects for gene therapy", Bioconjuage Chem 5:382-89.
5. Blaese et al. (1995) "Vectors in cancer therapy: how will they deliver", Cancer Gene Ther. 2:291-97.
6. Blaese et al. (1995) "T lympocyte-directed gene therapy for ADA-SCID: initial trial results after 4 years", Science 270(5235):475-80.
7. Briner et al. (2014) "Guide RNA functional modules direct Cas9 activity and orthognality", Molecular Cell 56:333-39.

8. Buchschacher and Panganiban (1992) "Human immunodeficiency virus vectors for inducible expression of foreign genes", J. Virol. 66:2731-39.
9. Burstein et al. (2017) "New CRISPR-Cas systems from uncultivated microbes", Nature 542:237-41.
10. Canver et al., (2015) "BCL11A enhancer dissection by Cas9-mediated in situ saturating mutagenesis", Nature Vol. 527, Pgs. 192-214.
11. Chang and Wilson (1987) "Modification of DNA ends can decrease end-joining relative to homologous recombination in mammalian cells", Proc. Natl. Acad. Sci. USA 84:4959-4963.
12. Charlesworth et al. (2019) "Identification of preexisting adaptive immunity to Cas9 proteins in humans", Nature Medicine, 25(2), 249.
13. Chung et al. (2006) "*Agrobacterium* is not alone: gene transfer to plants by viruses and other bacteria", Trends Plant Sci. 11(1):1-4.
14. Coelho et al. (2013) "Safety and efficacy of RNAi therapy for transthyretin amyloidosis" N. Engl. J. Med. 369, 819-829.
15. Crystal (1995) "Transfer of genes to humans: early lessons and obstacles to success", Science 270(5235): 404-10.
16. Dillon (1993) "Regulation gene expression in gene therapy" Trends in Biotechnology 11(5):167-173.
17. Dranoff et al. (1997) "A phase I study of vaccination with autologous, irradiated melanoma cells engineered to secrete human granulocyte macrophage colony stimulating factor", Hum. Gene Ther. 8(1):111-23.
18. Dunbar et al. (1995) "Retrovirally marked CD34-enriched peripheral blood and bone marrow cells contribute to long-term engraftment after autologous transplantation", Blood 85:3048-57.
19. Ellem et al. (1997) "A case report: immune responses and clinical course of the first human use of ganulocyte/macrophage-colony-stimulating-factor-transduced autologous melanoma cells for immunotherapy", Cancer Immunol Immunother 44:10-20.
20. Gao and Huang (1995) "Cationic liposome-mediated gene transfer" Gene Ther. 2(10):710-22.
21. Haddada et al. (1995) "Gene Therapy Using Adenovirus Vectors", in: The Molecular Repertoire of Adenoviruses III: Biology and Pathogenesis, ed. Doerfler and Bohm, pp. 297-306.
22. Han et al. (1995) "Ligand-directed retro-viral targeting of human breast cancer cells", Proc. Natl. Acad. Sci. USA 92(21):9747-51.
23. Humbert et al., (2019) "Therapeutically relevant engraftment of a CRISPR-Cas9—edited HSC-enriched population with HbF reactivation in nonhuman primates", Sci. Trans. Med., Vol. 11, Pgs. 1-13.
24. Inaba et al. (1992) "Generation of large numbers of dendritic cells from mouse bone marrow cultures supplemented with granulocyte/macrophage colony-stimulating factor", J Exp Med. 176(6):1693-702.
25. Jiang and Doudna (2017) "CRISPR-Cas9 Structures and Mechanisms", Annual Review of Biophysics 46:505-29.
26. Jinek et al. (2012) "A programmable dual-RNA-guided DNA endonuclease in adaptive bacterial immunity", Science 337(6096):816-21.
27. Johan et al. (1992) "GLVR1, a receptor for gibbon ape leukemia virus, is homologous to a phosphate permease of *Neurospora crassa* and is expressed at high levels in the brain and thymus", J Virol 66(3):1635-40.
28. Judge et al. (2006) "Design of noninflammatory synthetic siRNA mediating potent gene silencing in vivo", Mol Ther. 13(3):494-505.
29. Kohn et al. (1995) "Engraftment of gene-modified umbilical cord blood cells in neonates with adnosine deaminase deficiency", Nature Medicine 1:1017-23.
30. Kremer and Perricaudet (1995) "Adenovirus and adeno-associated virus mediated gene transfer", Br. Med. Bull. 51(1):31-44.
31. Macdiarmid et al. (2009) "Sequential treatment of drug-resistant tumors with targeted minicells containing siRNA or a cytotoxic drug", Nat Biotechnol. 27(7):643-51.
32. Malech et al. (1997) "Prolonged production of NADPH oxidase-corrected granulocyes after gene therapy of chronic granulomatous disease", PNAS 94(22):12133-38.
33. Maxwell et al. (2018) "A detailed cell-free transcription-translation-based assay to decipher CRISPR protospacer adjacent motifs", Methods 14348-57
34. Miller et al. (1991) "Construction and properties of retrovirus packaging cells based on gibbon ape leukemia virus", J Virol. 65(5):2220-24.
35. Miller (1992) "Human gene therapy comes of age", Nature 357:455-60.
36. Mir et al. (2019) "Type II-C CRISPR-Cas9 Biology, Mechanism and Application", ACS Chem. Biol. 13(2):357-365.
37. Mitani and Caskey (1993) "Delivering therapeutic genes—matching approach and application", Trends in Biotechnology 11(5):162-66.
38. Nabel and Felgner (1993) "Direct gene transfer for immunotherapy and immunization", Trends in Biotechnology 11(5):211-15.
39. Nehls et al. (1996) "Two genetically separable steps in the differentiation of thymic epithelium" Science 272: 886-889.
40. Nishimasu et al. "Crystal structure of Cas9 in complex with guide RNA and target DNA" (2014) Cell 156(5): 935-49.
41. Nishimasu et al. (2015) "Crystal Structure of *Staphylococcus aureus* Cas9" Cell 162(5):1113-26.
42. Palermo et al. (2018) "Key role of the REC lobe during CRISPR-Cas9 activation by 'sensing', 'regulating', and 'locking' the catalytic HNH domain" Quarterly Reviews of Biophysics 51, e9, 1-11.
43. Remy et al. (1994) "Gene Transfer with a Series of Lipophilic DNA-Binding Molecules", Bioconjugate Chem. 5(6):647-54.
44. Sentmanat et al. (2018) "A Survey of Validation Strategies for CRISPR-Cas9 Editing", Scientific Reports 8:888, doi:10.1038/s41598-018-19441-8.
45. Sommerfelt et al. (1990) "Localization of the receptor gene for type D simian retroviruses on human chromosome 19", J. Virol. 64(12):6214-20.
46. Van Brunt (1988) "Molecular framing: transgenic animals as bioactors" Biotechnology 6:1149-54.
47. Vigne et al. (1995) "Third-generation adenovectors for gene therapy", Restorative Neurology and Neuroscience 8(1,2): 35-36.
48. Wagner et al. (2019) "High prevalence of *Streptococcus pyogenes* Cas9-reactive T cells within the adult human population" Nature Medicine, 25(2), 242
49. Wilson et al. (1989) "Formation of infectious hybrid virion with gibbon ape leukemia virus and human T-cell leukemia virus retroviral envelope glycoproteins and the gag and pol proteins of Moloney murine leukemia virus", J. Virol. 63:2374-78.

50. Yu et al. (1994) "Progress towards gene therapy for HIV infection", Gene Ther. 1(1):13-26.

51. Zetsche et al. (2015) "Cpf1 is a single RNA-guided endonuclease of a class 2 CRIPSR-Cas system" Cell 163(3):759-71.

52. Zuris et al. (2015) "Cationic lipid-mediated delivery of proteins enables efficient protein based genome editing in vitro and in vivo" Nat Biotechnol. 33(1):73-80.

What is claimed is:

1. A non-naturally occurring composition comprising a Clustered Regularly Interspaced Short Palindromic Repeats (CRISPR) nuclease comprising a sequence having at least 95% identity to the amino acid sequence of SEQ ID NO: 3.

2. The composition of claim 1, further comprising a, a) a CRISPR RNA (crRNA) molecule and a transactivating CRISPR RNA (tracrRNA) molecule, wherein the crRNA molecule, tracrRNA molecule, and the CRISPR nuclease do not naturally occur together; or b) a single-guide RNA (sgRNA) molecule, wherein the crRNA molecule or sgRNA molecule comprises a guide sequence portion that is complementary to a sequence in a target region.

3. The composition of claim 2, wherein the guide sequence protein consists of 21-22 nucleotides.

4. The composition of claim 2, wherein the guide sequence portion consists of 19-23 nucleotides.

5. The composition of claim 2, wherein the guide sequence portion consists of 17-24 nucleotides.

6. The composition of claim 2, wherein the crRNA molecule or sgRNA molecule further comprises a repeat sequence portion which comprises the sequence of SEQ ID NO: 37, SEQ ID NO: 39, or GUUUGAGAG.

7. The composition of claim 2, wherein the tracrRNA molecule or the sgRNA molecule further comprises a tracrRNA sequence portion which comprises one or more sequences selected from SEQ ID NOs: 38, 40-43, and 149-154.

8. The composition of claim 2, wherein the sgRNA molecule further comprises a nucleotide sequence portion which comprises a sequence selected from the group of sequences set forth as SEQ ID NOs: 44, 45, 87, and 88.

9. The composition of claim 2, wherein the tracrRNA molecule comprises a nucleotide sequence that can form a complex with the CRISPR nuclease.

10. The composition of claim 2, wherein the target region is adjacent to a Protospacer Adjacent Motif (PAM) site selected from NGG, NAG, and NGA.

11. The composition of claim 2, further comprising a donor template molecule.

12. The composition of claim 11, wherein the donor template molecule is a DNA molecule.

13. The composition of claim 11, wherein the donor template molecule is an RNA molecule.

14. The composition of claim 1, wherein the CRISPR nuclease further comprises a nuclear localization sequence (NLS).

15. The composition of claim 1, wherein the CRISPR nuclease further comprises two or more nuclear localization sequences.

16. The composition of claim 1, wherein the CRISPR nuclease is linked to a further protein.

17. The composition of claim 1, further comprising a DNA molecule encoding a crRNA molecule, a tracrRNA molecule, both a crRNA molecule and a tracrRNA molecule, or a sgRNA molecule.

18. The composition of claim 1, further comprising a single-guide RNA (sgRNA) molecule, which comprises:

(i) a nuclease-binding RNA nucleotide sequence portion; and (ii) a guide sequence portion consisting of a 17-24 nucleotide sequence complementary to a sequence in a target DNA sequence, wherein the CRISPR nuclease is capable of complexing with the sgRNA molecule to form a complex capable of hybridizing with the target DNA sequence.

19. The composition of claim 18, wherein the guide sequence portion consists of 21-22 nucleotides.

20. The composition of claim 18, wherein the sgRNA molecule comprises a sequence selected from the group consisting of SEQ ID NOs: 37-45, 87-88, 149-154, and GUUUGAGAG.

21. The composition of claim 18, wherein the target DNA sequence is next to a PAM site selected from the group consisting of NGG, NAG, and NGA.

22. The composition of claim 18, wherein the sgRNA molecule has a length of 50 to 200 bases.

23. A composition comprising an engineered nucleic acid molecule encoding a Clustered Regularly Interspaced Short Palindromic Repeats (CRISPR) nuclease comprising a sequence having at least 95% identity to the amino acid sequence of SEQ ID NO: 3.

24. The composition of claim 23, wherein the engineered nucleic acid molecule is a DNA molecule.

25. The composition of claim 23, wherein the engineered nucleic acid molecule is an mRNA molecule.

26. The composition of claim 23, wherein the engineered nucleic acid molecule further encodes a single-guide RNA.

27. The composition of claim 23, further comprising a second nucleic acid molecule encoding a single-guide RNA molecule, a crRNA molecule, and/or a tracrRNA molecule.

28. The composition of claim 27, wherein the second nucleic acid molecule is a DNA molecule.

29. A method of targeting or modifying a nucleotide sequence at a target site in a genome of a cell comprising introducing into the cell a nucleic acid molecule which encodes a Clustered Regularly Interspaced Short Palindromic Repeats (CRISPR) nuclease comprising a sequence having at least 95% identity to the amino acid sequence of SEQ ID NO: 3.

30. The method of claim 29, further comprising introducing into the cell (a) a crRNA molecule and a tracrRNA molecule; or (b) a sgRNA molecule, wherein the crRNA molecule or sgRNA molecule comprises a guide sequence portion that is complementary to a sequence in a target region.

31. The method of claim 30, further comprising introducing into the cell a donor template molecule.

32. The method of claim 29, further comprising introducing into the cell a DNA molecule encoding a crRNA molecule, a tracrRNA molecule, both a crRNA molecule and a tracrRNA molecule, or a sgRNA molecule.

33. A method of targeting or modifying a nucleotide sequence at a target site in the genome of a mammalian cell comprising introducing into the cell the composition of claim 1, wherein the composition further comprises a single-guide RNA (sgRNA) molecule comprising a guide sequence portion having 17-24 nucleotides and that is complementary to a sequence in a target DNA site, wherein the target DNA site is next to a PAM site selected from the group consisting of NGG, NAG, and NGA.

34. The method of claim 33, wherein the guide sequence portion consists of 21-22 nucleotides.

35. The method of claim 33, wherein the sgRNA molecule further comprises a sequence selected from the group consisting of SEQ ID NOs: 37-45, 87-88, 149-154, and GUUUGAGAG.

36. The method of claim 33, further comprising introducing into the cell (iii) a donor template molecule.

37. The method of claim 36, wherein the donor template molecule is a DNA molecule.

38. The method of claim 36, wherein the donor template molecule is an RNA molecule.

39. A method of treating a subject having a mutation disorder comprising introducing the composition of claim 2 into a cell of the subject.

* * * * *